(12) United States Patent
Webb et al.

(10) Patent No.: US 11,337,981 B2
(45) Date of Patent: *May 24, 2022

(54) DUAL CLK/CDK1 INHIBITORS FOR CANCER TREATMENT

(71) Applicant: SRI INTERNATIONAL, Menlo Park, CA (US)

(72) Inventors: Thomas R. Webb, Mountain View, CA (US); Jaehyeon Park, Sunnyvale, CA (US); Chandraiah Lagisetti, Cupertino, CA (US)

(73) Assignee: SRI International, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/886,290

(22) Filed: May 28, 2020

(65) Prior Publication Data

US 2020/0390772 A1 Dec. 17, 2020

Related U.S. Application Data

(63) Continuation of application No. 16/334,229, filed as application No. PCT/US2017/054442 on Sep. 29, 2017, now Pat. No. 10,722,515.

(60) Provisional application No. 62/402,876, filed on Sep. 30, 2016.

(51) Int. Cl.

| | |
|---|---|
| *C07D 473/16* | (2006.01) |
| *A61K 31/52* | (2006.01) |
| *A61P 35/00* | (2006.01) |
| *C07D 473/32* | (2006.01) |
| *A61K 31/437* | (2006.01) |
| *C07D 487/04* | (2006.01) |

(52) U.S. Cl.
CPC ............ *A61K 31/52* (2013.01); *A61K 31/437* (2013.01); *A61P 35/00* (2018.01); *C07D 473/16* (2013.01); *C07D 473/32* (2013.01); *C07D 487/04* (2013.01)

(58) Field of Classification Search
CPC .............................. C07D 473/16; A61K 31/52
USPC ........................................ 546/262; 514/262.1
See application file for complete search history.

(56) References Cited

U.S. PATENT DOCUMENTS

| | | | |
|---|---|---|---|
| 10,722,515 B2* | 7/2020 | Webb ..................... | A61K 31/52 |
| 2015/0164933 A1 | 6/2015 | Chiao et al. | |

FOREIGN PATENT DOCUMENTS

| | | |
|---|---|---|
| CN | 201780067717 | 9/2017 |
| EP | 17857539.5 | 9/2017 |
| JP | 2019-517257 | 9/2017 |
| WO | WO 97/16452 A1 | 5/1997 |
| WO | WO-2013/144532 A1 | 10/2013 |
| WO | PCT/US2017/054442 | 9/2017 |
| WO | WO 2018/064545 | 4/2018 |
| WO | WO-2018/064545 A1 | 4/2018 |

OTHER PUBLICATIONS

Furet et. al., Journal of Computer-Aided Molecular Design (2000), 14(5), 403-409.*
Moravec, et. al., Bioorganic & Medicinal Chemistry Letters (2003), 13(18), 2993-2996.*
Araki, S. et al., Inhibitors of CLK protein kinases suppress cell growth and induce apoptosis by modulating pre-mRNA splicing. PLoS One 2015, 10, e0116929.
Bonnal, S.et al. The spliceosome as a target of novel antitumour drugs. Nat Rev Drug Discov 2012, 11, 847-859.
Boon, K. L. et al. prp8 mutations that cause human retinitis pigmentosa lead to a U5 snRNP maturation defect in yeast. Nat Struct Mol Blot 14, 1077-1083 (2007).
Cancer Genome Atlas Research, N. Genomic and epigenomic landscapes of adult de novo acute myeloid leukemia. N Engl J Med 2013, 368, 2059-74.
Cancer Genome Atlas, N. Comprehensive molecular portraits of human breast tumours. Nature 2012, 490, 61-70.
Chakarova, C. F. et al. Mutations in HPRP3, a third member of pre-mRNA splicing factor genes, implicated in autosomal dominant retinitis pigmentosa. Hum Mol Genet 11, 87-92 (2002).
Chang, Y. T. et al., Synthesis and application of functionally diverse 2,6,9-trisubstituted purine libraries as CDK inhibitors. Chem Biol 1999, 6, 361-75.
Convertini, P. et al., Sudemycin E influences alternative splicing and changes chromatin modifications. Nucleic Acids Res 2014, 42, 4947-61.
Dai, Y. et al., Induction of apoptosis in human leukemia cells by the CDK1 inhibitor CGP74514A. Cell Cycle 2002, 1, 143-52.
Damm, F. et al., Spliceosome and other novel mutations in chronic lymphocytic leukemia and myeloid malignancies. Leukemia 2012, 26, 2027-31.
David, C. J. et al., Alternative pre-mRNA splicing regulation in cancer: pathways and programs unhinged. Genes Dev 2010, 24, 2343-64.

(Continued)

*Primary Examiner* — Jeffrey H Murray
(74) *Attorney, Agent, or Firm* — Ballard Spahr LLP

(57) ABSTRACT

The disclosure generally relates to substituted purine analogs that are dual CLK2/CDK1 inhibitors or more potent and specific CLK inhibitors to target CLK2 and CDK1 kinases. These compounds may be useful in the treatment of germline mutations of the spliceosome leading to the development of cancers and other human disease. This abstract is intended as a scanning tool for purposes of searching in the particular art and is not intended to be limiting of the present invention.

17 Claims, 28 Drawing Sheets

Specification includes a Sequence Listing.

(56) References Cited

OTHER PUBLICATIONS

Delehouze et.al. CDK/CK1 inhibitors roscovitine and CR8 downregulate amplified MYCN in neuroblastoma cells in Oncogene, 2014, vol. 33, pp. 5675-5687.
Effenberger, K. et al. Interchangeable SF3B1 inhibitors interfere with pre-mRNA splicing at multiple stages. RNA 2016, 22, 350-9.
Eskens, F. A. et al., Phase I pharmacokinetic and pharmacodynamic study of the first-in-class spliceosome inhibitor E7107 in patients with advanced solid tumors. Clin Cancer Res 2013, 19, 6296-304.
Fabian, M. A. et al., A small molecule-kinase interaction map for clinical kinase inhibitors. Nat Biotechnol 2005, 23, 329-36.
Fan, L. et al., Sudemycins, novel small molecule analogues of FR901464, induce alternative gene splicing. ACS Chem Biol 2011, 6, 582-9.
Fedorov, O. et al., Specific CLK inhibitors from a novel chemotype for regulation of alternative splicing. Chem Biol 2011, 18, 67-76.
Fukuhara, T. et al., Utilization of host SR protein kinases and RNA-splicing machinery during viral replication. Proc Nall Acad Sci USA 2006, 103, 11329-33.
Gundluru, M. K.; Pourpak, A.; Cui, X.; Morris, S. W.; Webb, T. R. Design, synthesis and initial biological evaluation of a novel pladienolide analog scaffold. Medchemcomm 2011, 2, 904-908.
Hang, J., et al. Structural basis of pre-mRNA splicing. Science 2015.
Harbour, J. W. Genomic, prognostic, and cell-signaling advances in uveal melanoma. Am Soc Clin Oncol Educ Book 2013, 388-91.
Hasegawa, M. et al., Identification of SAP155 as the target of GEX1A (Herboxidiene), an antitumor natural product. ACS Chem Biol 2011, 6, 229-33.
He, H. et al. Mutations in U4atac snRNA, a component of the minor spliceosome, in the developmental disorder MOPD I. Science 332, 238-240, (2011).
Hsu, T. Y et al., The spliceosome is a therapeutic vulnerability in MYC-driven cancer. Nature 2015.
Hubert, C. G. et al., Genome-wide RNAi screens in human brain tumor isolates reveal a novel viability requirement for PHFSA. Genes Dev 2013, 27, 1032-45.
Imbach, P. et al., 2,6,9-trisubstituted purines: optimization towards highly potent and selective CDK1 inhibitors. Bioorg Med Chem Lett 1999, 9, 91-6.
Imielinski, M. et al., Mapping the hallmarks of lung adenocarcinoma with massively parallel sequencing. Cell 2012, 150, 1107-20.
Kaida, D. et al., Spliceostatin A targets SF3b and inhibits both splicing and nuclear retention of pre-mRNA. Nat Chem Biol 2007, 3, 576-83.
Kang, J. et al., Targeting cyclin-dependent kinase 1 (CDK1) but not CDK4/6 or CDK2 is selectively lethal to MYC-dependent human breast cancer cells. BMC Cancer 2014, 14, 32.
Kelso et.al. Cyclin-Dependent Kinase 7 Controls mRNA Synthesis by Affecting Stability of Preinitiation Complexes, Leading to Altered Gene Expression, Cell Cycle Progression, and Survival of Tumor Cells in Molecular and Cellular Biology, 2014, vol. 34, pp. 3675-3688. p. 3675.
Kotake, Y.et al., Splicing factor SF3b as a target of the antitumor natural product pladienolide. Nat Chem Biol 2007, 3, 570-5.
Kramer, A. The structure and function of proteins involved in mammalian pre-mRNA splicing. Annu Rev Biochem 1996, 65, 367-409.
Lagisetti, C. et al., Antitumor compounds based on a natural product consensus pharmacophore. J Med Chem 2008, 51, 6220-4.
Lagisetti, C. et al., Pre-mRNA splicing-modulatory pharmacophores: the total synthesis of herboxidiene, a pladienolide-herboxidiene hybrid analog and related derivatives. ACS Chem Biol 2014, 9, 643-8.
Lagisetti, C.; et al. Optimization of antitumor modulators of pre-mRNA splicing. .1 Med Chem 2013, 56, 10033-44.
Lagisetti, C. et al., . Synthetic mRNA splicing modulator compounds with in vivo antitumor activity. J Med Chem 2009, 52, 6979-90.
Liu, T. et al. A novel missense SNRNP200 mutation associated with autosomal dominant retinitis pigmentosa in a Chinese family. PloS one 7, e45464, (2012).
Liu, X. et al., Genomics-Guided Discovery of Thailanstatins A, B, and C as Pre-mRNA Splicing Inhibitors and Antiproliferative Agents from Burkholderia thailandensis MSMB43. Journal of Natural Products 2013, 76, 685-693.
Maguire, S. L. et al., SF3B1 mutations constitute a novel therapeutic target in breast cancer. J Pathol 2015, 235, 571-80.
Makishima, H. et al. Mutations in the spliceosome machinery, a novel and ubiquitous pathway in leukemogenesis. Blood 119, 3203-3210, (2012).
Mizui, Y. et al., Pladienolides, new substances from culture of Streptomyces platensis Mer-11107. III. In vitro and in vivo antitumor activities. JAntibiot (Tokyo) 2004, 57, 188-96.
Murati, A. et al., Myeloid malignancies: mutations, models and management. BMC Cancer 2012, 12, 304.
Nakajima, H. et al.. New antitumor substances, FR901463, FR901464 and FR901465. I. Taxonomy, fermentation isolation, physico-chemical properties and biological activities. JAntibiot (Tokyo) 1996, 49, 1196-203.
Ogawa, S. Splicing factor mutations in myelodysplasia. Int J Hematol 2012, 96, 438-42.
Oumata, N. et al., Roscovitine-derived, dual-specificity inhibitors of cyclin-dependent kinases and casein kinases 1. J Med Chem 2008, 51, 5229-42.
Parry, D. et al., Dinaciclib (SCH 727965), a novel and potent cyclin-dependent kinase inhibitor. Mol Cancer Ther 2010, 9, 2344-53.
Pawellek, A. et al., Identification of small molecule inhibitors of pre-mRNA splicing. .1 Biol Chem 2014, 289, 34683-98.
Popowycz, F. et al. Pyrazolo[1,5-a]-1,3,5-triazine as a Purine Bioisostere: Access to Potent Cyclin-Dependent Kinase Inhibitor (R)-Roscovitine Analogue. Journal of medicinal chemistry 52, 655-663, (2009).
Quesada, V. et al. Exome sequencing identifies recurrent mutations of the splicing factor SF3B1 gene in chronic lymphocytic leukemia. Nature genetics 44, 47-52,(2012).
Shi, Y. et al., Pharmacodynamic assays to facilitate preclinical and clinical development of pre-mRNA splicing modulatory drug candidates. Pharmacol Res Perspect 2015, 3, e00158.
Tanackovic, G. et al. A missense mutation in PRPF6 causes impairment of pre-mRNA splicing and autosomal-dominant retinitis pigmentosa. Am J Hum Genet 88, 643-649, (2011).
Uitdehaag, J. C. et al., A guide to picking the most selective kinase inhibitor tool compounds for pharmacological validation of drug targets. Br .J Pharmacol 2012, 166, 858-76.
Vithana, E. N. et al. A human homolog of yeast pre-mRNA splicing gene, PRP31, underlies autosomal dominant retinitis pigmentosa on chromosome 19q13.4 (RP11). Mol Cell 8, 375-381 (2001).
Wahl, M. C.; Will, C. L.; Luhrmann, R. The spliceosome: design principles of a dynamic RNP machine. Cell 2009, 136, 701-18.
Walters, B. J. et al., High-throughput screening reveals alsterpaullone, 2-cyanoethyl as a potent p27Kip1 transcriptional inhibitor. PLoS One 2014, 9, e91173.
Webb, T. R.et al. The development and application of small molecule modulators of SF3b as therapeutic agents for cancer. Drug Discovery Today 2013, 18, 43-49.
Yoshida, K. et al., Frequent pathway mutations of splicing machinery in myelodysplasia. Nature 2011, 478, 64-9.
Yoshida, T. et al., CLK2 is an Oncogenic Kinase and Splicing Regulator in Breast Cancer. Cancer Res 2015, 75, 1516-26.
International Search Report and Written Opinion were dated Dec. 26, 2017 by the International Searching Authority for International Application No. PCT/US2017/054442, filed on Sep. 29, 2017 and published as WO 2018/064545 on Apr. 5, 2018 (Applicant—SRI International) (8 Pages).
International Preliminary Report on Patentability was dated Apr. 2, 2019 by the International Searching Authority for International Application No. PCT/US2017/054442, filed on Sep. 29, 2017 and published as WO 2018/064545 on Apr. 5, 2018 (Applicant—SRI International) (5 Pages).
Extended European Search Report dated Mar. 17, 2020 by the European Patent Office for European Application No. 17857539.5,

(56) References Cited

OTHER PUBLICATIONS filed on Sep. 29, 2017 and published as EP 3518925 on Aug. 7, 2019 (Applicant—SRI International) (5 Pages).
U.S. Appl. No. 62/402,876, filed Sep. 30, 2016, Thomas R. Webb, et al.
U.S. Appl. No. 16/334,229 (US 2019/0255059 A1), filed Mar. 18, 2019 (Aug. 22, 2019), Thomas R. Webb, et al.
Chang Tae, et al. (1999) "Synthesis and application of functionally diverse 2,6,9-trisubstituted purine libraries as CDK inhibitors Young," *Chemistry and Biology* 6(6):361-375.
European Search Report dated Feb. 19, 2021 by the European Search Authority for EP Application No. 17857539.5, filed on Sep. 29, 2017 and published as EP 3518925 on Aug. 7, 2019 (Applicant—SRI International) (9 pages).

\* cited by examiner

DUAL CLK/CDK1 INHIBITORS FOR CANCER TREATMENT

CROSS-REFERENCE TO RELATED APPLICATIONS

This Application is a Continuation of U.S. application Ser. No. 16/334,229, filed on Mar. 18, 2019, which is a national stage filing under 35 U.S.C. § 371 of International Application No. PCT/US2017/054442, filed on Sep. 29, 2017, which claims the benefit of U.S. Provisional Application No. 62/402,876, filed on Sep. 30, 2016, the contents of which are incorporated herein by reference in their entireties.

STATEMENT REGARDING FEDERALLY SPONSORED RESEARCH

This invention was made with government support under Grant No. CA140474 awarded by the National Institutes of Health and a Stanford Cancer Institute Translational 2015-2016 Award from the Stanford Cancer Institute, The Leland J. Stanford University, Stanford, Calif. The government has certain rights in the invention.

REFERENCE TO SEQUENCE LISTING

The Sequence Listing submitted Aug. 4, 2020 as a text file named "37794_0001U3_ST25.txt," created on Mar. 22, 2020, and having a size of 3,930 bytes is hereby incorporated by reference pursuant to 37 C.F.R. § 1.52(e)(5).

BACKGROUND

The processing of pre-mRNA to mature mRNA in metazoans is a critical process for the development and normal functioning of cells. The pre-mRNA splicing process involves the removal of intervening sequences from pre-mRNA followed by the ligation of exons to form mature mRNA. This splicing process is catalyzed and regulated by a highly complex macromolecular protein-RNA complex called the spliceosome. The spliceosome is composed of five small nuclear ribonucleoproteins (snRNPs) (U1, U2, U4, U5 and U6) and over 150 associated proteins (Kramer, A. (1996) *Anny. Rev. Biochem.* 65: 367-409; Wahl et al. (2009) *Cell* 136: 701-18). The pre-mRNA maturation process includes alternative splicing (AS), which is the mechanism that allows for different forms of mature mRNAs to be generated from the same pre-mRNA. Commonly, alternative splicing patterns determine the inclusion or exclusion of portions of the coding sequence in the mRNA, giving rise to protein isoforms that differ in their peptide sequence. Alternate splicing is regulated by numerous spliceosomal transacting proteins, which are in turn regulated by cis-acting regulatory sites on pre-mRNA substrates (Kramer, A. (1996) *Anny. Rev. Biochem.* 65: 367-409). Since pre-mRNAs for a given gene may contain many different exon and intron combinations, there are often a very large number of possible mRNAs that can lead to a correspondingly large set of proteins with different, even opposing, biological functions within the cell. The complexity of the spliceosome and the current scarcity of molecular-resolution X-ray structures complicates a rapid advancement in the understanding of many of the important functional mechanisms that are critical to the normal functioning of the cells of higher organisms (Yan et al. (2015) *Science* 349: 1182-1191). Because of the importance of splicing in normal organismal development, the spliceosome is increasingly being recognized as a major frontier for molecular biology and is now accepted as a valid oncology target (Webb et al. (2013) *Drug Discovery Today* 18: 43-49; Bonnal et al. (2012) *Nat. Rev. Drug Discov.* 11: 847-859).

Interest in the spliceosome was dramatically bolstered when two independent groups reported that a pair of structurally divergent bacterial natural products, FR901464 and pladienolide, both target a similar site on the SF3B subunit of the spliceosome (Kaida et al. (2007) *Nat. Chem. Biol.* 3: 576-83; Kotake et al. (2007) *Nat. Chem. Biol.* 3: 570-5). Subsequent to those initial discoveries, the list of compounds that are known to target the SF3B subunit has grown to include additional bacterial natural products such as herboxidiene (GEX1A) (isolated from *Streptomyces* sp. A7847) (Hasegawa et al. (2011) *ACS Chem. Biol.* 6: 229-33) and the thailanstatins (isolated from *Burkholderia thailandensis*) (Liu et al. (2013) *Journal of Natural Products* 76: 685-693). These bacterial fermentation products show cytotoxic $IC_{50}$s in the low nanomolar range in tumor cell lines and were reported to have a similar distinctive effect on the cell cycle in mammalian cell lines, which includes cell cycle arrest in the G1 and G2/M phases (Nakajima et al. (1996) *J. Antibiot. (Tokyo)* 49: 1196-203). Several of these natural products have also been reported to show potent antitumor activity in vitro and in vivo (Nakajima et al. (1996) *J. Antibiot. (Tokyo)* 49: 1204-11; Mizui et al. (2004) *J. Antiobiot. (Tokyo)* 57: 188-96). Work in this area led to the development of the semisynthetic pladienolide analog E7107 that entered Phase I clinical studies (Kotake et al. (2007) *Nat. Chem. Biol.* 3: 570-5; Eskens et al. (2013) *Clin. Cancer Res.* 19: 6296-304; Yoshida et al. (2011) *Nature* 478: 64-9), without the benefit of many subsequent recent discoveries relevant to mechanism of action, tumor selectivity, and patient stratification (Webb et al. (2013) *Drug Discovery Today* 18: 43-49; Bonnal et al. (2012) *Nat. Rev. Drug Discov.* 11: 847-859).

Despite the increased interest in the spliceosome as a target for cancer therapeutics, small molecules that target specific sites on the spliceosome have thus far remained elusive. Therefore, there remains a need for the identification of new oncology drug targets and new small-molecule therapeutic leads for the diagnosis and treatment of multiple forms of cancer and other diseases involving aberrant spliceosome activities. These needs and others are met by the present invention.

SUMMARY OF THE INVENTION

In accordance with the purpose(s) of the invention, as embodied and broadly described herein, the invention, in one aspect, relates to compounds that are either dual CLK2/CDK1 inhibitors or more potent and specific CLK inhibitors to target CLK2 and CDK1 kinases. Surprisingly, it has been recently reported that CLK2[47] and CDK1[48] have been independently identified as potential targets for breast cancer. These compounds are potential probes and lead molecules in the treatment of germ-line mutations of the spliceosome, known etiologies in the development of cancers, including breast cancer and other human disease.

Disclosed are compounds having a structure represented by a formula selected from:

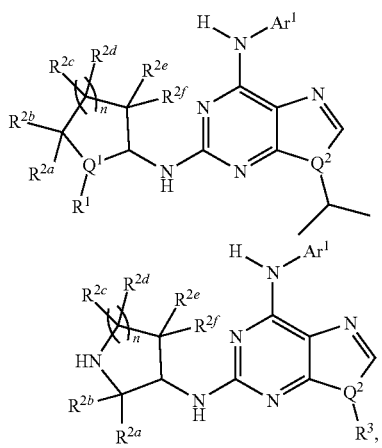

and

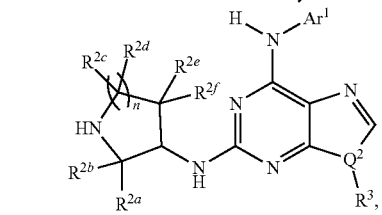

wherein n is selected from 1 and 2; wherein each of $Q^1$ and $Q^2$ is independently selected from N and CH; wherein $R^1$ is selected from —OH, —NHR$^4$, —(C1-C4 alkyl)OH, and —(C1-C4 alkyl)NHR$^4$; wherein $R^4$, when present, is selected from hydrogen and C1-C4 alkyl; wherein each occurrence of each of $R^{2a}$, $R^{2b}$, $R^{2c}$, $R^{2d}$, $R^{2e}$, and $R^{2f}$ is independently selected from hydrogen and C1-C8 alkyl; wherein $R^3$ is selected from ethyl and isopropyl; and wherein $Ar^1$ is selected from monocyclic aryl, 6-membered heteroaryl, and bicyclic heteroaryl, and is substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino, or a pharmaceutically acceptable derivative thereof.

Also disclosed are compounds having a structure represented by a formula:

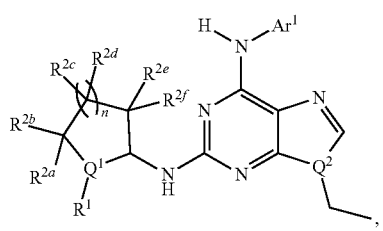

wherein n is selected from 1 and 2; wherein each of $Q^1$ and $Q^2$ is independently selected from N and CH; wherein $R^1$ is selected from —OH, —NHR$^4$, —(C1-C4 alkyl)OH, and —(C1-C4 alkyl)NHR$^4$; wherein $R^4$, when present, is selected from hydrogen and C1-C4 alkyl; wherein each occurrence of each of $R^{2a}$, $R^{2b}$, $R^{2c}$, $R^{2d}$, $R^{2e}$, and $R^{2f}$ is independently selected from hydrogen and C1-C8 alkyl; and wherein Art is selected from 6-membered heteroaryl and bicyclic heteroaryl, and is substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino; or wherein Art is phenyl meta-substituted with —Cl, or a pharmaceutically acceptable derivative thereof.

Also disclosed are compounds having a structure represented by a formula selected from:

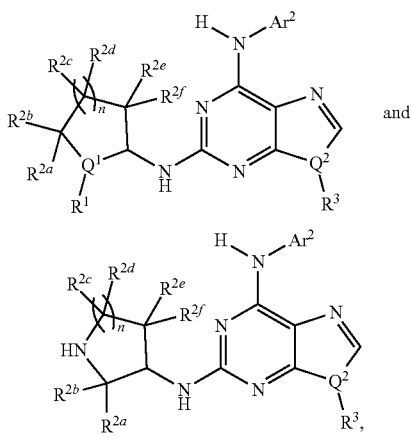

and wherein n is selected from 1 and 2; wherein each of $Q^1$ and $Q^2$ is independently selected from N and CH; wherein $R^1$ is selected from —OH, —NHR$^4$, —(C1-C4 alkyl)OH, and —(C1-C4 alkyl)NHR$^4$; wherein $R^4$, when present, is selected from hydrogen and C1-C4 alkyl; wherein each occurrence of each of $R^{2a}$, $R^{2b}$, $R^{2c}$, $R^{2d}$, $R^{2e}$, and $R^{2f}$ is independently selected from hydrogen and C1-C8 alkyl; wherein $R^3$ is selected from ethyl and isopropyl; and wherein $Ar^2$ is selected from 6-membered heteroaryl and bicyclic heteroaryl, and is substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4) (C1-C4) dialkylamino, or a pharmaceutically acceptable derivative thereof.

Also disclosed are compounds selected from:

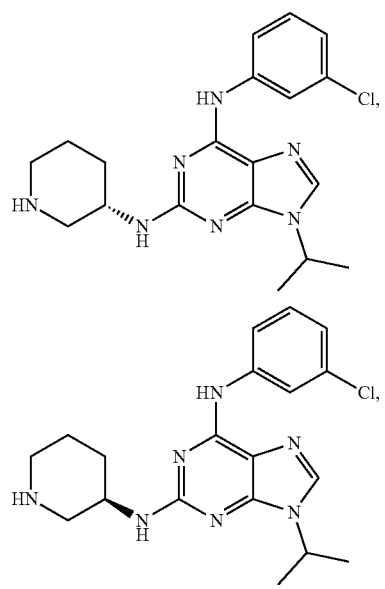

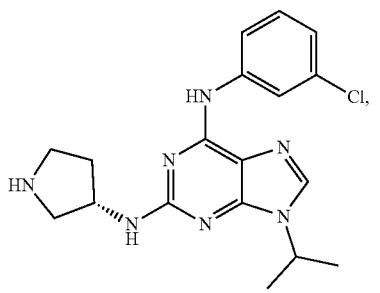

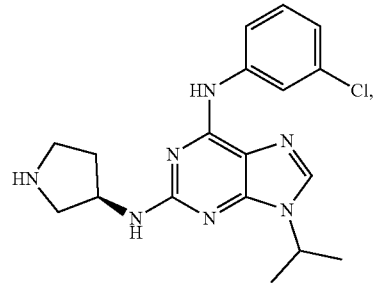

or a pharmaceutically acceptable derivative thereof.

Also disclosed are methods for treating a disorder having an aberrant germ-like mutation in a subject, the method comprising the step of administering to the subject a therapeutically effective amount of at least one compound that inhibits both CLK2 and CDK1.

Also disclosed are methods for treating a disorder having an aberrant germ-like mutation in a subject, the method comprising the step of administering to the subject a therapeutically effective amount of a compound selected from:

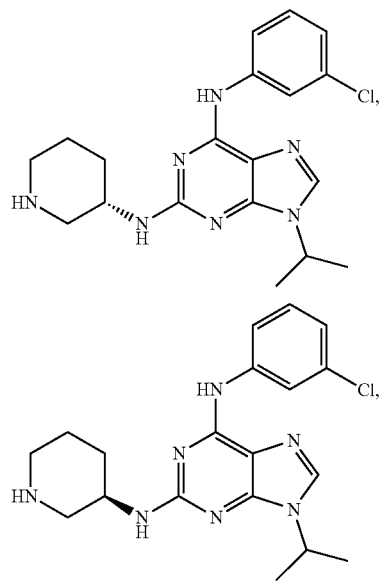

or a pharmaceutically acceptable derivative thereof.

Also disclosed are methods for inhibiting CLK2 and/or CDK1 in at least one cell, the method comprising the step of contacting at least one cell with an effective amount of a compound selected from:

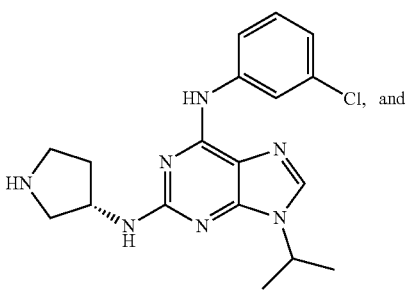

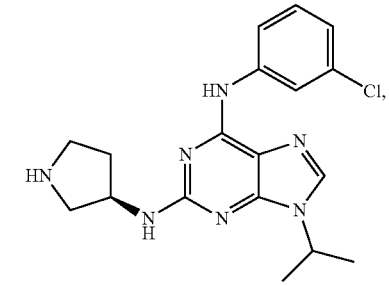

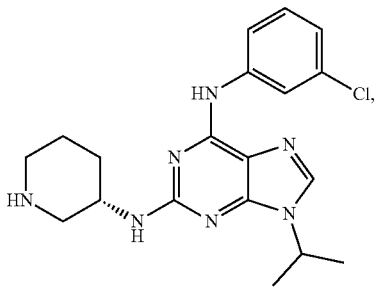

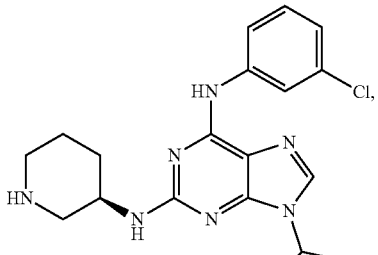

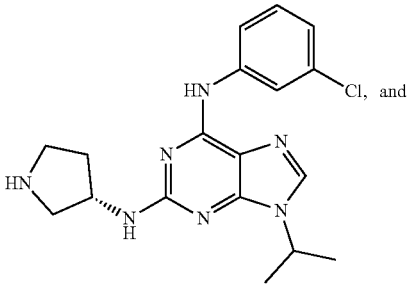

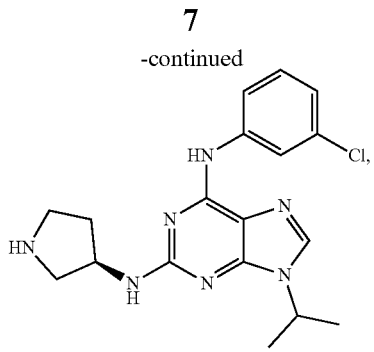

or a pharmaceutically acceptable salt thereof, thereby inhibiting CLK2 and/or CDK1 in at least one cell.

Also disclosed are methods of making a disclosed compound.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

The foregoing and other objects and aspects of the present invention are explained in greater detail in the drawings herein and the specification set forth below. The disclosures of all United States patent references cited herein are to be incorporated herein by reference.

BRIEF DESCRIPTION OF THE DRAWINGS

The accompanying figures, which are incorporated in and constitute a part of this specification, illustrate several aspects and together with the description serve to explain the principles of the invention.

Figure 1:
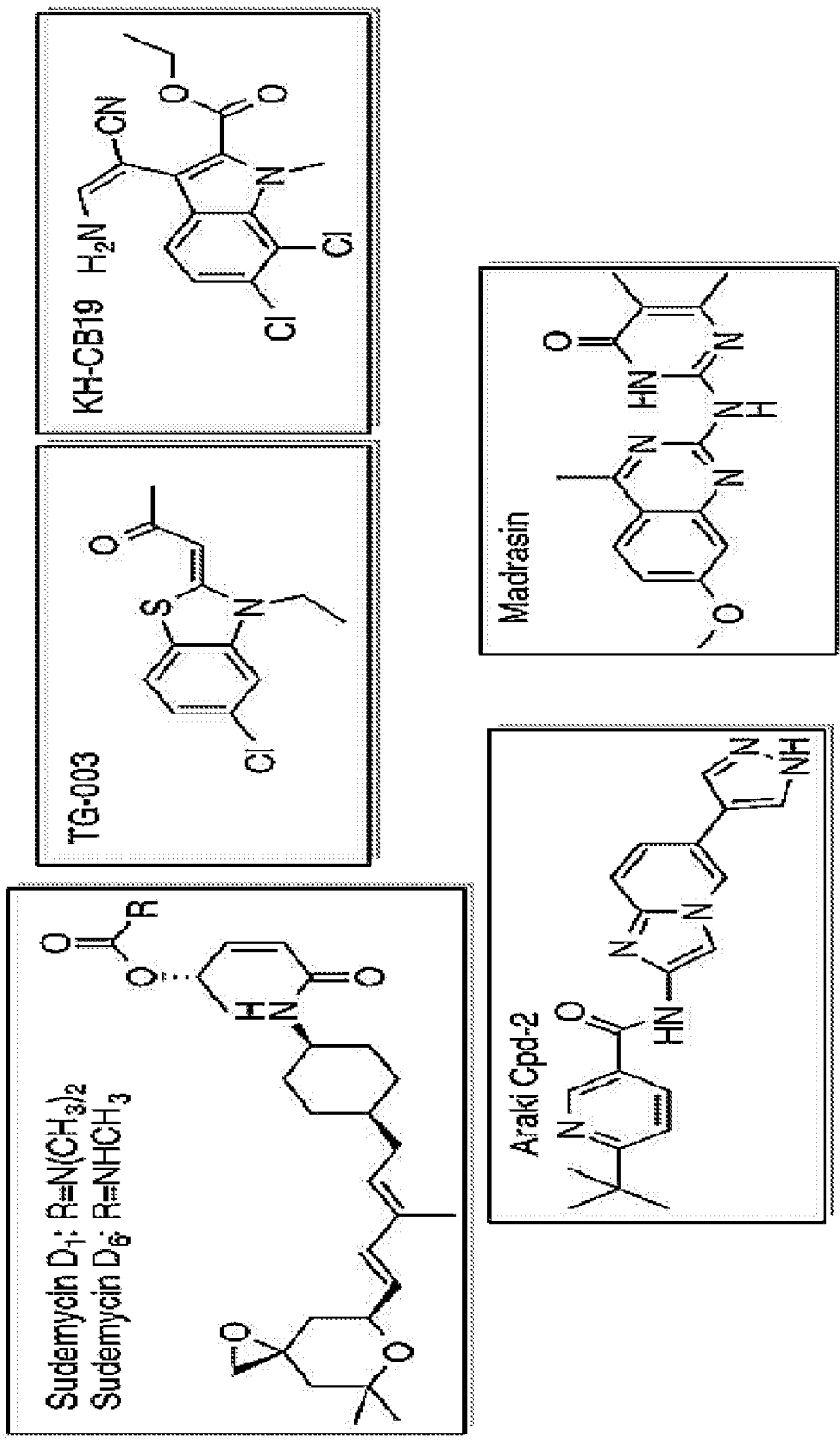
FIG. 1 shows representative recently reported synthetic alternate splicing modulators. See Lagisetti et al. (2013) *J. Med. Chem.* 56: 10033-44; Fedorov et al. (2011) *Chem. Vio.* 18: 67-76; Araki et al. (2015) *PLoS One* 10: e0116929; Pawellek et al. (2014) *J. Biol. Chem.* 289: 34683-98.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention now will be described more fully hereinafter with reference to the accompanying drawings, in which illustrative aspects of the invention are shown. In the drawings, the relative sizes of regions or features may be exaggerated for clarity. This invention may, however, be embodied in many different forms and should not be construed as limited to the aspects set forth herein; rather, these aspects are provided so that this disclosure will be thorough and complete, and will fully convey the scope of the invention to those skilled in the art.

This disclosure describes inventive concepts with reference to specific examples. However, the intent is to cover all modifications, equivalents, and alternatives of the inventive concepts that are consistent with this disclosure.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Further, the dates of publication provided herein may be different from the actual publication dates, which can require independent confirmation.

A. DEFINITIONS

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

As used in the specification and in the claims, the term "comprising" can include the aspects "consisting of" and "consisting essentially of." Said another way, when the application states the invention comprises A, B, and C, it would also be contemplated that the invention can be claimed as consisting of A, B, and C. Similarly, when the application states the invention comprises A, B, and C, it would also be contemplated that the invention can be claimed as consisting essentially of A, B, and C.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated 10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more disorder, e.g., diabetes or cancer, prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the phrase "identified to be in need of treatment for a disorder," or the like, refers to selection of a subject based upon need for treatment of the disorder. For example, a subject can be identified as having a need for treatment of a disorder (e.g., a disorder such as cancer) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, target of a disclosed peptide, or other biological entity together in such a manner that the compound can affect the activity of the target (e.g., receptor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage form can comprise a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), anti-foaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14$^{th}$ edition), the Physicians' Desk Reference (64$^{th}$ edition), and The Pharmacological Basis of Therapeutics (12$^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more CH$_2$ groups linked to one another. The polyalkylene group can be represented by the formula (CH$_2$)$_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —OA$^1$ where A$^1$ is alkyl or cycloalkyl as defined above. "Alkoxy" also includes polymers of alkoxy groups as just described; that is, an alkoxy can be a polyether such as —OA$^1$-OA$^2$ or —OA$^1$-(OA$^2$)$_a$-OA$^3$, where "a" is an integer of from 1 to 200 and A$^1$, A$^2$, and A$^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as (A$^1$A$^2$)C═C(A$^3$A$^4$) are intended to include both the E and Z isomers. This can be presumed in structural formulae herein wherein an asymmetric alkene is present, or it can be explicitly indicated by the bond symbol C═C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C═C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C═O.

The terms "amine" or "amino" as used herein are represented by the formula $NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula $N(-alkyl)_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$- or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula $—N_3$.

The term "nitro" as used herein is represented by the formula $—NO_2$.

The term "nitrile" or "cyano" as used herein is represented by the formula —CN or —C≡N.

The term "silyl" as used herein is represented by the formula $—SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $—S(O)A^1$, $—S(O)_2A^1$, $—OS(O)_2A^1$, or $—OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S═O. The term "sulfonyl" is used herein to refer to the sulfo-oxo group represented by the formula $—S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" is represented by the formula $A'S(O)_2A^2$, where A and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A'S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}OC(O)R$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, $-(haloR^\bullet)$, $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*_2, =NNHC(O)R*, =NNHC(O)OR*, =NNHS(O)_2R*, =NR*, =NOR*, $-O(C(R*_2))_{2-3}O-$, or $-S(C(R*_2))_{2-3}S-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR*_2)_{2-3}O-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $-R^\bullet$, $-(haloR^\bullet)$, $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-4}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

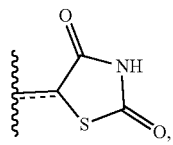

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

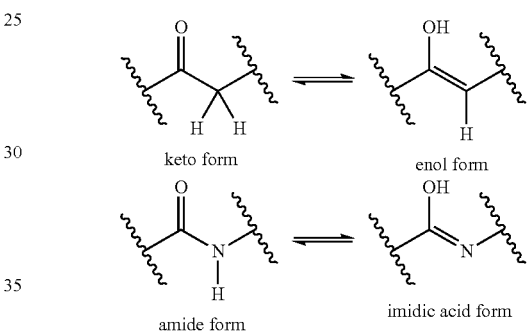

Likewise, amides with an N-hydrogen can exist in an equilibrium of the amide form and the imidic acid form. As another example, pyrazoles can exist in two tautomeric forms, $N^{1}$-unsubstituted, 3-$A^{3}$ and $N^{1}$-unsubstituted, 5-$A^{3}$ as shown below.

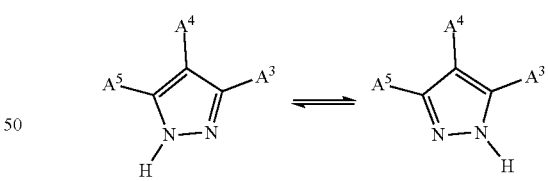

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

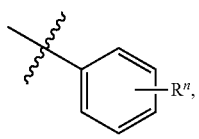

which is understood to be equivalent to a formula:

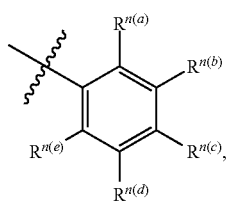

wherein n is typically an integer. That is, R is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. COMPOUNDS

In one aspect, disclosed are compounds useful in treating or preventing a disorder associated with CLK2 and/or CDK1 activity such as, for example, retinitis Pigmentosa, microcephalic osteodysplastic primordial dwarfism (MOPD) type 1, and cancer. In a further aspect, the disclosed compounds exhibit modulation of CLK2 and/or CDK1 activity. In a still further aspect, the disclosed compounds exhibit inhibition of CLK2 and/or CDK1 activity. In yet a further aspect, the disclosed compounds exhibit inhibition of CLK2 activity. In an even further aspect, the disclosed compounds exhibit inhibition of CDK1 activity.

In one aspect, the compounds of the invention are useful in the treatment or prevention of disorders associated with CLK2 and/or CDK1 dysfunction and other diseases in which CLK2s or CDK1s are involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, disclosed are compounds having a structure represented by a formula selected from:

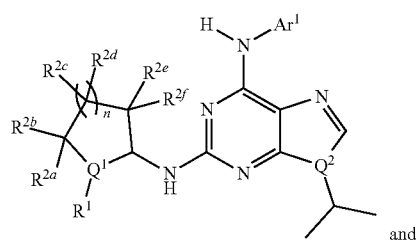

and

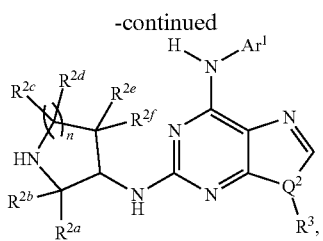

wherein n is selected from 1 and 2; wherein each of $Q^1$ and $Q^2$ is independently selected from N and CH; wherein $R^1$ is selected from —OH, —NHR$^4$, —(C1-C4 alkyl)OH, and —(C1-C4 alkyl)NHR$^4$; wherein $R^4$, when present, is selected from hydrogen and C1-C4 alkyl; wherein each occurrence of each of $R^{2a}$, $R^{2b}$, $R^{2c}$, $R^{2d}$, $R^{2e}$, and $R^{2f}$ is independently selected from hydrogen and C1-C8 alkyl; wherein $R^3$ is selected from ethyl and isopropyl; and wherein Ar$^1$ is selected from monocyclic aryl, 6-membered heteroaryl, and bicyclic heteroaryl, and is substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino, or a pharmaceutically acceptable derivative thereof.

In one aspect, disclosed are compounds having a structure represented by a formula:

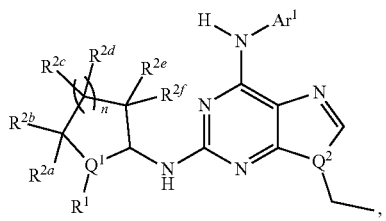

wherein n is selected from 1 and 2; wherein each of $Q^1$ and $Q^2$ is independently selected from N and CH; wherein $R^1$ is selected from —OH, —NHR$^4$, —(C1-C4 alkyl)OH, and —(C1-C4 alkyl)NHR$^4$; wherein $R^4$, when present, is selected from hydrogen and C1-C4 alkyl; wherein each occurrence of each of $R^{2a}$, $R^{2b}$, $R^{2c}$, $R^{2d}$, $R^{2e}$, and $R^{2f}$ is independently selected from hydrogen and C1-C8 alkyl; and wherein Ar$^1$ is selected from 6-membered heteroaryl and bicyclic heteroaryl, and is substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino; or wherein Ar$^1$ is phenyl meta-substituted with —Cl, or a pharmaceutically acceptable derivative thereof.

In one aspect, disclosed are compounds having a structure represented by a formula selected from:

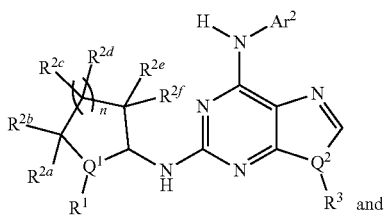

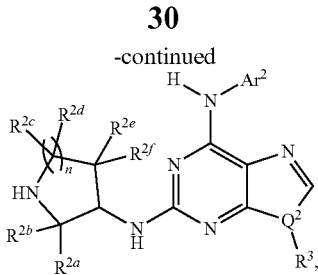

wherein n is selected from 1 and 2; wherein each of $Q^1$ and $Q^2$ is independently selected from N and CH; wherein $R^1$ is selected from —OH, —NHR$^4$, —(C1-C4 alkyl)OH, and —(C1-C4 alkyl)NHR$^4$; wherein $R^4$, when present, is selected from hydrogen and C1-C4 alkyl; wherein each occurrence of each of $R^{2a}$, $R^{2b}$, $R^{2c}$, $R^{2d}$, $R^{2e}$, and $R^{2f}$ is independently selected from hydrogen and C1-C8 alkyl; wherein $R^3$ is selected from ethyl and isopropyl; and wherein Ar$^2$ is selected from 6-membered heteroaryl and bicyclic heteroaryl, and is substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino, or a pharmaceutically acceptable derivative thereof.

In one aspect, disclosed are compounds selected from:

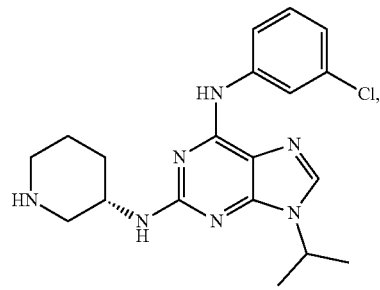

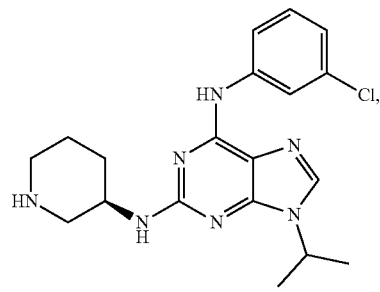

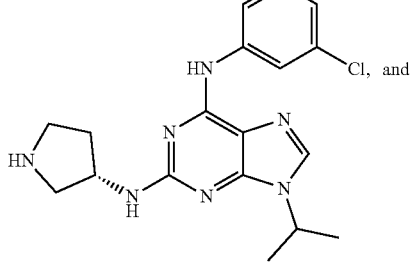

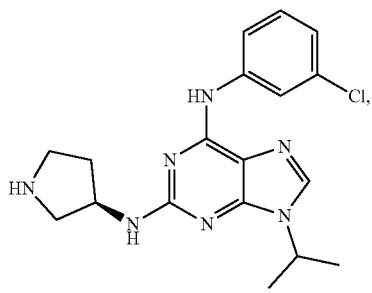
or a pharmaceutically acceptable derivative thereof.
In a further aspect, the compound has a structure represented by a formula selected from.
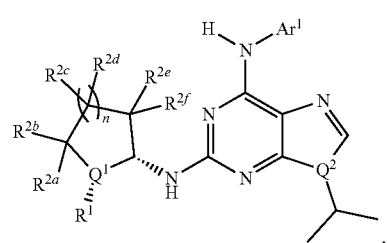
,
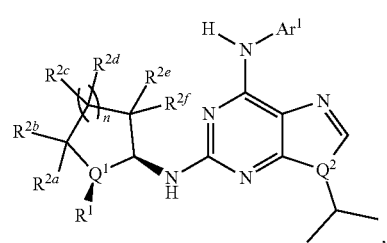
,
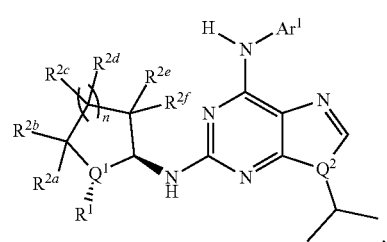
,
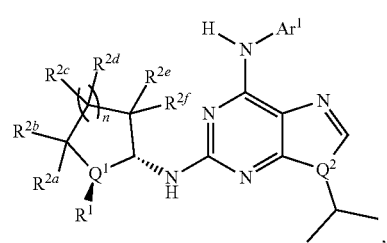
,
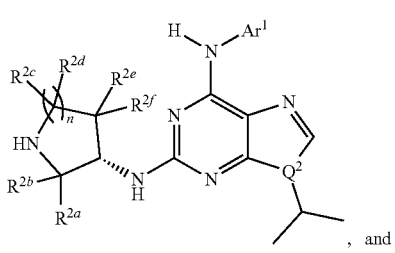
, and
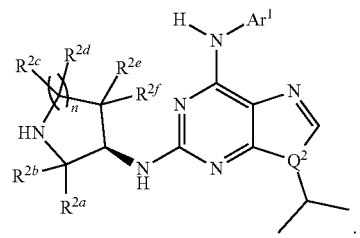
.
In a further aspect, the compound has a structure represented by a formula selected from:
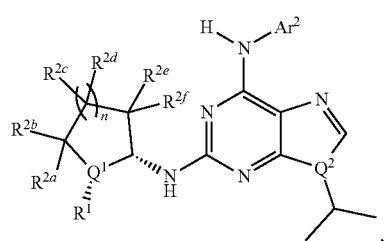
,
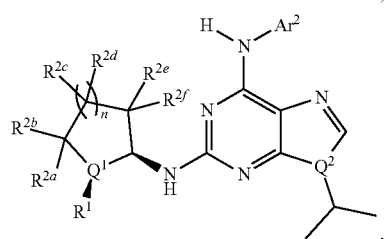
,
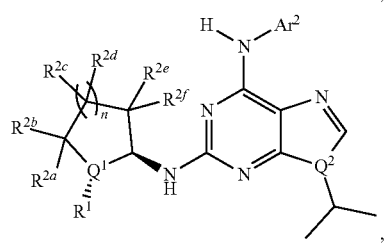
,
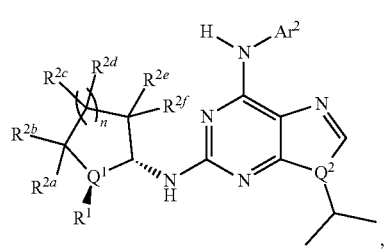
,
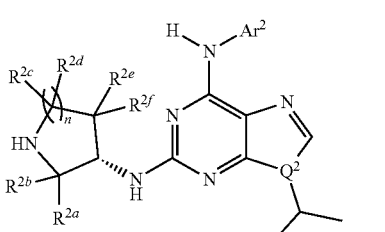
, and -continued

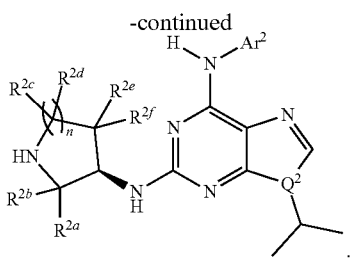

In a further aspect, the compound has a structure represented by a formula:

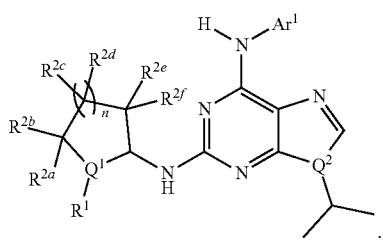

In a further aspect, the compound has a structure represented by a formula:

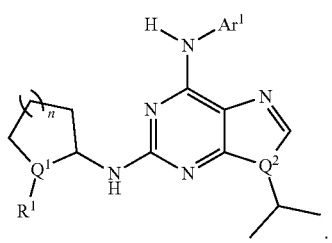

In a further aspect, the compound has a structure represented by a formula:

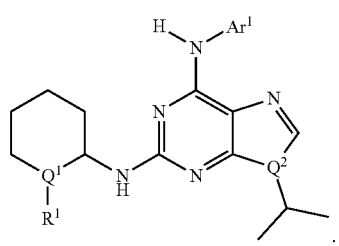

In a further aspect, the compound has a structure represented by a formula:

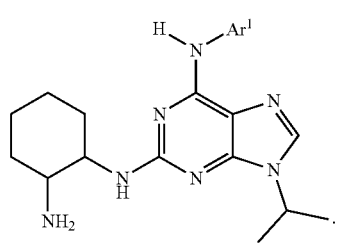

In a further aspect, the compound has a structure represented by a formula:

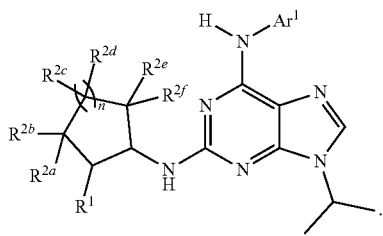

In a further aspect, the compound has a structure represented by a formula:

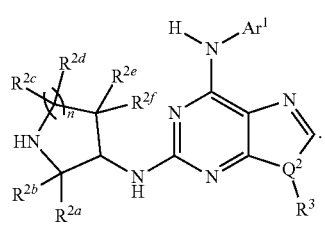

In a further aspect, the compound has a structure represented by a formula:

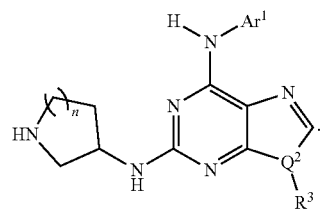

In a further aspect, the compound has a structure represented by a formula:

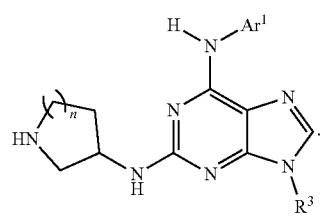

In a further aspect, the compound has a structure represented by a formula:

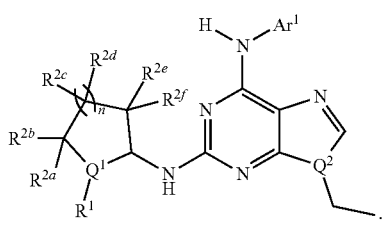

In a further aspect, the compound has a structure represented by a formula:

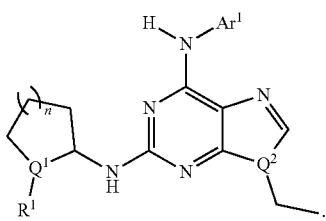

In a further aspect, the compound has a structure represented by a formula:]

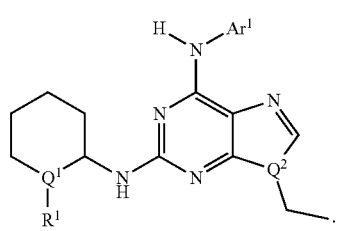

In a further aspect, the compound has a structure represented by a formula:

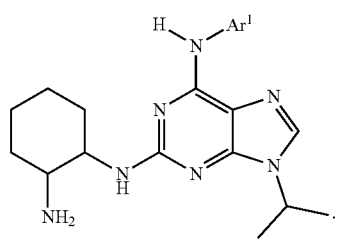

In a further aspect, the compound has a structure represented by a formula:

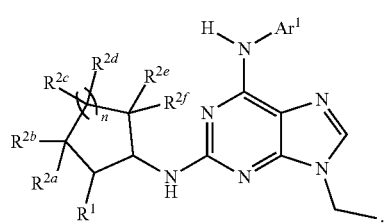

In a further aspect, the compound has a structure represented by a formula:

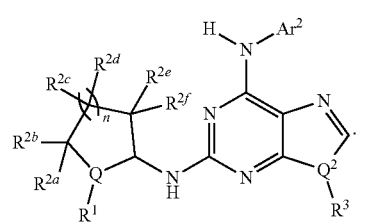

In a further aspect, the compound has a structure represented by a formula:

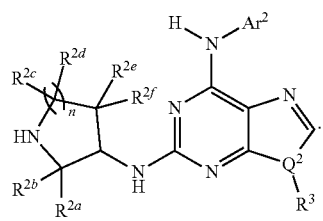

In a further aspect, the compound has a structure represented by a formula:

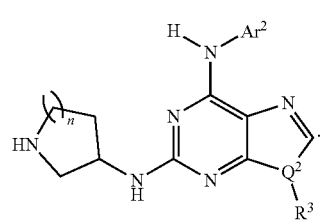

In a further aspect, the compound has a structure represented by a formula:

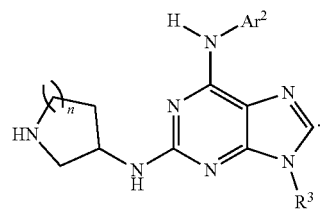

In a further aspect, the compound is selected from:

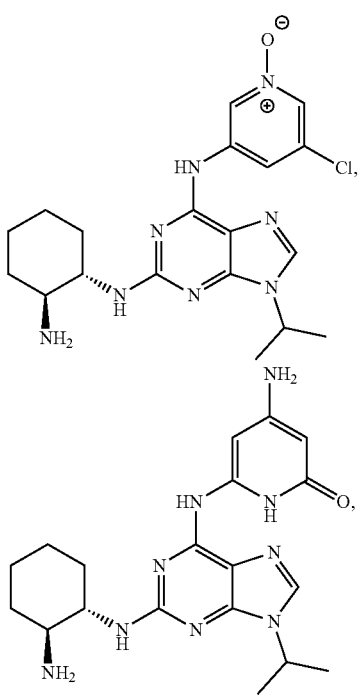

-continued
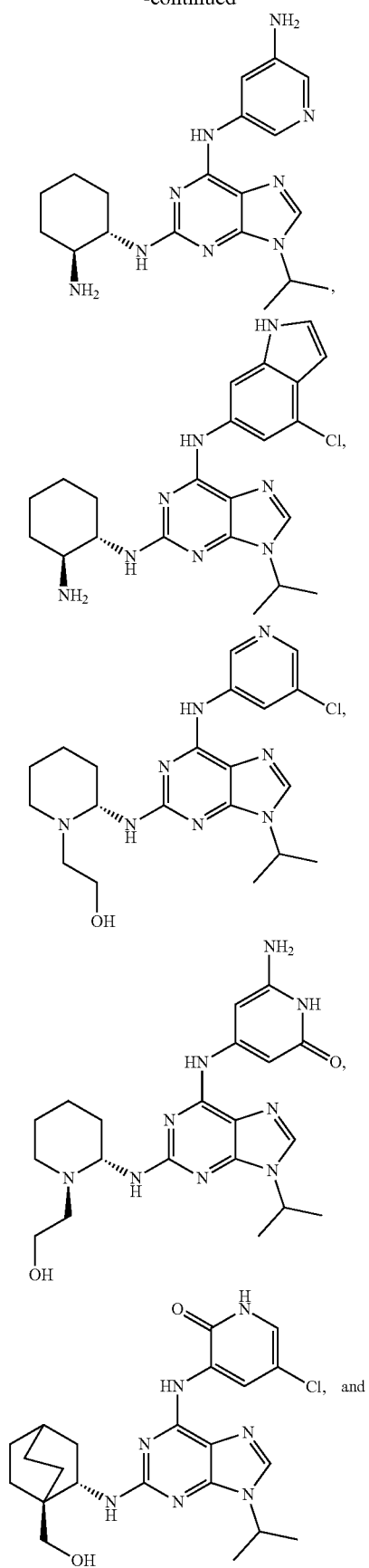
-continued
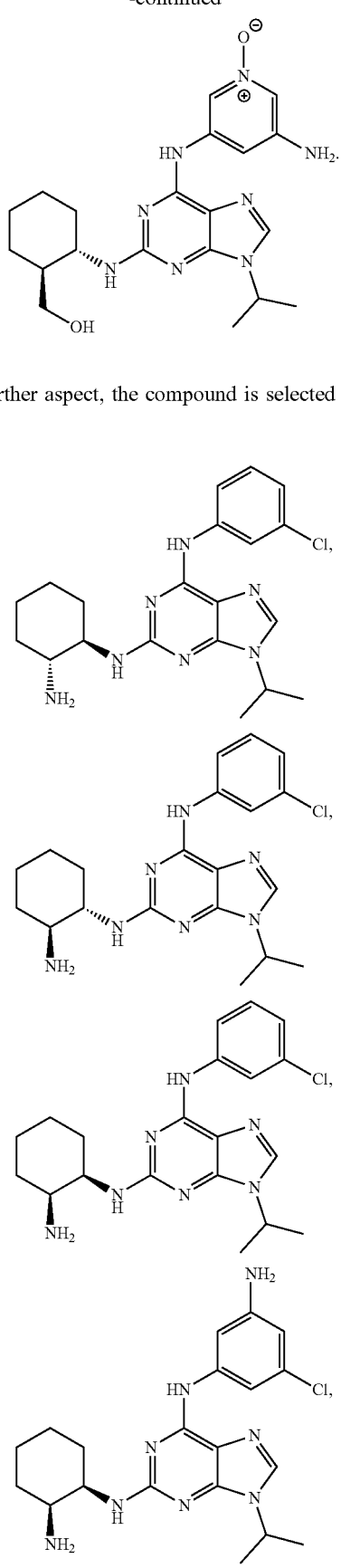
In a further aspect, the compound is selected from:

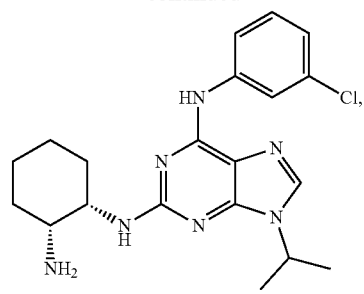
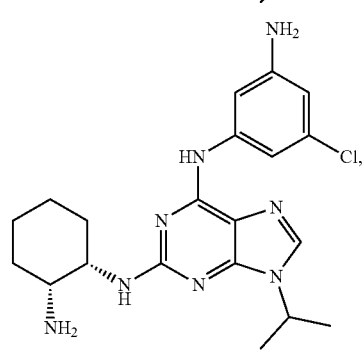
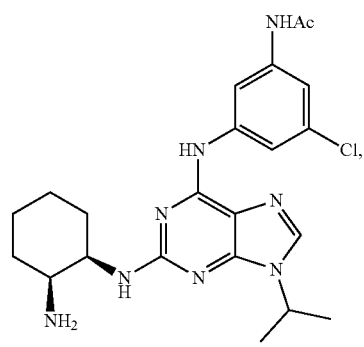
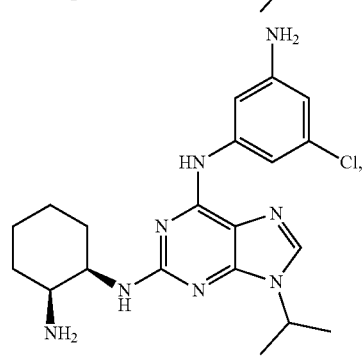
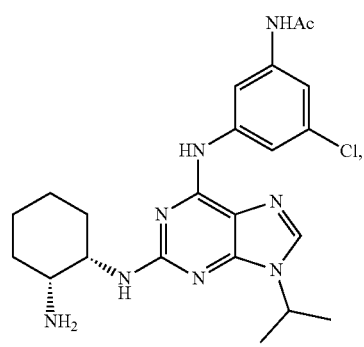
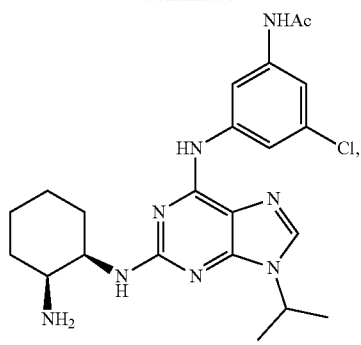
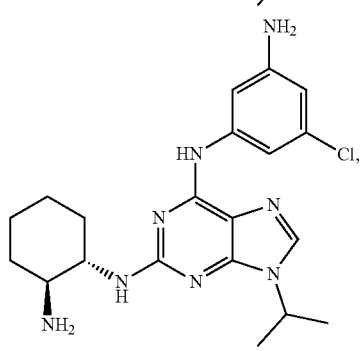
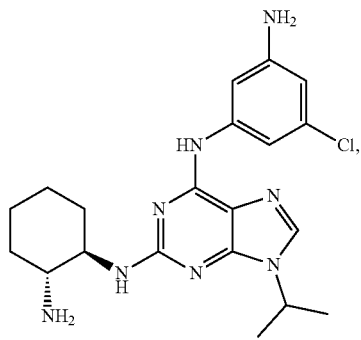
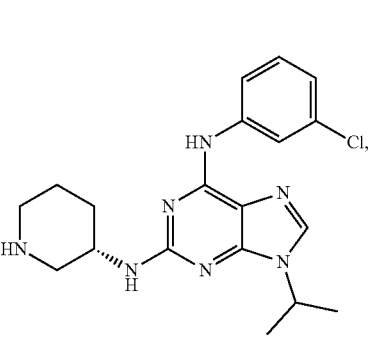
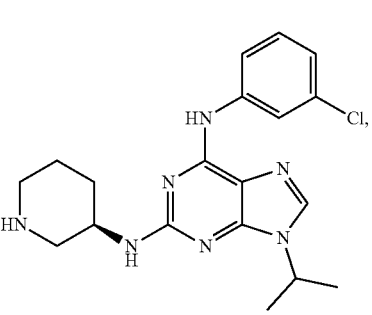

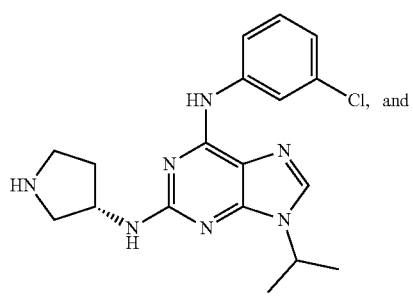
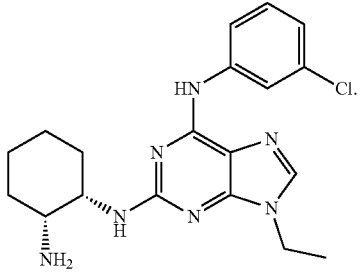
In a further aspect, the compound is selected from:
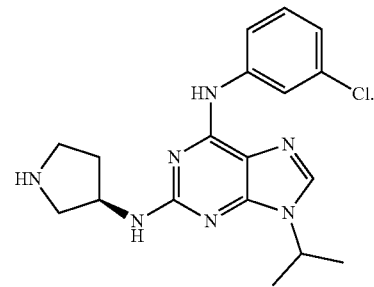
In a further aspect, the compound is selected from:
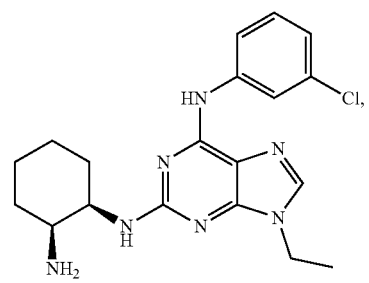
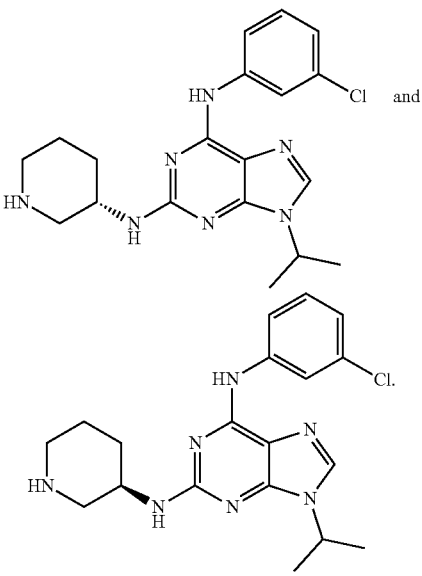
In a further aspect, the compound is selected from:
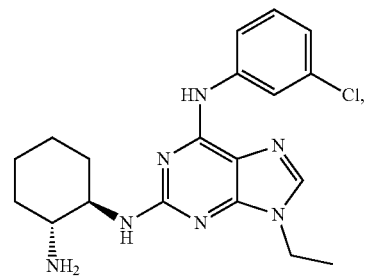
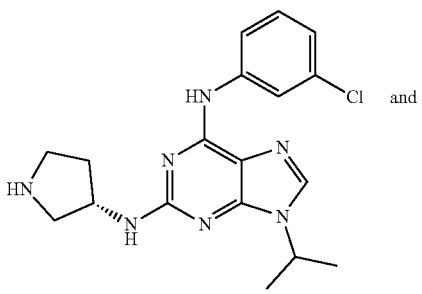
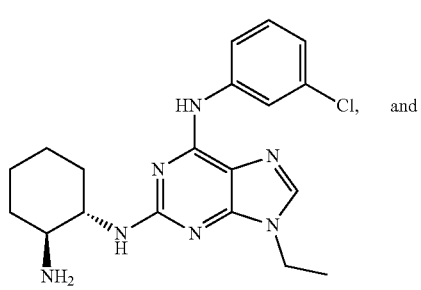
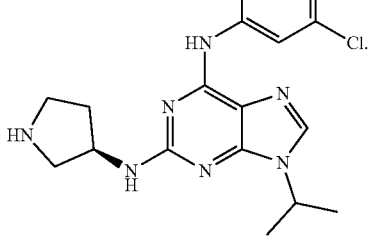
In a further aspect, n is selected from 1 and 2. In a still further aspect, n is 1. In yet a further aspect, n is 2.

a. $Q^1$ and $Q^2$ Groups

In one aspect, each of $Q^1$ and $Q^2$ is independently selected from N and CH. In a further aspect, $Q^1$ is N and $Q^2$ is CH. In a still further aspect, $Q^1$ is CH and $Q^2$ is N. In yet a further aspect, each of $Q^1$ and $Q^2$ is N. In an even further aspect, each of $Q^1$ and $Q^2$ is CH.

In a further aspect, $Q^2$ is N. In a still further aspect, $Q^2$ is CH.

In a further aspect, $Q^1$ is N. In a still further aspect, $Q^1$ is CH.

b. $Z^1$ and $Z^2$ Groups

In one aspect, $Z^1$ is selected from CH and N and $Z^2$ is selected from $CH_2$ and NH. In a further aspect, $Z^1$ is CH and $Z^2$ is $CH_2$. In a still further aspect, $Z^1$ is CH and $Z^2$ is NH. In yet a further aspect, $Z^1$ is N and $Z^2$ is $CH_2$. In an even further aspect, $Z^1$ is N and $Z^2$ is NH.

In a further aspect, $Z^1$ is CH and $Z^2$ is selected from $CH_2$ and NH. In a still further aspect, $Z^1$ is N and $Z^2$ is selected from $CH_2$ and NH.

In a further aspect, $Z^2$ is $CH_2$ and $Z^1$ is selected from CH and N. In a still further aspect, $Z^2$ is NH and $Z^1$ is selected from CH and N.

In a further aspect, $Z^1$ is selected from CH and N. In a still further aspect, $Z^1$ is CH. In yet a further aspect, $Z^1$ is N.

In a further aspect, $Z^2$ is selected from $CH_2$ and NH. In a still further aspect, $Z^2$ is $CH_2$. In yet a further aspect, $Z^2$ is NH.

c. $R^1$ Groups

In one aspect, $R^1$ is selected from —OH, —$NHR^4$, —(C1-C4 alkyl)OH, and —(C1-C4 alkyl)$NHR^4$.

In a further aspect, $R^1$ is selected from —OH, —$NHR^4$, —$CH_2OH$, —$CH_2CH_2OH$, —$CH_2CH_2CH_2OH$, —CH($CH_3$)($CH_2OH$), —$CH_2NHR^4$, —$CH_2CH_2NHR^4$, —$CH_2CH_2CH_2NHR^4$, and —CH($CH_3$)($CH_2NHR^4$). In a still further aspect, $R^1$ is selected from —OH, —$NHR^4$, —$CH_2OH$, —$CH_2CH_2OH$, —$CH_2NHR^4$, and —$CH_2CH_2NHR^4$. In yet a further aspect, $R^1$ is selected from —OH, —$NHR^4$, —$CH_2OH$, and —$CH_2NHR^4$.

In a further aspect, $R^1$ is selected from —OH and —$NHR^4$. In a still further aspect, $R^1$ is —OH. In a further aspect, $R^1$ is —$NHR^4$. In a still further aspect, $R^1$ is —$NH_2$.

In a further aspect, $R^1$ is selected from —(C1-C4 alkyl)OH and —(C1-C4 alkyl)$NHR^4$. In a still further aspect, $R^1$ is selected from —$CH_2OH$, —$CH_2CH_2OH$, —$CH_2CH_2CH_2OH$, —CH($CH_3$)($CH_2OH$), —$CH_2NHR^4$, —$CH_2CH_2NHR^4$, —$CH_2CH_2CH_2NHR^4$, and —CH($CH_3$)($CH_2NHR^4$). In yet a further aspect, $R^1$ is selected from —$CH_2OH$, —$CH_2CH_2OH$, —$CH_2NHR^4$, and —$CH_2CH_2NHR^4$. In an even further aspect, $R^1$ is selected from —$CH_2OH$ and —$CH_2NHR^4$.

In a further aspect, $R^1$ is —(C1-C4 alkyl)OH. In a still further aspect, $R^1$ is selected from —$CH_2OH$, —$CH_2CH_2OH$, —$CH_2CH_2CH_2OH$, and —CH($CH_3$)($CH_2H$). In yet a further aspect, $R^1$ is selected from —$CH_2OH$ and —$CH_2CH_2H$. In an even further aspect, $R^1$ is —$CH_2CH_2OH$. In a still further aspect, $R^1$ is —$CH_2OH$.

In a further aspect, $R^1$ is —(C1-C4 alkyl)$NHR^4$. In a still further aspect, $R^1$ is selected from —$CH_2NHR^4$, —$CH_2CH_2NHR^4$, —$CH_2CH_2CH_2NHR^4$, and —CH($CH_3$)($CH_2NHR^4$). In yet a further aspect, $R^1$ is selected from —$CH_2NHR^4$ and —$CH_2CH_2NHR^4$. In an even further aspect, $R^1$ is —$CH_2CH_2NHR^4$. In a still further aspect, $R^1$ is —$CH_2NHR^4$.

d. $R^{2A}$, $R^{2B}$, $R^{2C}$, $R^{2D}$, $R^{2E}$, and $R^{2F}$ Groups

In one aspect, each occurrence of each of $R^{2a}$, $R^{2b}$, $R^{2c}$, $R^{2d}$, $R^{2e}$, and $R^{2f}$ is independently selected from hydrogen and C1-C8 alkyl. In a further aspect, each occurrence of each of $R^{2a}$, $R^{2b}$, $R^{2c}$, $R^{2d}$, $R^{2e}$, and $R^{2f}$ is independently selected from hydrogen and C1-C4 alkyl. In a still further aspect, each of $R^{2a}$, $R^{2b}$, $R^{2c}$, $R^{2d}$, $R^{2e}$, and $R^{2f}$ is hydrogen.

In a further aspect, each occurrence of each of $R^{2a}$, $R^{2b}$, $R^{2c}$, $R^{2d}$, $R^{2e}$, and $R^{2f}$ is independently selected from hydrogen, methyl, ethyl, n-propyl, isopropyl, n-butyl, isobutyl, s-butyl, and t-butyl. In a still further aspect, each occurrence of each of $R^{2a}$, $R^{2b}$, $R^{2c}$, $R^{2d}$, $R^{2e}$, and $R^{2f}$ is independently selected from hydrogen, methyl, ethyl, n-propyl, and isopropyl. In yet a further aspect, each occurrence of each of $R^{2a}$, $R^{2b}$, $R^{2c}$, $R^{2d}$, $R^{2e}$, and $R^{2f}$ is independently selected from hydrogen, methyl, and ethyl. In an even further aspect, each occurrence of each of $R^{2a}$, $R^{2b}$, $R^{2c}$, $R^{2d}$, $R^{2e}$, and $R^{2f}$ is independently selected from hydrogen and ethyl. In a still further aspect, each occurrence of each of $R^{2a}$, $R^{2b}$, $R^{2c}$, $R^{2d}$, $R^{2e}$, and $R^{2f}$ is independently selected from hydrogen and methyl.

e. $R^3$ Groups

In one aspect, $R^3$ is selected from ethyl and isopropyl. In a further aspect, $R^3$ is ethyl. In a still further aspect, $R^3$ is isopropyl.

f. $R^4$ Groups

In one aspect, $R^4$, when present, is selected from hydrogen and C1-C4 alkyl. In a further aspect, $R^4$, when present, is hydrogen.

In a further aspect, $R^4$, when present, is selected from hydrogen, methyl, ethyl, isopropyl, n-propyl, isobutyl, n-butyl, s-butyl, and t-butyl. In a still further aspect, $R^4$, when present, is selected from hydrogen, methyl, ethyl, isopropyl, and n-propyl. In yet a further aspect, $R^4$, when present, is selected from hydrogen, methyl, and ethyl. In an even further aspect, $R^4$, when present, is selected from hydrogen and ethyl. In a still further aspect, $R^4$, when present, is selected from hydrogen and methyl.

In a further aspect, $R^4$, when present, is selected from methyl, ethyl, isopropyl, n-propyl, isobutyl, n-butyl, s-butyl, and t-butyl. In a still further aspect, $R^4$, when present, is selected from methyl, ethyl, isopropyl, and n-propyl. In yet a further aspect, $R^4$, when present, is selected from methyl and ethyl. In an even further aspect, $R^4$, when present, is ethyl. In a still further aspect, $R^4$, when present, is methyl.

g. $R^5$ Groups

In one aspect, $R^5$ is selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a further aspect, $R^5$ is selected from —F, —Cl, —Br, —OH, —$NH_2$, —CN, —$NO_2$, methyl, ethyl, n-propyl, isopropyl, —$CH_2F$, —$CH_2Cl$, —$CH_2CH_2F$, —$CH_2CH_2Cl$, —$CHF_2$, —$CF_3$, —$CHCl_2$, —$CCl_3$, —$OCH_3$, —$OCH_2CH_3$, —$NHC(O)CH_3$, —$NHC(O)CH_2CH_3$, —$NHCH_3$, —$NHCH_2CH_3$, —$N(CH_3)_2$, —$N(CH_2CH_3)_2$, and —$N(CH_2CH_3)(CH_3)$. In a still further aspect, $R^5$ is selected from —F, —Cl, —Br, —OH, —$NH_2$, —CN, —$NO_2$, methyl, ethyl, —$CH_2F$, —$CH_2Cl$, —$CH_2CH_2F$, —$CH_2CH_2Cl$, —$CHF_2$, —$CF_3$, —$CHCl_2$, —$CCl_3$, —$OCH_3$, —$OCH_2CH_3$, —$NHC(O)CH_3$, —$NHC(O)CH_2CH_3$, —$NHCH_3$, —$NHCH_2CH_3$, —$N(CH_3)_2$, —$N(CH_2CH_3)_2$, and —$N(CH_2CH_3)(CH_3)$. In yet a further aspect, $R^5$ is selected from —F, —Cl, —Br, —OH, —$NH_2$, —CN, —$NO_2$, methyl, —$CH_2F$, —$CH_2Cl$, —$CHF_2$, —$CF_3$, —$CHCl_2$, —$CCl_3$, —$OCH_3$, —NHC(O)$CH_3$, —$NHCH_3$, and —$N(CH_3)_2$.

In a further aspect, $R^5$ is selected from halogen, —$NH_2$, C1-C4 haloalkyl, —NHC(O)(C1-C4 alkyl), C1-C4 alkylamino, and (C1-C4)(C1-C4) dialkylamino. In a still further aspect, $R^5$ is selected from —F, —Cl, —Br, —$NH_2$, —$CH_2F$, —$CH_2Cl$, —$CH_2CH_2F$, —$CH_2CH_2Cl$, —$CHF_2$, —CF₃, —CHCl₂, —CCl₃, —NHC(O)CH₃, —NHC(O)CH₂CH₃, —NHCH₃, —NHCH₂CH₃, —N(CH₃)₂, —N(CH₂CH₃)₂, and —N(CH₂CH₃)(CH₃). In yet a further aspect, R⁵ is selected from —F, —Cl, —Br, —NH₂, —CH₂F, —CH₂Cl, —CH₂CH₂F, —CH₂CH₂Cl, —CHF₂, —CF₃, —CHCl₂, —CCl₃, —NHC(O)CH₃, —NHC(O)CH₂CH₃, —NHCH₃, —NHCH₂CH₃, —N(CH₃)₂, —N(CH₂CH₃)₂, and —N(CH₂CH₃)(CH₃). In an even further aspect, R⁵ is selected from —F, —Cl, —Br, —NH₂, —CH₂F, —CH₂Cl, —CHF₂, —CF₃, —CHCl₂, —CCl₃, —NHC(O)CH₃, —NHCH₃, and —N(CH₃)₂.

In a further aspect, R⁵ is selected from halogen and C1-C4 haloalkyl. In a still further aspect, R⁵ is selected from —F, —Cl, —Br, —CH₂F, —CH₂Cl, —CH₂CH₂F, —CH₂CH₂Cl, —CHF₂, —CF₃, —CHCl₂, and —CCl₃. In yet a further aspect, R⁵ is selected from —F, —Cl, —Br, —CH₂F, —CH₂Cl, —CHF₂, —CF₃, —CHCl₂, and —CCl₃.

In a further aspect, R⁵ is halogen. In a still further aspect, R⁵ is selected from —F, —Cl, and —Br. In yet a further aspect, R⁵ is selected from —F and —Cl. In an even further aspect, R⁵ is —F. In a still further aspect, R⁵ is —Cl.

In a further aspect, R⁵ is selected from —NH₂ and —NHC(O)(C1-C4 alkyl). In a still further aspect, R⁵ is selected from —NH₂, —NHC(O)CH₃, and —NHC(O)CH₂CH₃. In yet a further aspect, R⁵ is selected from —NH₂ and —NHC(O)CH₃. In an even further aspect, R⁵ is NH₂. In a still further aspect, R⁵ is —NHC(O)CH₃.

h. AR¹ Groups

In one aspect, Ar¹ is selected from monocyclic aryl, 6-membered heteroaryl, and bicyclic heteroaryl, and is substituted with 0-4 groups independently selected from halogen, —OH, —NH₂, —CN, —NO₂, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a further aspect, Ar¹ is selected from monocyclic aryl, 6-membered heteroaryl, and bicyclic heteroaryl, and is substituted with 0-3 groups independently selected from halogen, —OH, —NH₂, —CN, —NO₂, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, Ar¹ is selected from monocyclic aryl, 6-membered heteroaryl, and bicyclic heteroaryl, and is substituted with 0-2 groups independently selected from halogen, —OH, —NH₂, —CN, —NO₂, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, Ar¹ is selected from monocyclic aryl, 6-membered heteroaryl, and bicyclic heteroaryl, and is substituted with 0-1 group selected from halogen, —OH, —NH₂, —CN, —NO₂, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In an even further aspect, Ar¹ is selected from monocyclic aryl, 6-membered heteroaryl, and bicyclic heteroaryl, and is monosubstituted with a group selected from halogen, —OH, —NH₂, —CN, —NO₂, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In still further aspect, Ar¹ is selected from monocyclic aryl, 6-membered heteroaryl, and bicyclic heteroaryl, and is unsubstituted.

In one aspect, Ar¹ is selected from 6-membered heteroaryl and bicyclic heteroaryl, and is substituted with 0-4 groups independently selected from halogen, —OH, —NH₂, —CN, —NO₂, C1-C4 alkyl, C1-C4 haloalkyl, C1-C4 alkoxy, —NHC(O)(C1-C4 alkyl), C1-C4 alkylamino, and (C1-C4)(C1-C4) dialkylamino; or Ar¹ is phenyl meta-substituted with —Cl.

In a further aspect, Ar¹ is selected from monocyclic aryl, 6-membered heteroaryl, and bicyclic heteroaryl, and is substituted with 0-4 groups independently selected from —F, —Cl, —NH₂, and —NHC(O)CH₃. In a further aspect, Ar¹ is selected from monocyclic aryl, 6-membered heteroaryl, and bicyclic heteroaryl, and is substituted with 0-3 groups independently selected from —F, —Cl, —NH₂, and —NHC(O)CH₃. In a still further aspect, Ar¹ is selected from monocyclic aryl, 6-membered heteroaryl, and bicyclic heteroaryl, and is substituted with 0-2 groups independently selected from —F, —Cl, —NH₂, and —NHC(O)CH₃. In yet a further aspect, Ar¹ is selected from monocyclic aryl, 6-membered heteroaryl, and bicyclic heteroaryl, and is substituted with 0-1 group selected from —F, —Cl, —NH₂, and —NHC(O)CH₃. In an even further aspect, Ar¹ is selected from monocyclic aryl, 6-membered heteroaryl, and bicyclic heteroaryl, and is monosubstituted with a group selected from —F, —Cl, —NH₂, and —NHC(O)CH₃. In a still further aspect, Ar¹ is selected from monocyclic aryl, 6-membered heteroaryl, and bicyclic heteroaryl, and is monosubstituted with a —F group. In yet a further aspect, Ar¹ is selected from monocyclic aryl, 6-membered heteroaryl, and bicyclic heteroaryl, and is monosubstituted with a —Cl group. In an even further aspect, Ar¹ is selected from monocyclic aryl, 6-membered heteroaryl, and bicyclic heteroaryl, and is monosubstituted with a —NH₂ group.

In a further aspect, Ar¹ is monocyclic aryl substituted with 0-4 groups independently selected from halogen, —OH, —NH₂, —CN, —NO₂, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, Ar¹ is monocyclic aryl substituted with 0-3 groups independently selected from halogen, —OH, —NH₂, —CN, —NO₂, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, Ar¹ is monocyclic aryl substituted with 0-2 groups independently selected from halogen, —OH, —NH₂, —CN, —NO₂, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In an even further aspect, Ar¹ is monocyclic aryl substituted with 0-1 group selected from halogen, —OH, —NH₂, —CN, —NO₂, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, Ar¹ is monocyclic aryl monosubstituted with a group selected from halogen, —OH, —NH₂, —CN, —NO₂, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, Ar¹ is unsubstituted monocyclic aryl.

In a further aspect, Ar¹ is monocyclic aryl substituted with 0-4 groups independently selected from —F, —Cl, —NH₂, and —NHC(O)CH₃. In a further aspect, Ar¹ is monocyclic aryl substituted with 0-3 groups independently selected from —F, —Cl, —NH₂, and —NHC(O)CH₃. In a still further aspect, Ar¹ is monocyclic aryl substituted with 0-2 groups independently selected from —F, —Cl, —NH₂, and —NHC(O)CH₃. In yet a further aspect, Ar¹ is monocyclic aryl substituted with 0-1 group selected from —F, —Cl, —NH₂, and —NHC(O)CH₃. In an even further aspect, Ar¹ is monocyclic aryl monosubstituted with a group selected from —F, —Cl, —NH₂, and —NHC(O)CH₃. In a still further aspect, Ar¹ is monocyclic aryl monosubstituted with a —F group. In yet a further aspect, Ar¹ is monocyclic aryl monosubstituted with a —Cl group. In an even further aspect, Ar¹ is monocyclic aryl monosubstituted with a —NH₂ group.

In a further aspect, Ar$^1$ is phenyl substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, Ar$^1$ is phenyl substituted with 0-3 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, Ar$^1$ is phenyl substituted with 0-2 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In an even further aspect, Ar$^1$ is phenyl substituted with 0-1 group selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, Ar$^1$ is phenyl monosubstituted with a group selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, Ar$^1$ is unsubstituted phenyl.

In a further aspect, Ar$^1$ is phenyl substituted with 0-4 groups independently selected from —F, —Cl, —NH$_2$, and —NHC(O)CH$_3$. In a further aspect, Ar$^1$ is phenyl substituted with 0-3 groups independently selected from —F, —Cl, —NH$_2$, and —NHC(O)CH$_3$. In a still further aspect, Ar$^1$ is phenyl substituted with 0-2 groups independently selected from —F, —Cl, —NH$_2$, and —NHC(O)CH$_3$. In yet a further aspect, Ar$^1$ is phenyl substituted with 0-1 group selected from —F, —Cl, —NH$_2$, and —NHC(O)CH$_3$. In an even further aspect, Ar$^1$ is phenyl monosubstituted with a group selected from —F, —Cl, —NH$_2$, and —NHC(O)CH$_3$. In a still further aspect, Ar$^1$ is phenyl monosubstituted with a —F group. In yet a further aspect, Ar$^1$ is phenyl monosubstituted with a —Cl group. In an even further aspect, Ar$^1$ is phenyl monosubstituted with a —NH$_2$ group.

In a further aspect, Ar$^1$ is selected from 6-membered heteroaryl and bicyclic heteroaryl, and is substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, Ar$^1$ is selected from 6-membered heteroaryl and bicyclic heteroaryl, and is substituted with 0-3 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, Ar$^1$ is selected from 6-membered heteroaryl and bicyclic heteroaryl, and is substituted with 0-2 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In an even further aspect, Ar$^1$ is selected from 6-membered heteroaryl and bicyclic heteroaryl, and is substituted with 0-1 group selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, Ar$^1$ is selected from 6-membered heteroaryl and bicyclic heteroaryl, and is monosubstituted with a group selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, Ar$^1$ is selected from 6-membered heteroaryl and bicyclic heteroaryl, and is unsubstituted.

In a further aspect, Ar$^1$ is selected from 6-membered heteroaryl and bicyclic heteroaryl, and is substituted with 0-4 groups independently selected from —F, —Cl, —NH$_2$, and —NHC(O)CH$_3$. In a further aspect, Ar$^1$ is selected from 6-membered heteroaryl and bicyclic heteroaryl, and is substituted with 0-3 groups independently selected from —F, —Cl, —NH$_2$, and —NHC(O)CH$_3$. In a still further aspect, Ar$^1$ is selected from 6-membered heteroaryl and bicyclic heteroaryl, and is substituted with 0-2 groups independently selected from —F, —Cl, —NH$_2$, and —NHC(O)CH$_3$. In yet a further aspect, Ar$^1$ is selected from 6-membered heteroaryl and bicyclic heteroaryl, and is substituted with 0-1 group selected from —F, —Cl, —NH$_2$, and —NHC(O)CH$_3$. In an even further aspect, Ar$^1$ is selected from 6-membered heteroaryl and bicyclic heteroaryl, and is monosubstituted with a group selected from —F, —Cl, —NH$_2$, and —NHC(O)CH$_3$. In a still further aspect, Ar$^1$ is selected from 6-membered heteroaryl and bicyclic heteroaryl, and is monosubstituted with a —F group. In yet a further aspect, Ar$^1$ is selected from 6-membered heteroaryl and bicyclic heteroaryl, and is monosubstituted with a —Cl group. In an even further aspect, Ar$^1$ is selected from 6-membered heteroaryl and bicyclic heteroaryl, and is monosubstituted with a —NH$_2$ group.

In a further aspect, Ar$^1$ is 6-membered heteroaryl substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, Ar$^1$ is 6-membered heteroaryl substituted with 0-3 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, Ar$^1$ is 6-membered heteroaryl substituted with 0-2 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In an even further aspect, Ar$^1$ is 6-membered heteroaryl substituted with 0-1 group selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, Ar$^1$ is 6-membered heteroaryl monosubstituted with a group selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, Ar$^1$ is unsubstituted 6-membered heteroaryl.

In a further aspect, Ar$^1$ is 6-membered heteroaryl substituted with 0-4 groups independently selected from —F, —Cl, —NH$_2$, and —NHC(O)CH$_3$. In a further aspect, Ar$^1$ is 6-membered heteroaryl substituted with 0-3 groups independently selected from —F, —Cl, —NH$_2$, and —NHC(O)CH$_3$. In a still further aspect, Ar$^1$ is 6-membered heteroaryl substituted with 0-2 groups independently selected from —F, —Cl, —NH$_2$, and —NHC(O)CH$_3$. In yet a further aspect, Ar$^1$ is 6-membered heteroaryl substituted with 0-1 group selected from —F, —Cl, —NH$_2$, and —NHC(O)CH$_3$. In an even further aspect, Ar$^1$ is 6-membered heteroaryl monosubstituted with a group selected from —F, —Cl, —NH$_2$, and —NHC(O)CH$_3$. In a still further aspect, Ar$^1$ is 6-membered heteroaryl monosubstituted with a —F group. In yet a further aspect, Ar$^1$ is 6-membered heteroaryl monosubstituted with a —Cl group. In an even further aspect, $Ar^1$ is 6-membered heteroaryl monosubstituted with a —NH$_2$ group.

In a further aspect, $Ar^1$ is pyridinyl substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, $Ar^1$ is pyridinyl substituted with 0-3 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, $Ar^1$ is pyridinyl substituted with 0-2 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In an even further aspect, $Ar^1$ is pyridinyl substituted with 0-1 group selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, $Ar^1$ is pyridinyl monosubstituted with a group selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, $Ar^1$ is unsubstituted pyridinyl.

In a further aspect, $Ar^1$ is pyridinyl substituted with 0-4 groups independently selected from —F, —Cl, —NH$_2$, and —NHC(O)CH$_3$. In a further aspect, $Ar^1$ is pyridinyl substituted with 0-3 groups independently selected from —F, —Cl, —NH$_2$, and —NHC(O)CH$_3$. In a still further aspect, $Ar^1$ is pyridinyl substituted with 0-2 groups independently selected from —F, —Cl, —NH$_2$, and —NHC(O)CH$_3$. In yet a further aspect, $Ar^1$ is pyridinyl substituted with 0-1 group selected from —F, —Cl, —NH$_2$, and —NHC(O)CH$_3$. In an even further aspect, $Ar^1$ is pyridinyl monosubstituted with a group selected from —F, —Cl, —NH$_2$, and —NHC(O)CH$_3$. In a still further aspect, $Ar^1$ is pyridinyl monosubstituted with a —F group. In yet a further aspect, $Ar^1$ is pyridinyl monosubstituted with a —Cl group. In an even further aspect, $Ar^1$ is pyridinyl monosubstituted with a —NH$_2$ group.

In a further aspect, $Ar^1$ is pyridinonyl substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, $Ar^1$ is pyridinonyl substituted with 0-3 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, $Ar^1$ is pyridinonyl substituted with 0-2 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In an even further aspect, $Ar^1$ is pyridinonyl substituted with 0-1 group selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, $Ar^1$ is pyridinonyl monosubstituted with a group selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, $Ar^1$ is unsubstituted pyridinonyl.

In a further aspect, $Ar^1$ is pyridinonyl substituted with 0-4 groups independently selected from —F, —Cl, —NH$_2$, and —NHC(O)CH$_3$. In a further aspect, $Ar^1$ is pyridinonyl substituted with 0-3 groups independently selected from —F, —Cl, —NH$_2$, and —NHC(O)CH$_3$. In a still further aspect, $Ar^1$ is pyridinonyl substituted with 0-2 groups independently selected from —F, —Cl, —NH$_2$, and —NHC(O)CH$_3$. In yet a further aspect, $Ar^1$ is pyridinonyl substituted with 0-1 group selected from —F, —Cl, —NH$_2$, and —NHC(O)CH$_3$. In an even further aspect, $Ar^1$ is pyridinonyl monosubstituted with a group selected from —F, —Cl, —NH$_2$, and —NHC(O)CH$_3$. In a still further aspect, $Ar^1$ is pyridinonyl monosubstituted with a —F group. In yet a further aspect, $Ar^1$ is pyridinonyl monosubstituted with a —Cl group. In an even further aspect, $Ar^1$ is pyridinonyl monosubstituted with a —NH$_2$ group.

In a further aspect, $Ar^1$ is pyridine 1-oxidyl substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, $Ar^1$ is pyridine 1-oxidyl substituted with 0-3 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, $Ar^1$ is pyridine 1-oxidyl substituted with 0-2 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In an even further aspect, $Ar^1$ is pyridine 1-oxidyl substituted with 0-1 group selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, $Ar^1$ is pyridine 1-oxidyl monosubstituted with a group selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, $Ar^1$ is unsubstituted pyridine 1-oxidyl.

In a further aspect, $Ar^1$ is pyridine 1-oxidyl substituted with 0-4 groups independently selected from —F, —Cl, —NH$_2$, and —NHC(O)CH$_3$. In a further aspect, $Ar^1$ is pyridine 1-oxidyl substituted with 0-3 groups independently selected from —F, —Cl, —NH$_2$, and —NHC(O)CH$_3$. In a still further aspect, $Ar^1$ is pyridine 1-oxidyl substituted with 0-2 groups independently selected from —F, —Cl, —NH$_2$, and —NHC(O)CH$_3$. In yet a further aspect, $Ar^1$ is pyridine 1-oxidyl substituted with 0-1 group selected from —F, —Cl, —NH$_2$, and —NHC(O)CH$_3$. In an even further aspect, $Ar^1$ is pyridine 1-oxidyl monosubstituted with a group selected from —F, —Cl, —NH$_2$, and —NHC(O)CH$_3$. In a still further aspect, $Ar^1$ is pyridine 1-oxidyl monosubstituted with a —F group. In yet a further aspect, $Ar^1$ is pyridine 1-oxidyl monosubstituted with a —Cl group. In an even further aspect, $Ar^1$ is pyridine 1-oxidyl monosubstituted with a —NH$_2$ group.

In a further aspect, $Ar^1$ is bicyclic heteroaryl substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, $Ar^1$ is bicyclic heteroaryl substituted with 0-3 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, $Ar^1$ is bicyclic heteroaryl substituted with 0-2 groups independently selected from halogen, —OH, —NH$_2$, —CN, —NO$_2$, C1-C4 alkyl, C1-C4 haloalkyl, C1-C4 alkoxy, —NHC(O) (C1-C4 alkyl), C1-C4 alkylamino, and (C1-C4)(C1-C4) dialkylamino. In an even further aspect, Ar$^1$ is bicyclic heteroaryl substituted with 0-1 group selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, Ar$^1$ is bicyclic heteroaryl monosubstituted with a group selected from halogen, —OH, —NH$_2$, —CN, —NO$_2$, C1-C4 alkyl, C1-C4 haloalkyl, C1-C4 alkoxy, —NHC(O) (C1-C4 alkyl), C1-C4 alkylamino, and (C1-C4)(C1-C4) dialkylamino. In yet a further aspect, Ar$^1$ is unsubstituted bicyclic heteroaryl.

In a further aspect, Ar$^1$ is bicyclic heteroaryl substituted with 0-4 groups independently selected from —F, —Cl, —NH$_2$, and —NHC(O)CH$_3$. In a further aspect, Ar$^1$ is bicyclic heteroaryl substituted with 0-3 groups independently selected from —F, —Cl, —NH$_2$, and —NHC(O)CH$_3$. In a still further aspect, Ar$^1$ is bicyclic heteroaryl substituted with 0-2 groups independently selected from —F, —Cl, —NH$_2$, and —NHC(O)CH$_3$. In yet a further aspect, Ar$^1$ is bicyclic heteroaryl substituted with 0-1 group selected from —F, —Cl, —NH$_2$, and —NHC(O)CH$_3$. In an even further aspect, Ar$^1$ is bicyclic heteroaryl monosubstituted with a group selected from —F, —Cl, —NH$_2$, and —NHC(O)CH$_3$. In a still further aspect, Ar$^1$ is bicyclic heteroaryl monosubstituted with a —F group. In yet a further aspect, Ar$^1$ is bicyclic heteroaryl monosubstituted with a —Cl group. In an even further aspect, Ar$^1$ is bicyclic heteroaryl monosubstituted with a —NH$_2$ group.

In a further aspect, Ar$^1$ is indolyl substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, Ar$^1$ is indolyl substituted with 0-3 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, Ar$^1$ is indolyl substituted with 0-2 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In an even further aspect, Ar$^1$ is indolyl substituted with 0-1 group selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, Ar$^1$ is indolyl monosubstituted with a group selected from halogen, —OH, —NH$_2$, —CN, —NO$_2$, C1-C4 alkyl, C1-C4 haloalkyl, C1-C4 alkoxy, —NHC(O) (C1-C4 alkyl), C1-C4 alkylamino, and (C1-C4)(C1-C4) dialkylamino. In yet a further aspect, Ar$^1$ is unsubstituted indolyl.

In a further aspect, Ar$^1$ is indolyl substituted with 0-4 groups independently selected from —F, —Cl, —NH$_2$, and —NHC(O)CH$_3$. In a further aspect, Ar$^1$ is indolyl substituted with 0-3 groups independently selected from —F, —Cl, —NH$_2$, and —NHC(O)CH$_3$. In a still further aspect, Ar$^1$ is indolyl substituted with 0-2 groups independently selected from —F, —Cl, —NH$_2$, and —NHC(O)CH$_3$. In yet a further aspect, Ar$^1$ is indolyl substituted with 0-1 group selected from —F, —Cl, —NH$_2$, and —NHC(O)CH$_3$. In an even further aspect, Ar$^1$ is indolyl monosubstituted with a group selected from —F, —Cl, —NH$_2$, and —NHC(O)CH$_3$.

In a still further aspect, Ar$^1$ is indolyl monosubstituted with a —F group. In yet a further aspect, Ar$^1$ is indolyl monosubstituted with a —Cl group. In an even further aspect, Ar$^1$ is indolyl monosubstituted with a —NH$_2$ group.

In a further aspect, Ar$^1$ is a moiety having a structure represented by a formula selected from:

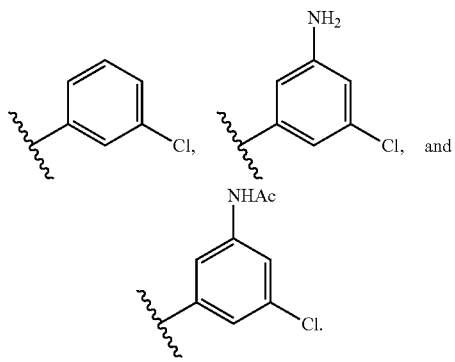

In a further aspect, Ar$^1$ is a moiety having a structure represented by a formula:

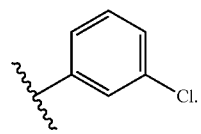 [SMILES: *c1cccc(Cl)c1]

In a further aspect, Ar$^1$ is a moiety having a structure represented by a formula selected from:

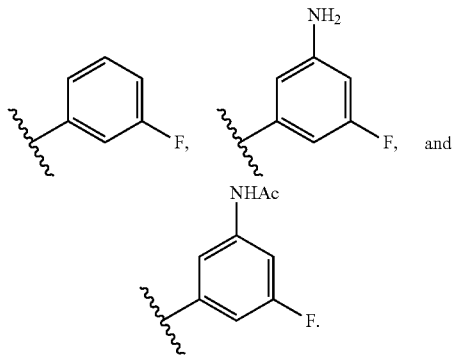

In a further aspect, Ar$^1$ is a moiety having a structure represented by a formula:

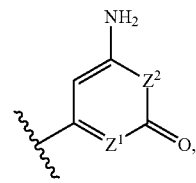

wherein Z$^1$ is selected from CH and N; and wherein Z$^2$ is selected from CH$_2$ and NH.

In a further aspect, Ar¹ is a moiety having a structure represented by a formula selected from:

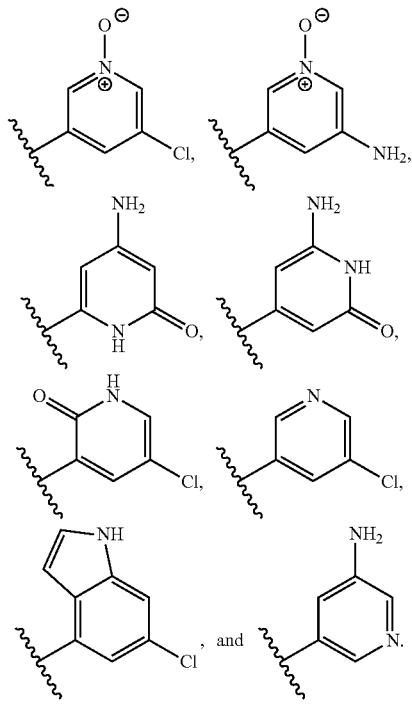

i. AR² Groups

In one aspect, Ar² is selected from 6-membered heteroaryl and bicyclic heteroaryl, and is substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, Ar² is selected from 6-membered heteroaryl and bicyclic heteroaryl, and is substituted with 0-3 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, Ar² is selected from 6-membered heteroaryl and bicyclic heteroaryl, and is substituted with 0-2 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In an even further aspect, Ar² is selected from 6-membered heteroaryl and bicyclic heteroaryl, and is substituted with 0-1 group selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, Ar² is selected from 6-membered heteroaryl and bicyclic heteroaryl, and is monosubstituted with a group selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, Ar² is selected from 6-membered heteroaryl and bicyclic heteroaryl, and is unsubstituted.

In a further aspect, Ar² is selected from 6-membered heteroaryl and bicyclic heteroaryl, and is substituted with 0-4 groups independently selected from —F, —Cl, —NH$_2$, and —NHC(O)CH$_3$. In a further aspect, Ar² is selected from 6-membered heteroaryl and bicyclic heteroaryl, and is substituted with 0-3 groups independently selected from —F, —Cl, —NH$_2$, and —NHC(O)CH$_3$. In a still further aspect, Ar² is selected from 6-membered heteroaryl and bicyclic heteroaryl, and is substituted with 0-2 groups independently selected from —F, —Cl, —NH$_2$, and —NHC(O)CH$_3$. In yet a further aspect, Ar² is selected from 6-membered heteroaryl and bicyclic heteroaryl, and is substituted with 0-1 group selected from —F, —Cl, —NH$_2$, and —NHC(O)CH$_3$. In an even further aspect, Ar² is selected from 6-membered heteroaryl and bicyclic heteroaryl, and is monosubstituted with a group selected from —F, —Cl, —NH$_2$, and —NHC(O)CH$_3$. In a still further aspect, Ar² is selected from 6-membered heteroaryl and bicyclic heteroaryl, and is monosubstituted with a —F group. In yet a further aspect, Ar² is selected from 6-membered heteroaryl and bicyclic heteroaryl, and is monosubstituted with a —Cl group. In an even further aspect, Ar² is selected from 6-membered heteroaryl and bicyclic heteroaryl, and is monosubstituted with a —NH$_2$ group.

In a further aspect, Ar² is 6-membered heteroaryl substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, Ar¹ is 6-membered heteroaryl substituted with 0-3 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, Ar¹ is 6-membered heteroaryl substituted with 0-2 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In an even further aspect, Ar¹ is 6-membered heteroaryl substituted with 0-1 group selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, Ar² is 6-membered heteroaryl monosubstituted with a group selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, Ar² is unsubstituted 6-membered heteroaryl.

In a further aspect, Ar² is 6-membered heteroaryl substituted with 0-4 groups independently selected from —F, —Cl, —NH$_2$, and —NHC(O)CH$_3$. In a further aspect, Ar² is 6-membered heteroaryl substituted with 0-3 groups independently selected from —F, —Cl, —NH$_2$, and —NHC(O)CH$_3$. In a still further aspect, Ar¹ is 6-membered heteroaryl substituted with 0-2 groups independently selected from —F, —Cl, —NH$_2$, and —NHC(O)CH$_3$. In yet a further aspect, Ar² is 6-membered heteroaryl substituted with 0-1 group selected from —F, —Cl, —NH$_2$, and —NHC(O)CH$_3$. In an even further aspect, Ar² is 6-membered heteroaryl monosubstituted with a group selected from —F, —Cl, —NH$_2$, and —NHC(O)CH$_3$. In a still further aspect, Ar² is 6-membered heteroaryl monosubstituted with a —F group. In yet a further aspect, Ar² is 6-membered heteroaryl monosubstituted with a —Cl group. In an even further aspect, Ar² is 6-membered heteroaryl monosubstituted with a —NH$_2$ group.

In a further aspect, Ar² is pyridinyl substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, $Ar^2$ is pyridinyl substituted with 0-3 groups independently selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, $Ar^2$ is pyridinyl substituted with 0-2 groups independently selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In an even further aspect, $Ar^2$ is pyridinyl substituted with 0-1 group selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, $Ar^2$ is pyridinyl monosubstituted with a group selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, $Ar^2$ is unsubstituted pyridinyl.

In a further aspect, $Ar^2$ is pyridinyl substituted with 0-4 groups independently selected from —F, —Cl, —$NH_2$, and —NHC(O)$CH_3$. In a further aspect, $Ar^2$ is pyridinyl substituted with 0-3 groups independently selected from —F, —Cl, —$NH_2$, and —NHC(O)$CH_3$. In a still further aspect, $Ar^2$ is pyridinyl substituted with 0-2 groups independently selected from —F, —Cl, —$NH_2$, and —NHC(O)$CH_3$. In yet a further aspect, $Ar^1$ is pyridinyl substituted with 0-1 group selected from —F, —Cl, —$NH_2$, and —NHC(O)$CH_3$. In an even further aspect, $Ar^2$ is pyridinyl monosubstituted with a group selected from —F, —Cl, —$NH_2$, and —NHC(O)$CH_3$. In a still further aspect, $Ar^2$ is pyridinyl monosubstituted with a —F group. In yet a further aspect, $Ar^2$ is pyridinyl monosubstituted with a —Cl group. In an even further aspect, $Ar^2$ is pyridinyl monosubstituted with a —$NH_2$ group.

In a further aspect, $Ar^2$ is pyridinonyl substituted with 0-4 groups independently selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, $Ar^2$ is pyridinonyl substituted with 0-3 groups independently selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, $Ar^2$ is pyridinonyl substituted with 0-2 groups independently selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In an even further aspect, $Ar^2$ is pyridinonyl substituted with 0-1 group selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, $Ar^2$ is pyridinonyl monosubstituted with a group selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, $Ar^2$ is unsubstituted pyridinonyl.

In a further aspect, $Ar^2$ is pyridinonyl substituted with 0-4 groups independently selected from —F, —Cl, —$NH_2$, and —NHC(O)$CH_3$. In a further aspect, $Ar^2$ is pyridinonyl substituted with 0-3 groups independently selected from —F, —Cl, —$NH_2$, and —NHC(O)$CH_3$. In a still further aspect, $Ar^2$ is pyridinonyl substituted with 0-2 groups independently selected from —F, —Cl, —$NH_2$, and —NHC(O)$CH_3$. In yet a further aspect, $Ar^2$ is pyridinonyl substituted with 0-1 group selected from —F, —Cl, —$NH_2$, and —NHC(O)$CH_3$. In an even further aspect, $Ar^2$ is pyridinonyl monosubstituted with a group selected from —F, —Cl, —$NH_2$, and —NHC(O)$CH_3$. In a still further aspect, $Ar^2$ is pyridinonyl monosubstituted with a —F group. In yet a further aspect, $Ar^2$ is pyridinonyl monosubstituted with a —Cl group. In an even further aspect, $Ar^2$ is pyridinonyl monosubstituted with a —$NH_2$ group.

In a further aspect, $Ar^2$ is pyridine 1-oxidyl substituted with 0-4 groups independently selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, $Ar^2$ is pyridine 1-oxidyl substituted with 0-3 groups independently selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, $Ar^2$ is pyridine 1-oxidyl substituted with 0-2 groups independently selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In an even further aspect, $Ar^2$ is pyridine 1-oxidyl substituted with 0-1 group selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, $Ar^2$ is pyridine 1-oxidyl monosubstituted with a group selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, $Ar^2$ is unsubstituted pyridine 1-oxidyl.

In a further aspect, $Ar^2$ is pyridine 1-oxidyl substituted with 0-4 groups independently selected from —F, —Cl, —$NH_2$, and —NHC(O)$CH_3$. In a further aspect, $Ar^2$ is pyridine 1-oxidyl substituted with 0-3 groups independently selected from —F, —Cl, —$NH_2$, and —NHC(O)$CH_3$. In a still further aspect, $Ar^2$ is pyridine 1-oxidyl substituted with 0-2 groups independently selected from —F, —Cl, —$NH_2$, and —NHC(O)$CH_3$. In yet a further aspect, $Ar^2$ is pyridine 1-oxidyl substituted with 0-1 group selected from —F, —Cl, —$NH_2$, and —NHC(O)$CH_3$. In an even further aspect, $Ar^2$ is pyridine 1-oxidyl monosubstituted with a group selected from —F, —Cl, —$NH_2$, and —NHC(O)$CH_3$. In a still further aspect, $Ar^2$ is pyridine 1-oxidyl monosubstituted with a —F group. In yet a further aspect, $Ar^2$ is pyridine 1-oxidyl monosubstituted with a —Cl group. In an even further aspect, $Ar^2$ is pyridine 1-oxidyl monosubstituted with a —$NH_2$ group.

In a further aspect, $Ar^2$ is bicyclic heteroaryl substituted with 0-4 groups independently selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, $Ar^2$ is bicyclic heteroaryl substituted with 0-3 groups independently selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, $Ar^2$ is bicyclic heteroaryl substituted with 0-2 groups independently selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In an even further aspect, $Ar^2$ is bicyclic heteroaryl substituted with 0-1 group selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, Ar² is bicyclic heteroaryl monosubstituted with a group selected from halogen, —OH, —NH₂, —CN, —NO₂, C1-C4 alkyl, C1-C4 haloalkyl, C1-C4 alkoxy, —NHC(O) (C1-C4 alkyl), C1-C4 alkylamino, and (C1-C4)(C1-C4) dialkylamino. In yet a further aspect, Ar² is unsubstituted bicyclic heteroaryl.

In a further aspect, Ar² is bicyclic heteroaryl substituted with 0-4 groups independently selected from —F, —Cl, —NH₂, and —NHC(O)CH₃. In a further aspect, Ar¹ is bicyclic heteroaryl substituted with 0-3 groups independently selected from —F, —Cl, —NH₂, and —NHC(O) CH₃. In a still further aspect, Ar² is bicyclic heteroaryl substituted with 0-2 groups independently selected from —F, —Cl, —NH₂, and —NHC(O)CH₃. In yet a further aspect, Ar² is bicyclic heteroaryl substituted with 0-1 group selected from —F, —Cl, —NH₂, and —NHC(O)CH₃. In an even further aspect, Ar² is bicyclic heteroaryl monosubstituted with a group selected from —F, —Cl, —NH₂, and —NHC(O)CH₃. In a still further aspect, Ar² is bicyclic heteroaryl monosubstituted with a —F group. In yet a further aspect, Ar² is bicyclic heteroaryl monosubstituted with a —Cl group. In an even further aspect, Ar² is bicyclic heteroaryl monosubstituted with a —NH₂ group.

In a further aspect, Ar² is indolyl substituted with 0-4 groups independently selected from halogen, —OH, —NH₂, —CN, —NO₂, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, Ar² is indolyl substituted with 0-3 groups independently selected from halogen, —OH, —NH₂, —CN, —NO₂, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In yet a further aspect, Ar² is indolyl substituted with 0-2 groups independently selected from halogen, —OH, —NH₂, —CN, —NO₂, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In an even further aspect, Ar² is indolyl substituted with 0-1 group selected from halogen, —OH, —NH₂, —CN, —NO₂, C1-C4 alkyl, C1-C4 haloalkyl, C1-C4 alkoxy, —NHC(O)(C1-C4 alkyl), C1-C4 alkylamino, and (C1-C4)(C1-C4) dialkylamino. In a still further aspect, Ar² is indolyl monosubstituted with a group selected from halogen, —OH, —NH₂, —CN, —NO₂, C1-C4 alkyl, C1-C4 haloalkyl, C1-C4 alkoxy, —NHC(O) (C1-C4 alkyl), C1-C4 alkylamino, and (C1-C4)(C1-C4) dialkylamino. In yet a further aspect, Ar² is unsubstituted indolyl.

In a further aspect, Ar² is indolyl substituted with 0-4 groups independently selected from —F, —Cl, —NH₂, and —NHC(O)CH₃. In a further aspect, Ar² is indolyl substituted with 0-3 groups independently selected from —F, —Cl, —NH₂, and —NHC(O)CH₃. In a still further aspect, Ar² is indolyl substituted with 0-2 groups independently selected from —F, —Cl, —NH₂, and —NHC(O)CH₃. In yet a further aspect, Ar² is indolyl substituted with 0-1 group selected from —F, —Cl, —NH₂, and —NHC(O)CH₃. In an even further aspect, Ar² is indolyl monosubstituted with a group selected from —F, —Cl, —NH₂, and —NHC(O)CH₃. In a still further aspect, Ar² is indolyl monosubstituted with a —F group. In yet a further aspect, Ar² is indolyl monosubstituted with a —Cl group. In an even further aspect, Ar² is indolyl monosubstituted with a —NH₂ group.

In a further aspect, Ar² is a moiety having a structure represented by a formula:

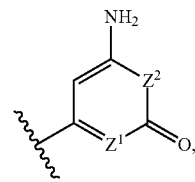

wherein $Z^1$ is selected from CH and N; and wherein $Z^2$ is selected from $CH_2$ and NH.

In a further aspect, Ar² is a moiety having a structure represented by a formula selected from:

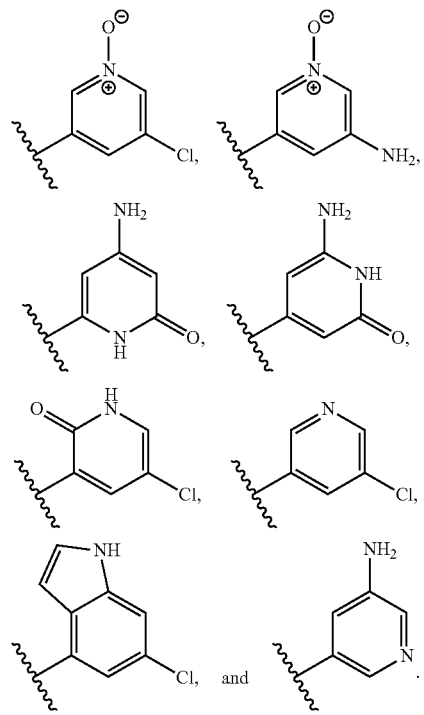

In a further aspect, Ar² is a moiety having a structure represented by a formula:

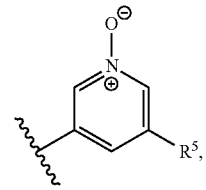

wherein $R^5$ is selected from halogen, —OH, —NH₂, —CN, —NO₂, C1-C4 alkyl, C1-C4 haloalkyl, C1-C4 alkoxy, —NHC(O)(C1-C4 alkyl), C1-C4 alkylamino, and (C1-C4) (C1-C4) dialkylamino.

In a still further aspect, Ar² is a moiety having a structure represented by a formula selected from:

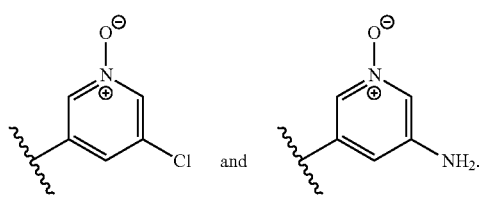 [SMILES: *c1cc(Cl)c[n+]([O-])c1 ; "and" ; *c1cc(N)c[n+]([O-])c1] and
2. Example Compounds
In one aspect, a compound can be present as one or more of the following structures:
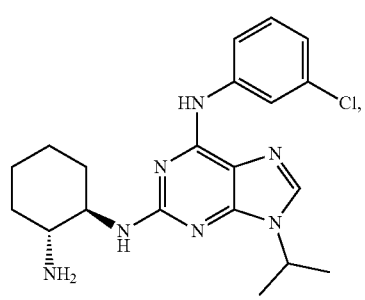
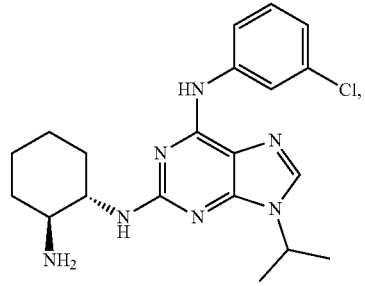
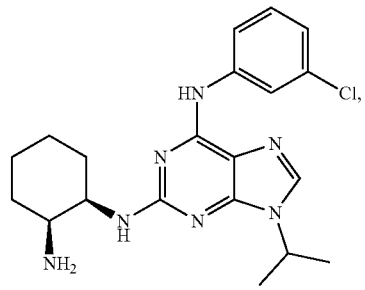
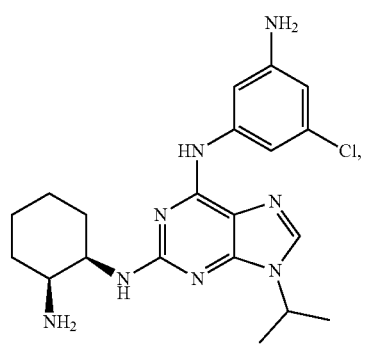
-continued
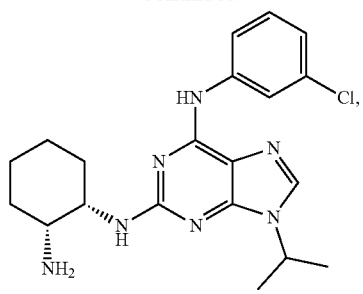
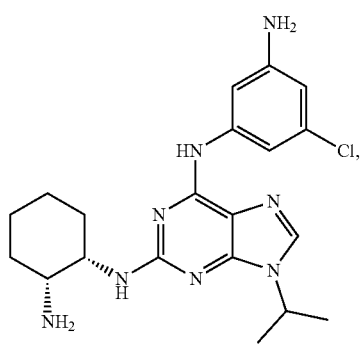
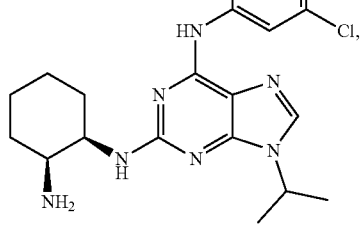
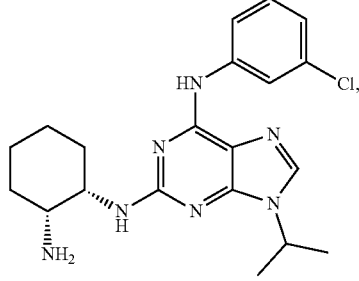
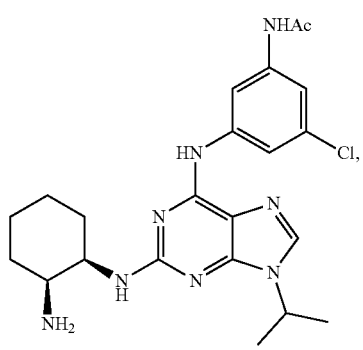

-continued
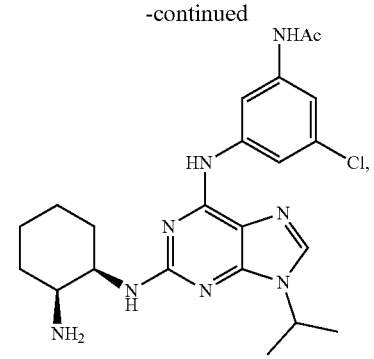
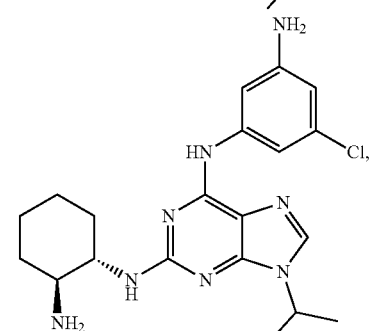
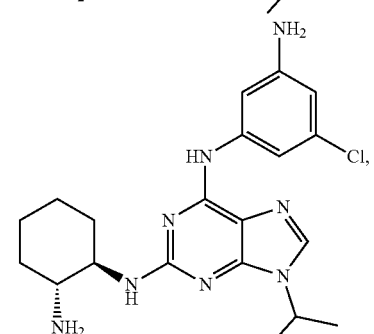
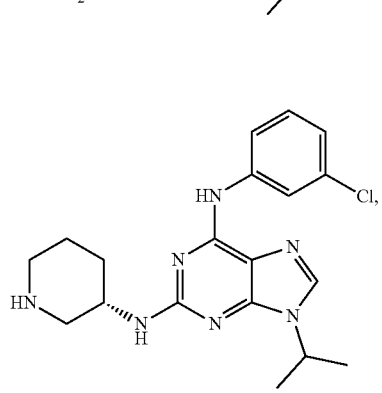
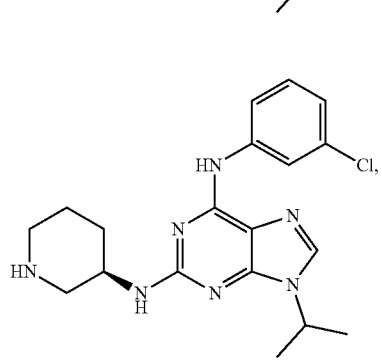
-continued
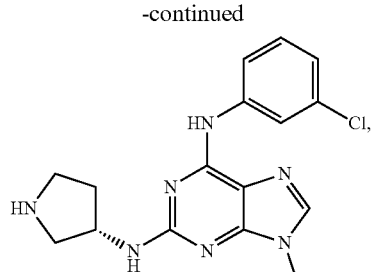
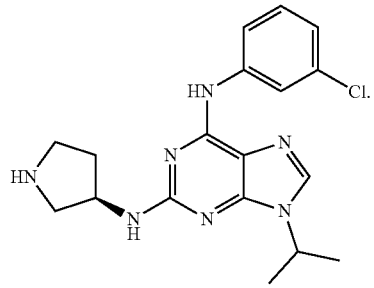
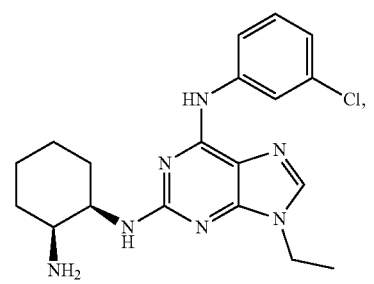
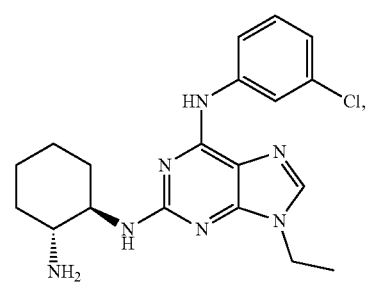
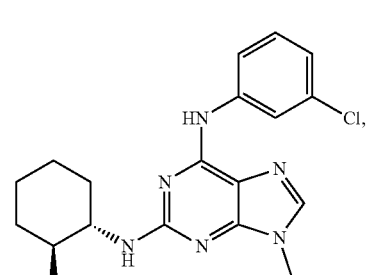

-continued

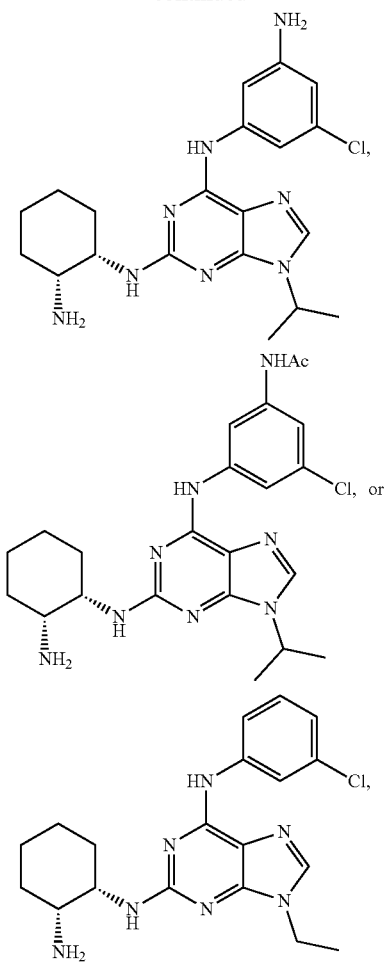

or a pharmaceutically acceptable salt thereof.

In one aspect, a compound can be present as one or more of the following structures:

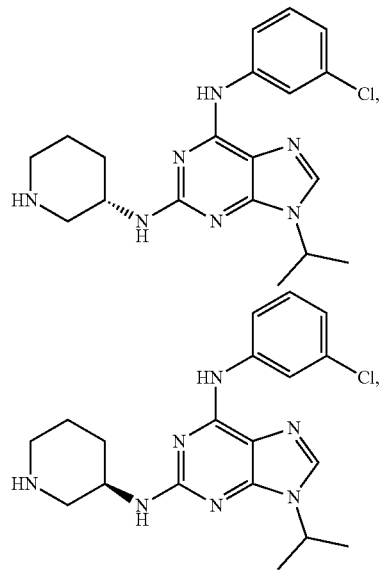

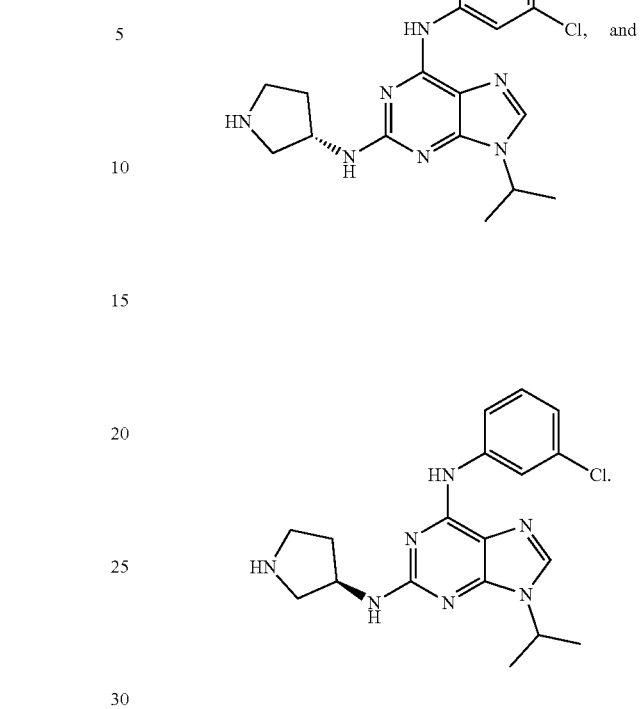

or a pharmaceutically acceptable salt thereof.

In one aspect, a compound can be present as one or more of the following structures:

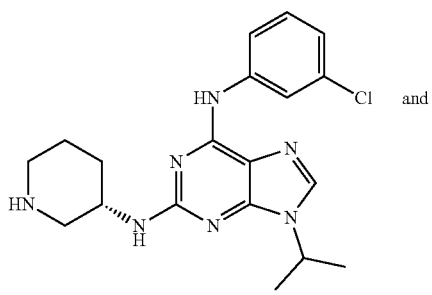

or a pharmaceutically acceptable salt thereof.

In one aspect, a compound can be present as one or more of the following structures:

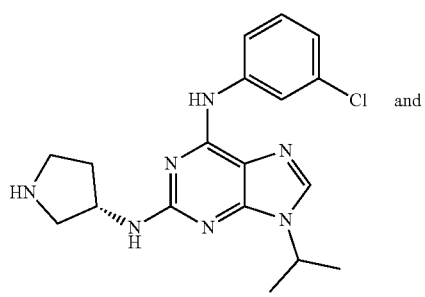
and
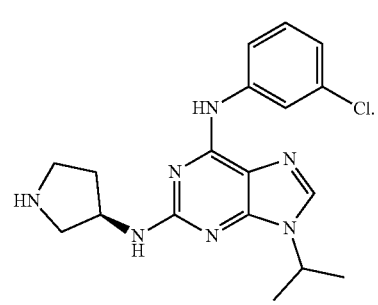
or a pharmaceutically acceptable salt thereof.
In one aspect, a compound can be present as one or more of the following structures:
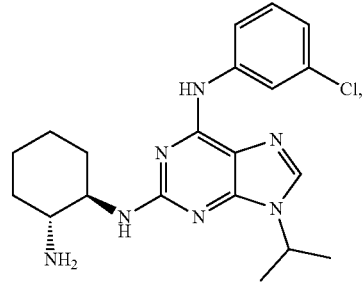
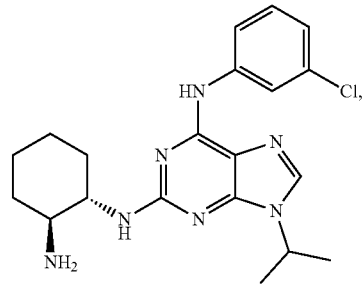
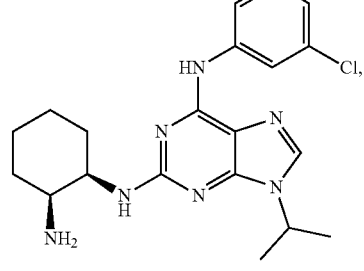
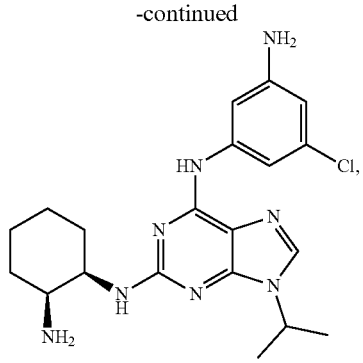
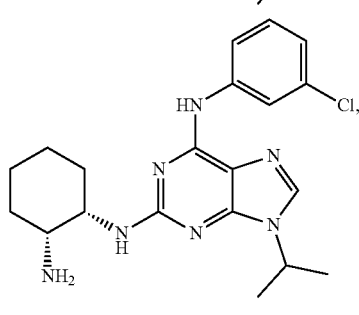
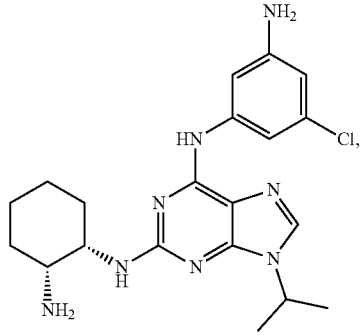
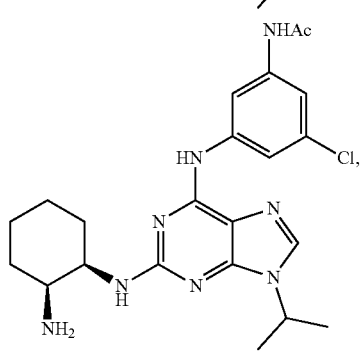
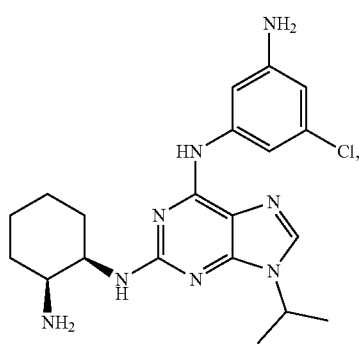

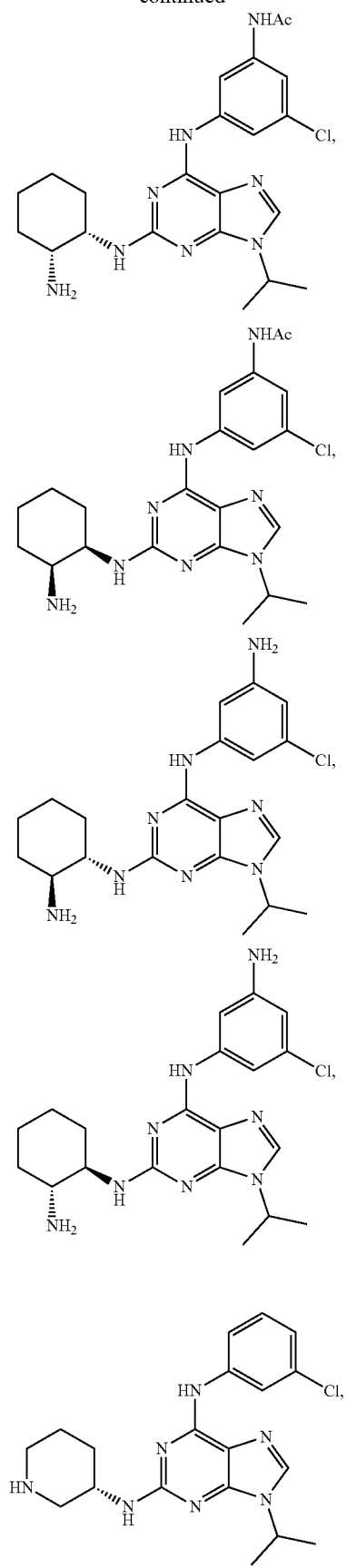
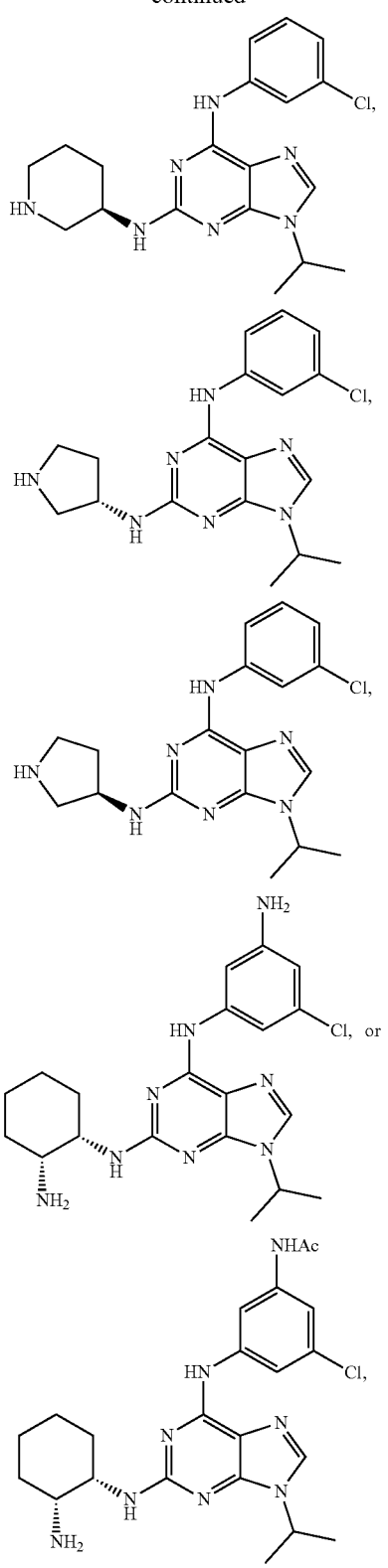
or a pharmaceutically acceptable salt thereof.
In one aspect, a compound can be present as one or more of the following structures:

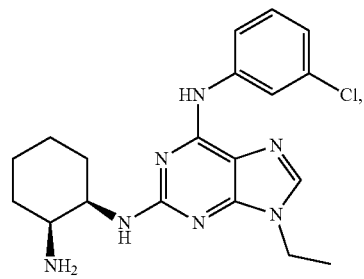

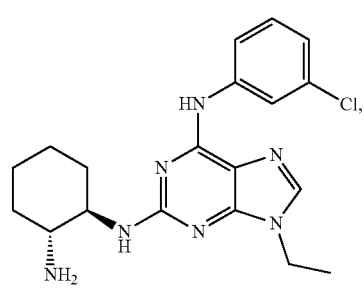

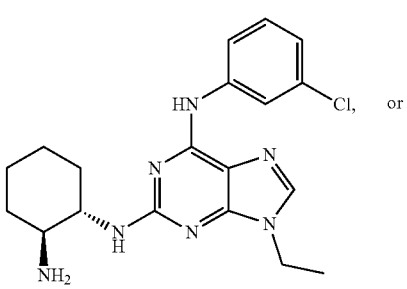 or

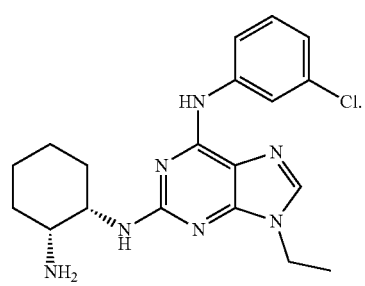

or a pharmaceutically acceptable salt thereof.

3. Prophetic Examples

The following compound examples are prophetic, and can be prepared using the synthesis methods described herein above and other general methods as needed as would be known to one skilled in the art. It is anticipated that the prophetic compounds would be active as PanK antagonists, and such activity can be determined using the assay methods described herein.

In one aspect, a compound can be selected from:

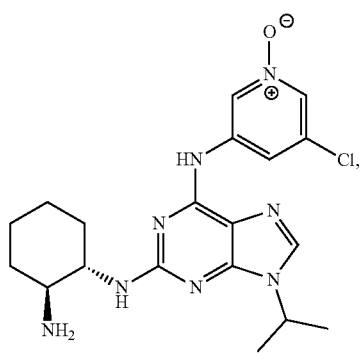

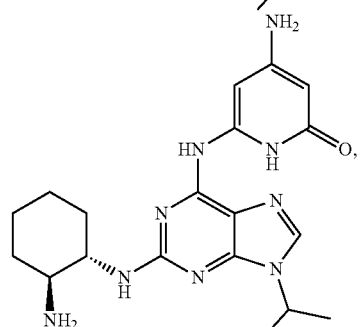

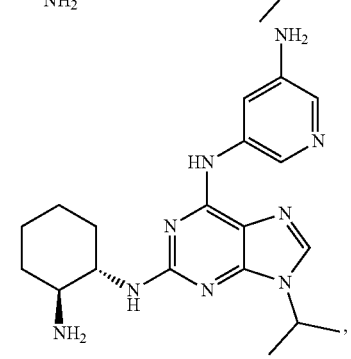

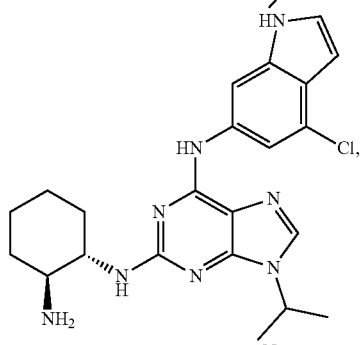

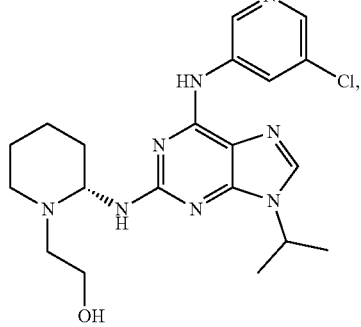

71
-continued
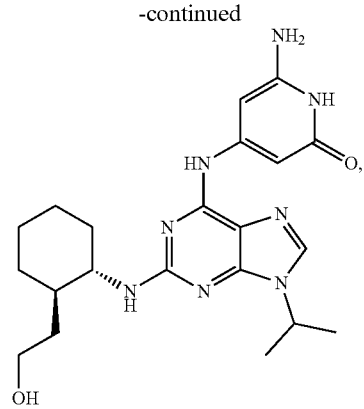
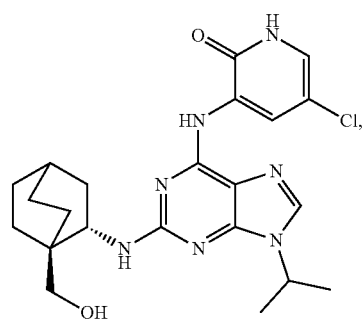
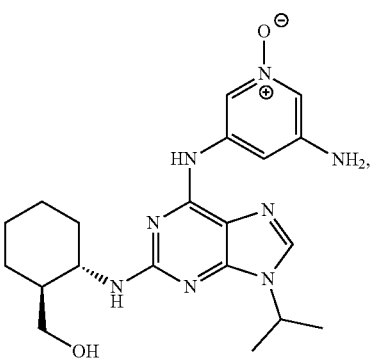
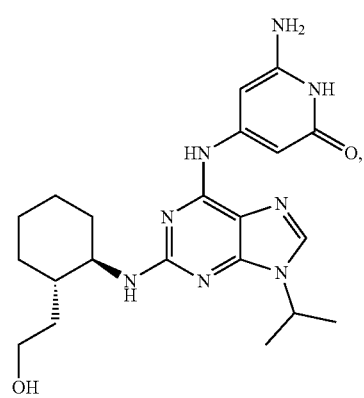
72
-continued
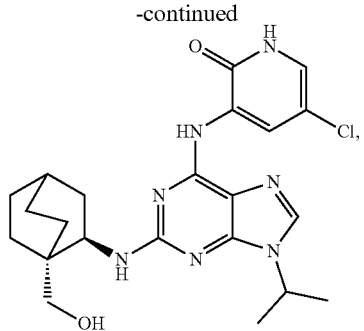
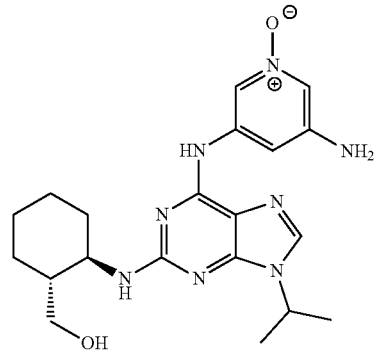
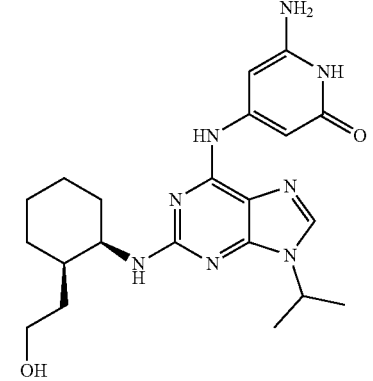
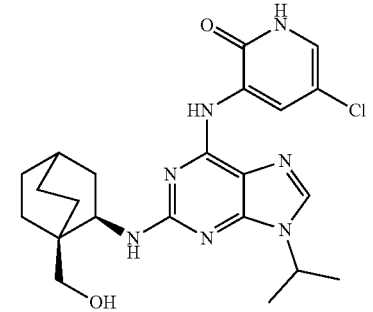
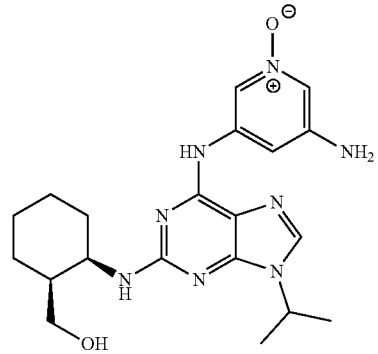

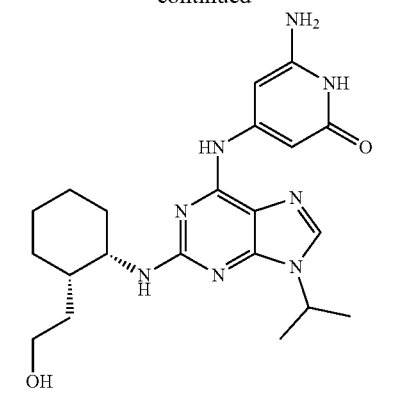

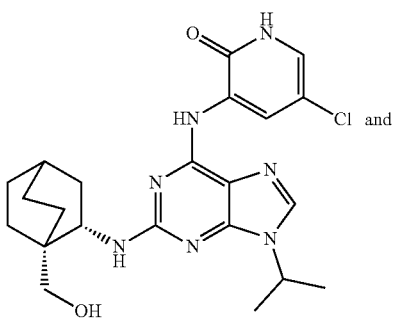

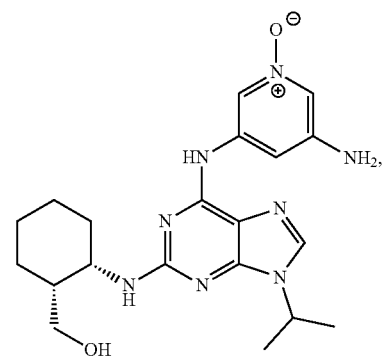

or a pharmaceutically acceptable salt thereof.

In one aspect, a compound can be selected from:

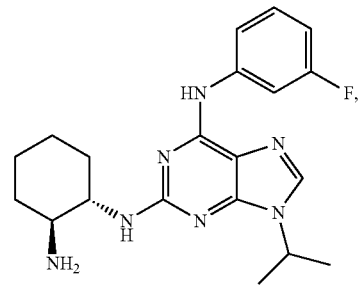

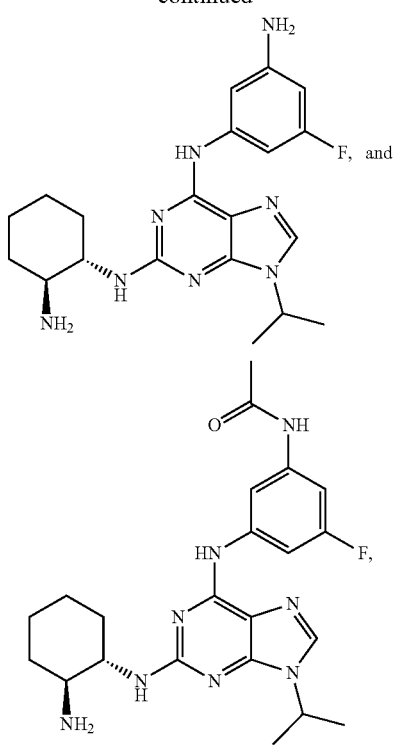

or a pharmaceutically acceptable salt thereof.

C. METHODS OF MAKING THE COMPOUNDS

The compounds of this invention can be prepared by employing reactions as shown in the following schemes, in addition to other standard manipulations that are known in the literature, exemplified in the experimental sections or clear to one skilled in the art. For clarity, examples having a single substituent are shown where multiple substituents are allowed under the definitions disclosed herein.

Reactions used to generate the compounds of this invention are prepared by employing reactions as shown in the following Reaction Schemes, as described and exemplified below. The following examples are provided so that the invention might be more fully understood, are illustrative only, and should not be construed as limiting.

1. Route I

In one aspect, substituted purine derivatives can be prepared as shown below.

SCHEME 1A.

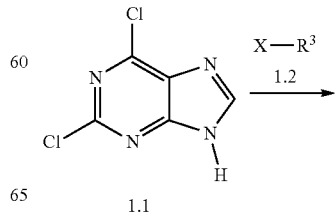

-continued

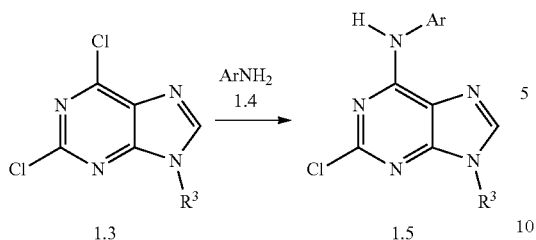

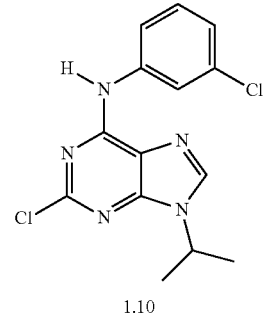

Compounds are represented in generic form, with substituents as noted in compound descriptions elsewhere herein; wherein X is halogen and wherein Ar is either $Ar^1$ or $Ar^2$. A more specific example is set forth below.

SCHEME 1B.

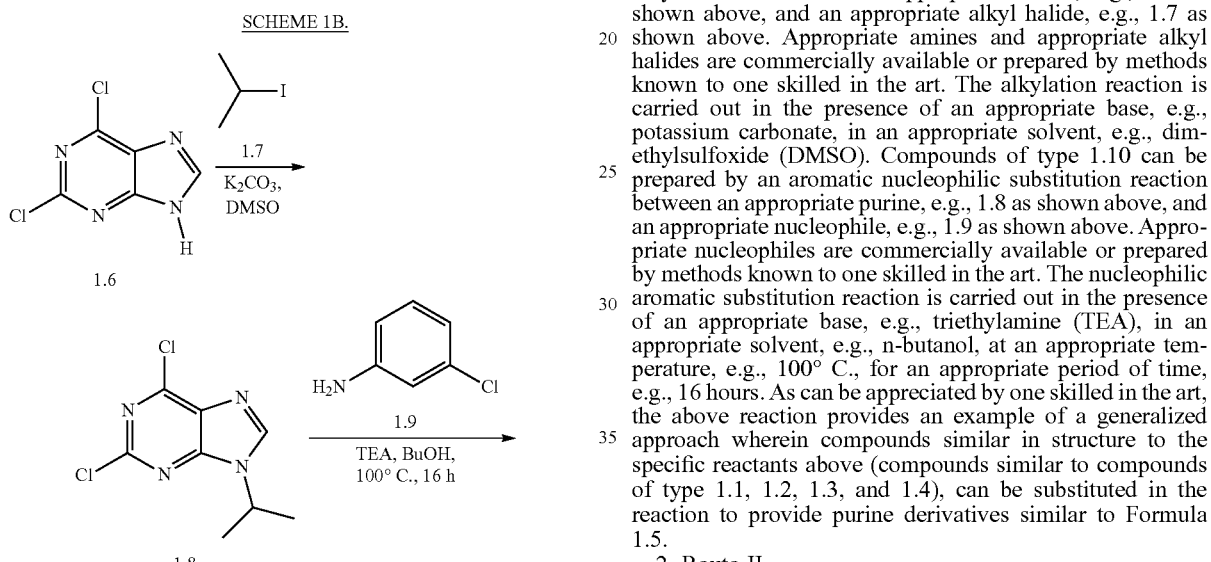

In one aspect, compounds of type 1.5, and similar compounds, can be prepared according to reaction Scheme 1B above. Thus, compounds of type 1.8 can be prepared by an alkylation reaction of an appropriate amine, e.g., 1.6 as shown above, and an appropriate alkyl halide, e.g., 1.7 as shown above. Appropriate amines and appropriate alkyl halides are commercially available or prepared by methods known to one skilled in the art. The alkylation reaction is carried out in the presence of an appropriate base, e.g., potassium carbonate, in an appropriate solvent, e.g., dimethylsulfoxide (DMSO). Compounds of type 1.10 can be prepared by an aromatic nucleophilic substitution reaction between an appropriate purine, e.g., 1.8 as shown above, and an appropriate nucleophile, e.g., 1.9 as shown above. Appropriate nucleophiles are commercially available or prepared by methods known to one skilled in the art. The nucleophilic aromatic substitution reaction is carried out in the presence of an appropriate base, e.g., triethylamine (TEA), in an appropriate solvent, e.g., n-butanol, at an appropriate temperature, e.g., 100° C., for an appropriate period of time, e.g., 16 hours. As can be appreciated by one skilled in the art, the above reaction provides an example of a generalized approach wherein compounds similar in structure to the specific reactants above (compounds similar to compounds of type 1.1, 1.2, 1.3, and 1.4), can be substituted in the reaction to provide purine derivatives similar to Formula 1.5.

2. Route II

In one aspect, substituted purine and substituted pyrrolopyrimidine derivatives can be prepared as shown below.

SCHEME 2A.

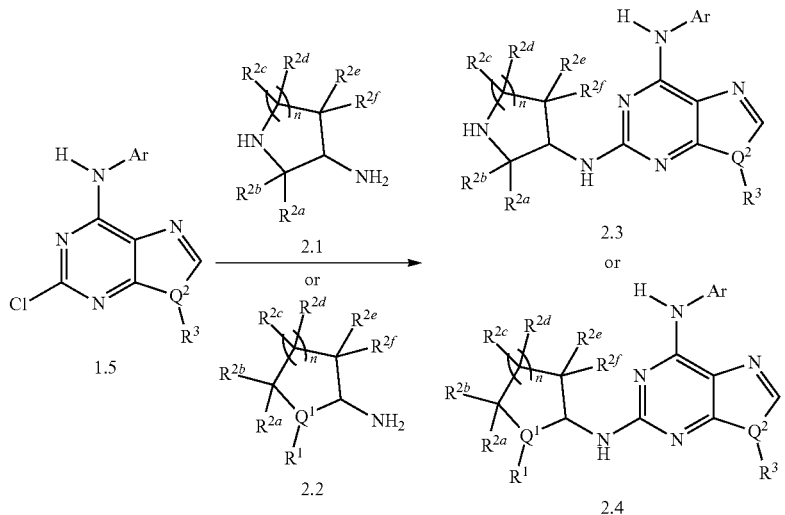

Compounds are represented in generic form, with substituents as noted in compound descriptions elsewhere herein; wherein Ar is either Ar¹ or Ar². A more specific example is set forth below.

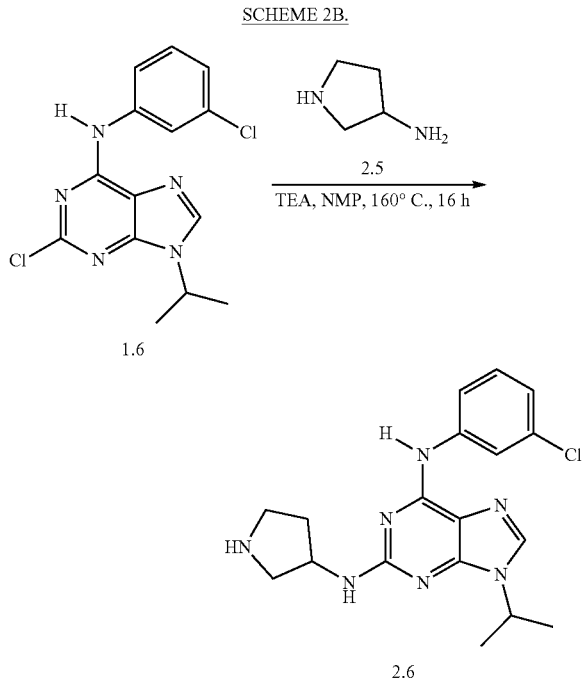

SCHEME 2B.

1.6

2.5

TEA, NMP, 160° C., 16 h 2.6

In one aspect, compounds of type 2.3 or 2.4, and similar compounds, can be prepared according to reaction Scheme 2B above. Thus, compounds of type 2.6 can be prepared by an aromatic nucleophilic substitution reaction of an appropriate purine or pyrrolopyrimidine, e.g., 1.6 as shown above, and an appropriate amine, e.g., 2.5 as shown above. Appropriate amines are commercially available or prepared by methods known to one skilled in the art. The aromatic nucleophilic substitution reaction is carried out in the presence of an appropriate base, e.g., triethylamine (TEA), in an appropriate solvent, e.g., N-methyl-2-pyrrolidone (NMP), at an appropriate temperature, e.g., 160° C., for an appropriate period of time, e.g., 16 hours. As can be appreciated by one skilled in the art, the above reaction provides an example of a generalized approach wherein compounds similar in structure to the specific reactants above (compounds similar to compounds of type 1.5, 2.1, and 2.2), can be substituted in the reaction to provide purine and pyrrolopyrimidine derivatives similar to Formula 2.3 or 2.4.

3. Route III

In one aspect, substituted purine and substituted pyrrolopyrimidine can be prepared as shown below.

SCHEME 3A.

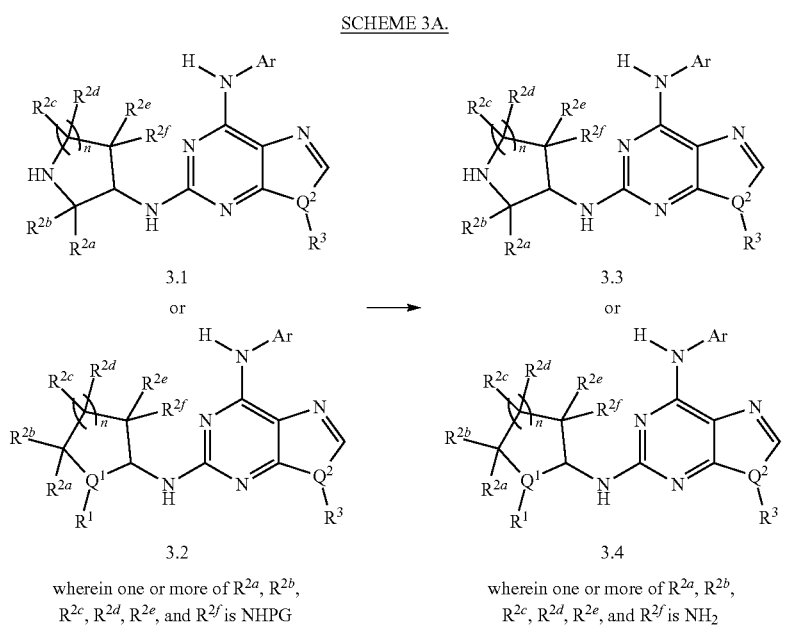

3.1
or
3.2 wherein one or more of R²ᵃ, R²ᵇ, R²ᶜ, R²ᵈ, R²ᵉ, and R²ᶠ is NHPG 3.3
or
3.4 wherein one or more of R²ᵃ, R²ᵇ, R²ᶜ, R²ᵈ, R²ᵉ, and R²ᶠ is NH₂

Compounds are represented in generic form, with substituents as noted in compound descriptions elsewhere herein; wherein Ar is either Ar¹ or Ar². A more specific example is set forth below.

SCHEME 3B.

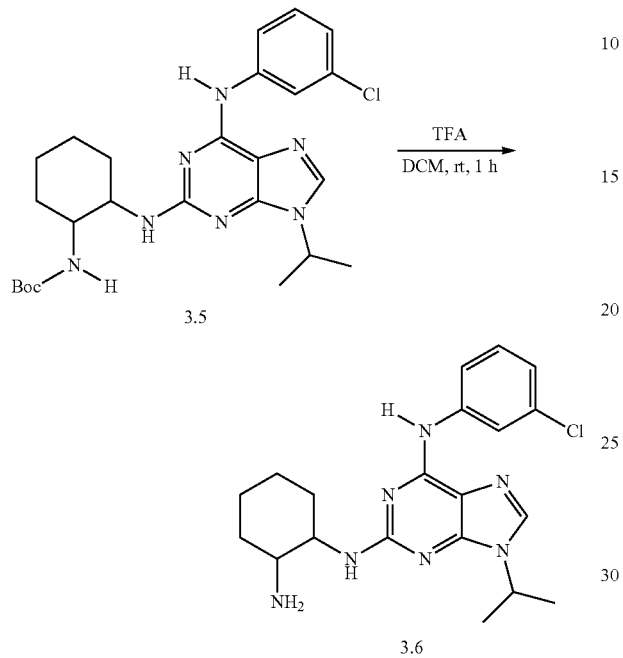

In one aspect, compounds of type 3.3 or 3.4, and similar compounds, can be prepared according to reaction Scheme 3B above. Thus, compounds of type 3.6 can be prepared by a deprotection reaction of an appropriate amine, e.g., 3.5 as shown above. The deprotection reaction is carried out in the presence of an appropriate deprotecting agent, e.g., trifluoroacetic acid (TFA), in an appropriate solvent, e.g., dichloromethane (DCM), for an appropriate period of time, e.g., 1 hour. As can be appreciated by one skilled in the art, the above reaction provides an example of a generalized approach wherein compounds similar in structure to the specific reactants above (compounds similar to compounds of type 3.1 and 3.2), can be substituted in the reaction to provide purine and pyrrolopyrimidine derivatives similar to Formula 3.3 or 3.4.

4. Route IV

In one aspect, substituted pyrrolopyrimidine derivatives can be prepared as shown below.

SCHEME 4A.

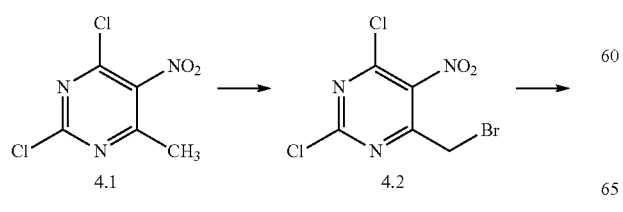

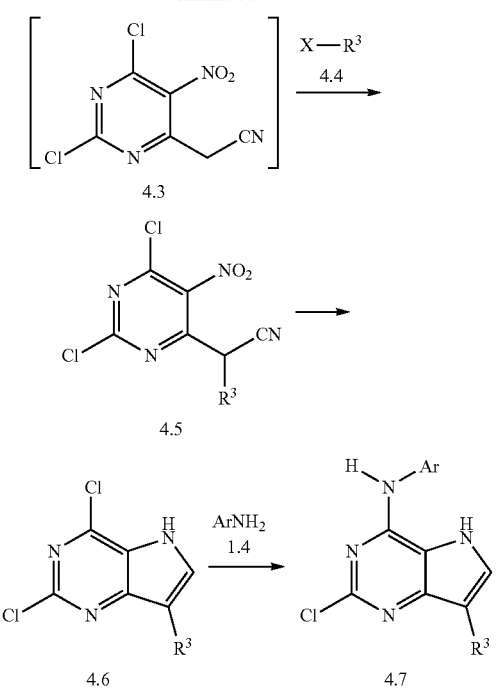

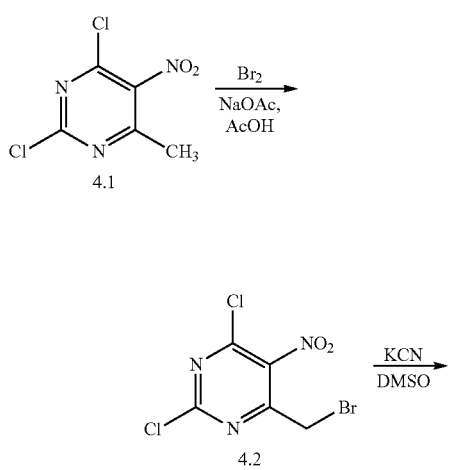

Compounds are represented in generic form, with substituents as noted in compound descriptions elsewhere herein; wherein X is halogen and wherein Ar is either Ar¹ or Ar². A more specific example is set forth below.

SCHEME 4B.

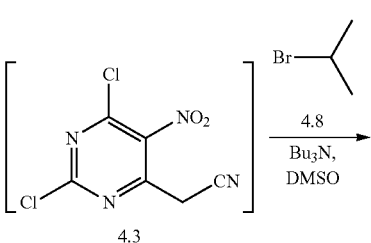

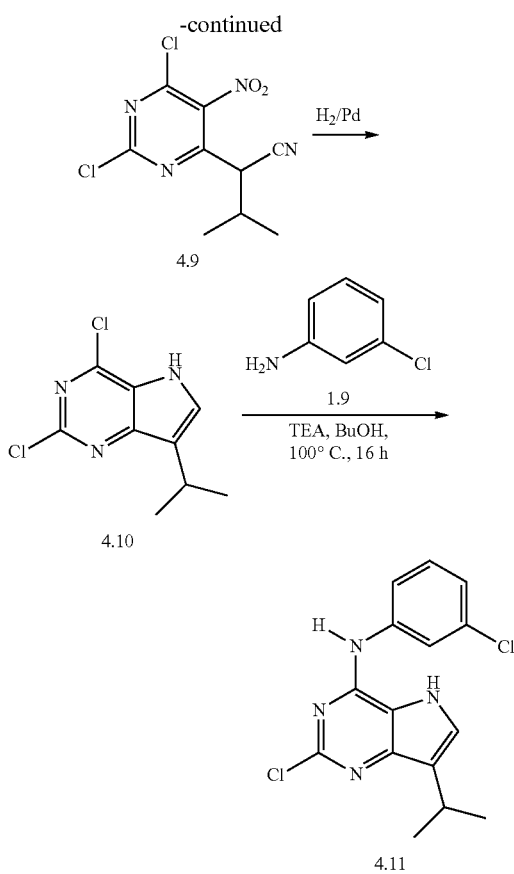

In one aspect, compounds of type 1.5, and similar compounds, can be prepared according to reaction Scheme 4B above. Thus, compounds of type 4.2 can be prepared by a halogenation reaction of an appropriate pyrimidine, e.g., 4.1 as shown above. Appropriate pyrimidines are commercially available or prepared by methods known to one skilled in the art. The halogenation reaction is carried out in the presence of an appropriate halide, e.g., bromine, and an appropriate salt, e.g., sodium acetate, in an appropriate solvent, e.g., acetic acid. Compounds of type 4.3 can be prepared by a nucleophilic substitution reaction between an appropriate halide, e.g., 4.2 as shown above, and an appropriate nucleophile, e.g., potassium cyanide as shown above. The nucleophilic substitution reaction is carried out in an appropriate solvent, e.g., n-dimethylsulfoxide (DMSO). Compounds of type 4.9 can be prepared by alkylation of an appropriate pyrimidine, e.g., 4.3 as shown above. The alkylation is carried out in the presence of an appropriate alkyl halide, e.g., 4.8 as shown above, and an appropriate base, e.g., N,N-dibutylbutan-1-amine, an appropriate solvent, e.g., n-dimethylsulfoxide. Compounds of type 4.10 can be prepared by cyclization of an appropriate pyrimidine, e.g., 4.9 as shown above. The cyclization is carried out in the presence of an appropriate reducing agent, e.g., hydrogen gas, and an appropriate catalyst, e.g., palladium. Compounds of type 4.11 can be prepared by an aromatic nucleophilic substitution reaction between an appropriate pyrrolopyrimidine, e.g., 4.10 as shown above, and an appropriate nucleophile, e.g., 1.9 as shown above. Appropriate nucleophiles are commercially available or prepared by methods known to one skilled in the art. The nucleophilic aromatic substitution reaction is carried out in the presence of an appropriate base, e.g., triethylamine (TEA), in an appropriate solvent, e.g., n-butanol, at an appropriate temperature, e.g., 100° C., for an appropriate period of time, e.g., 16 hours. As can be appreciated by one skilled in the art, the above reaction provides an example of a generalized approach wherein compounds similar in structure to the specific reactants above (compounds similar to compounds of type 1.4, 4.1, 4.2, 4.3, 4.4, 4.5, and 4.6), can be substituted in the reaction to provide pyrrolopyrimidine derivatives similar to Formula 4.7.

D. PHARMACEUTICAL COMPOSITIONS

In one aspect, disclosed are pharmaceutical compositions comprising at least one disclosed compound, or a pharmaceutically acceptable salt thereof and a pharmaceutically acceptable carrier.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients. For example, a pharmaceutical composition can be formulated for local or systemic administration, e.g., administration by drops or injection into the ear, insufflation (such as into the ear), intravenous, topical, or oral administration.

The nature of the pharmaceutical compositions for administration is dependent on the mode of administration and can readily be determined by one of ordinary skill in the art. In various aspects, the pharmaceutical composition is sterile or sterilizable. The therapeutic compositions featured in the invention can contain carriers or excipients, many of which are known to skilled artisans. Excipients that can be used include buffers (for example, citrate buffer, phosphate buffer, acetate buffer, and bicarbonate buffer), amino acids, urea, alcohols, ascorbic acid, phospholipids, polypeptides (for example, serum albumin), EDTA, sodium chloride, liposomes, mannitol, sorbitol, water, and glycerol. The nucleic acids, polypeptides, small molecules, and other modulatory compounds featured in the invention can be administered by any standard route of administration. For example, administration can be parenteral, intravenous, subcutaneous, or oral. A modulatory compound can be formulated in various ways, according to the corresponding route of administration. For example, liquid solutions can be made for administration by drops into the ear, for injection, or for ingestion; gels or powders can be made for ingestion or topical application. Methods for making such formulations are well known and can be found in, for example, Remington's Pharmaceutical Sciences, 18th Ed., Gennaro, ed., Mack Publishing Co., Easton, Pa. 1990.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A$^1$ suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to treat a disorder associated with CLK2 and/or CDK1 activity such as, for example, retinitis Pigmentosa, microcephalic osteodysplastic primordial dwarfism (MOPD) type 1, and cancer.

It is understood that the disclosed compositions can be prepared from the disclosed compounds. It is also understood that the disclosed compositions can be employed in the disclosed methods of using.

E. METHODS FOR TREATING A DISORDER IN A SUBJECT

In various aspects, the compounds and compositions disclosed herein are useful for treating, preventing, ameliorating, controlling or reducing the risk of a variety of disorders associated with CLK2 and/or CDK1 activity, including, for example, retinitis Pigmentosa, microcephalic osteodysplastic primordial dwarfism (MOPD) type 1, and cancer. Thus, in one aspect, disclosed are methods of treating a disorder associated with CLK2 and/or CDK1 activity in a subject, the method comprising administering to the subject an effective amount of at least one disclosed compound or a pharmaceutically acceptable salt thereof.

In one aspect, disclosed are methods for treating a disorder having an aberrant germ-like mutation in a subject, the method comprising the step of administering to the subject a therapeutically effective amount of at least one compound that inhibits both CLK2 and CDK1.

In one aspect, disclosed are methods for treating a disorder having an aberrant germ-like mutation in a subject, the method comprising the step of administering to the subject a therapeutically effective amount of a compound selected from:

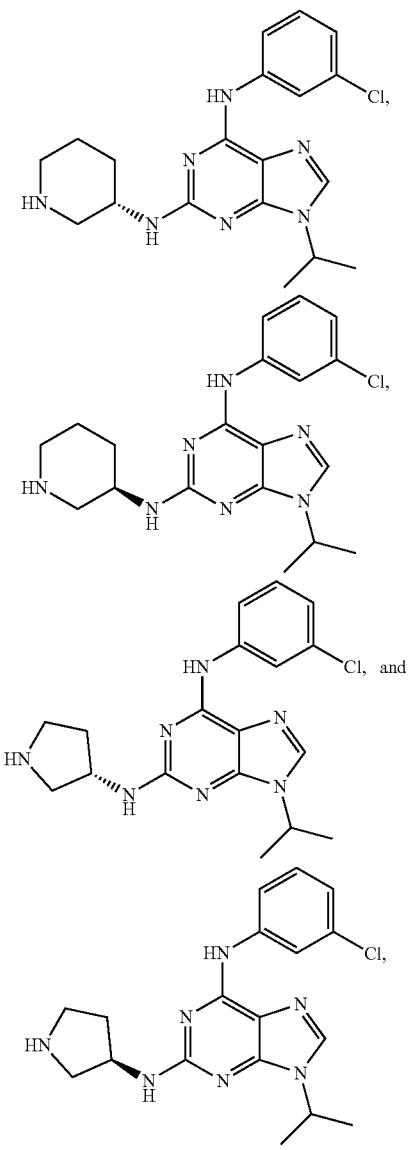

or a pharmaceutically acceptable derivative thereof.

The design and synthesis of FR analogs that contain only 3 chiral centers (the sudemycins) (Lagisetti et al. (2013) *J Med Chem* 56: 10033-44; Lagisetti et al. (2008) *J Med Chem* 51: 6220-4; Lagisetti et al. (2009) *J Med Chem* 52: 6979-90; Fan et al. (2011) *ACS Chem Biol* 6: 582-9), pladienolide analogs (Gundluru et al. (2011) *Medchemcomm* 2: 904-908), and recently several herboxidiene analogs (Lagisetti et al. (2014) *ACS Chem Biol* 9: 643-8), all of which are active compounds that effectively modulate alternate splicing (Fan et al. (2011) *ACS Chem Biol* 6: 582-9), has been recently reported. More recently, however, details regarding the mechanism of action of SF3B1 targeted agents has been elucidated (Effenberger et al. (2016) *RNA* 22: 350-9). Additionally, these results were also reported on the genome-wide array analysis of sudemycin treated tumor cells, which shows that sudemycins cause a rapid wide-ranging change in alternate pre-mRNA splicing and that a biotin-labeled sudemycin probe directly interacts with the SF3B1 protein (Convertini et al. (2014) *Nucleic Acids Res* 42: 4947-61). This collaborative project ultimately led to sudemycin D6 (SD6) (Lagisetti et al. (2013) *J Med Chem* 56: 10033-44), which is currently in preclinical development as an anticancer agent (see FIG. 1). Other groups have independently discovered new diverse small molecule structural classes that effect pre-mRNA splicing, using a range of screening strategies (see FIG. 1). These compounds include KH-CB19 (Fedorov et al. (2011) *Chem Biol* 18: 67-76), Ariki Cpd-2 (Araki et al. (2015) *PLoS One* 10: e0116929), and Madrasin (Pawellek et al. (2014) *J Biol Chem* 289: 34683-98) (see FIG. 1). Compounds KH-CB19 and the Araki Cpd-2 have been reported to be highly selective inhibitors of the of cdc2-like kinase (CLK) family (Fedorov et al. (2011) *Chem Biol* 18: 67-76; Araki et al. (2015) *PLoS One* 10: e0116929), while the molecular target of Madrasin has not been reported (Pawellek et al. (2014) *J Biol Chem* 289: 34683-98).

In parallel to the work described above, strong evidence has continued to mount that aberrant splicing of pre-mRNA is a driver of tumorigenesis (David and Manley (2010) *Genes Dev* 24: 2343-64) and that the spliceosome is a valid target for cancer therapy (Webb et al. (2013) *Drug Discovery Today* 18: 43-49; Bonnal et al. (2012) *Nat Rev Drug Discov* 11: 847-859). Recent groundbreaking discoveries have identified recurrent mutations in SF3B1 (and/or other splicing factors) in multiple forms of cancer including: myelodysplastic syndromes (MDS) (Yoshida et al. (2011) *Nature* 478: 64-9; Ogawa, S. (2012) *Int J Hematol* 96: 438-42), chronic lymphocytic leukemia (CLL) (Damm et al. (2012) *Leukemia* 26: 2027-31), acute myeloid leukemia (AML) (Murati et al. (2012) *BMC Cancer* 12: 304; Cancer Genome Atlas Research (2013) *N Engl J Med* 368: 2059-74), breast cancer (Cancer Genome Atlas (2012) *Nature* 490: 61-70; Maguire et al. (2015) *J Pathol* 235: 571-80), lung adenosarcoma (Imielinski et al. (2012) *Cell* 150: 1107-20), and uveal melanoma (Harbour, J. W. (2013) *Am Soc Clin Oncol Educ Book* pgs. 388-91). These genetic studies have also fueled complementary research in the therapeutic significance of spliceosome recurrent mutations. Very recently the selective sensitivity of tumors to agents that target SF3B1 have also been linked *Nature* 525: 384-8). The collective progress in natural product screening, target identification, spliceosome related medicinal chemistry, and high-throughput transcriptome sequencing has led to a remarkable convergence of independent research areas.

Human diseases having aberrant germ-line mutations of the spliceosome are listed in Table 1 and somatic mutations identified in cancer are listed in Table 2. Further descriptions of human disease and the modulation of alternative splicing can be found in K. Ohe and M. Haghwara, "Modulation of Alternative Splicing with Chemical Compounds in New Therapeutics for Human Diseases" (2015) ACS Chem. Biol. 10:914-924, incorporated by reference herein in its entirety.

TABLE 1

| gene | function | disease | reference |
|---|---|---|---|
| PRP3 U4/U6 SnRNP 90 KDa Protein | Part of the U4/U5/U6 tri-snRNP | retinitis Pigmentosa | Chakarova et al. (2002) *Hum. Mol. Genet.* 11: 87-92. |
| PRP6 U5 SnRNP-Associated 102 KDa Protein | Part of the U4/U5/U6 tri-snRNP | retinitis Pigmentosa | Tanackovic et al. (2011) *Am. J. Hum. Genet.* 88: 643-649. |
| PRP8 U5 SnRNP-Specific Protein (220 KD) | Scaffold for snRNPs during the splicing reaction | retinitis Pigmentosa | Boon et al. (2007) *Nat. Struct. Mol. Biol.* 14: 1077-1083. |
| Brr2 U5 SnRNP-Specific 200 KDa | RNA helicase | retinitis Pigmentosa | Liu et al. (2012) *PloS one* 7 : e45464. |
| PRP31 | U4/U6 SnRNP 61 Kda Protein | retinitis Pigmentosa | Vithana et al. (2001) *Mol. Cell* 8: 375-381. |
| U4atac | snRNA in the minor spliceosome | microcephalic osteodysplastic primordial dwarfism (MOPD) type I | He et al. (2011) *Science* 332: 238-240. |

TABLE 2

| gene | function | disease | reference |
|---|---|---|---|
| SF3B1 | U2 component, recognition of 3' splice site | Chronic lymphocytic leukemia | Quesada et al. (2012) *Nature genetics* 44: 47-52. |
|  |  | Myelodysplasia | Yoshida et al. (2011) *Nature* 478: 64-69. |
| SF3A1 | U2 component, recognition of 3' splice site | Myelodysplasia | Yoshida et al. (2011) *Nature* 478: 64-69. |
| PRPF40B | U1 and U2 component | Myelodysplasia | Yoshida et al. (2011) *Nature* 478: 64-69. |
| SF1 | Recognizes branchpoint, 3' splice site | Myelodysplasia | Yoshida et al. (2011) *Nature* 478: 64-69. |
| U2AF35 | recognition of 3' splice site | Myelodysplasia | Yoshida et al. (2011) *Nature* 478: 64-69. |
| U2AF65 | recognition of 3' splice site | Myelodysplasia | Yoshida et al. (2011) *Nature* 478: 64-69. |
| ZRSR2 zinc Finger (CCCH Type), RNA-Binding Motif And Serine/Arginine Rich 2 | Second step of splicing in major splicesome; recognition of 3' splice site in minor spliceosome | Myelodysplasia | Yoshida et al. (2011) *Nature* 478: 64-69. |
| SRSF2 (SC35) | Promotes exon inclusion | Myelodysplastic syndromes | Makishima et al. (2012) *Blood* 119: 3203-3210. |

Thus, in one aspect, disclosed are focused library compounds that can be used to test and explore different pharmacophore hypotheses (see, e.g., FIGS. 6A-H). The synthesis of these analogs can be done using, for example, the reported literature methods (Popowycz et al. (2009) *Journal of medicinal chemistry* 52: 655-663).

In a further aspect, the compound has a structure represented by a formula selected from:

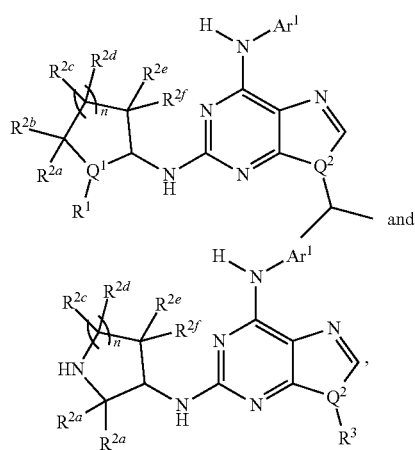

wherein n is selected from 1 and 2; wherein each of $Q^1$ and $Q^2$ is independently selected from N and CH; wherein $R^1$ is selected from —OH, —NHR$^4$, —(C1-C4 alkyl)OH, and —(C1-C4 alkyl)NHR$^4$; wherein $R^4$, when present, is selected from hydrogen and C1-C4 alkyl; wherein each occurrence of each of $R^{2a}$, $R^{2b}$, $R^{2c}$, $R^{2d}$, $R^{2e}$, and $R^{2f}$ is independently selected from hydrogen and C1-C8 alkyl; wherein $Ar^1$ is selected from monocyclic aryl, 6-membered heteroaryl, and bicyclic heteroaryl, and is substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino, or a pharmaceutically acceptable derivative thereof.

In a further aspect, the compound has a structure represented by a formula:

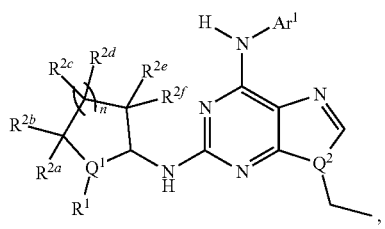

wherein n is selected from 1 and 2; wherein each of $Q^1$ and $Q^2$ is independently selected from N and CH; wherein $R^1$ is selected from —OH, —NHR$^4$, —(C1-C4 alkyl)OH, and —(C1-C4 alkyl)NHR$^4$; wherein $R^4$, when present, is selected from hydrogen and C1-C4 alkyl; wherein each occurrence of each of $R^{2a}$, $R^{2b}$, $R^{2c}$, $R^{2d}$, $R^{2e}$, and $R^{2f}$ is independently selected from hydrogen and C1-C8 alkyl; and wherein $Ar^1$ is selected from 6-membered heteroaryl and bicyclic heteroaryl, and is substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino; or wherein $Ar^1$ is phenyl meta-substituted with —Cl, or a pharmaceutically acceptable derivative thereof.

In a further aspect, the compound has a structure represented by a formula selected from:

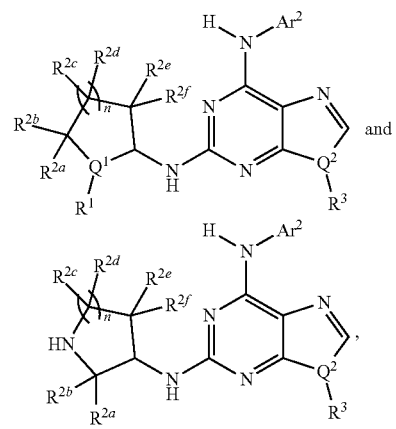

wherein n is selected from 1 and 2; wherein each of $Q^1$ and $Q^2$ is independently selected from N and CH; wherein $R^1$ is selected from —OH, —NHR$^4$, —(C1-C4 alkyl)OH, and —(C1-C4 alkyl)NHR$^4$; wherein $R^4$, when present, is selected from hydrogen and C1-C4 alkyl; wherein each occurrence of each of $R^{2a}$, $R^{2b}$, $R^{2c}$, $R^{2d}$, $R^{2e}$, and $R^{2f}$ is independently selected from hydrogen and C1-C8 alkyl; wherein $R^3$ is selected from ethyl and isopropyl; and wherein $Ar^2$ is selected from 6-membered heteroaryl and bicyclic heteroaryl, and is substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino, or a pharmaceutically acceptable derivative thereof.

In various aspects, the disclosed compounds can be used in combination with one or more other drugs in the treatment, prevention, control, amelioration, or reduction of risk of disorders associated with CLK2 and/or CDK1 activity for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly. Accordingly, the pharmaceutical compositions include those that contain one or more other active ingredients, in addition to a compound of the present invention.

In a further aspect, the compound exhibits inhibition of CLK2 and/or CDK1 activity. In a still further aspect, the compound exhibits inhibition of CLK2 and CDK1 activity. In yet a further aspect, the compound exhibits inhibition of CLK2 activity. In an even further aspect, the compound exhibits inhibition of CDK1 activity. In a still further aspect, the compound exhibits inhibition of CLK2 or CDK1 activity.

In a further aspect, the compound exhibits a decrease in CLK2 and/or CDK1 activity. In a still further aspect, the compound exhibits a decrease in CLK2 and CDK1 activity. In yet a further aspect, the compound exhibits a decrease in CLK2 activity. In an even further aspect, the compound exhibits a decrease in CDK1 activity. In a still further aspect, the compound exhibits a decrease in CLK2 or CDK1 activity.

In a further aspect, the compound exhibits inhibition of CLK2 activity with an $IC_{50}$ of from about 0.001 µM to about 25 µM. In a still further aspect, the compound exhibits inhibition of CLK2 activity with an $IC_{50}$ of from about 0.001 µM to about 15 µM. In yet a further aspect, the compound exhibits inhibition of CLK2 activity with an $IC_{50}$ of from about 0.001 µM to about 10 µM. In an even further aspect, the compound exhibits inhibition of CLK2 activity with an $IC_{50}$ of from about 0.001 µM to about 5 µM. In a still further aspect, the compound exhibits inhibition of CLK2 activity with an $IC_{50}$ of from about 0.001 µM to about 1 µM. In yet a further aspect, the compound exhibits inhibition of CLK2 activity with an $IC_{50}$ of from about 0.001 µM to about 0.5 µM. In an even further aspect, the compound exhibits inhibition of CLK2 activity with an $IC_{50}$ of from about 0.001 µM to about 0.1 µM. In a still further aspect, the compound exhibits inhibition of CLK2 activity with an $IC_{50}$ of from about 0.001 µM to about 0.05 µM. In yet a further aspect, the compound exhibits inhibition of CLK2 activity with an $IC_{50}$ of from about 0.001 µM to about 0.01 µM. In an even further aspect, the compound exhibits inhibition of CLK2 activity with an $IC_{50}$ of from about 0.001 µM to about 0.005 µM. In a still further aspect, the compound exhibits inhibition of CLK2 activity with an $IC_{50}$ of from about 0.005 µM to about 25 µM. In yet a further aspect, the compound exhibits inhibition of CLK2 activity with an $IC_{50}$ of from about 0.01 µM to about 25 µM. In an even further aspect, the compound exhibits inhibition of CLK2 activity with an $IC_{50}$ of from about 0.05 µM to about 25 µM. In a still further aspect, the compound exhibits inhibition of CLK2 activity with an $IC_{50}$ of from about 0.1 µM to about 25 µM. In yet a further aspect, the compound exhibits inhibition of CLK2 activity with an $IC_{50}$ of from about 0.5 µM to about 25 µM. In an even further aspect, the compound exhibits inhibition of CLK2 activity with an $IC_{50}$ of from about 1 µM to about 25 µM. In a still further aspect, the compound exhibits inhibition of CLK2 activity with an $IC_{50}$ of from about 5 µM to about 25 µM. In yet a further aspect, the compound exhibits inhibition of CLK2 activity with an $IC_{50}$ of from about 10 µM to about 25 µM. In an even further aspect, the compound exhibits inhibition of CLK2 activity with an $IC_{50}$ of from about 15 µM to about 25 µM.

In a further aspect, the compound exhibits inhibition of CDK1 activity with an $IC_{50}$ of from about 0.001 µM to about 25 µM. In a still further aspect, the compound exhibits inhibition of CDK1 activity with an $IC_{50}$ of from about 0.001 µM to about 15 µM. In yet a further aspect, the compound exhibits inhibition of CDK1 activity with an $IC_{50}$ of from about 0.001 µM to about 10 µM. In an even further aspect, the compound exhibits inhibition of CDK1 activity with an $IC_{50}$ of from about 0.001 µM to about 5 µM. In a still further aspect, the compound exhibits inhibition of CDK1 activity with an $IC_{50}$ of from about 0.001 µM to about 1 µM. In yet a further aspect, the compound exhibits inhibition of CDK1 activity with an $IC_{50}$ of from about 0.001 µM to about 0.5 µM. In an even further aspect, the compound exhibits inhibition of CDK1 activity with an $IC_{50}$ of from about 0.001 µM to about 0.1 µM. In a still further aspect, the compound exhibits inhibition of CDK1 activity with an $IC_{50}$ of from about 0.001 µM to about 0.05 µM. In yet a further aspect, the compound exhibits inhibition of CDK1 activity with an $IC_{50}$ of from about 0.001 µM to about 0.01 µM. In an even further aspect, the compound exhibits inhibition of CDK1 activity with an $IC_{50}$ of from about 0.001 µM to about 0.005 µM. In a still further aspect, the compound exhibits inhibition of CDK1 activity with an $IC_{50}$ of from about 0.005 µM to about 25 µM. In yet a further aspect, the compound exhibits inhibition of CDK1 activity with an $IC_{50}$ of from about 0.01 µM to about 25 µM. In an even further aspect, the compound exhibits inhibition of CDK1 activity with an $IC_{50}$ of from about 0.05 µM to about 25 µM. In a still further aspect, the compound exhibits inhibition of CDK1 activity with an $IC_{50}$ of from about 0.1 µM to about 25 µM. In yet a further aspect, the compound exhibits inhibition of CDK1 activity with an $IC_{50}$ of from about 0.5 µM to about 25 µM. In an even further aspect, the compound exhibits inhibition of CDK1 activity with an $IC_{50}$ of from about 1 µM to about 25 µM. In a still further aspect, the compound exhibits inhibition of CDK1 activity with an $IC_{50}$ of from about 5 µM to about 25 µM. In yet a further aspect, the compound exhibits inhibition of CDK1 activity with an $IC_{50}$ of from about 10 µM to about 25 µM. In an even further aspect, the compound exhibits inhibition of CDK1 activity with an $IC_{50}$ of from about 15 µM to about 25 µM.

In a further aspect, the disorder is selected from retinitis Pigmentosa, microcephalic osteodysplastic primordial dwarfism (MOPD) type 1, and cancer. In a still further aspect, the disorder is retinitis Pigmentosa. In yet a further aspect, the disorder is MOPD type 1. In an even further aspect, the disorder is cancer. In a still further aspect, the cancer is selected from chronic lymphocytic leukemia (CLL), myelodysplasia, myelodysplastic syndromes (MDS), acute myeloid leukemia (AML), breast cancer, lung adenosarcoma, and uveal melanoma.

In a further aspect, the subject is a mammal. In a still further aspect, the subject is a human.

In a further aspect, the subject has been diagnosed with a need for treatment of a disorder having an aberrant germ-line mutation prior to the administering step. In a still further aspect, the subject is at risk for developing the disorder prior to the administering step.

In a further aspect, the method further comprises the step of identifying a subject in need of treatment of a disorder having an aberrant germ-line mutation.

F. METHODS FOR INHIBITING CLK2 AND/OR CDK1 IN AT LEAST ONE CELL

In one aspect, disclosed are methods of inhibiting CLK2 and/or CDK1 activity in at least one cell, the method comprising the step of contacting the at least one cell with an effective amount of at least one disclosed compound, or a pharmaceutically acceptable salt thereof.

In one aspect, disclosed are methods for inhibiting CLK2 and/or CDK1 in a subject, the method comprising the step of administering to the subject an effective amount of at least one compound having a structure represented by formula selected from:

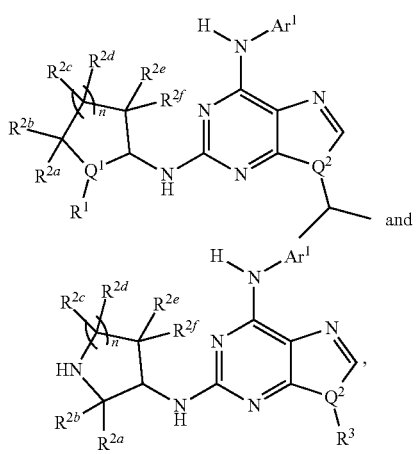

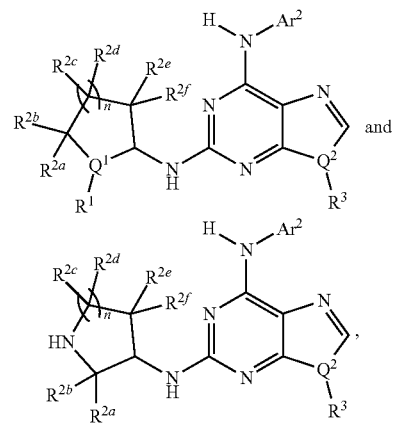

and wherein n is selected from 1 and 2; wherein each of $Q^1$ and $Q^2$ is independently selected from N and CH; wherein $R^1$ is selected from —OH, —NHR$^4$, —(C1-C4 alkyl)OH, and —(C1-C4 alkyl)NHR$^4$; wherein $R^4$, when present, is selected from hydrogen and C1-C4 alkyl; wherein each occurrence of each of $R^{2a}$, $R^{2b}$, $R^{2c}$, $R^{2d}$, $R^{2e}$, and $R^{2f}$ is independently selected from hydrogen and C1-C8 alkyl; wherein $R^3$ is selected from ethyl and isopropyl; and wherein Ar$^1$ is selected from monocyclic aryl, 6-membered heteroaryl, and bicyclic heteroaryl, and is substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino, or a pharmaceutically acceptable derivative thereof.

In one aspect, disclosed are methods for inhibiting CLK2 and/or CDK1 in a subject, the method comprising the step of administering to the subject an effective amount of at least one compound having a structure represented by a formula:

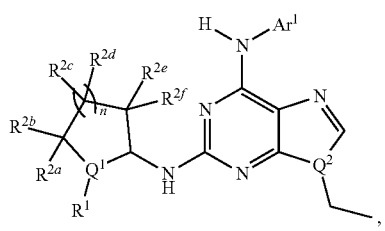

wherein n is selected from 1 and 2; wherein each of $Q^1$ and $Q^2$ is independently selected from N and CH; wherein $R^1$ is selected from —OH, —NHR$^4$, —(C1-C4 alkyl)OH, and —(C1-C4 alkyl)NHR$^4$; wherein $R^4$, when present, is selected from hydrogen and C1-C4 alkyl; wherein each occurrence of each of $R^{2a}$, $R^{2b}$, $R^{2c}$, $R^{2d}$, $R^{2e}$, and $R^{2f}$ is independently selected from hydrogen and C1-C8 alkyl; and wherein Ar$^1$ is selected from 6-membered heteroaryl and bicyclic heteroaryl, and is substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino; or wherein Ar$^1$ is phenyl meta-substituted with —Cl, or a pharmaceutically acceptable derivative thereof.

In one aspect, disclosed are methods for inhibiting CLK2 and/or CDK1 in a subject, the method comprising the step of administering to the subject an effective amount of at least one compound having a structure represented by a formula selected from:

wherein n is selected from 1 and 2; wherein each of $Q^1$ and $Q^2$ is independently selected from N and CH; wherein $R^1$ is selected from —OH, —NHR$^4$, —(C1-C4 alkyl)OH, and —(C1-C4 alkyl)NHR$^4$; wherein $R^4$, when present, is selected from hydrogen and C1-C4 alkyl; wherein each occurrence of each of $R^{2a}$, $R^{2b}$, $R^{2c}$, $R^{2d}$, $R^{2e}$, and $R^{2f}$ is independently selected from hydrogen and C1-C8 alkyl; wherein $R^3$ is selected from ethyl and isopropyl; and wherein Ar$^2$ is selected from 6-membered heteroaryl and bicyclic heteroaryl, and is substituted with 0-4 groups independently selected from halogen, —OH, —NH$_2$, —CN, —NO$_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino, or a pharmaceutically acceptable derivative thereof.

In one aspect, disclosed are methods for inhibiting CLK2 and/or CDK1 in at least one cell, the method comprising the step of contacting at least one cell with an effective amount of a compound selected from:

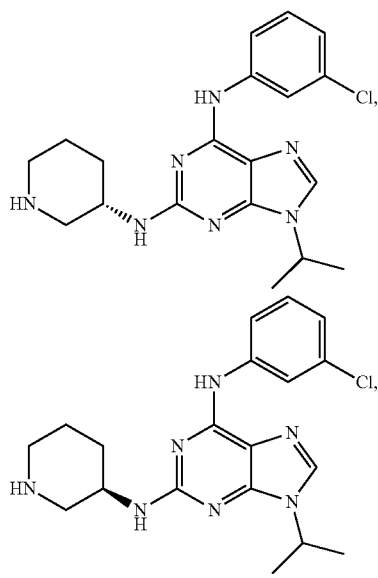

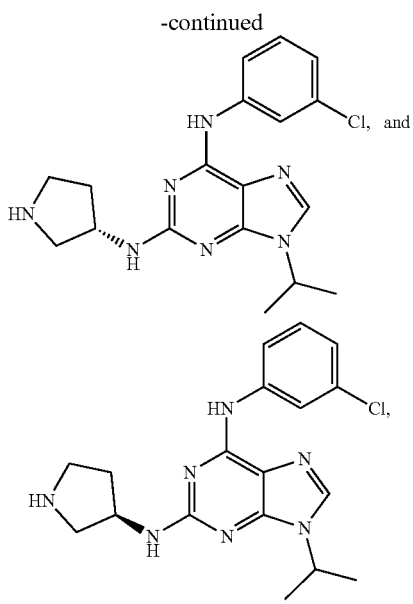

or a pharmaceutically acceptable salt thereof, thereby inhibiting CLK2 and/or CDK1 in at least one cell.

In a further aspect, each of CLK2 and CDK1 are inhibited. In a still further aspect, one of CLK2 and CDK1 are inhibited. In yet a further aspect, CLK2 is inhibited. In an even further aspect, CDK1 is inhibited.

In a further aspect, the cell is mammalian. In a still further aspect, the cell is human. In yet a further aspect, the cell has been isolated from a human prior to the administering step. In an even further aspect, the cell is a cancer cell.

In a further aspect, contacting is via administration to a subject.

In a further aspect, the subject has been diagnosed with a need for inhibition of CLK2 and/or CDK1 prior to the administering step. In a still further aspect, the subject has been diagnosed with a need for inhibition of CLK2 and CDK1 prior to the administering step. In yet a further aspect, the subject has been diagnosed with a need for inhibition of CLK2 prior to the administering step. In an even further aspect, the subject has been diagnosed with a need for inhibition of CDK1 prior to the administering step. In a still further aspect, the subject has been diagnosed with a need for inhibition of CLK2 or CDK1 prior to the administering step.

In a further aspect, the subject has been diagnosed with a need for treatment of a disorder associated with activation of CLK2 and/or CDK1 prior to the administering step. In a still further aspect, the subject has been diagnosed with a need for treatment of a disorder associated with activation of CLK2 and CDK1 prior to the administering step. In yet a further aspect, the subject has been diagnosed with a need for treatment of a disorder associated with activation of CLK2 prior to the administering step. In an even further aspect, the subject has been diagnosed with a need for treatment of a disorder associated with activation of CDK1 prior to the administering step. In a still further aspect, the subject has been diagnosed with a need for treatment of a disorder associated with activation of CLK2 or CDK1 prior to the administering step.

G. METHODS OF USING THE COMPOUNDS AND COMPOSITIONS

Provided are methods of using of a disclosed composition or medicament. In one aspect, the method of use is directed to the treatment of a disorder. In a further aspect, the disclosed compounds can be used as single agents or in combination with one or more other drugs in the treatment, prevention, control, amelioration, or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

The pharmaceutical compositions and methods of the present invention can further comprise other therapeutically active compounds as noted herein which are usually applied in the treatment of the above mentioned pathological conditions.

1. Manufacture of a Medicament

In one aspect, disclosed are methods for the manufacture of a medicament for treating a disorder associated with CLK2 and/or CDK1 dysfunction in a mammal, the method comprising combining a therapeutically effective amount of a disclosed compound or product of a disclosed method with a pharmaceutically acceptable carrier or diluent.

As regards these applications, the present method includes the administration to an animal, particularly a mammal, and more particularly a human, of a therapeutically effective amount of the compound effective in the inhibition of protein and especially CLK2 and/or CDK1. The dose administered to an animal, particularly a human, in the context of the present invention should be sufficient to affect a therapeutic response in the animal over a reasonable time frame. One skilled in the art will recognize that dosage will depend upon a variety of factors including the condition of the animal, the body weight of the animal, as well as the severity and stage of the disorder.

Thus, in one aspect, the invention relates to the manufacture of a medicament comprising combining a disclosed compound or a product of a disclosed method of making, or a pharmaceutically acceptable salt, solvate, or polymorph thereof, with a pharmaceutically acceptable carrier or diluent.

2. Use of Compounds and Compositions

Also provided are the uses of the disclosed compounds and compositions. Thus, in one aspect, the invention relates to the uses of inhibitors of CLK2 and/or CDK1.

In a further aspect, the invention relates to the use of a disclosed compound or product of a disclosed method in the manufacture of a medicament for the treatment of a disorder associated with CLK2 and/or CDK1 activity such as, for example, retinitis Pigmentosa, microcephalic osteodysplastic primordial dwarfism (MOPD) type 1, and cancer.

In a further aspect, the use relates to a process for preparing a pharmaceutical composition comprising a therapeutically effective amount of a disclosed compound or a product of a disclosed method, and a pharmaceutically acceptable carrier, for use as a medicament.

In a further aspect, the use relates to a process for preparing a pharmaceutical composition comprising a therapeutically effective amount of a disclosed compound or a product of a disclosed method, wherein a pharmaceutically acceptable carrier is intimately mixed with a therapeutically effective amount of the disclosed compound or the product of a disclosed method.

In various aspects, the use relates to the treatment of retinitis Pigmentosa. In a further aspect, the use relates to the treatment of retinitis Pigmentosa in a vertebrate animal. In a further aspect, the use relates to the treatment of retinitis Pigmentosa in a human subject.

In various aspects, the use relates to the treatment of MOPD type 1. In a further aspect, the use relates to the treatment of MOPD type 1 in a vertebrate animal. In a further aspect, the use relates to the treatment of MOPD type 1 in a human subject.

In various aspects, the use relates to the treatment of cancer. In a further aspect, the use relates to the treatment of cancer in a vertebrate animal. In a further aspect, the use relates to the treatment of cancer in a human subject. Examples of cancers for which the compounds and compositions can be useful in treating, include, but are not limited to, leukemia, acute leukemia, acute lymphocytic leukemia, acute myelocytic leukemia, myeloblastic, promyelocytic, myelomonocytic, monocytic, erythroleukemia, chronic leukemia, chronic myelocytic (granulocytic) leukemia, chronic lymphocytic leukemia, Polycythemia vera, Lymphoma, Hodgkin's disease, non-Hodgkin's disease, Multiple myeloma, Waldenstrom's macroglobulinemia, Heavy chain disease, Solid tumors, sarcomas and carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, glioblastoma, osteosarcoma, colorectal, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

It is understood that the disclosed uses can be employed in connection with the disclosed compounds, methods, compositions, and kits. In a further aspect, the invention relates to the use of a disclosed compound or composition of a medicament for the treatment of a disorder associated with CLK2 and/or CDK1 activity in a mammal.

In a further aspect, the invention relates to the use of a disclosed compound or composition in the manufacture of a medicament for the treatment of a disorder associated with CLK2 and/or CDK1 activity selected from retinitis Pigmentosa, microcephalic osteodysplastic primordial dwarfism (MOPD) type 1, and cancer.

3. Kits

In one aspect, disclosed are kits comprising an effective amount of a disclosed compound, and one or more of: (a) at least one agent known to treat a disorder having an aberrant germ-like mutation; (b) at least one agent known to activate CLK2 and/or CDK1; (c) at least one agent known to inhibit CLK2 and/or CDK1; and (d) instructions for treating a disorder having an aberrant germ-like mutation.

In various aspects, the agents and pharmaceutical compositions described herein can be provided in a kit. The kit can also include combinations of the agents and pharmaceutical compositions described herein.

In various aspects, the informational material can be descriptive, instructional, marketing or other material that relates to the methods described herein and/or to the use of the agents for the methods described herein. For example, the informational material may relate to the use of the agents herein to treat a subject who has, or who is at risk for developing, a disorder associated with CLK2 and/or CDK1 activity. The kits can also include paraphernalia for administering the agents of this invention to a cell (in culture or in vivo) and/or for administering a cell to a patient.

In various aspects, the informational material can include instructions for administering the pharmaceutical composition and/or cell(s) in a suitable manner to treat a human, e.g., in a suitable dose, dosage form, or mode of administration (e.g., a dose, dosage form, or mode of administration described herein). In a further aspect, the informational material can include instructions to administer the pharmaceutical composition to a suitable subject, e.g., a human having, or at risk for developing, a disorder associated with CLK2 and/or CDK1 activity.

In various aspects, the composition of the kit can include other ingredients, such as a solvent or buffer, a stabilizer, a preservative, a fragrance or other cosmetic ingredient. In such aspects, the kit can include instructions for admixing the agent and the other ingredients, or for using one or more compounds together with the other ingredients.

In a further aspect, the disorder having an aberrant germ-like mutation is selected from retinitis Pigmentosa, microcephalic osteodysplastic primordial dwarfism (MOPD) type 1, and cancer.

In a further aspect, the compound and the at least one agent known to treat a disorder having an aberrant germ-like mutation are co-formulated. In a still further aspect, the compound and the at least one agent known to treat disorder having an aberrant germ-like mutation are co-packaged.

In a further aspect, the compound and the at least one agent known to activate CLK2 and/or CDK1 are co-formulated. In a still further aspect, the compound and the at least one agent known to activate CLK2 and/or CDK1 are co-packaged.

In a further aspect, the compound and the at least one agent known to inhibit CLK2 and/or CDK1 are co-formulated. In a still further aspect, the compound and the at least one agent known to inhibit CLK2 and/or CDK1 are co-packaged.

In a further aspect, the disorder having an aberrant germ-like mutation is selected from retinitis Pigmentosa, microcephalic osteodysplastic primordial dwarfism (MOPD) type 1, and cancer.

In a further aspect, the at least one agent known to treat cancer is selected from one or more of the group consisting of an alkylating agent, an antimetabolite agent, an antineoplastic antibiotic agent, a mitotic inhibitor agent, a mTor inhibitor agent or other chemotherapeutic agent, or a pharmaceutically acceptable salt thereof. In yet a further aspect, the antineoplastic antibiotic agent is selected from one or more of the group consisting of doxorubicin, mitoxantrone, bleomycin, daunorubicin, dactinomycin, epirubicin, idarubicin, plicamycin, mitomycin, pentostatin, and valrubicin, or a pharmaceutically acceptable salt thereof. In an even further aspect, the antimetabolite agent is selected from one or more of the group consisting of gemcitabine, 5-fluorouracil, capecitabine, hydroxyurea, mercaptopurine, pemetrexed, fludarabine, nelarabine, cladribine, clofarabine, cytarabine, decitabine, pralatrexate, floxuridine, methotrexate, and thioguanine, or a pharmaceutically acceptable salt thereof. In a still further aspect, the alkylating agent is selected from one or more of the group consisting of carboplatin, cisplatin, cyclophosphamide, chlorambucil, melphalan, carmustine, busulfan, lomustine, dacarbazine, oxaliplatin, ifosfamide, mechlorethamine, temozolomide, thiotepa, bendamustine, and streptozocin, or a pharmaceutically acceptable salt, hydrate, solvate, or polymorph thereof. In yet a further aspect, the mitotic inhibitor agent is selected from one or more of the group consisting of irinotecan, topotecan, rubitecan, cabazitaxel, docetaxel, paclitaxel, etopside, vincristine, ixabepilone, vinorelbine, vinblastine, and teniposide, or a pharmaceutically acceptable salt thereof. In an even further aspect, the mTor inhibitor agent is selected from one or more of the group consisting of everolimus, siroliumus, and temsirolimus, or a pharmaceutically acceptable salt thereof.

In a further aspect, the kit further comprises a plurality of dosage forms, the plurality comprising one or more doses; wherein each dose comprises an effective amount of the compound and the at least one agent known to treat a disorder having an aberrant germ-like mutation. In a still further aspect, the effective amount is a therapeutically effective amount. In yet a further aspect, the effective amount is a prophylactically effective amount. In an even further aspect, each dose of the compound and at least one agent known to treat a disorder having an aberrant germ-like mutation are co-packaged. In a still further aspect, each dose of the compound and the at least one agent known to treat a disorder having an aberrant germ-like mutation are co-formulated.

In a further aspect, the kit further comprises a plurality of dosage forms, the plurality comprising one or more doses; wherein each dose comprises an effective amount of the compound and the at least one agent known to activate CLK2 and/or CDK1. In a still further aspect, the effective amount is a therapeutically effective amount. In yet a further aspect, the effective amount is a prophylactically effective amount. In an even further aspect, each dose of the compound and at least one agent known to activate CLK2 and/or CDK1 are co-packaged. In a still further aspect, each dose of the compound and the at least one agent known to activate CLK2 and/or CDK1 are co-formulated.

In a further aspect, the kit further comprises a plurality of dosage forms, the plurality comprising one or more doses; wherein each dose comprises an effective amount of the compound and the at least one agent known to inhibit CLK2 and/or CDK1. In a still further aspect, the effective amount is a therapeutically effective amount. In yet a further aspect, the effective amount is a prophylactically effective amount. In an even further aspect, each dose of the compound and at least one agent known to inhibit CLK2 and/or CDK1 are co-packaged. In a still further aspect, each dose of the compound and the at least one agent known to inhibit CLK2 and/or CDK1 are co-formulated.

4. Subjects

In various aspects, the subject of the herein disclosed methods is a vertebrate, e.g., a mammal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment prior to the administering step. In some aspects of the disclosed method, the subject has been diagnosed with a disorder associated with PanK activity prior to the administering step. In some aspects of the disclosed methods, the subject has been identified with a need for treatment prior to the administering step. In one aspect, a subject can be treated prophylactically with a compound or composition disclosed herein, as discussed herein elsewhere.

a. Dosage

Toxicity and therapeutic efficacy of the agents and pharmaceutical compositions described herein can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio $LD_{50}/ED_{50}$. Polypeptides or other compounds that exhibit large therapeutic indices are preferred.

Data obtained from cell culture assays and further animal studies can be used in formulating a range of dosage for use in humans. The dosage of such compounds lies preferably within a range of circulating concentrations that include the $ED_{50}$ with little or no toxicity, and with little or no adverse effect on a human's ability to hear. The dosage may vary within this range depending upon the dosage form employed and the route of administration utilized. For any agents used in the methods described herein, the therapeutically effective dose can be estimated initially from cell culture assays. A dose can be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Exemplary dosage amounts of a differentiation agent are at least from about 0.01 to 3000 mg per day, e.g., at least about 0.00001, 0.0001, 0.001, 0.01, 0.1, 1, 2, 5, 10, 25, 50, 100, 200, 500, 1000, 2000, or 3000 mg per kg per day, or more.

The formulations and routes of administration can be tailored to the disease or disorder being treated, and for the specific human being treated. For example, a subject can receive a dose of the agent once or twice or more daily for one week, one month, six months, one year, or more. The treatment can continue indefinitely, such as throughout the lifetime of the human. Treatment can be administered at regular or irregular intervals (once every other day or twice per week), and the dosage and timing of the administration can be adjusted throughout the course of the treatment. The dosage can remain constant over the course of the treatment regimen, or it can be decreased or increased over the course of the treatment.

In various aspects, the dosage facilitates an intended purpose for both prophylaxis and treatment without undesirable side effects, such as toxicity, irritation or allergic response. Although individual needs may vary, the determination of optimal ranges for effective amounts of formulations is within the skill of the art. Human doses can readily be extrapolated from animal studies (Katocs et al., (1990) Chapter 27 in Remington's Pharmaceutical Sciences, 18th Ed., Gennaro, ed., Mack Publishing Co., Easton, Pa.). In general, the dosage required to provide an effective amount of a formulation, which can be adjusted by one skilled in the art, will vary depending on several factors, including the age, health, physical condition, weight, type and extent of the disease or disorder of the recipient, frequency of treatment, the nature of concurrent therapy, if required, and the nature and scope of the desired effect(s) (Nies et al., (1996) Chapter 3, In: Goodman & Gilman's The Pharmacological Basis of Therapeutics, 9th Ed., Hardman et al., eds., McGraw-Hill, New York, N.Y.).

b. Routes of Administration

Also provided are routes of administering the disclosed compounds and compositions. The compounds and compositions of the present invention can be administered by direct therapy using systemic administration and/or local administration. In various aspects, the route of administration can be determined by a patient's health care provider or clinician, for example following an evaluation of the patient. In various aspects, an individual patient's therapy may be customized, e.g., the type of agent used, the routes of administration, and the frequency of administration can be personalized. Alternatively, therapy may be performed using a standard course of treatment, e.g., using pre-selected agents and pre-selected routes of administration and frequency of administration.

Systemic routes of administration can include, but are not limited to, parenteral routes of administration, e.g., intravenous injection, intramuscular injection, and intraperitoneal injection; enteral routes of administration e.g., administration by the oral route, lozenges, compressed tablets, pills, tablets, capsules, drops (e.g., ear drops), syrups, suspensions and emulsions; rectal administration, e.g., a rectal suppository or enema; a vaginal suppository; a urethral suppository; transdermal routes of administration; and inhalation (e.g., nasal sprays).

In various aspects, the modes of administration described above may be combined in any order.

H. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Chemistry Experimentals a. General

Unless otherwise noted, all commercial reagents were obtained from commercially available sources and used without purification. Flash column chromatography was performed on a Biotage SP-1 chromatography system. TLC plates were visualized by exposure to ultraviolet light (254 nm). $^1$H and $^{13}$C spectra were recorded using 400 MHz, and 300 MHz, respectively, using CDCl$_3$, CD$_3$OD, or DMSO-d$_6$ as a solvent. The chemical shifts are reported in parts per million (ppm) relative to residual solvent (for chloroform, δ 7.24 ppm for $^1$H NMR and δ 77.02 ppm for carbon NMR. For DMSO, δ 2.47 ppm for $^1$H NMR. For CD$_3$OD, δ 49.00 ppm for $^{13}$C NMR). Coupling constants are reported in hertz (Hz). The following abbreviations are used to designate the multiplicities: s=singlet, d=doublet, t=triplet, q=quartet, m=multiplet. Mass spectra with electrospray ionization (ESI) were recorded on LCQ Fleet Ion Trap Mass Spectrometer (Thermo Scientific) coupled to the Finnigan Surveyor Plus HPLC System (Thermo Scientific). High-resolution mass spectra were recorded on LTQ-Orbitrap XL (Thermo Scientific) using static nanoelectrospray ionization in positive-ion profile mode at a nominal resolution setting of 100,000. Approximately 50 scans were averaged for each sample and the resulting Fourier-transformed frequency-domain spectrum was mass-assigned with calibration constants from an external calibration mixture. Experimental masses and isotope distributions were compared to theoretical values. All compounds reported are of at least 95% purity, as judged by HPLC (Waters XBridge C18, 250 mm×4.6 mm ID, 5 μm column; 10 μL injection; 10-100% MeCN/H$_2$O+0.1% TFA gradient over 15 min; 1 mL/min flow; ESI; positive ion mode; UV detection at 310 nM or 340 nM). Optical rotations were measured from an automatic Autopol® IV polarimeter at the Na D-line (λ=589 nm) using a 1 dm cell. When applicable the separation of enantiomers was done by supercritical fluid chromatography (SFC) (Jasco PU-2088 Plus system and Chiralpak® chiral column (AD-H) 21×250 mm, 5 μm) using CO$_2$ and HPLC grade MeOH as mobile phase.

Additional Abbreviations: CLK, cdc2-like kinase. MDM2, mouse double minute 2 homolog. Luc, luciferase. TEA, triethylamine. DIPEA, diisopropylethylamine. EtOAc, ethyl acetate.

b. Synthesis of 2,6-dichloro-9-isopropyl-9H-purine

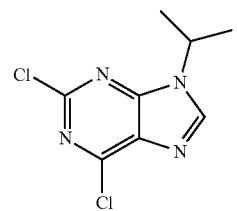

To a solution of 2,6-dichloro-9H-purine (12.5 g, 66.1 mmol) in 75 mL of DMSO were added potassium carbonate (27.4 g, 198 mmol), and 2-iodopropane (33 mL, 330 mmol) at rt. The reaction mixture was stirred at rt for 5 days, quenched with water, and extracted with EtOAc (4×500 mL). The combined organic layers were washed with water and brine, dried (MgSO$_4$), concentrated, and purified by automated flash column chromatography (hexane-EtOAc: 20-60% gradient) to give the title compound (10.6 g, 70%) as a white solid. mp 153-156° C.; $^1$H NMR (399 MHz, CDCl$_3$) δ 8.16 (s, 1H), 4.91 (hept, J=6.8 Hz, 1H), 1.65 (dd, J=6.8, 1 Hz, 8H); $^{13}$C NMR (75 MHz, CDCl$_3$) δ 152.7, 152.6, 151.6, 143.5, 131.0, 48.4, 22.5; HRMS (ESI) m/z calcd for C$_8$H$_8$Cl$_2$N$_4$ (M+H)$^+$ 231.0199; found, 231.0199.

c. Synthesis of 2,6-dichloro-9-ethyl-9H-purine

The title compound was prepared in a similar way to that for 2,6-dichloro-9-isopropyl-9H-purine using bromoethane in the alkylation. Yield 69%, white solid. mp 105-106° C.; $^1$H NMR (399 MHz, CDCl$_3$) δ 8.12 (s, 1H), 4.33 (q, J=7.4 Hz, 3H), 1.65-1.45 (m, 6H); $^{13}$C NMR (75 MHz, CDCl$_3$) δ 153.0, 152.9, 151.7, 145.3, 130.8, 39.7, 15.3; HRMS (ESI) m/z calcd for C$_7$H$_6$Cl$_2$N$_4$ (M+H)$^+$217.0042; found, 217.0040.

d. Synthesis of 2-chloro-N-(3-chlorophenyl)-9-isopropyl-9H-purin-6-amine

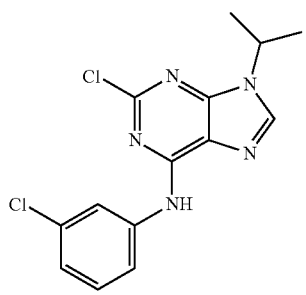 [SMILES: CC(C)n1cnc2c(Nc3cccc(Cl)c3)nc(Cl)nc21]

To a solution of 2,6-dichloro-9-isopropyl-9H-purine (1.30 g, 5.63 mmol) in 8.4 mL of n-butanol was treated with TEA (1.30 mL, 9.01 mmol), and 3-chloroaniline (0.71 mL, 6.75 mmol) at rt. The reaction mixture was stirred at 100° C. for 18 h, cooled to rt, and concentrated. The residue was dispersed in water and extracted with EtOAc (50 mL×2). The combined organic layers were washed with brine, dried (MgSO$_4$), and concentrated. The residue was purified by automated flash column chromatography (hexane-EtOAc: 20-60% gradient) to give the title compound (1.47 g, 81%) as a yellow solid. mp. 134-136° C.; $^1$H NMR (399 MHz, CDCl$_3$) δ 7.93 (s, 1H), 7.88 (2s, 2H), 7.67 (dd, J=8.3, 2.9 Hz, 1H), 7.31 (t, J=8.3 Hz, 1H), 7.13-7.07 (d, J=2.9 Hz, 1H), 4.87 (p, J=6.9 Hz, 1H), 1.61 (d, J=6.7 Hz, 6H); $^{13}$C NMR (75 MHz, CDCl$_3$) δ 153.8, 151.9, 150.4, 139.4, 138.5, 134.6, 130.0, 123.8, 120.1, 119.1, 118.1, 47.5, 22.7; HRMS (ESI) m/z calcd for C$_{14}$H$_{13}$Cl$_2$N$_5$ (M+H)$^+$322.0621; found, 322.0621.

e. Synthesis of 2-chloro-N-(3-chlorophenyl)-9-ethyl-9H-purin-6-amine

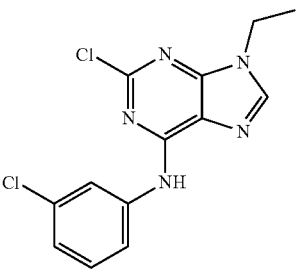 [SMILES: CCn1cnc2c(Nc3cccc(Cl)c3)nc(Cl)nc21]

The title compound was prepared in a similar way to that for 2-chloro-N-(3-chlorophenyl)-9-isopropyl-9H-purin-6-amine from 2,6-dichloro-9-ethyl-9H-purine. Yield 66%, yellow solid. mp 134-136° C.; $^1$H NMR (CDCl$_3$) δ 7.95-7.85 (m, 1H), 7.83 (s, 1H), 7.71-7.60 (m, 1H), 7.31 (t, J=8.1 Hz, 1H), 7.10 (ddd, J=7.9, 2.0, 1.0 Hz, 1H), 4.27 (q, J=7.3 Hz, 2H), 1.55 (t, J=7.3 Hz, 3H); $^{13}$C NMR (75 MHz, CDCl$_3$) δ 154.1, 151.9, 150.7, 140.5, 139.3, 134.6, 130.0, 123.9, 120.1, 118.9, 118.2, 39.2, 15.5; HRMS (ESI) m/z calcd for C$_{13}$H$_{11}$Cl$_2$N$_5$ (M+H)$^+$308.0464; found, 308.0464.

f. Example General Procedure: Synthesis of Racemic N$^2$-(cis-2-aminocyclohexyl)-N$^6$-(3-chlorophenyl)-9-ethyl-9H-purine-2,6-diamine (1)

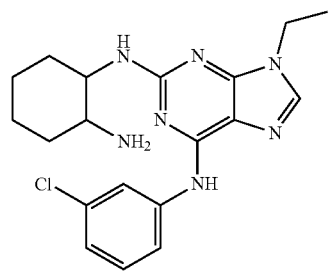 [SMILES: CCn1cnc2c(Nc3cccc(Cl)c3)nc(NC3CCCCC3N)nc21]

To a solution of 2-chloro-N-(3-chlorophenyl)-9-ethyl-9H-purin-6-amine (0.360 g, 1.17 mmol) in 6.0 mL of NMP were added TEA (0.33 mL, 2.3 mmol), and cis-cyclohexane-1,2-diamine (0.400 g, 3.50 mmol) at rt. The reaction mixture was stirred at 160° C. for 12 h, allowed to cool to rt, then partitioned between water and dichloromethane. The organic layer was washed with brine, dried (MgSO$_4$), and concentrated, and finally purified by automated flash column chromatography (dichloromethane-methanol with 10% NH$_4$OH: 0-10% gradient) to give 1 (0.244 g, 54%) as a brownish solid. mp 90-91° C.; $^1$H NMR (399 MHz, CDCl$_3$) $^1$H NMR (399 MHz, CDCl$_3$) δ 8.11 (br s, 1H), 7.59 (br s, 1H), 7.46 (s, 1H), 7.35 (d, J=8.2 Hz, 1H), 7.17 (t, J=8.2 Hz, 1H), 6.89-6.98 (m, 1H), 5.23 (d, J=7.8 Hz, 1H), 3.83-4.11 (m, 3H), 3.21 (br s, 1H), 1.69 (br s, 5H), 1.46-1.66 (m, 5H), 1.42 (t, J=7.2 Hz, 3H); $^{13}$C NMR (75 MHz, DMSO-d$_6$) δ 158.7, 152.4, 152.1, 142.4, 138.7, 133.1, 130.3, 121.7, 119.6, 118.7, 114.4, 52.7, 49.7, 38.0, 31.3, 27.1, 23.9, 20.5, 15.7; HRMS (ESI) m/z calcd for C$_{19}$H$_{24}$ClN$_7$ (M+H)$^+$ 386.1855; found, 386.1855.

g. Synthesis of N²-((1R,2R)-2-aminocyclohexyl)-N⁶-(3-chlorophenyl)-9-ethyl-9H-purine-2,6-diamine (5)

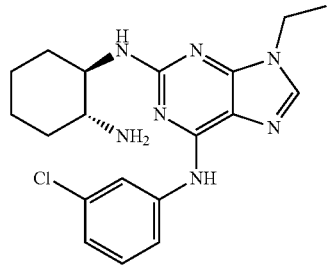 [SMILES: CCn1cnc2c(Nc3cccc(Cl)c3)nc(N[C@@H]3CCCC[C@H]3N)nc21]

The title compound was prepared in a similar way to that for 1 from 2-chloro-N-(3-chlorophenyl)-9-ethyl-9H-purin-6-amine and optically pure (1R,2R)-cyclohexane-1,2-diamine. Yield 41%, off white solid. mp 90-91° C.; $[\alpha]_D^{24}$=−23.2° (c 1.0, CHCl$_3$); $^1$H NMR (399 MHz, CDCl$_3$) δ 8.25 (br s, 1H), 7.59 (br s, 1H), 7.54 (s, 1H), 7.36 (d, J=8.2 Hz, 1H), 7.19-7.25 (m, 1H), 7.02 (d, J=7.8 Hz, 1H), 4.81 (d, J=9.0 Hz, 1H), 4.10 (q, J=7.3 Hz, 2H), 3.75 (d, J=8.6 Hz, 1H), 2.52 (d, J=9.4 Hz, 1H), 2.18 (d, J=12.5 Hz, 1H), 2.04 (br s, 2H), 1.77 (m, 4H), 1.50 (t, J=7.3 Hz, 3H), 1.12-1.40 (m, 4H); $^{13}$C NMR (75 MHz, CDCl$_3$) δ 159.6, 151.8, 140.6, 137.3, 134.3, 129.6, 122.4, 119.7, 117.4, 114.7, 58.2, 56.0, 38.2, 35.0, 32.9, 25.3, 25.2, 15.3; HRMS (ESI) m/z calcd for C$_{19}$H$_{24}$ClN$_7$ (M+H)$^+$386.1855; found, 386.1855.

h. Synthesis of N²-((1S,2S)-2-aminocyclohexyl)-N⁶-(3-chlorophenyl)-9-ethyl-9H-purine-2,6-diamine (6)

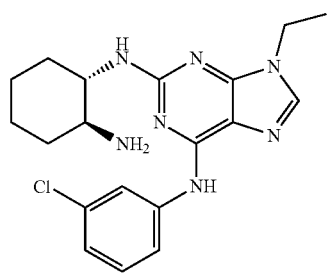 [SMILES: CCn1cnc2c(Nc3cccc(Cl)c3)nc(N[C@H]3CCCC[C@@H]3N)nc21]

The title compound was prepared in a similar way to that for 1 from 2-chloro-N-(3-chlorophenyl)-9-ethyl-9H-purin-6-amine and optically pure (1S,2S)-cyclohexane-1,2-diamine. Yield 42%, brownish solid. mp 90-91° C.; $[\alpha]_D^{24}$=+25.6° (c 1.0, CHCl$_3$); $^1$H NMR (399 MHz, CDCl$_3$) δ 8.25 (br s, 1H), 7.64 (br s, 1H), 7.49-7.56 (m, 1H), 7.37 (d, J=7.8 Hz, 1H), 7.19-7.24 (m, 1H), 7.02 (d, J=6.7 Hz, 1H), 4.80 (d, J=9.0 Hz, 1H), 4.10 (q, J=7.2 Hz, 2H), 3.74 (dd, J=9.6, 5.7 Hz, 1H), 2.52 (d, J=4.7 Hz, 1H), 2.18 (d, J=12.9 Hz, 1H), 2.05 (br s, 2H), 1.77 (br s, 3H), 1.49 (q, J=6.8 Hz, 4H), 1.09-1.35 (m, 4H); $^{13}$C NMR (75 MHz, CDCl$_3$) δ 159.6, 151.8, 151.7, 140.6, 137.3, 134.3, 129.6, 122.4, 119.7, 117.5, 114.7, 58.1, 56.1, 38.3, 34.9, 32.9, 25.3, 25.1, 15.3; HRMS (ESI) m/z calcd for C$_{19}$H$_{24}$ClN$_7$ (M+H)$^+$386.1855; found, 386.1858.

i. Synthesis of N²-((1R,2R)-2-aminocyclohexyl)-N⁶-(3-chlorophenyl)-9-isopropyl-9H-purine-2,6-diamine (7)

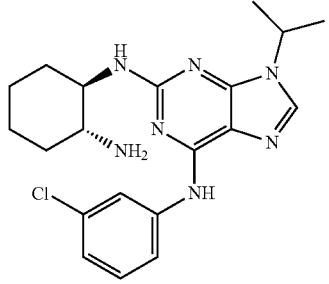 [SMILES: CC(C)n1cnc2c(Nc3cccc(Cl)c3)nc(N[C@@H]3CCCC[C@H]3N)nc21]

The title compound was prepared in a similar way to that for 1 from 2-chloro-N-(3-chlorophenyl)-9-isopropyl-9H-purin-6-amine and optically pure (1R,2R)-cyclohexane-1,2-diamine. Yield 48%, brownish solid. mp 106-108° C.; $[\alpha]_D^{24}$=−22.7° (c 1.0, CHCl$_3$); $^1$H NMR (399 MHz, CDCl$_3$) δ 8.21 (br s, 1H), 7.70 (br s, 1H), 7.52-7.62 (m, 1H), 7.38 (d, J=8.2 Hz, 1H), 7.18-7.25 (m, 1H), 7.02 (d, J=8.2 Hz, 1H), 4.82 (d, J=9.4 Hz, 1H), 4.63-4.73 (m, 1H), 4.04-4.16 (m, 1H), 3.68-3.81 (m, 1H), 2.52-2.63 (m, 1H), 2.18 (d, J=13.3 Hz, 1H), 2.03-2.13 (m, 2H), 1.78 (d, J=10.2 Hz, 2H), 1.56 (dd, J=6.7, 1.2 Hz, 6H), 1.19-1.49 (m, 4H); $^{13}$C NMR (75 MHz, CDCl$_3$) δ 159.2, 151.9, 140.5, 135.5, 134.3, 129.7, 122.6, 119.8, 117.7, 115.0, 111.0, 57.2, 56.3, 46.4, 33.8, 32.7, 25.1, 24.9, 22.6; HRMS (ESI) m/z calcd for C$_{20}$H$_{26}$ClN$_7$ (M+H)$^+$400.2011; found, 400.2011.

j. Synthesis of N²-((1S,2S)-2-aminocyclohexyl)-N⁶-(3-chlorophenyl)-9-isopropyl-9H-purine-2,6-diamine (8)

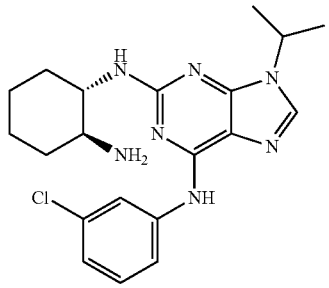 [SMILES: CC(C)n1cnc2c(Nc3cccc(Cl)c3)nc(N[C@H]3CCCC[C@@H]3N)nc21]

The title compound was prepared in a similar way to that for 1 from 2-chloro-N-(3-chlorophenyl)-9-isopropyl-9H-purin-6-amine and optically pure (1S,2S)-cyclohexane-1,2-diamine. Yield 45%, off white solid. mp 103-105° C.; $[\alpha]_D^{24}$=+26.5° (c 1.0, CHCl$_3$); $^1$H NMR (399 MHz, CDCl$_3$) δ 8.24 (br s, 1H), 7.66 (br s, 1H), 7.53-7.61 (m, 1H), 7.37 (br s, 1H), 7.25 (br s, 1H), 7.02 (d, J=7.0 Hz, 1H), 4.80 (d, J=9.4 Hz, 1H), 4.67 (d, J=6.7 Hz, 1H), 4.12 (d, J=7.0 Hz, 1H), 3.73 (br s, 1H), 2.53 (br s, 1H), 2.17 (br s, 1H), 2.04 (d, J=4.3 Hz, 2H), 1.77 (br s, 2H), 1.57 (d, J=6.7 Hz, 6H), 1.47 (br s, 1H), 1.12-1.39 (m, 4H); $^{13}$C NMR (75 MHz, CDCl$_3$) δ 169.4, 159.4, 151.9, 151.4, 140.6, 135.4, 134.3, 129.6, 122.4, 119.7, 117.5, 58.2, 56.0, 46.3, 35.0, 32.8, 25.3, 25.1, 22.6; HRMS (ESI) m/z calcd for C$_{20}$H$_{26}$ClN$_7$ (M+H)$^+$400.2011, found, 400.2013.

k. Method 1: Synthesis of N²-((1R,2S)-2-aminocyclohexyl)-N⁶-(3-chlorophenyl)-9-isopropyl-9H-purine-2,6-diamine (9)

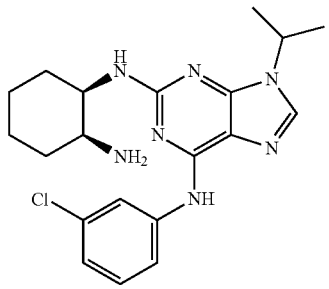 [SMILES: CC(C)n1cnc2c(Nc3cccc(Cl)c3)nc(N[C@@H]3CCCC[C@@H]3N)nc21]

The mixture of 2-chloro-N-(3-chlorophenyl)-9-isopropyl-9H-purin-6-amine (247 mg, 0.77 mmol) and tert-butyl ((1R,2S)-2-aminocyclohexyl)carbamate (328 mg, 1.53 mmol) in 0.75 mL of DIPEA was added and stirred at 110° C. for 5 days, cooled to rt, diluted with dichloromethane, the organic phase concentrated under vacuum and the residue was purified by automated flash column chromatography (hexane-EtOAc: 0-100% gradient) to give a mixture of starting material and product, which was reacted with 1 mL of TFA in 5 mL of dichloromethane for 17 h, then concentrated. The residue was diluted with dichloromethane and washed with aqueous saturated sodium bicarbonate solution. The organic layer was concentrated and purified by automated flash column chromatography (dichloromethane-methanol with 10% NH₄OH: 0-10% gradient) to give 9 (81 mg, 26%) as an off white solid. mp 100-102° C.; $[\alpha]_D^{24}$=+3.1° (c 1.0, CHCl₃); ¹H NMR (399 MHz, DMSO-d₆) δ 9.62 (s, 1H), 8.25 (s, 1H), 7.96 (s, 1H), 7.85 (s, 1H), 7.25 (t, J=8.1 Hz, 1H), 6.97 (ddd, J=7.9, 2.1, 0.9 Hz, 1H), 6.23 (d, J=7.6 Hz, 1H), 4.56 (p, J=6.7 Hz, 1H), 3.84 (s, 1H), 3.10 (m, 1H), 1.69-1.51 (m, 6H), 1.46 (d, J=6.8 Hz, 6H), 1.31 (m, 2H); ¹³C NMR (75 MHz, CDCl₃) δ 158.9, 151.9, 151.4, 140.5, 135.4, 134.4, 129.7, 122.5, 119.6, 117.6, 115.1, 52.4, 50.0, 46.4, 30.1, 27.3, 23.4, 22.6, 20.6; HRMS (ESI) m/z calcd for $C_{20}H_{26}ClN_7$ (M+H)⁺400.2011; found, 400.2007.

l. Method 1: Synthesis of N²-((1S,2R)-2-aminocyclohexyl)-N⁶-(3-chlorophenyl)-9-isopropyl-9H-purine-2,6-diamine (10)

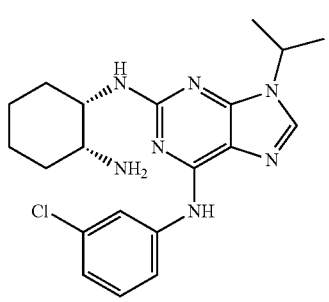 [SMILES: CC(C)n1cnc2c(Nc3cccc(Cl)c3)nc(N[C@H]3CCCC[C@H]3N)nc21]

The title compound was prepared in a similar way to that for 9 from tert-butyl 24 ((1S,2R)-2-aminocyclohexyl)carbamate. Yield 21%, off-white solid. mp 100-102° C.; $[\alpha]_D^{24}$=−2.4° (c 1.0, CHCl₃); ¹H NMR (DMSO-d₆) δ 9.61 (s, 1H), 8.26 (s, 1H), 7.95 (s, 1H), 7.85 (s, 1H), 7.25 (t, J=8.1 Hz, 1H), 6.96 (ddd, J=8.0, 2.1, 0.9 Hz, 1H), 6.19 (d, J=7.7 Hz, 1H), 4.56 (p, J=6.8 Hz, 1H), 3.81 (s, 1H), 3.08 (m, 1H), 1.70-1.50 (m, 6H), 1.46 (d, J=6.8 Hz, 6H), 1.30 (m, 2H); ¹³C NMR (75 MHz, CDCl₃) δ 158.9, 151.9, 151.6, 140.7, 135.4, 134.3, 129.6, 122.3, 119.6, 117.4, 114.8, 52.8, 49.8, 46.2, 31.9, 27.6, 23.4, 22.6, 21.0; HRMS (ESI) m/z calcd for $C_{20}H_{26}ClN_7$ (M+H)⁺400.2011; found, 400.2011.

m. Method 2 for the Preparation of 9 and 10

(1) Step 1

The title compound was prepared in a similar way to that for 1 from 2-chloro-N-(3-chlorophenyl)-9-isopropyl-9H-purin-6-amine and cis-cyclohexane-1,2-diamine. Yield 52%, brownish solid. mp 102-104° C.; ¹H NMR (399 MHz, CDCl₃) δ 8.17 (br s, 1H), 7.67 (br s, 1H), 7.58 (s, 1H), 7.43 (d, J=8.2 Hz, 1H), 7.19-7.25 (m, 1H), 7.01 (d, J=8.2 Hz, 1H), 5.27 (d, J=7.8 Hz, 1H), 4.67 (dt, J=13.8, 7.0 Hz, 1H), 4.00-4.18 (m, 1H), 3.28 (br s, 1H), 1.70-1.82 (m, 6H), 1.56 (d, J=7.0 Hz, 6H), 1.36-1.52 (m, 4H); ¹³C NMR (75 MHz, CDCl₃) δ 158.9, 151.9, 151.5, 140.7, 135.3, 134.4, 129.6, 122.4, 119.6, 117.4, 114.8, 52.9, 49.8, 46.3, 32.0, 27.7, 23.4, 22.6, 21.0; HRMS (ESI) m/z calcd for $C_{20}H_{26}ClN_7$ (M+H)⁺ 400.2011; found, 400.2010.

(2) Step 2

A solution of N²-(cis-2-aminocyclohexyl)-N⁶-(3-chlorophenyl)-9-isopropyl-9H-purine-2,6-diamine (0.105 g, 0.263 mmol) in 5.2 mL of THF was treated with TEA (0.092 mL, 0.66 mmol), and di-tert-butyl dicarbonate (0.069 g, 0.32 mmol) at rt. The reaction mixture was allowed to stir at rt for 16 h, and concentrated. Purification of crude was done by flash column chromatography using hexane-EtOAc (10-80% gradient) to obtain racemic tert-butyl (cis-2-((6-((3-chlorophenyl)amino)-9-isopropyl-9H-purin-2-yl)amino)cyclohexyl)carbamate (0.102 g, 78%) as a brownish solid. mp 160-161° C.; ¹H NMR (399 MHz, DMSO-d₆) δ 9.65 (s, 1H), 8.23 (s, 1H), 8.02-7.94 (m, 1H), 7.84 (s, 1H), 7.26 (t, J=8.1 Hz, 1H), 6.97 (ddd, J=8.0, 2.2, 0.9 Hz, 1H), 6.58 (s, 1H), 6.18 (s, 1H), 4.56 (p, J=6.8 Hz, 1H), 3.98 (br s, 1H), 3.80 (br s, 1H), 1.78 (s, 2H), 1.63-1.41 (m, 4H), 1.46 (dd, J=6.8, 5.3 Hz, 6H), 1.31 (s, 9H), 1.15-1.04 (m, 2H); ¹³C NMR (75 MHz, CDCl₃) δ 158.8, 155.7, 151.9, 151.1, 140.5, 135.4, 134.3, 129.7, 122.6, 119.8, 117.7, 114.9, 79.0, 51.4, 51.0, 47.2, 46.6, 46.5, 45.9, 29.4, 28.8, 28.3, 22.8, 22.6, 22.5, 21.8; HRMS (ESI) m/z calcd for $C_{25}H_{34}ClN_7O_2$ (M+H)⁺ 500.2535; found, 500.2534.

(3) Step 3

The racemic mixture prepared from Step 2 was separated by SFC (Jasco PU-2088 Plus system, Chiralpak® AD-H 19445, 21×250 mm, 5 µm, 10% MeOH/CO₂, flow rate: 50 mL/min) to give PEAK1 ($R_t$=12 min) and PEAK2 ($R_t$=13.3 min). The stereochemistry of PEAK1 and PEAK2 were determined by comparing $R_t$ with chiral products of method 1.

(4) Step 4: Synthesis of $N^2$-((1R,2S)-2-aminocyclohexyl)-$N^6$-(3-chlorophenyl)-9-isopropyl-9H-purine-2,6-diamine (9)

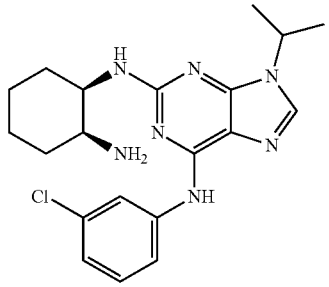 [SMILES: CC(C)n1cnc2c(Nc3cccc(Cl)c3)nc(N[C@@H]3CCCC[C@@H]3N)nc21]

To a solution of PEAK1 (6.0 mg, 0.01 mmol) prepared from Step 3 in 2 mL of dichloromethane was added TFA (0.2 mL) at rt. The reaction mixture was stirred at rt for 20 h, and concentrated. The residue was washed with ethyl ether, decanted, and dried under high vacuum to give trifluoroacetate salt of 9 (5.0 mg, 81%) as an off white solid. $^1$H NMR (399 MHz, DMSO-$d_6$) δ 9.74 (s, 1H), 8.12 (s, 1H), 8.05 (s, 1H), 7.67 (s, 3H), 7.28 (t, J=8.1 Hz, 1H), 7.00 (ddd, J=7.9, 2.2, 0.9 Hz, 1H), 6.51 (d, J=6.6 Hz, 1H), 4.61 (p, J=6.9 Hz, 1H), 4.15 (s, 1H), 1.81 (s, 2H), 1.72-1.52 (m, 2H), 1.47 (dd, J=6.8, 2.3 Hz, 6H), 1.39 (d, J=8.8 Hz, 2H); MS (ESI) m/z 400.33 (M+H)$^+$.

(5) Step 4: Synthesis of $N^2$-((1S,2R)-2-aminocyclohexyl)-$N^6$-(3-chlorophenyl)-9-isopropyl-9H-purine-2,6-diamine (10)

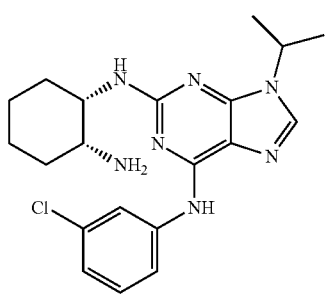 [SMILES: CC(C)n1cnc2c(Nc3cccc(Cl)c3)nc(N[C@H]3CCCC[C@H]3N)nc21]

The title compound was prepared as a trifluoroacetate salt in a similar way to that for 9 from PEAK2 prepared from Step 3, Yield 78%, as an off white solid. $^1$H NMR (399 MHz, DMSO-$d_6$) δ 9.74 (s, 1H), 8.12 (s, 1H), 8.05 (s, 1H), 7.67 (s, 3H), 7.28 (t, J=8.1 Hz, 1H), 7.00 (ddd, J=7.9, 2.2, 0.9 Hz, 1H), 6.51 (d, J=6.6 Hz, 1H), 4.61 (p, J=6.9 Hz, 1H), 4.15 (s, 1H), 1.81 (s, 2H), 1.72-1.52 (m, 2H), 1.47 (dd, J=6.8, 2.3 Hz, 6H), 1.39 (d, J=8.8 Hz, 2H); MS (ESI) m/z 400.35 (M+H)$^+$.

n. Synthesis of 2-chloro-N-(3-chlorophenyl)-7-isopropyl-7H-pyrrolo[2,3-D]pyrimidin-4-amine

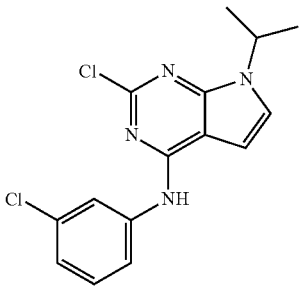 [SMILES: CC(C)n1ccc2c(Nc3cccc(Cl)c3)nc(Cl)nc21]

The title compound was prepared from 2,4-dichloro-7-isopropyl-7H-pyrrolo[2,3-d]pyrimidine (500 mg, 2.0 mmol) and 3-chloroaniline (329 mg, 2.5 mmol) following the procedure for compound 2-chloro-N-(3-chlorophenyl)-9-isopropyl-9H-purin-6-amine. Yield: 382 mg (55%) of title compound as a solid. $^1$H NMR (CDCl$_3$) δ 7.58 (t, J=2.1 Hz, 1H), 7.47-7.43 (m, 1H), 7.37-7.32 (m, 1H), 7.29 (t, J=8.0 Hz, 1H), 7.17-7.13 (m, 1H), 7.00 (d, J=3.7 Hz, 1H), 6.06 (d, J=3.6 Hz, 1H), 5.04 (p, J=6.8 Hz, 1H), 1.45 (d, J=6.8 Hz, 6H); HRMS (ESI) m/z calcd for C$_{15}$H$_{14}$C2N$_4$ (M+H)$^+$, 321.0668; found, 321.0672.

o. Synthesis of Racemic $N^2$-cis((2-aminocyclohexyl)-N4-(3-chlorophenyl)-7-isopropyl-7H-pyrrolo[2,3-D]pyrimidine-2,4-diamine (11)

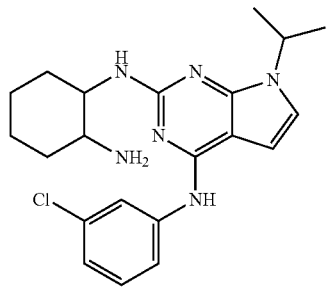 [SMILES: CC(C)n1ccc2c(Nc3cccc(Cl)c3)nc(NC3CCCCC3N)nc21]

The title compound was prepared from 2-chloro-N-(3-chlorophenyl)-7-isopropyl-7H-pyrrolo[2,3-d]pyrimidin-4-amine (120 mg, 0.37 mmol) and cis-1,2-cyclohexanediamine (255 mg, 2.24 mmol) following the procedure for compound 1. Yield: 60 mg (40%) of 11 as a solid. mp 96-98° C.; $^1$H NMR (399 MHz, CDCl$_3$) δ 7.46 (t, J=2.0 Hz, 1H), 7.30-7.25 (m, 1H), 7.20 (t, J=8.0 Hz, 1H), 7.06 (t, J=7.9 Hz, 1H), 6.67 (d, J=3.7 Hz, 1H), 5.84 (d, J=3.7 Hz, 1H), 5.10 (s, 1H), 4.78 (hept, J=6.9 Hz, 1H), 4.29 (s, 1H), 3.55-3.50 (m, 1H), 2.02-1.59 (m, 6H), 1.55-1.44 (m, 2H), 1.36 (dd, J=6.7, 3.0 Hz, 6H); $^{13}$C NMR (75 MHz, CDCl$_3$) δ 157.7, 154.0, 140.2, 134.3, 129.8, 124.2, 122.6, 120.7, 118.5, 99.7, 97.8, 53.0, 50.6, 45.5, 29.1, 26.2, 22.8, 22.6, 22.6, 20.7; HRMS (ESI) m/z calcd for C$_{21}$H$_{27}$ClN$_6$ (M+H)$^+$, 399.2059; found, 399.2059.

p. Synthesis of Racemic N-cis(2-((6-((3-chlorophenyl)amino)-9-ethyl-9H-purin-2-yl)amino)cyclohexyl) acetamide (12)

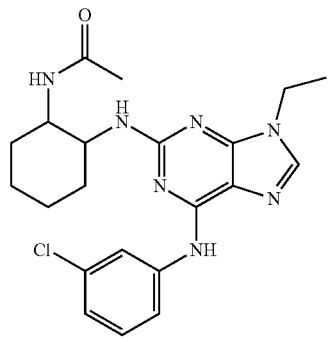 [SMILES: CCn1cnc2c(Nc3cccc(Cl)c3)nc(NC3CCCCC3NC(C)=O)nc21]

A stirred solution of CGP-74514A (1) (20 mg, 0.05 mmol) in EtOAc (0.2 mL) at rt was treated with acetic anhydride (6.3 μL, 0.06 mmol). The solution was cooled to 0° C. and treated with aqueous 10% NaHCO$_3$ (120 μL, 0.15 mmol). The resulting suspension was allowed to stir at 0° C. for an hour by which time TLC and LC/MS showed that starting material has been consumed. The reaction mixture was diluted with water (2 mL) and the product was extracted with EtOAc (2×4 mL). The combined organic layers were washed with brine (3 mL), dried over MgSO$_4$ and concentrated. The residue was purified on silica column (1-10% methanol (10% NH$_4$OH) in dichloromethane) to give 7 mg of 12 as a solid in 31% yield. mp 75-77° C.; $^1$H NMR (399 MHz, CDCl$_3$) δ 7.98 (s, 1H), 7.75 (s, 1H), 7.57 (s, 1H), 7.50 (d, J=8.0 Hz, 1H), 7.28-7.21 (m, 1H), 7.01 (d, J=8 Hz, 1H), 6.37 (br d, J=6.8 Hz, 1H), 5.17 (d, J=8.7 Hz, 1H), 4.46-4.38 (m, 1H), 4.14-4.06 (m, 3H), 1.86-1.80 (m, 2H), 1.78 (s, 3H), 1.62-1.58 (m, 3H), 1.54-1.48 (m, 6H); HRMS (ESI) m/z calcd for C$_{21}$H$_{26}$ClN$_7$O (M+H)$^+$, 428.1960; found, 428.1960.

q. Synthesis of N$^6$-(3-chlorophenyl)-9-isopropyl-N$^2$-(2-methoxyethyl)-9H-purine-2,6-diamine (13)

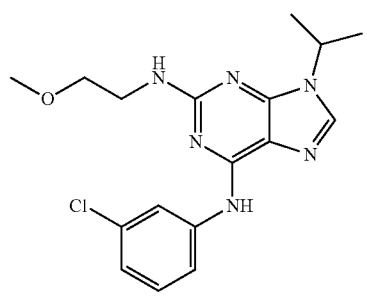 [SMILES: COCCNc1nc(Nc2cccc(Cl)c2)c2ncn(C(C)C)c2n1]

The title compound was prepared from 2-chloro-N-(3-chlorophenyl)-9-isopropyl-9H-purin-6-amine (75 mg, 0.23 mmol) and 2-methoxyethan-1-amine (167 mg, 0.23 mmol) by following the procedure for compound 1. Yield: 35 mg (42%) of 13 as a white solid. mp 101-103° C.; $^1$H NMR (399 MHz, CDCl$_3$) δ 8.11 (s, 1H), 7.64 (s, 1H), 7.59 (s, 1H), 7.52-7.45 (m, 1H), 7.23 (t, J=8.1 Hz, 1H), 7.01 (ddd, J=7.9, 2.0, 0.9 Hz, 1H), 5.25 (t, J=5.6 Hz, 1H), 4.68 (hept, J=6.7 Hz, 1H), 3.72-3.60 (m, 4H), 3.41 (s, 3H), 1.57 (d, J=6.8 Hz, 6H); $^{13}$C NMR (75 MHz, CDCl$_3$) δ 159.1, 151.7, 140.5, 135.1, 135.0, 134.4, 129.7, 122.6, 119.8, 119.8, 117.6, 71.5, 58.7, 46.7, 41.8, 22.5, 22.5; HRMS (ESI) m/z calcd for C$_{17}$H$_{21}$ClN$_6$O (M+H)$^+$, 361.1538; found, 361.1538.

r. Synthesis of 5-chloro-N$^1$-(2-chloro-9-isopropyl-9H-purin-6-yl)benzene-1,3-diamine

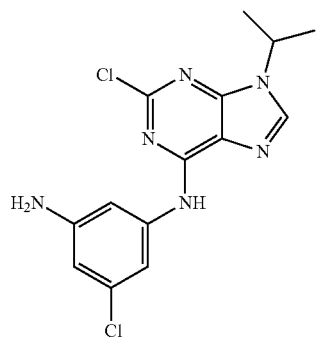 [SMILES: CC(C)n1cnc2c(Nc3cc(N)cc(Cl)c3)nc(Cl)nc21]

A suspension of 2,6-dichloro-9-isopropyl-9H-purine (3.0 g, 12 mmol) and 5-chloro m-phenylethylenediamine (1.8 g, 12 mmol) in n-butanol (21 mL) was stirred at rt as DIPEA (4.1 mL, 24 mmol) was added drop-wise. The resulting suspension was allowed to stir at 100° C. and the suspension became a clear solution. After 8 h heating, the solution became a suspension. This suspension was allowed to cool to rt and filtered. The solids were washed with EtOAc (2×10 mL) and dried under vacuum. The title compound (3.6 g) was recovered as solid in 83% yield. $^1$H NMR (399 MHz, DMSO-d$_6$) δ 10.08 (s, 1H), 8.42 (s, 1H), 7.10 (t, J=1.9 Hz, 1H), 6.96 (t, J=1.9 Hz, 1H), 6.33 (t, J=2.0 Hz, 1H), 5.41 (s, 2H), 4.71 (p, J=6.8 Hz, 1H), 1.51 (d, J=6.7 Hz, 6H); $^{13}$C NMR (75 MHz, DMSO-d$_6$) δ 152.7, 152.3, 150.7, 150.6, 141.0, 140.9, 133.4, 119.6, 109.2, 108.9, 105.4, 47.4, 22.6, 22.5; HRMS (ESI) m/z calcd for C$_{14}$H$_{14}$Cl$_2$N$^6$ (M+H)$^+$, 337.0730; found, 337.0727.

s. Synthesis of N-(3-CHLORO-5-((2-CHLORO-9-isopropyl-9H-purin-6-yl)amino)phenyl)acetamide

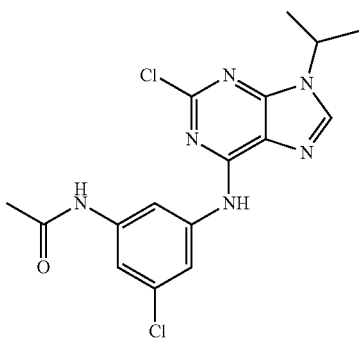 [SMILES: CC(=O)Nc1cc(Cl)cc(Nc2nc(Cl)nc3c2ncn3C(C)C)c1]

A stirred solution of 5-chloro-N$^1$-(2-chloro-9-isopropyl-9H-purin-6-yl)benzene-1,3-diamine (100 mg, 0.29 mmol) and pyridine (0.2 mL) in DMF (1.5 mL) at rt was treated with acetic anhydride (90 mg, 0.89 mmol). The solution was allowed to stir at rt for an hour and poured into ice-cold water. The resulting solids were filtered and washed with dichloromethane and hexanes. The title compound was obtained as a solid (78 mg) 70% yield. $^1$H NMR (399 MHz, DMSO-d$_6$) δ 10.44 (s, 1H), 10.12 (s, 1H), 8.46 (s, 1H), 7.87 (t, J=1.9 Hz, 1H), 7.68 (t, J=2.0 Hz, 1H), 7.52 (t, J=1.8 Hz, 1H), 4.73 (p, J=6.7 Hz, 1H), 2.05 (s, 3H), 1.52 (d, J=6.8 Hz, 6H); $^{13}$C NMR (75 MHz, DMSO-d$_6$) δ 169.1, 152.6, 152.2, 151.0, 141.2, 141.1, 141.0, 133.1, 119.7, 115.9, 114.1, 110.6, 47.4, 24.5, 22.6, 22.5; HRMS (ESI) m/z calcd for C$_{16}$H$_{16}$Cl$_2$N$^{60}$ (M+H)$^+$, 379.0835; found, 379.0834.

t. Synthesis of Racemic N$^6$-cis-(3-amino-5-chlorophenyl)-N$^2$-(2-aminocyclohexyl)-9-isopropyl-9H-purine-2,6-diamine (14)

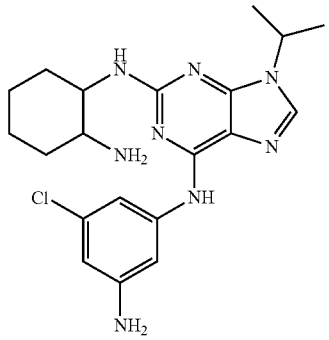 [SMILES: CC(C)n1cnc2c(Nc3cc(N)cc(Cl)c3)nc(NC3CCCCC3N)nc21]

The title compound was prepared from 5-chloro-N$^1$-(2-chloro-9-isopropyl-9H-purin-6-yl)benzene-1,3-diamine (100 mg, 0.21 mmol) and cis-1,2-cyclohexanediamine (169 mg, 1.2 mmol) by following the procedure for compound 1. Yield: 43 mg (35%) of 14 as brown solid. mp 115-117° C.; $^1$H NMR (399 MHz, CDCl$_3$) δ 7.55 (s, 2H), 7.40 (s, 1H), 6.92 (s, 1H), 6.35 (t, J=1.9 Hz, 1H), 5.23 (d, J=7.9 Hz, 1H), 4.63 (h, J=6.8 Hz, 1H), 4.09 (tt, J=7.9, 3.8 Hz, 1H), 3.75 (s, 2H), 3.25 (dt, J=6.9, 3.7 Hz, 1H), 1.84-1.58 (m, 8H), 1.53 (d, J=6.8 Hz, 6H), 1.45 (s, 2H); HRMS (ESI) m/z calcd for C$_{20}$H$_{27}$ClN$_8$ (M+H)$^+$, 415.2120; found, 415.2120.

u. Synthesis of Racemic N-cis(3-((2-((2-aminocyclohexyl)amino)-9-isopropyl-9H-purin-6-yl)amino)-5-chlorophenyl)acetamide (15)

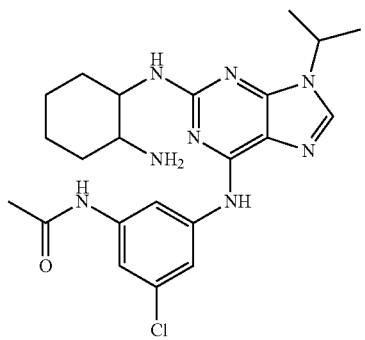 [SMILES: CC(=O)Nc1cc(Cl)cc(Nc2nc(NC3CCCCC3N)nc3c2ncn3C(C)C)c1]

The title compound was prepared from N-(3-chloro-5-((2-chloro-9-isopropyl-9H-purin-6-yl)amino)phenyl)acetamide (60 mg, 0.15 mmol) and cis-1,2-cyclohexanediamine (90 mg, 0.78 mmol) by following the procedure for compound 1. Yield: 25 mg (35%) of 15 as a solid. mp 142-144° C.; $^1$H NMR (399 MHz, CDCl$_3$) δ 7.98 (br s, 1H), 7.95 (s, 1H), 7.78 (s, 1H), 7.58-7.55 (m, 2H), 7.40 (s, 1H), 5.24 (d, J=8.1 Hz, 1H), 4.64 (p, J=6.8 Hz, 1H), 4.20-4.12 (m, 1H), 3.24-3.16 (m, 1H), 2.14 (s, 3H), 1.84-1.58 (m, 8H), 1.54 (d, J=6.8 Hz, 6H), 1.47-1.42 (m, 2H); HRMS (ESI) m/z calcd for C$_{22}$H$_{29}$ClN$_8$O (M+H)$^+$, 457.2226; found, 457.2227.

v. Synthesis of N$^6$-(3-amino-5-chlorophenyl)-N$^2$-((1R,2S)-2-aminocyclohexyl)-9-isopropyl-9H-purine-2,6-diamine (16)

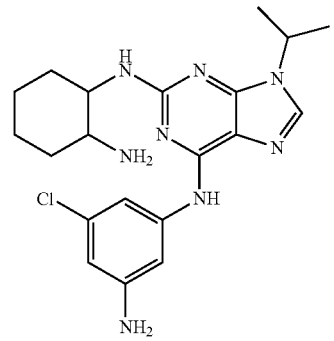

The title compound was prepared from 5-chloro-N$^1$-(2-chloro-9-isopropyl-9H-purin-6-yl)benzene-1,3-diamine and tert-butyl ((1S,2R)-2-aminocyclohexyl)carbamate by following the procedure for compound 9. Yield 2.3%, brown solid. mp 120-122° C.; [α]$_D^{24}$=+3.5° (c 0.18, CHCl$_3$); $^1$H NMR (399 MHz, CDCl$_3$) δ 7.57 (s, 1H), 7.49 (s, 1H), 7.38 (s, 1H), 6.96 (s, 1H), 6.37 (s, 1H), 5.28 (d, J=7.9 Hz, 1H), 4.70-4.61 (m, 1H), 4.14-4.05 (m, 1H), 3.78 (s, 2H), 3.30-3.25 (m, 1H), 1.90-1.79 (m, 2H), 1.78-1.58 (m, 6H), 1.55 (d, J=6.7 Hz 6H), 1.50-1.41 (m, 2H); HRMS (ESI) m/z calcd for C$_{20}$H$_{27}$ClN$_8$ (M+H)$^+$, 415.2120; found, 415.2119.

w. Synthesis of N$^6$-(3-amino-5-chlorophenyl)-N$^2$-((1S,2R)-2-aminocyclohexyl)-9-isopropyl-9H-purine-2,6-diamine (17)

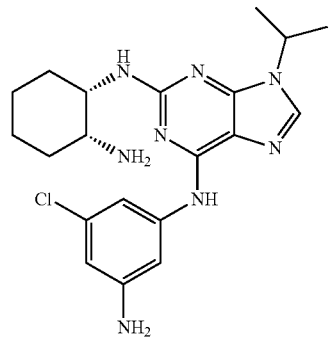

The title compound was prepared from 5-chloro-N$^1$-(2-chloro-9-isopropyl-9H-purin-6-yl)benzene-1,3-diamine and tert-butyl ((1R,2S)-2-aminocyclohexyl)carbamate by following the procedure for compound 9. Yield 3%, brown solid. mp 113-116° C.; [α]$_D^{24}$=−5.2° (c 0.2, CHCl$_3$); $^1$H NMR (399 MHz, CDCl$_3$) δ 7.62 (br s, J=4.7 Hz, 1H), 7.56 (s, 1H), 7.41 (s, 1H), 6.93 (s, 1H), 6.37 (td, J=1.9, 0.8 Hz, 1H), 5.26 (d, J=7.8 Hz, 1H), 4.73-4.60 (m, 1H), 4.10 (tt, J=8.0, 3.9 Hz, 1H), 3.78 (s, 2H), 3.26 (dt, J=6.7, 3.5 Hz, 1H), 1.90-1.58 (m, 8H), 1.55 (dd, J=6.7, 1.0 Hz, 6H), 1.50-1.38 (m, 2H); HRMS (ESI) m/z calcd for $C_{20}H_{27}ClN_8$ (M+H)$^+$, 415.2120; found, 415.2119.

x. Synthesis of N-(3-((2-(((1R,2S)-2-aminocyclohexyl)amino)-9-isopropyl-9H-purin-6-yl)amino)-5-chlorophenyl)acetamide (18)

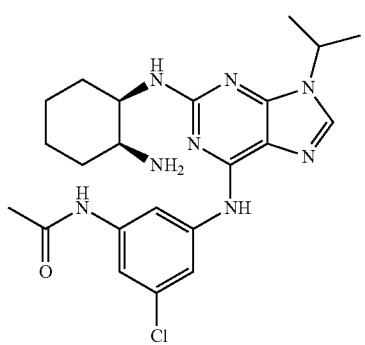 [SMILES: CC(=O)Nc1cc(Cl)cc(Nc2nc(N[C@@H]3CCCC[C@@H]3N)nc3c2ncn3C(C)C)c1]

The title compound was prepared from N-(3-chloro-5-((2-chloro-9-isopropyl-9H-purin-6-yl)amino)phenyl)acetamide and tert-butyl ((1S,2R)-2-aminocyclohexyl)carbamate by following the procedure for compound 9. Yield 2.5%, brown solid. mp=145-146° C.; $[\alpha]_D^{24}$=+1.6° (c 0.25, CHCl$_3$); $^1$H NMR (399 MHz, CDCl$_3$) δ 8.36 (s, 1H), 7.96 (s, 2H), 7.58 (s, 1H), 7.49 (s, 1H), 7.43 (s, 1H), 5.39 (s, 1H), 4.64 (p, J=6.8 Hz, 1H), 4.17 (s, 1H), 3.25-3.20 (m, 1H), 2.12 (s, 3H), 1.73-1.65 (m, 3H), 1.63-1.57 (m, 3H), 1.56 (d, J=6.8 Hz, 6H), 1.50-1.40 (m, 2H); HRMS (ESI) m/z calcd for $C_{22}H_{29}ClN_8O$ (M+H)$^+$, 457.2226; found, 457.2224.

y. Synthesis of N-(3-((2-(((1S,2R)-2-aminocyclohexyl)amino)-9-isopropyl-9H-purin-6-yl)amino)-5-chlorophenyl)acetamide (19)

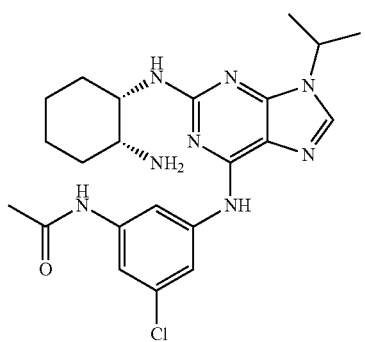

The title compound was prepared from N-(3-chloro-5-((2-chloro-9-isopropyl-9H-purin-6-yl)amino)phenyl)acetamide and tert-butyl ((1R,2S)-2-aminocyclohexyl)carbamate by following the procedure for compound 9. Yield 3.3%, brown solid. mp=148-150° C.; $[\alpha]_D^{24}$=−2.2° (c 0.35, CHCl$_3$); $^1$H NMR (399 MHz, CDCl$_3$) δ 8.14 (s, 1H), 7.92 (s, 1H), 7.88 (s, 1H), 7.59 (s, 1H), 7.56 (s, 1H), 7.40 (s, 1H), 5.29 (d, J=8.0 Hz, 1H), 4.66 (p, J=6.8 Hz, 1H), 4.17 (s, 1H), 3.24-3.18 (m, 1H), 2.13 (s, 3H), 1.74-1.67 (m, 3H), 1.64- 1.56 (m, 3H), 1.55 (d, J=6.8 Hz, 6H), 1.50-1.41 (m, 2H); HRMS (ESI) m/z calcd for $C_{22}H_{29}ClN_8O$ (M+H)$^+$, 457.2226; found, 457.2225.

z. Synthesis of N$^6$-(3-amino-5-chlorophenyl)-N$^2$-((1S,2)-2-aminocyclohexyl)-9-isopropyl-9H-purine-2,6-diamine (20)

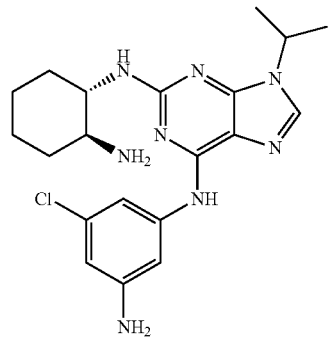 [SMILES: CC(C)n1cnc2c(Nc3cc(N)cc(Cl)c3)nc(N[C@H]3CCCC[C@@H]3N)nc21]

The title compound was prepared from 5-chloro-N$^1$-(2-chloro-9-isopropyl-9H-purin-6-yl)benzene-1,3-diamine (169 mg, 0.500 mmol) and (1S,2S)-cyclohexane-1,2-diamine (171 mg, 1.50 mmol) by following the procedure for compound 1. Yield: 103 mg (50%) of 20 as an off white solid. mp 142-144° C.; $[\alpha]_D^{24}$=26.8° (c 1.0, MeOH); $^1$H NMR (399 MHz, DMSO-d$_6$) δ 9.19 (s, 1H), 7.91 (s, 1H), 7.61-6.80 (m, 2H), 6.38 (s, 1H), 6.21 (t, J=1.9 Hz, 1H), 5.19 (s, 2H), 4.54 (hept, J=6.9 Hz, 1H), 3.49 (q, J=11.3 Hz, 1H), 2.64-2.50 (m, 1H), 2.01 (d, J=12.2 Hz, 1H), 1.88-1.77 (m, 1H), 1.62 (d, J=10.0 Hz, 2H), 1.45 (d, J=6.7 Hz, 6H), 1.39-1.01 (m, 4H); $^{13}$C NMR (75 MHz, CD$_3$OD) δ 160.8, 153.3, 152.5, 150.8, 142.7, 137.4, 135.6, 115.2, 110.3, 110.1, 105.3, 58.0, 55.9, 47.9, 34.5, 33.3, 26.3, 25.9, 22.6, 22.6; HRMS (ESI) m/z calcd for $C_{20}H_{27}ClN_8$ (M+H)$^+$, 415.2120; found, 415.2119.

aa. Synthesis of N$^6$-(3-amino-5-chlorophenyl)-N$^2$-((1R,2R)-2-aminocyclohexyl)-9-isopropyl-9H-purine-2,6-diamine (21)

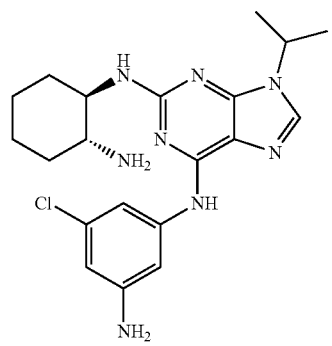 [SMILES: CC(C)n1cnc2c(Nc3cc(N)cc(Cl)c3)nc(N[C@@H]3CCCC[C@H]3N)nc21]

The title compound was prepared from 5-chloro-N$^1$-(2-chloro-9-isopropyl-9H-purin-6-yl)benzene-1,3-diamine (169 mg, 0.500 mmol) and (1R,2R)-cyclohexane-1,2-diamine (171 mg, 1.50 mmol) by following the procedure for compound 1. Yield: 114 mg (55%) of 21 as brownish solid. mp 142-144° C.; $[\alpha]_D^{24}$=−31.9° (c 1.0, MeOH); $^1$H NMR (399 MHz, DMSO-d$_6$) δ 9.20 (s, 1H), 7.91 (s, 1H), 7.61-6.80 (m, 2H), 6.39 (s, 1H), 6.21 (t, J=2.0 Hz, 1H), 5.20 (s, 2H), 4.54 (p, J=6.7 Hz, 1H), 3.60-3.43 (m, 1H), 2.64-2.50 (m, 1H), 2.01 (d, J=12.2 Hz, 1H), 1.88-1.77 (m, 1H), 1.62 (d, J=9.7 Hz, 2H), 1.45 (d, J=6.7 Hz, 6H), 1.39-1.01 (m, 4H); $^{13}$C NMR (75 MHz, CD$_3$OD) δ 160.9, 153.3, 152.5, 150.8, 142.7, 137.3, 135.6, 115.2, 110.4, 110.1, 105.3, 58.2, 55.9, 48.0, 34.6, 33.4, 26.3, 26.0, 22.6, 22.6; HRMS (ESI) m/z calcd for C$_{20}$H$_{27}$ClN$_8$ (M+H)$^+$, 415.2120; found, 415.2120.

bb. Synthesis of (S)—N$^6$-(3-amino-5-chlorophenyl)-9-isopropyl-N$^2$-(piperidin-3-yl)-9H-purine-2,6-diamine (22)

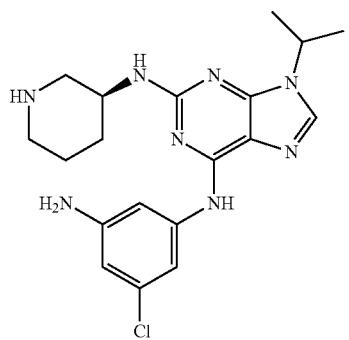 [SMILES: CC(C)n1cnc2c(Nc3cc(N)cc(Cl)c3)nc(N[C@H]3CCCNC3)nc21]

The title compound was prepared from 5-chloro-N$^1$-(2-chloro-9-isopropyl-9H-purin-6-yl)benzene-1,3-diamine (102 mg, 0.302 mmol) and (S)-piperidin-3-amine dihydrochloride (105 mg, 0.604 mmol) by following the procedure for compound 1. Yield: 45 mg (37%) of 22 as an off white solid. mp 104-106° C.; [α]$_D^{24}$=26.7° (c 1.0, MeOH); $^1$H NMR (399 MHz, DMSO-d$_6$) δ 9.32 (s, 1H), 7.95 (s, 1H), 7.22 (t, J=1.9 Hz, 1H), 7.04 (t, J=1.9 Hz, 1H), 6.21 (t, J=1.9 Hz, 1H), 5.29 (s, 2H), 4.58 (h, J=6.7 Hz, 1H), 4.47 (d, J=9.3 Hz, 1H), 4.40 (d, J=13.1 Hz, 1H), 2.91-2.80 (m, 1H), 2.72-2.58 (m, 4H), 1.90-1.81 (m, 1H), 1.70-1.61 (m, 1H), 1.47 (d, J=6.8 Hz, 6H), 1.42-1.36 (m, 1H), 1.30-1.16 (m, 1H); $^{13}$C NMR (75 MHz, CD$_3$OD) δ 160.0, 152.8, 152.7, 150.7, 142.8, 137.8, 137.6, 135.6, 114.8, 110.3, 105.2, 57.6, 52.1, 48.1, 46.0, 33.3, 24.4, 22.5; HRMS (ESI) m/z calcd for C$_{19}$H$_{25}$ClN$_8$ (M+H)$^+$, 401.1964; found, 401.1963.

cc. Synthesis of (R)—N$^6$-(3-amino-5-chlorophenyl)-9-isopropyl-N$^2$-(piperidin-3-yl)-9H-purine-2,6-diamine (23)

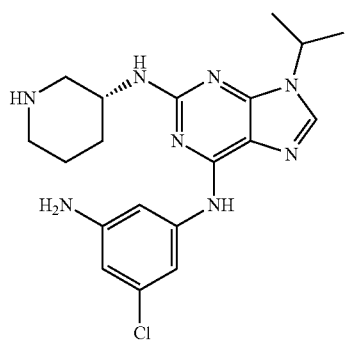 [SMILES: CC(C)n1cnc2c(Nc3cc(N)cc(Cl)c3)nc(N[C@@H]3CCCNC3)nc21]

The title compound was prepared from 5-chloro-N$^1$-(2-chloro-9-isopropyl-9H-purin-6-yl)benzene-1,3-diamine (97 mg, 0.29 mmol) and (R)-piperidin-3-amine dihydrochloride (100 mg, 0.58 mmol) by following the procedure for compound 1. Yield: 30 mg (26%) of 23 as an off white solid. mp 104-106° C.; [α]$_D^{24}$=−31.9° (c 1.0, MeOH); $^1$H NMR (399 MHz, DMSO-d$_6$) δ ppm (s, 1H), 7.95 (s, 1H), 7.22 (t, J=1.9 Hz, 1H), 7.04 (t, J=1.9 Hz, 1H), 6.21 (t, J=2.0 Hz, 1H), 5.29 (s, 2H), 4.59 (p, J=6.7 Hz, 1H), 4.47 (d, J=9.8 Hz, 1H), 4.41 (d, J=13.0 Hz, 1H), 2.83 (t, J=12.1 Hz, 1H), 2.70-2.49 (m, 4H), 1.85 (d, J=10.8 Hz, 1H), 1.65 (d, J=13.3 Hz, 1H), 1.46 (d, J=6.8 Hz, 6H), 1.43-1.32 (m, 1H), 1.21 (d, J=10.2 Hz, 1H); $^{13}$C NMR (75 MHz, CDCl$_3$) δ 158.7, 151.6, 151.4, 147.9, 141.3, 135.5, 134.6, 114.2, 109.8, 109.1, 104.1, 52.8, 47.6, 46.4, 44.9, 34.1, 23.5, 22.5; HRMS (ESI) m/z calcd for C$_{19}$H$_{25}$ClN$_8$ (M+H)$^+$, 401.1964; found, 401.1963.

dd. Synthesis of (S)—N$^6$-(3-amino-5-chlorophenyl)-9-isopropyl-N$^2$-(pyrrolidin-3-yl)-9H-purine-2,6-diamine (24)

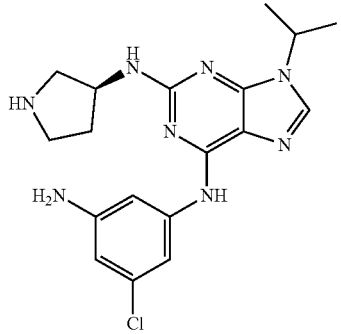 [SMILES: CC(C)n1cnc2c(Nc3cc(N)cc(Cl)c3)nc(N[C@H]3CCNC3)nc21]

The title compound was prepared from 5-chloro-N$^1$-(2-chloro-9-isopropyl-9H-purin-6-yl)benzene-1,3-diamine (150 mg, 0.449 mmol) and (S)-pyrrolidin-3-amine dihydrochloride (143 mg, 0.898 mmol) by following the procedure for compound 1. Yield: 63 mg (36%) of 24 as an off white solid. mp 143-145° C.; [α]$_D^{24}$=4.6° (c 1.0, MeOH); $^1$H NMR (399 MHz, DMSO-d$_6$) δ 9.23 (s, 1H), 8.02-7.80 (m, 1H), 7.42 (s, 1H), 7.17 (t, J=1.9 Hz, 1H), 6.21 (q, J=1.7 Hz, 1H), 5.23 (s, 2H), 4.60 (p, J=6.6 Hz, 1H), 3.66 (dd, J=11.0, 6.0 Hz, 2H), 3.55 (t, J=5.5 Hz, 2H), 3.22 (d, J=10.5 Hz, 1H), 2.03 (dt, J=13.2, 6.4 Hz, 1H), 1.69 (dq, J=12.6, 6.3 Hz, 1H), 1.49 (dd, J=6.8, 1.4 Hz, 6H); $^{13}$C NMR (75 MHz, CD$_3$OD) δ 158.8, 152.8, 152.7, 150.6, 143.1, 136.9, 135.6, 114.3, 109.9, 109.8, 104.7, 55.7, 52.1, 48.0, 46.4, 34.9, 22.5; HRMS (ESI) m/z calcd for C$_{18}$H$_{23}$ClN$_8$ (M+H)$^+$, 387.1807; found, 387.1806.

ee. Synthesis of (R)—N$^6$-(3-amino-5-chlorophenyl)-9-isopropyl-N$^2$-(pyrrolidin-3-yl)-9H-purine-2,6-diamine (25)

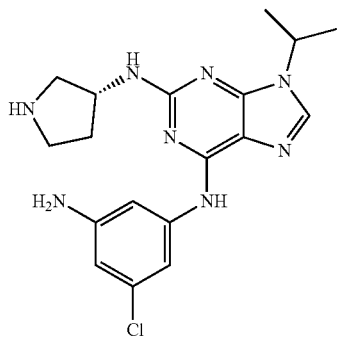 [SMILES: CC(C)n1cnc2c(Nc3cc(N)cc(Cl)c3)nc(N[C@@H]3CCNC3)nc21]

The title compound was prepared from 5-chloro-$N^1$-(2-chloro-9-isopropyl-9H-purin-6-yl)benzene-1,3-diamine (150 mg, 0.449 mmol) and (R)-pyrrolidin-3-amine dihydrochloride (143 mg, 0.898 mmol) by following the procedure for compound 1. Yield: 65 mg (37%) of 25 as an off white solid. mp 145-147° C.; $[\alpha]_D^{24}$=−4.6° (c 1.0, MeOH); $^1$H NMR (399 MHz, DMSO-$d_6$) δ 9.24 (s, 1H), 7.92 (d, J=2.2 Hz, 1H), 7.42 (s, 1H), 7.17 (t, J=1.9 Hz, 1H), 6.21 (t, J=2.0 Hz, 1H), 5.23 (s, 2H), 4.60 (p, J=6.8 Hz, 1H), 3.74-3.60 (m, 2H), 3.60-3.46 (m, 2H), 3.24 (d, J=11.2 Hz, 1H), 2.04 (dt, J=13.1, 6.4 Hz, 1H), 1.71 (dd, J=12.2, 6.3 Hz, 1H), 1.49 (dd, J=6.8, 1.8 Hz, 6H); $^{13}$C NMR (75 MHz, $CD_3OD$) δ 158.9, 152.8, 152.7, 150.6, 143.2, 136.9, 135.6, 114.3, 109.9, 109.8, 104.7, 55.7, 52.1, 48.0, 46.4, 34.9, 22.5; HRMS (ESI) m/z calcd for $C_{18}H_{23}ClN_8$ $(M+H)^+$, 387.1807; found, 387.1807.

2. In Vitro Kinase Assays

Enzymatic biochemical activities were evaluated in radiometric protein kinase assays (Eurofins, Dundee, Scotland). Kinases are incubated with buffer, substrate and [$\gamma$-$^{33}$P]-ATP (specific activity approx. 500 cpm/pmol, concentration as required). The reaction is initiated by the addition of the MgATP mix. After incubation for 40 minutes at room temperature, the reaction is stopped by the addition of 3% phosphoric acid solution. 10 μL of the reaction is then spotted onto a P30 filtermat and washed three times for 5 minutes in 75 mM phosphoric acid and once in methanol prior to drying and scintillation counting.

All compounds are prepared to 50× final assay concentration in 100% DMSO. Positive control wells contain all components of the reaction with 2% DMSO. Blank wells contain all components of the reaction, with a reference inhibitor replacing the compound of interest. Each kinase is assigned a standard assay concentration of ATP within 20 μM of its apparent KM. Compounds were screened at 1 μM in duplicate or tested at 10 concentrations at half log dilution starting from 10 μM in singlicate. Dose response curves were fitted with four parameter logistic curve to obtain $IC_{50}$ values. The average coefficient of variation (CV) of the conducted assay is 4.4%.

3. Cell-Based Exon-Skipping Reporter Assay

SK-MEL-2/MDM2-Luc stable cells were cultured in MEM medium with Earle's salts and L-glutamine containing 1 mM sodium pyruvate, 10% FCS and 10 mM Hepes and plated at a density of 10,000/well in 96-well plates and incubated overnight at 37° C. in 5% $CO_2$. The following day, cells were treated with serial dilutions of compounds for 4 hours and ONE-Glo™ reagents (Promega) were added to measure the luciferase activity by EnVision™ plate reader. Sudemycin D6 and 0.5% DMSO were used as positive and negative controls, respectively. Relative luminescent units were plotted against corresponding drug concentrations and fitted with a standard four parameter sigmoidal curve with GraphPad Prism™ program.

4. HTS Establishment, Initial Screen, and Hit Validation

The development of a novel luc-MDM2 construct and the exon-skipping luciferase reporter assay was previously reported (Shi et al. (2015) *Pharmacol. Res. Perspect.* 3: e00158). After the successful development of the reporter assay, a screen was implemented using the reporter plasmid with transfections into SK-MEL2. It was determined that the splicing reporter activity showed a strong signal in SK-MEL-2 cells at a constant sudemycin D1 dose of 1 μM at a 4 hour time point. It was also found that the Luc-MDM2 splicing reporter expressed consistent levels of luciferase and could tolerate concentrations of DMSO up to 1% (see FIG. 2A). Next, a HTS assay validation procedure was performed for the Luc-MDM2 reporter in transiently transfected SK-MEL-2 cells using three different sudemycin D1 doses (4 μM for high control, 400 nM for medium control, and DMSO for low control) with 4 h incubations (see FIG. 2B and FIG. 2C). This was performed in a 384-well format with a Wellmate and a Biomek liquid handling system. The HTS procedure was validated by assessment of the plate uniformity and signal variability. The calculated Z' factors were all above 0.5. This assay was then used to screen the St. Jude Bioactive Small Molecule Library (composed of 830 known drugs and 4,359 unique bioactive compounds (Walters et al. (2014) *PLoS One* 9: e91173)) at a single concentration (10 μM) in triplicate (see FIG. 3). 12 'hits' were initially identified from the screen and 8 'hits' were validated and showed a good dose response curve. More interestingly, from this initial screen, two 'hits' having a similar structure were identified.

Figure 2A:
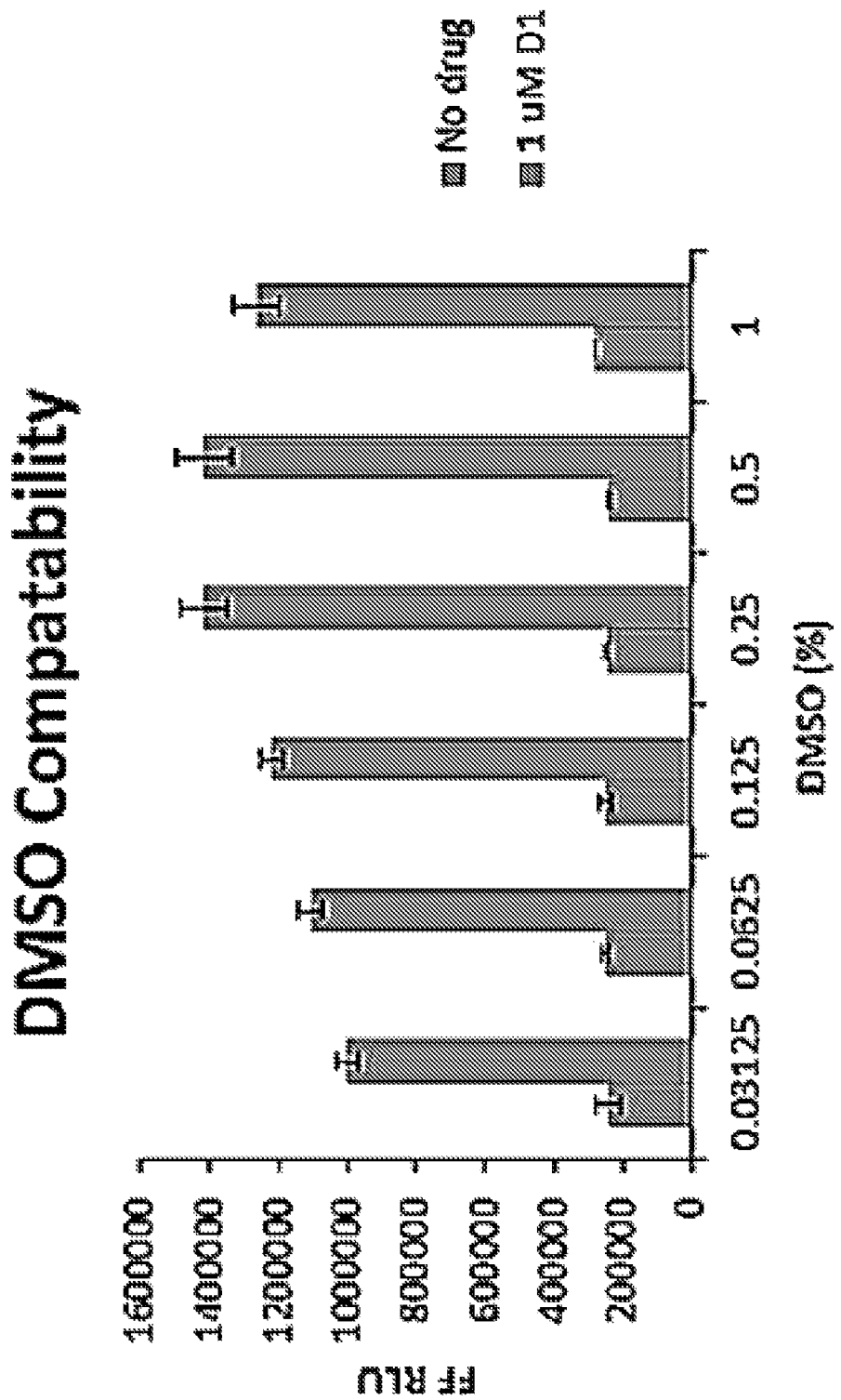
FIG. 2A-C shows representative data pertaining to the HTS validation.

Referring to FIG. 2A, SK-MEL-2 cells were transiently transfected with the Luc-MDM-2 reporter. The transfected cells were then incubated for 4 h with either different concentrations of DMSO alone, or with 1 μM of sudemycin D1 with increasing concentrations of DMSO (to 1%), as shown. The ONE-Glo™ reagent was then added and the luminescent signals were measured on an EnVision® plate reader.

Figure 2B:
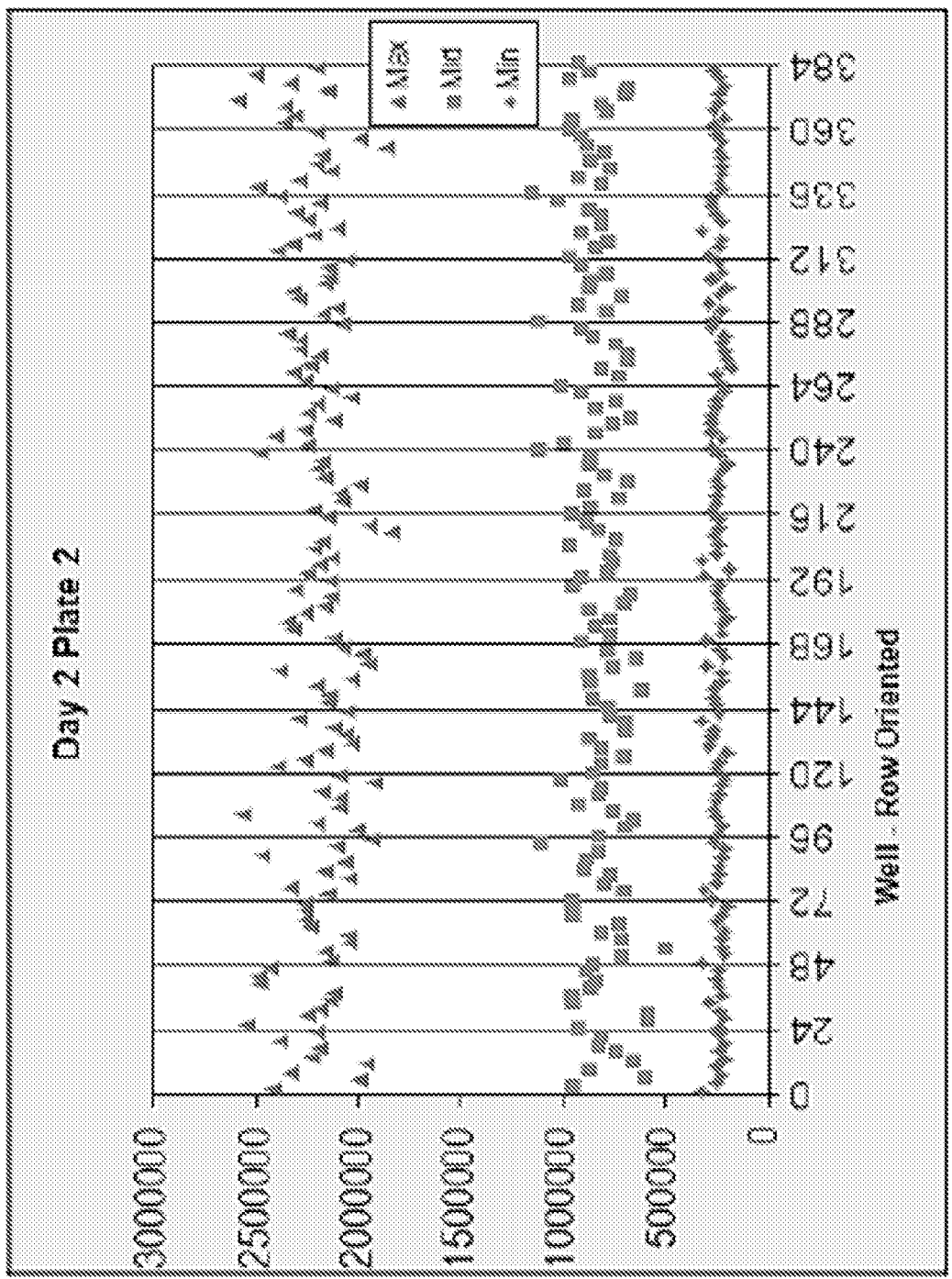
Figure 2C:
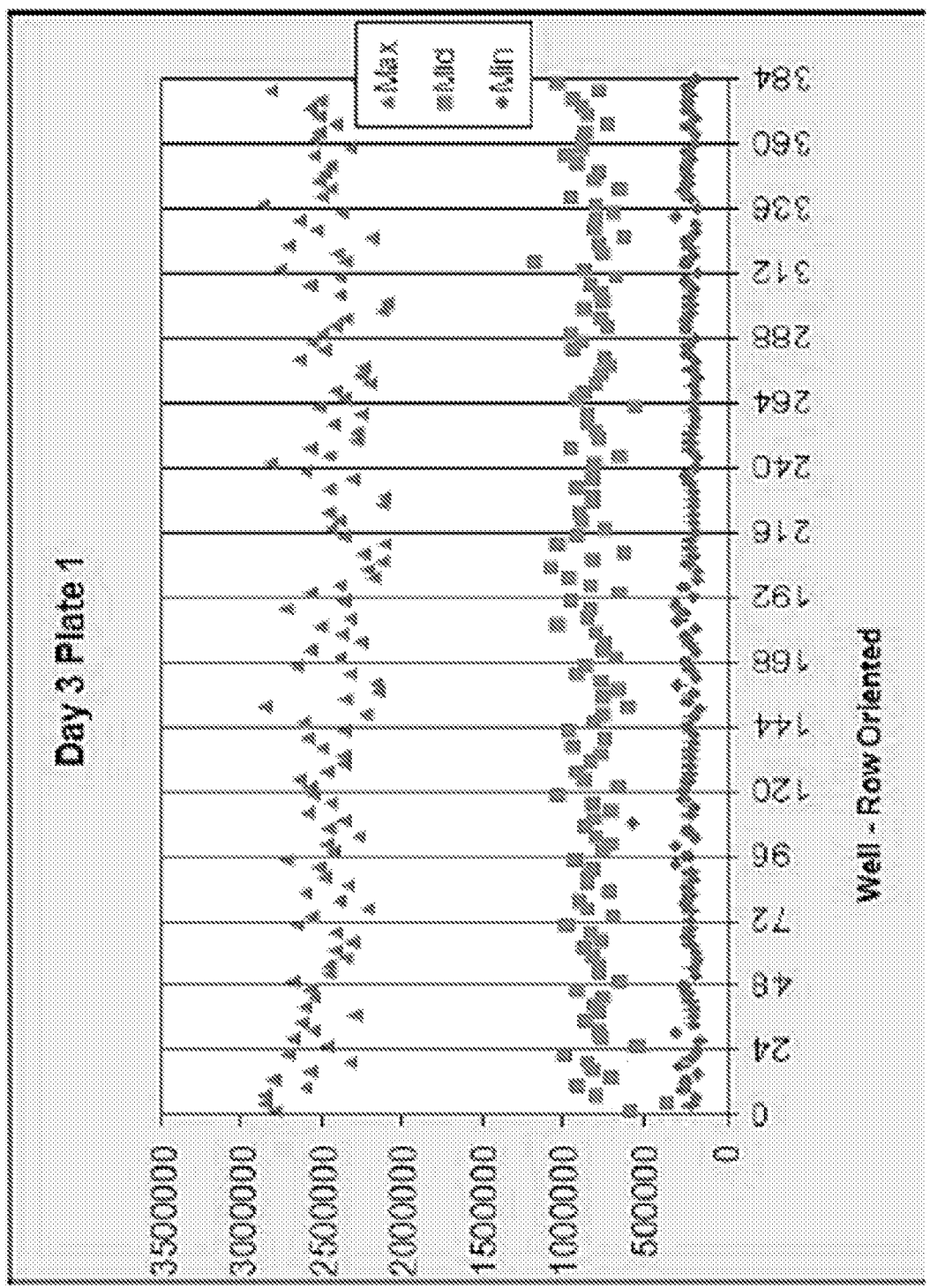

Referring to FIG. 2B and FIG. 2C, scatter plots of the activity values in two HTS validation plates are shown. Cells were transiently transfected with Luc-MDM-2 reporter and treated with 4 μM (Max), 400 nM (Mid) of sudemycin D1, or DMSO (Min).

Figure 3:
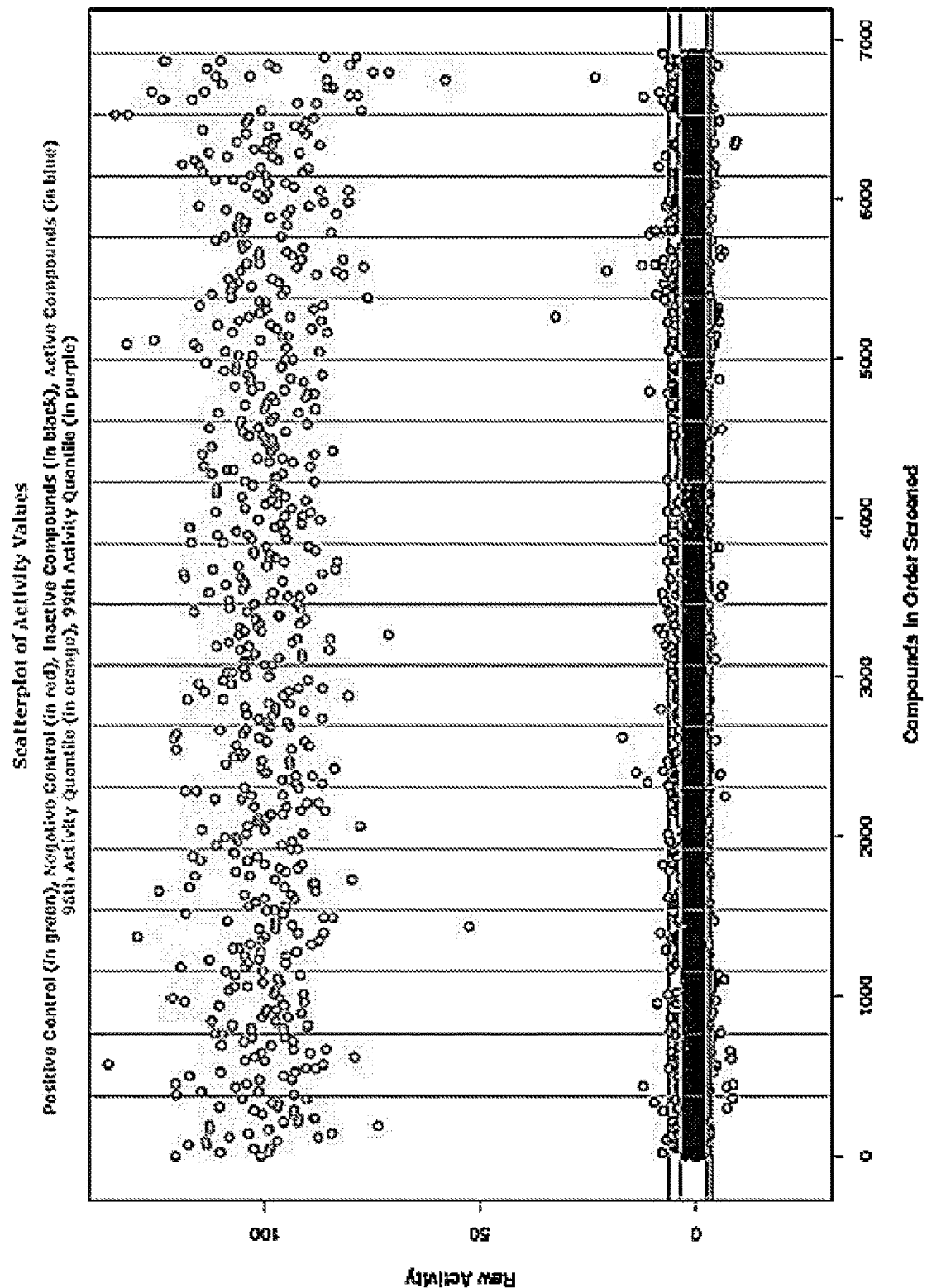
FIG. 3 shows a representative scatter plot of activity values in the HTS.

Referring to FIG. 3, cells were treated with sudemycin D1 as the positive control (4 μM) and DMSO as the negative control (0.1%). The assay was performed in a 384-well format on a Biomek liquid handling system at a single concentration (10 μM), in duplicate, with a 4 h incubation time. The cutoff value for activity was set at 10% of the positive control, which yielded 12 hits, two of which are different batches of the same drug. The SJ Bioactive Library contains many duplicates of the same compounds (Walters et al. (2014) *PLoS One* 9: e91173_.

5. Establishment of a Stable Cell Line Expressing the Luc-MDM2 Reporter and Validation of the HTS Luc-MDM2 Reporter Stable Cell Line Assay In order to facilitate the discovery of new splicing modulator drugs in full scale HTS, a stable SK-MEL-2 cell line expressing the Luc-MDM2 reporter (SK-MEL-2/Luc-MDM2) was established, as previously described (Shi et al. (2015) *Pharmacol. Res. Perspect.* 3: e00158). Without wishing to be bound by theory, the establishment of this stable cell line expressing a triple exon-skipping reporter provides a valuable tool for HTS screening and evaluation of splicing modulators. To validate the assay for HTS in the stable cell line, plate statistics were measured using 10 μM sudemycin D6 as high control and 0.1% DMSO as low control. The mean, standard deviation, coefficient of variance (% CV), Z' factor, signal:background (S/B) metrics were determined and the assay performance parameter was assessed, including plate uniformity, day-to-day, and plate-to-plate variability. Z' factors obtained from the assays were all >0.5, which meet the criteria for HTS assay validation and ensure the screening assay is sufficiently robust. Three sample plate statistics data were as illustrated in Table 3 and FIG. 4A-C.

TABLE 3

| | Statistics | Low Control | High Control |
|---|---|---|---|
| Plate 1 | # of wells | 192 | 192 |
| | Mean | 2798.5 | 57036.0 |
| | S.D. | 1668.9 | 5992.9 |
| | Cv | 60% | 11% |
| | Z' | | 0.58 |
| Plate 2 | # of wells | 192 | 192 |
| | Mean | 2258.5 | 50431.5 |
| | S.D. | 1490.6 | 4741.8 |
| | Cv | 66% | 9% |
| | Z' | | 0.61 |
| Plate 3 | # of wells | 192 | 192 |
| | Mean | 2900.4 | 80639.0 |
| | S.D. | 1330.5 | 11058.3 |
| | Cv | 46% | 14% |
| | Z' | | 0.52 |

Figures 4A, 4B:
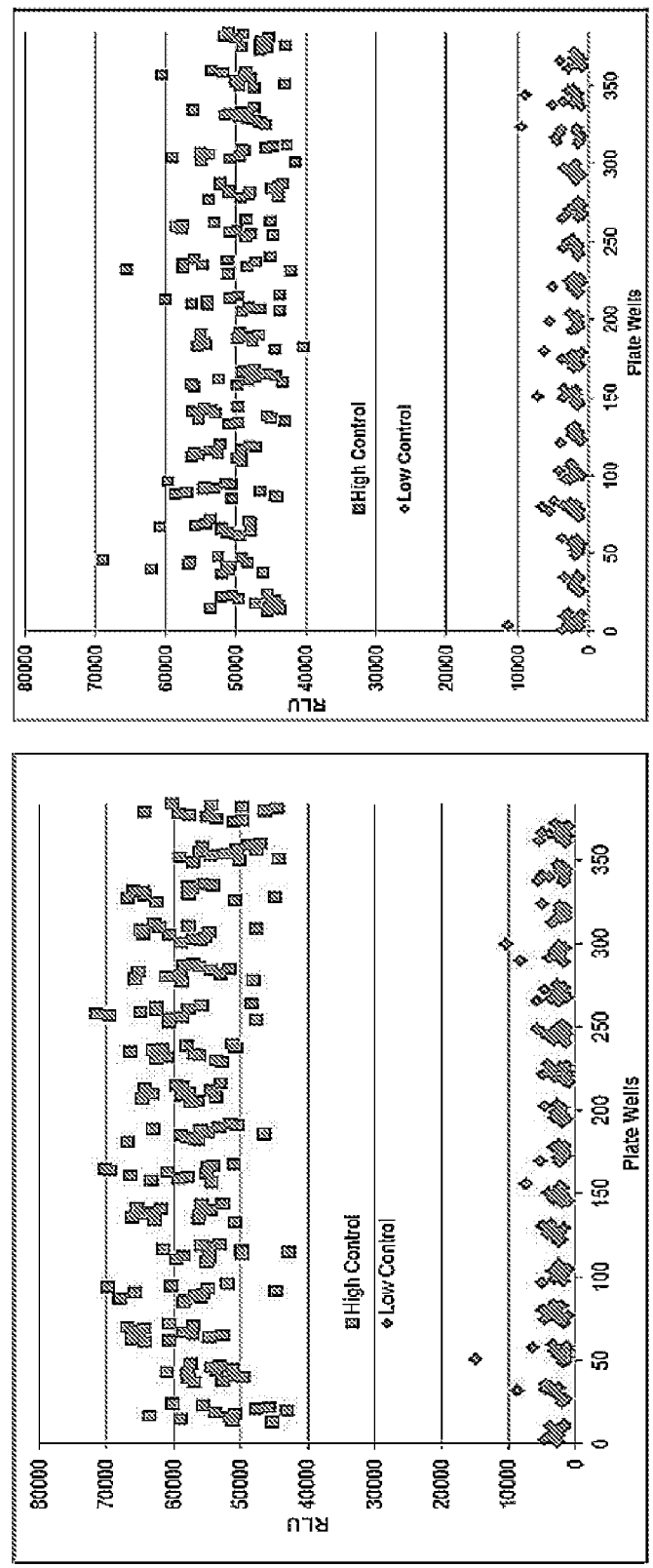
FIG. 4A-C show representative plate statistics in the stable SK-MEL-2/Luc-MDM2 cell line.
Figure 4C:
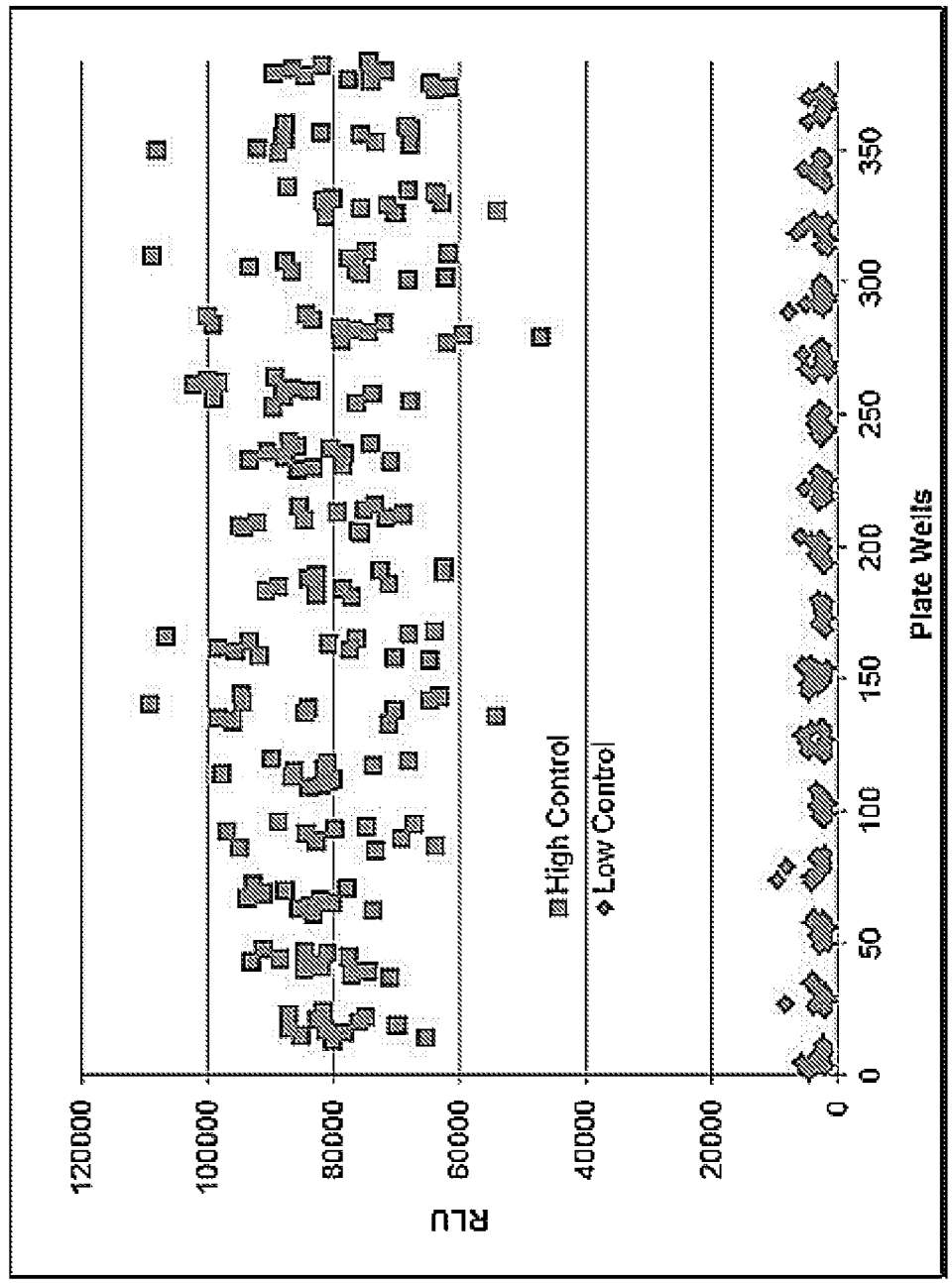

Referring to FIG. 4A-C, cells (4000/well) were seeded in 384-well plates by Wellmate and cultured overnight at 37° C. Cells were dosed either with 10 µM sudemycin D6 as the high control or 0.1% DMSO as the low control and cultured for 4 h. ONE-Glo reagent was added and luminescent signals were measured on an EnVision plate reader. The statistic data summarized in Table 3 was derived from the plates with the scatter plot shown FIG. 4A-C, with Plate 1 corresponding to FIG. 4A, Plate 2 corresponding to FIG. 4B, and Plate 3 corresponding to FIG. 4C.

6. Orthogonal Secondary Assay

Figure 6:
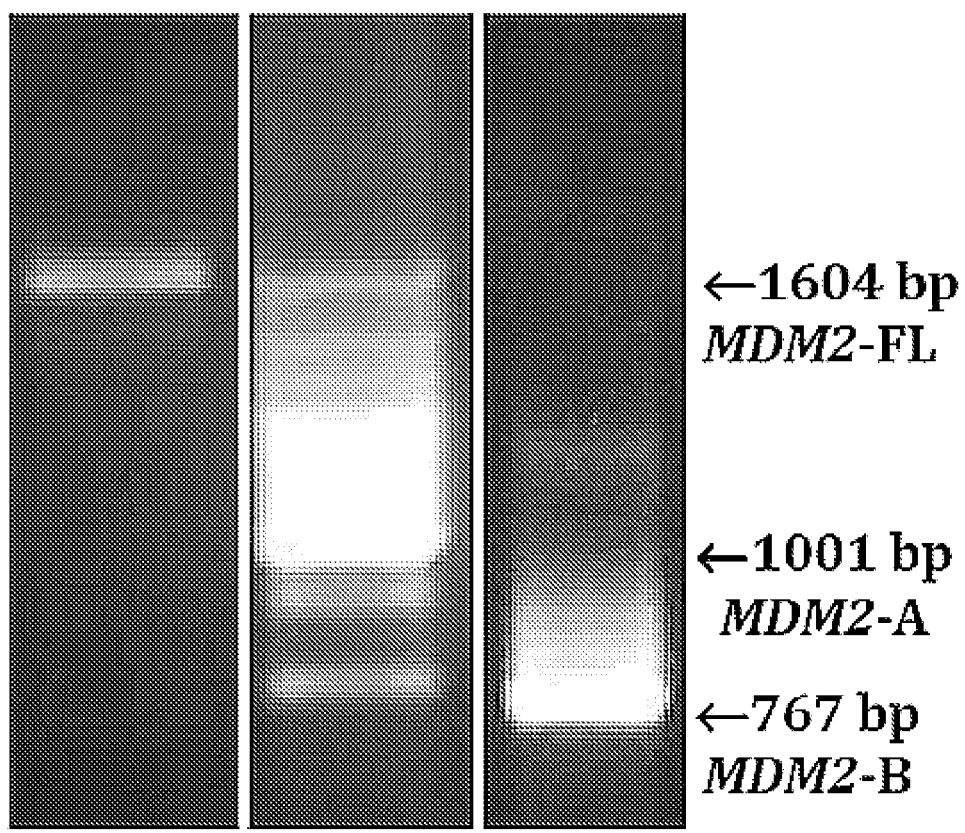
FIG. 6 shows representative data pertaining to the RT-PCR assay performed in Rh-18 cells with cells exposed to 0.5% DMSO, 0.2 µM sudemycin D6, or 10 µM CGP-74514A, respectively, for 8 hours.
Figure 7:
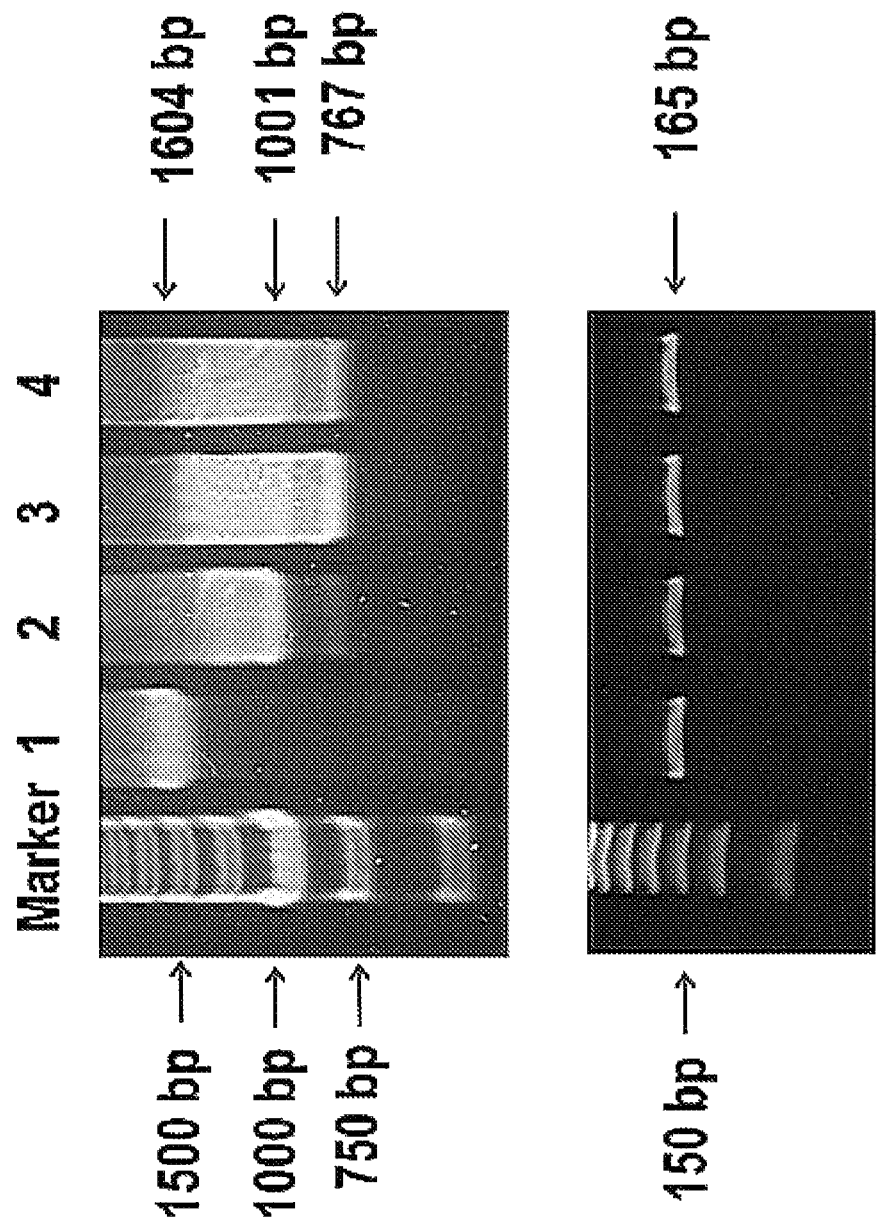
FIG. 7 shows representative data pertaining to the RT-PCR assay performed in Rh-18 cells with cells exposed to 0.5% DMSO (lane 1), 1 µM sudemycin D6 (lane 2), 10 µM compound 14 (lane 3), or 10 µM compound 15 (lane 4), respectively, for 8 hours.

Eight of the initial unconfirmed hits showed an initial dose response (see FIG. 5 below). These hits were then subjected to a confirmatory assay in the Rh-18 MDM2 RT-PCR gel-based assay at a concentration of 10 µM. Two hits showed clear activity in this confirmatory assay, CGP-74514A and Aminopurvalanol A. Sudemycins are used as a positive control in this assay (Fan et al. (2011) ACS Chem. Biol. 6: 582-9; Lagisetti et al. (2013) J. Med. Chem. 56: 10033-44). Rh-18 cells were chosen for the RT-PCR gel-based assay since endogenous MDM2 gene expression is abundant and much higher in Rh-18 than in other cell lines investigated. Two structurally related "hits" showed activity in this secondary screen, which is similar to that of sudemycins but less potent. The results of the confirmation of the most potent of these two hits (CGP-74514A) is shown in FIG. 6 below. FIG. 7 shows confirmation for analogs 14 and 15.

Figure 5:
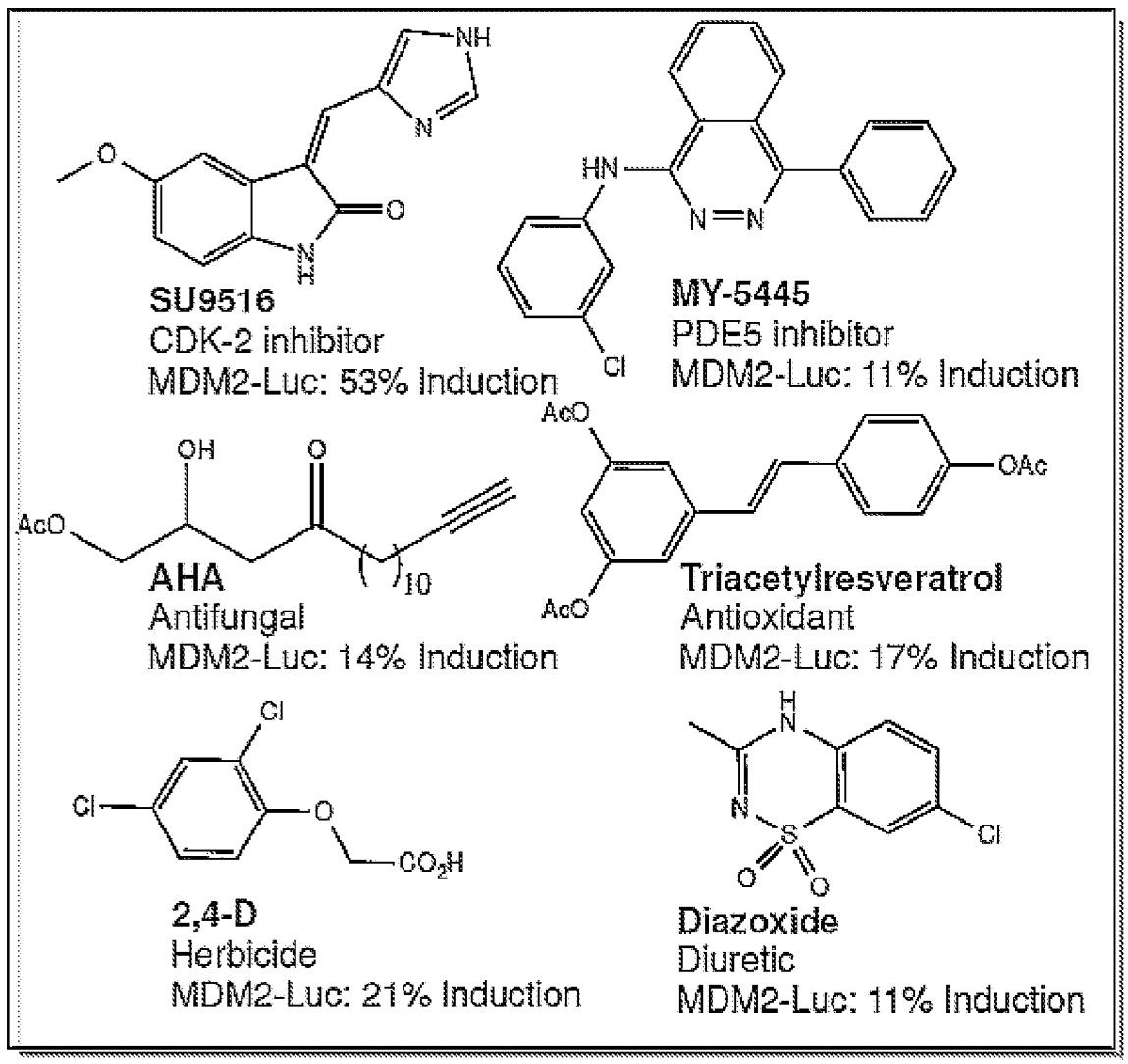
FIG. 5 shows representative structures of the initial hits that did not confirm in both assays.

Referring to FIG. 5, the initial percentage of maximum Luc signal induced at 10 µM of test compound in the screen is shown for the hits that did not confirm.

Referring to FIG. 6, cells were exposed to 0.5% DMSO, 0.2 µM sudemycin D6 or 10 µM CGP-74514A for 8 h. Total RNA was extracted by RNeasy Mini Kit (Qiagen). High capacity RNA-to-cDNA kit (Life technologies) was used to convert the RNA to cDNA. PCR products of full length MDM2 (1604 bp, MDM2-FL) and two major MDM2 splicing alternates (1001 bp, MDM2-A and 767 bp, MDM2-B) are indicated by arrows.

Referring to FIG. 7, cells were exposed to 0.5% DMSO (lane 1), 1 µM sudemycin D6 (lane 2), 10 µM Compound 14 (lane 3), and 10 µM Compound 15 (lane 4) for 8 h. The total RNA was extracted by RNeasy Mini Kit (Qiagen). High capacity RNA-to-cDNA kit (Life technologies) was used to convert the RNA to cDNA. PCR products (in bp) indicated by the arrows. Ubiquitin transcripts (165 bp) in the same cells were used as a control (Fan et al. (2011) ACS Chem. Biol. 6: 582-9).

7. Dose Response Curves for Confirmed Hits

Figure 8B:
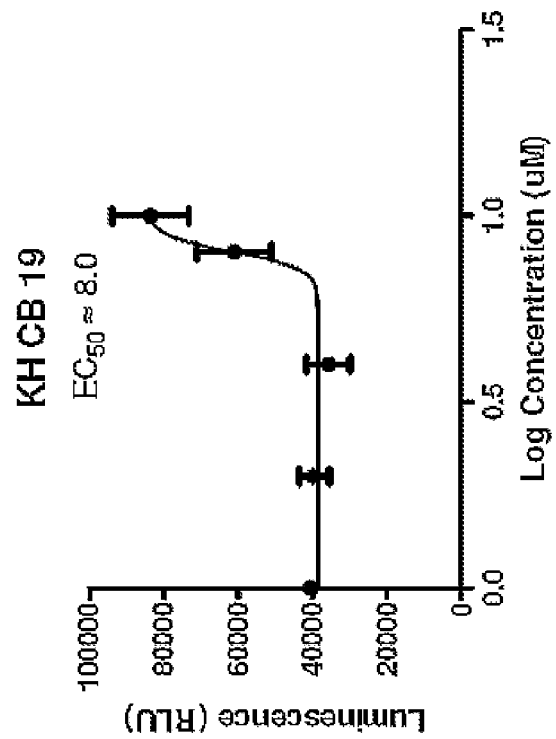
FIG. 8A-X show representative examples of MDM2-Luc Curves and $EC_{50}$ values for the standards and hits.
Figure 8A:
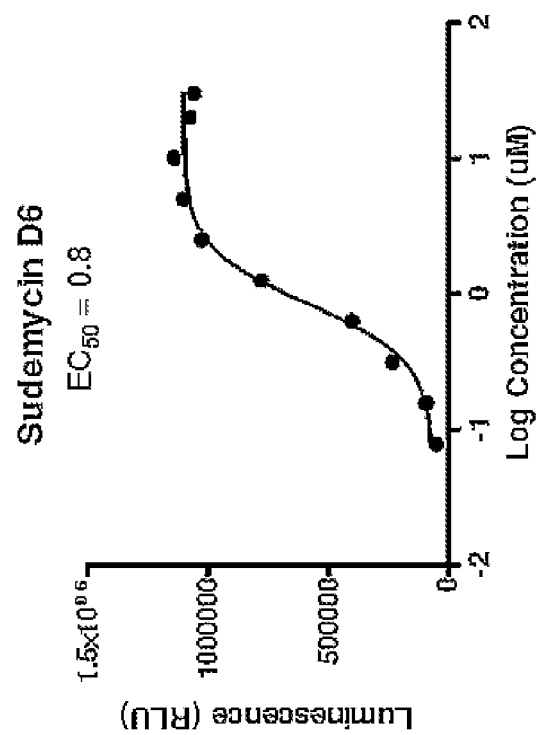
Figure 8C:
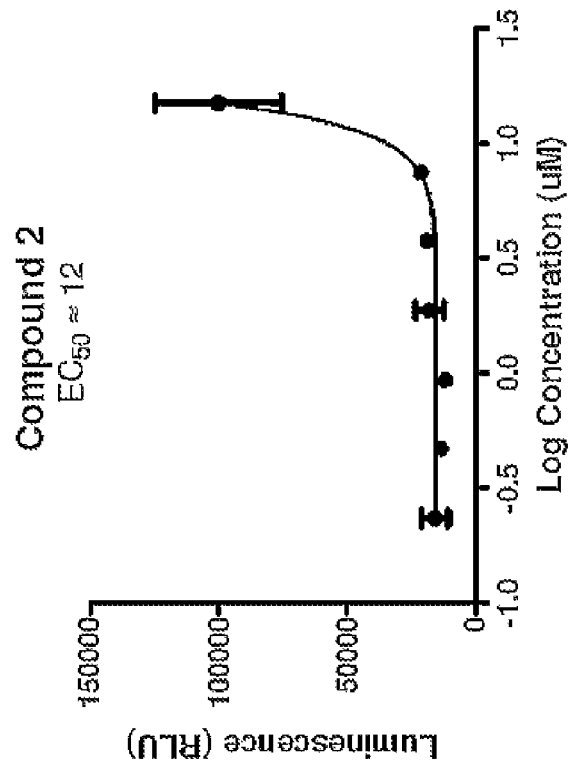
Figure 8D:
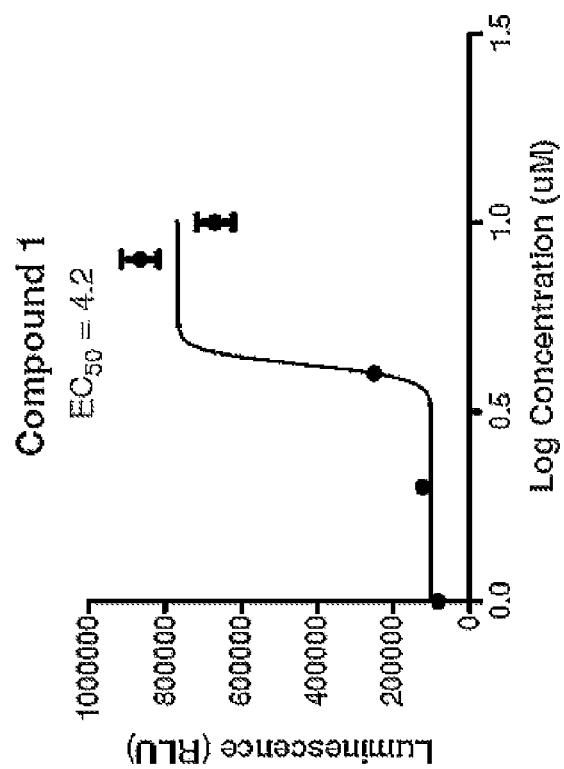
Figure 8F:
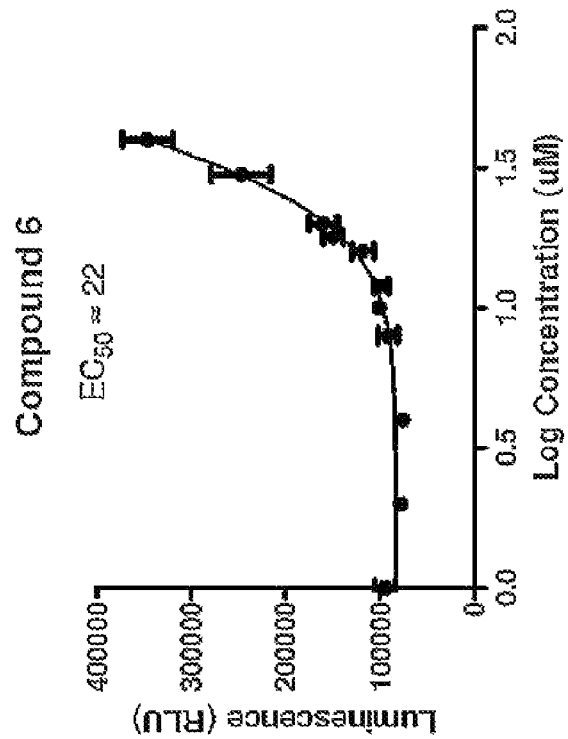
Figure 8E:
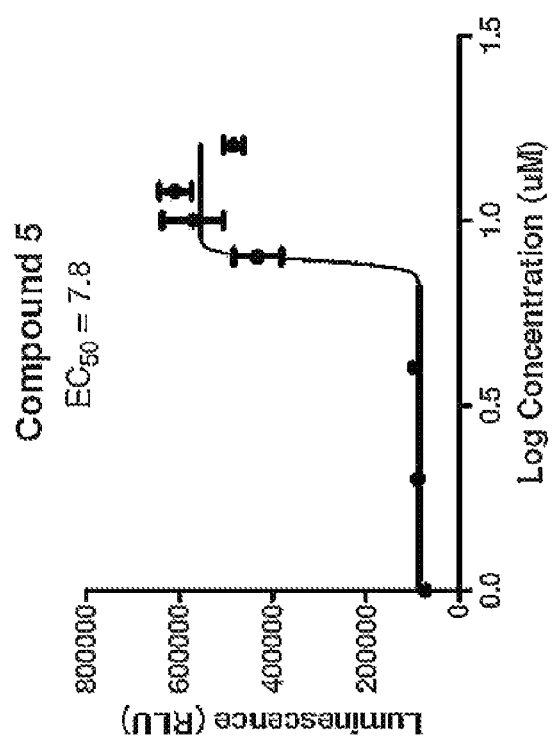
Figure 8H:
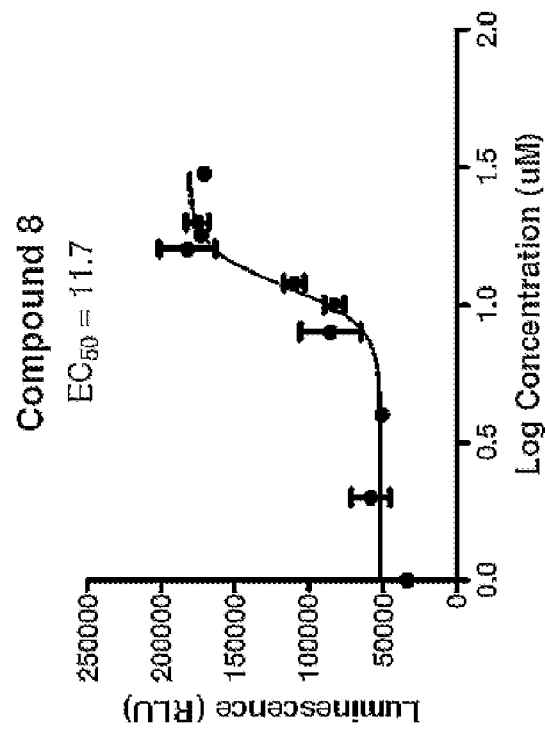
Figure 8G:
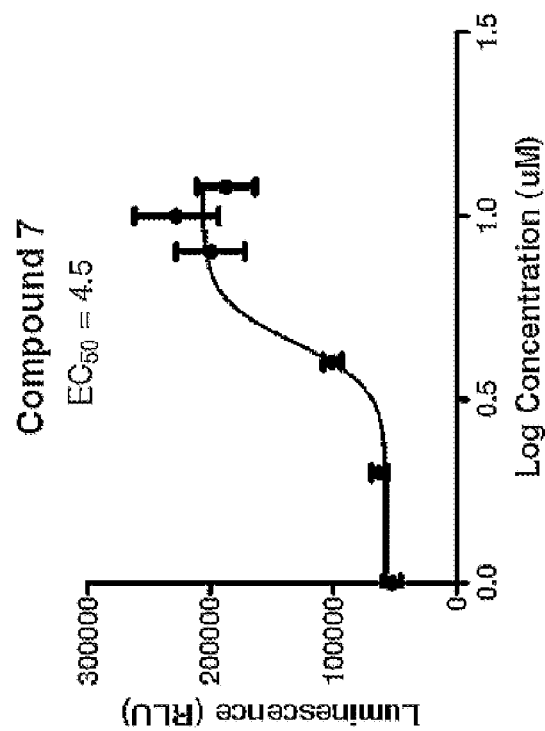
Figure 8J:
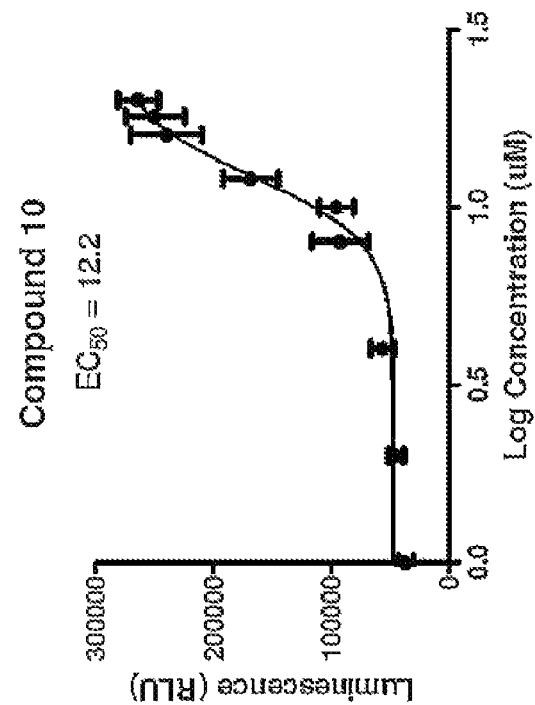
Figure 8I:
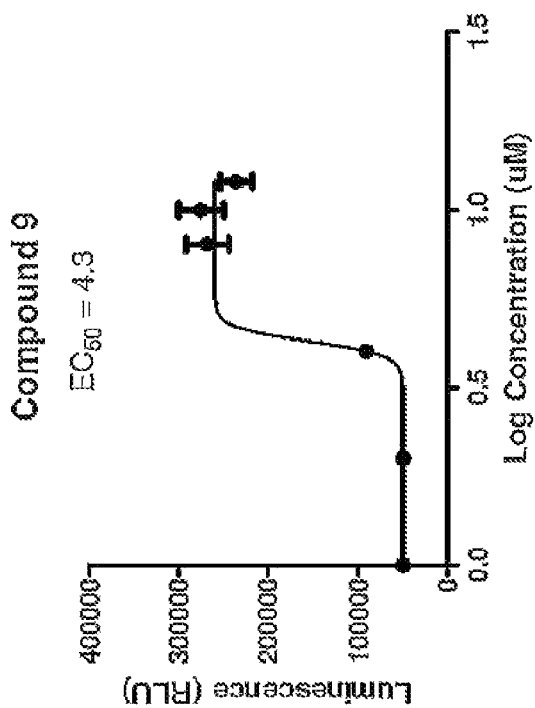
Figure 8L:
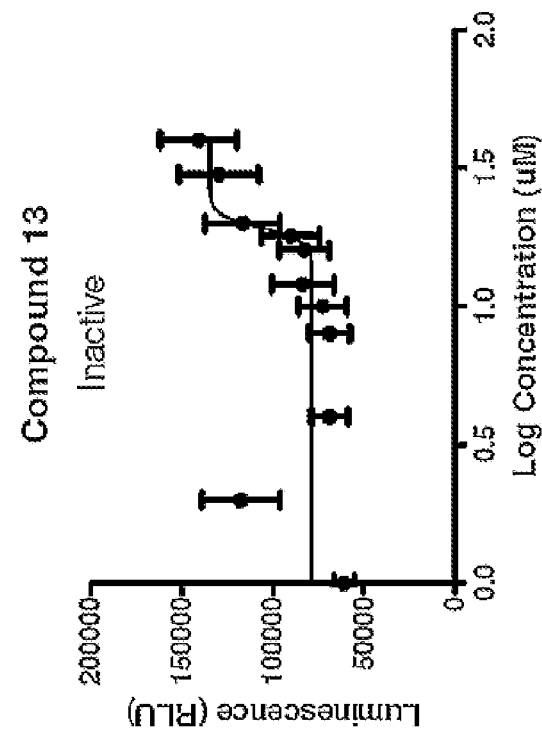
Figure 8K:
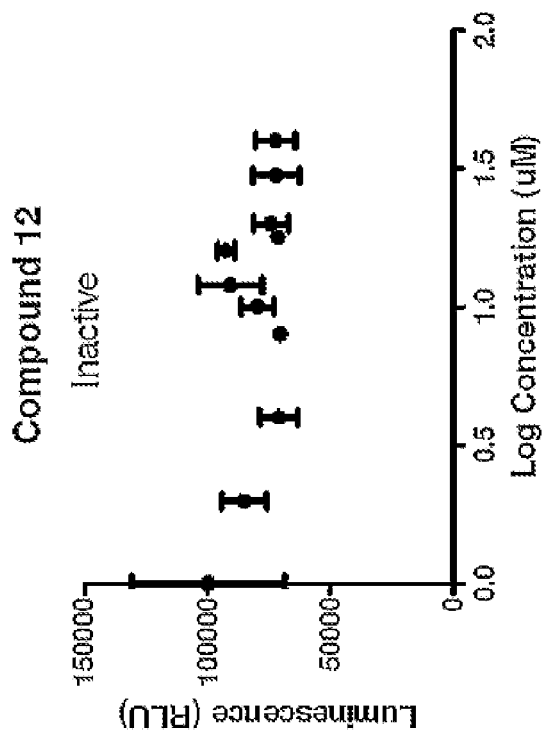
Figure 8N:
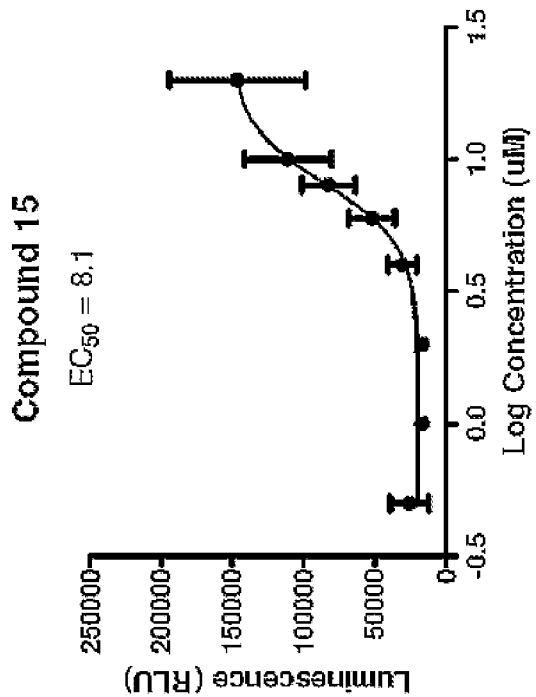
Figure 8M:
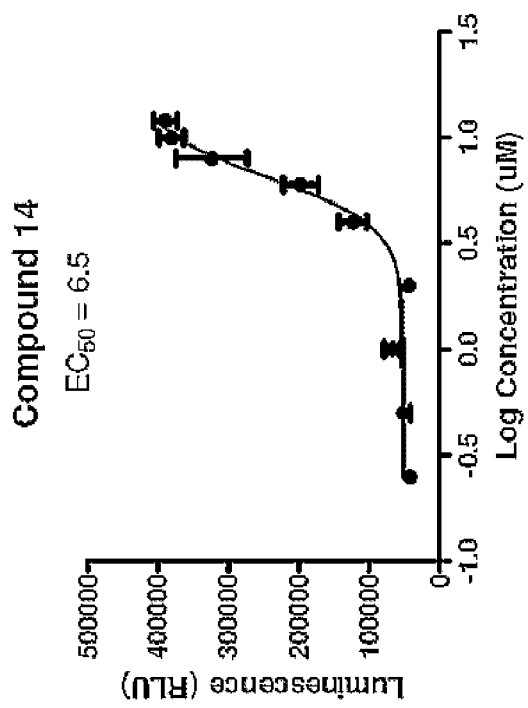
Figure 8P:
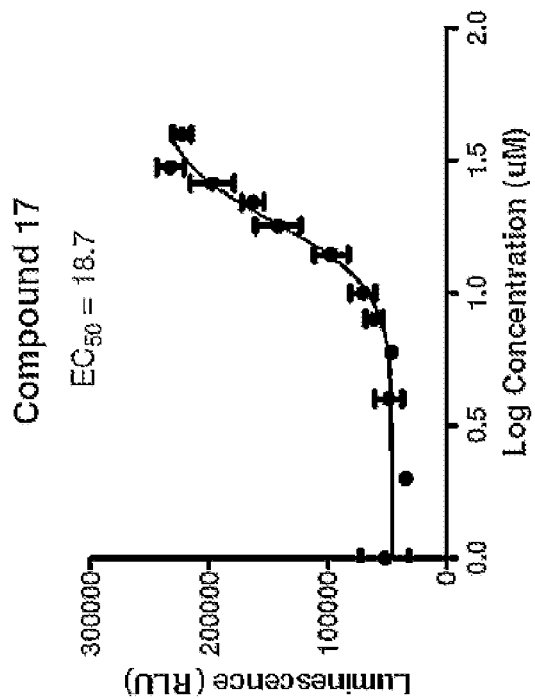
Figure 8O:
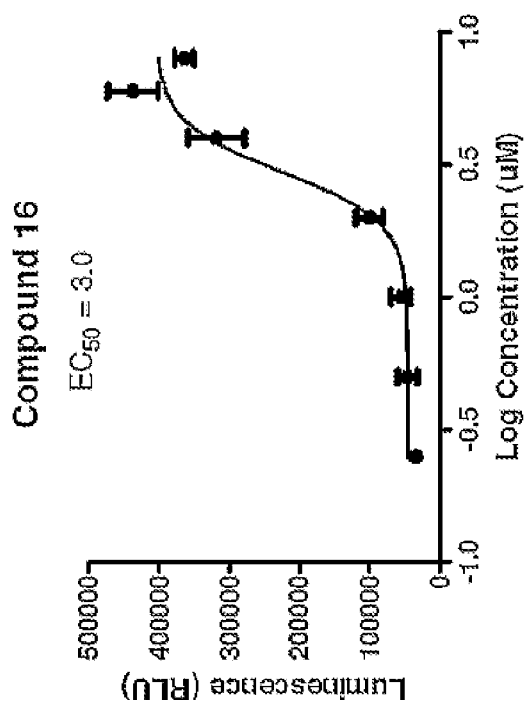
Figures 8Q, 8R:
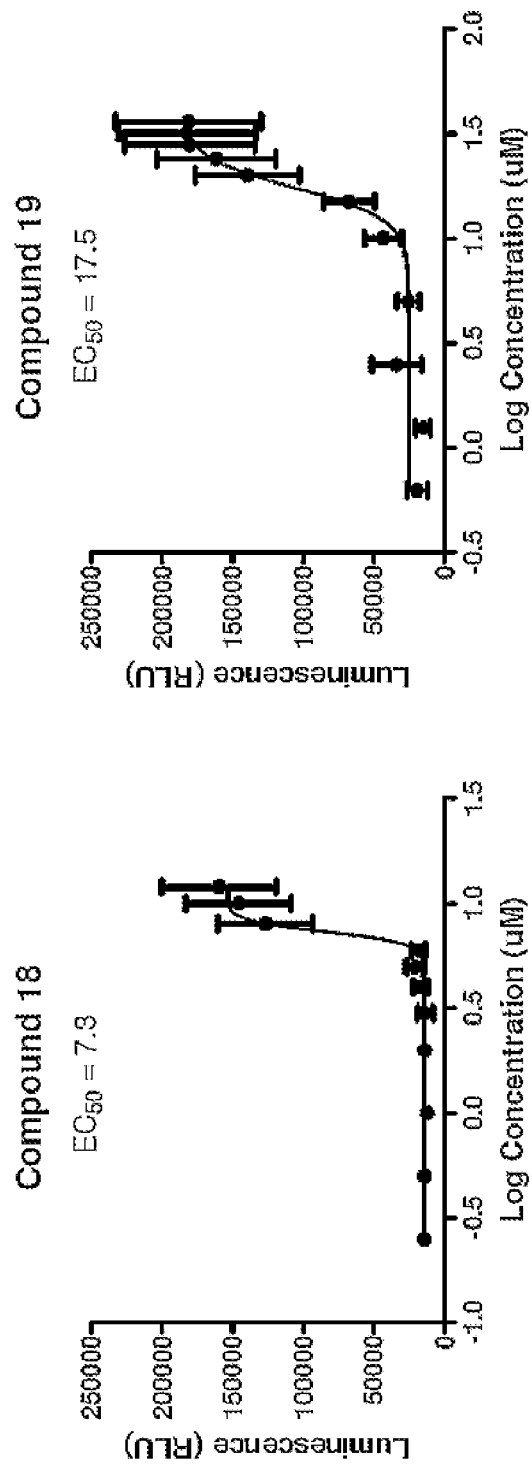
Figures 8S, 8T:
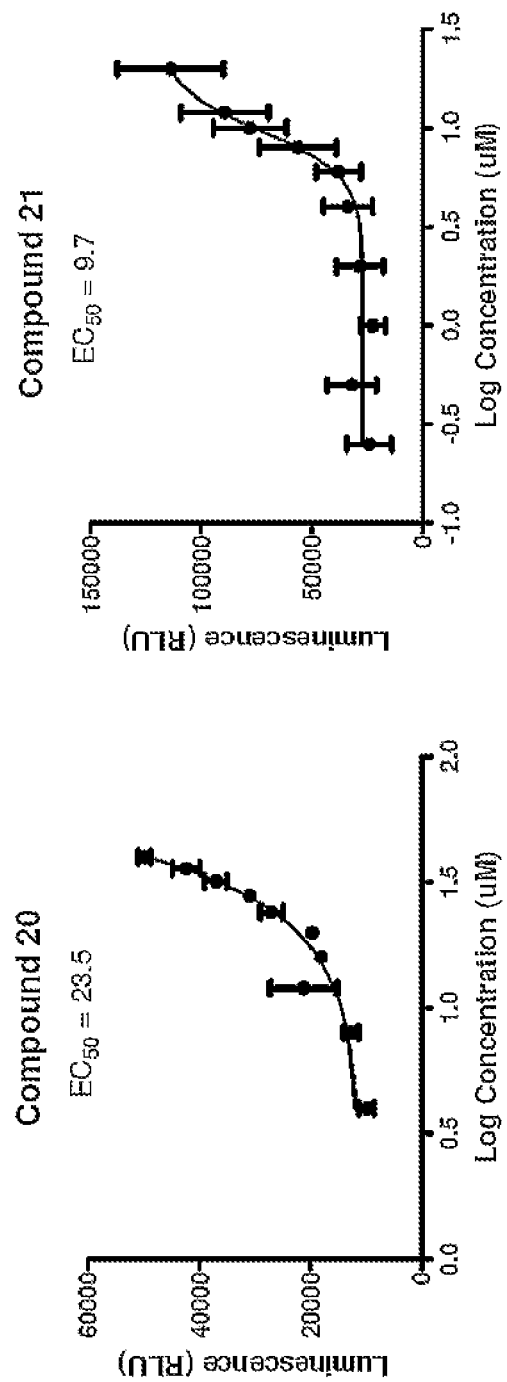
Figure 8V:
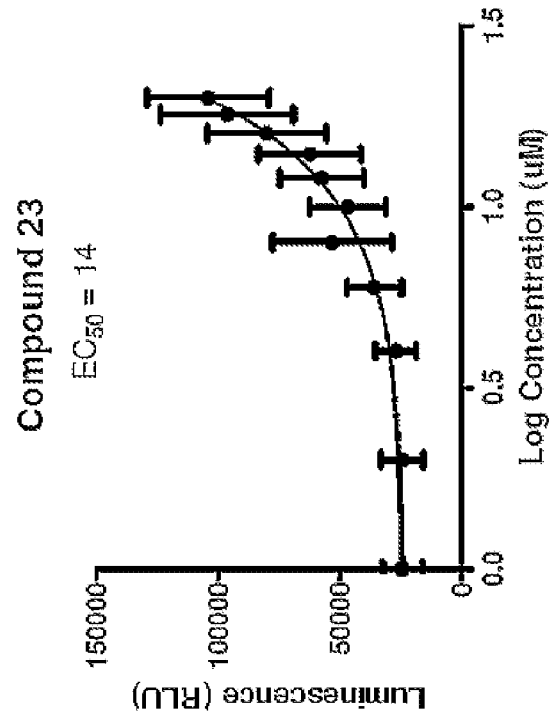
Figure 8U:
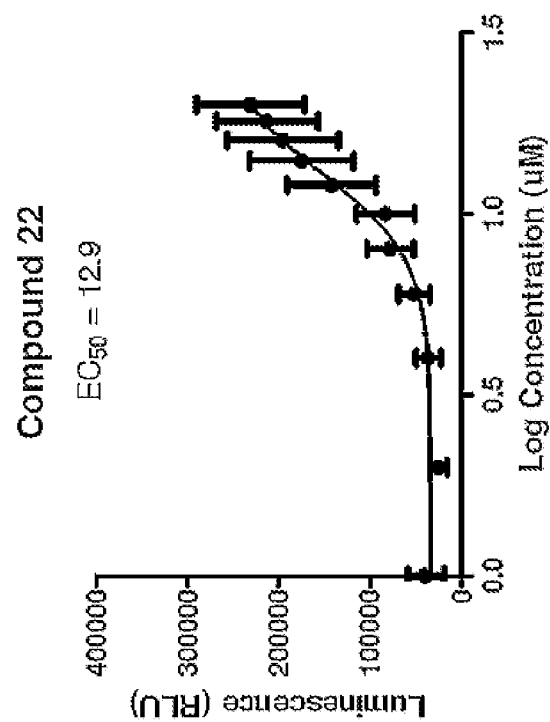
Figure 8W:
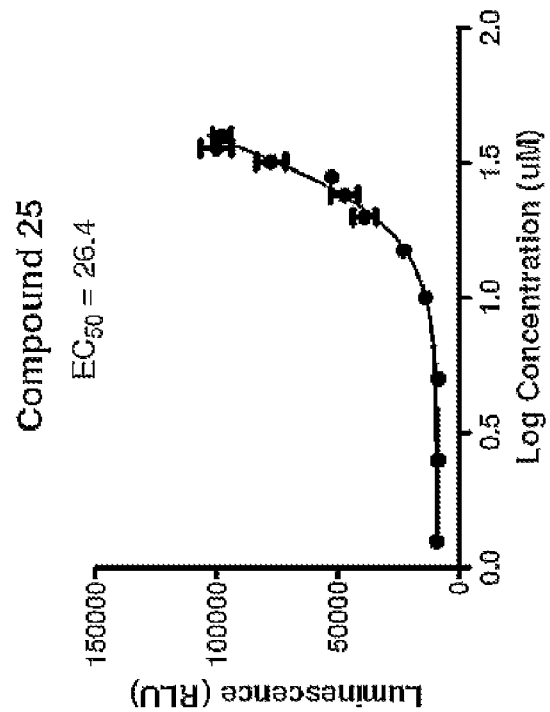
Figure 8X:
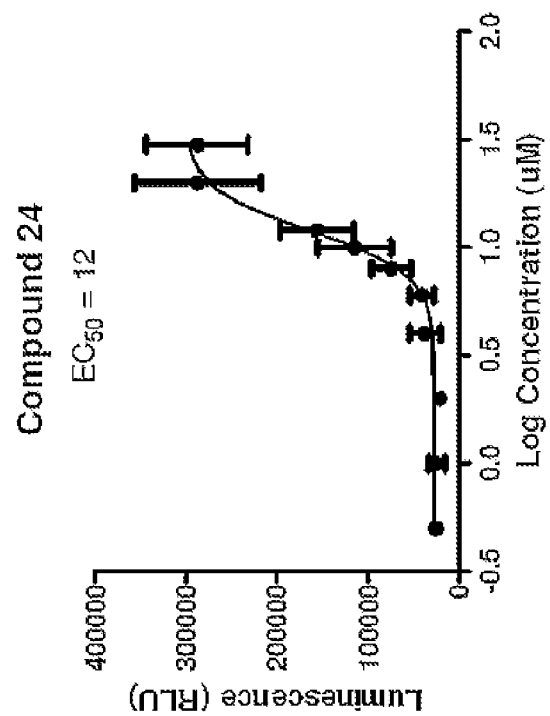

Compounds with confirmed activity were tested in a concentration response format using the MDM2-Luc exon-skipping assay. The SK-MEL-2/Luc-MDM2 cell line was incubated with serial dilutions of each compound and incubated for four hours before measuring luciferase activity as described below (FIG. 8A-X). Graphical analysis was used to estimate the concentration that produced half maximal luciferase induction ($EC_{50}$) for each compound.

Referring to FIG. 8A-X, SK-MEL-2/Luc-MDM2 stable cells were cultured in MEM medium with Earle's salts and L-glutamine containing 1 M sodium pyruvate, FCS and 10 mM Hepes and plated at a density of 10,000/well in 96-well plates and incubated overnight at 37° C. in $500CO_2$. The following day, cells were treated with serial dilutions of compounds for 4 hours and ONE-Glo reagents (Promega) were added to measure the luminescent signal (Relative Luminescent Unit, RLU) by EnVision plate reader. The $EC_{50}$ for luciferase activity of the SK-MEL-2/Luc-MDM2 reporter was analyzed by GraphPad Prism.

The kinase profile of compounds 8, 9, and 14 is shown in Table 4 below.

TABLE 4

| % Inhibition | Compound 8 at 1 µM | Compound 9 at 1 µM | Compound 14 at 1 µM |
|---|---|---|---|
| Abl(h)[a] | -2 | 2 | 8 |
| ALK(h)[a] | 7 | -2 | 10 |
| Aurora-A(h)[a] | 4 | -5 | 13 |
| Aurora-B(h)[a] | -15 | -16 | -16 |
| B-Raf(h)[a] | 10 | 21 | 5 |
| EGFR(h)[a] | -6 | 3 | -1 |
| ErbB2(h)[a] | 2 | 0 | 3 |
| Flt3(h)[a] | 19 | 90 | 93 |
| Fms(h)[a] | -1 | -16 | 9 |
| IKKβ(h)[a] | -2 | -5 | -9 |
| JAK2(h)[a] | -6 | 2 | 8 |
| JAK3(h)[a] | 0 | 4 | 0 |
| JNKα1(h)[a] | 3 | -1 | -6 |
| JNK2a2(h)[a] | 1 | 4 | -6 |
| KDR(h)[a] | 16 | -6 | 4 |
| MEK1(h)[a] | 10 | 8 | 6 |
| MEKK2(h)[a] | 47 | 18 | 48 |
| Plk1(h)[a] | 49 | 9 | 60 |
| Src(1-530)(h)[a] | 22 | 69 | 78 |
| PI3 Kinase (p110f3/p85α)(h)[b] | 5 | 4 | 4 |
| PI3 Kinase (p110f3/p85α)(h)[b] | 2 | 3 | 0 |
| PI3 Kinase (p110f3/p85α)(h)[b] | 2 | 5 | 1 |

[a]Radiometric assays were conducted as described in the experimental section. Percent inhibition was calculated by comparing to the positive control wells that contain all components of the reaction and 2% DMSO (0% inhibition), as well as the blank wells that contain all components of the reaction, with a reference inhibitor (100% inhibition). Staurosporine is used as reference for all tested enzymes except for Abl(h) (PKR inhibitor as reference compound), JNKlαl(h) and JNKlα2(h) (K-252a as reference compound).
[b]PI3 kinases were examined with the non-radiometric HTRF assay and reactions without enzyme were used as blanks (100% inhibition). The assay buffer contains 10 µ M phosphatidylinositol 4,5-bisphosphate and Mg ATP. The reaction is initiated by ATP, followed by incubation for 30 minutes at room temperature, then stopped by stop solution containing EDTA and biotinylated phosphatidylinositol-3,4,5-trisphosphate. Finally, detection buffer is added, which contains europium-labeled anti-GST monoclonal antibody, GST-tagged GRP1 PH domain and streptavidin allophycocyanin. The plate is then read in time-resolved fluorescence mode and the homogeneous time-resolved fluorescence (HTRF) signal is determined according to the formula HTRF =10000 x (Em665 nm/Em620 nm).

The kinase assay conditions are shown in Table 5 below.

TABLE 5

| Enzyme[a] | Substrate (concentration) | ATP (µM) | % CV |
|---|---|---|---|
| CLK1(h)[b] | ERMRPRKRQGSVRRRV (200 µM) (SEQ. ID NO. 1) | 10 | 6 |
| CLK2(h) | YRRAAVPPSPSLSRHSSPHQS(p)EDEEE (20 µM) (SEQ. ID NO. 2) | 10 | 6 |
| CLK3(h)[c] | ERMRPRKRQGSVRRRV (250 µM) (SEQ. ID NO. 3) | 90 | 3 |
| CLK4(h) | YRRAAVPPSPSLSRHSSPHQS(p)EDEEE (200 µM) (SEQ. ID NO. 4) | 10 | 6 |
| CDK1/cyclinB(h) | Histone H1 (0.1 mg/ml) | 45 | 5 |
| CDK4/cyclinD3(h) | Histone H1 (0.1 mg/ml) | 20 | 5 |
| CDK6/cyclinD3(h) | Histone H1 (0.1 mg/ml) | 20 | 6 |
| Abl(h) | EAIYAAPFAKKK (50 µM) (SEQ. ID NO. 5) | 45 | 7 |
| ALK(h) | casein (2 mg/ml) | 200 | 7 |
| Aurora-A(h) | LRRASLG (Kemptide) (200 µM) (SEQ. ID NO. 6) | 15 | 7 |
| Aurora-B(h) | AKRRRLSSLRA (30 µM) (SEQ. ID NO. 7) | 10 | 15 |
| B-Raf(h)[d] | myelin basic protein (0.5 mg/mL) | 120 | 8 |
| EGFR(h)[e] | poly(Glu, Tyr) 4:1 (0.1 mg/mL) | 10 | 9 |
| ErbB2(h)[f] | poly(Glu, Tyr) (0.1 mg/mL) | 10 | 6 |
| Flt3(h) | EAIYAAPFAKKK (50 µM) (SEQ. ID NO. 8) | 200 | 7 |
| Fms(h) | KKKSPGEYVNIEFG (250 µM) (SEQ. ID NO. 9) | 200 | 7 |
| IKKβ(h) | KKKKERLLDDRHDSGLDSMKDEE (100 µM) (SEQ. ID NO. 10) | 10 | 5 |
| JAK2(h) | KTFCGTPEYLAPEVRREPRILSEEEQEMFRDFDYI ADWC (100 µM) (SEQ. ID NO. 11) | 45 | 13 |
| JAK3(h) | GGEEEEYFELVKKKK (500 µM) (SEQ. ID NO. 12) | 10 | 7 |
| JNK1α1(h)[g] | ATF2 (3 µM) | 45 | 6 |
| JNK2α2(h)[g] | ATF2 (3 µM) | 45 | 8 |
| KDR(h) | myelin basic protein (0.33 mg/mL) | 90 | 7 |
| MEK1(h)[h] | unactive MAPK2(m) (1 µM) | 10 | 9 |
| MEKK2(h) | myelin basic protein (1 mg/ml) | 11 | 15 |
| Plk1(h)[i] | casein (1.25 mg/ml) | 70 | 5 |
| Src(1-530)(h) | GGEEEEYFELVKKKK (500 µM) (SEQ. ID NO. 13) | 45 | 10 |
| PI3 Kinase (p110β/p85α)(h)[j] | phosphatidylinositol 4,5-bisphosphate (10 µM) | 200 | 0 |

TABLE 5-continued

| Enzyme[a] | Substrate (concentration) | ATP (µM) | % CV |
|---|---|---|---|
| P13 Kinase (p110β/p85α) (h)[j] | phosphatidylinositol 4,5-bisphosphate (10 µM) | 200 | 1 |
| P13 Kinase (p110β/p85α) (h)[j] | phosphatidylinositol 4,5-bisphosphate (10 µM) | 200 | 2 |

[a]The standard enzyme reaction buffer contains mM MOPS pH 7.0, 10 mM Mg Acetate, 0.2 mM EDTA. The additional components of any specific enzyme are described from b-k.
[b]The enzyme reaction buffer for CLK1(h) also contains 1 mM sodium orthovanadate, 5 mM sodium 6-glycerophosphate.
[c]The enzyme reaction buffer for CLK3(h) also contains 30 mM NaCl.
[d]The enzyme reaction buffer for B-Raf(h) also contains 0.2 mM EGTA, 10 mM DTT, 0.01% Triton X-100, 0.5 mM sodium, orthovandate, 0.5 mM 6-glycerophosphate, 1% glycerol, 34 nM unactive MEK1, 69 nM unactive MAPK2.
[e]The enzyme reaction buffer for EGFR(h) also contains 10 mM MnCl$_2$.
[f]The enzyme reaction buffer for ErB2(h) also contains 5 mM MnCl$_2$.
[g]The enzyme reaction buffer for JNK1α1(h) or JNK1α2(h) also contains 0.1 mM EGTA (no EDTA), 0.1% 6-mercaptoethanol.
[h]The enzyme reaction buffer for MEK1(h) also contains 0.2 mM EGTA, 0.1% 6-mercaptoethanol, 0.01% Brij-35.
[i]The enzyme reaction buffer for Plkl(h) also contains 20 mM DTT.
[j]The enzyme reaction buffer for PI3 kinases are described in Supplementary Table 1.

8. Evaluation of Inhibitor Tool Compounds

Figure 9:
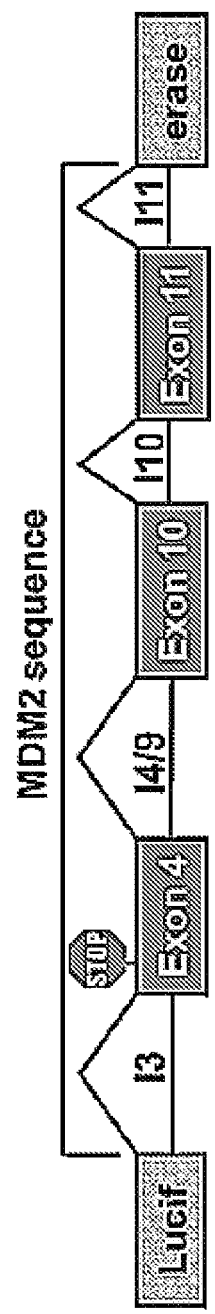
FIG. 9 shows a representative schematic diagram of the chemical structure of an MDM2-Luc construct that contains parts of the MDM2 intronic and exonic sequences in the luciferase gene (Fan et al. (2011) *ACS Chem. Bio.* 6: 582-9).
Figure 10:
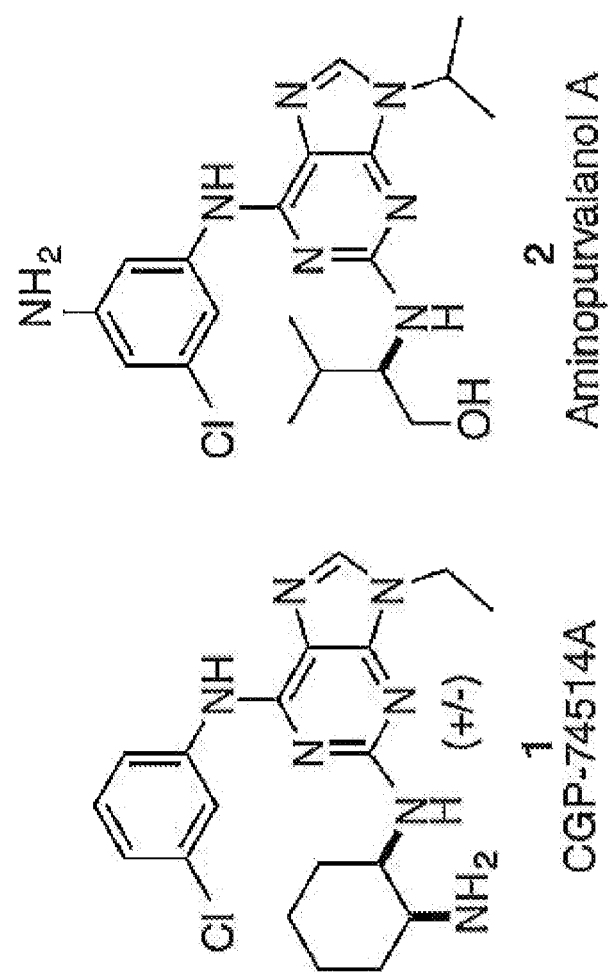
FIG. 10 shows representative chemical structures of compounds 1 and 2, which are PCR validated hits from a run of the MDM2-Luc exon-skipping screen.

It was previously demonstrated that the SF3B1 targeted splicing modulator drugs potently induce exon skipping in MDM2 pre-mRNA (Fan et al. (2011) ACS Chem Biol 6: 582-9; Lagisetti et al. (2014) ACS Chem Biol 9: 643-8). More specifically, splicing of MDM2 is altered in response to treatment with the sudemycins, and other SF3B1 active agents, such that exons 4-11 are skipped (Fan et al. (2011) ACS Chem Biol 6: 582-9). Based on these observations, an exon-skipping MDM2-Luc reporter was designed (see FIG. 9) (Shi et al. (2015) Pharmacol Res Perspect 3: e00158). The principal strategy in the design of this reporter is that, when expressed, cellular luminescence is dependent on the production of a correctly spliced full-length luciferase transcript due to the drug induced skipping of MDM2 cassette exons 4, 10, and 11, which interrupt the luciferase gene in this construct in the absence of a splicing modulator drug (see FIG. 9). The use of this construct as a reporter for the real time pharmacodynamics of SF3B1 targeted agents in vivo, via a stable reporter cell line, was recently reported (Shi et al. (2015) Pharmacol Res Perspect 3: e00158). Using a stable cell line expressing this reporter, luminescent signals are generated in a dose-dependent fashion in the presence of splicing modulations (such as the sudemycins, herboxidiene and pladienolide B) (Shi et al. (2015) Pharmacol Res Perspect 3: e00158). This assay was previously used to screen a small molecule library (composed of 830 known drugs and 4,359 bioactive compounds) (Walters et al. (2014) PLoS One 9: e91173) and identified several active "hit" compounds. These hits were then subjected to dose-response assays in the MDM2-Luc exon-skipping assay and those actives were then confirmed in an orthogonal PCR based MDM2 alternate splicing assay in Rh-18 cells (as detailed above) (Fan et al. (2011) ACS Chem Biol 6: 582-9). Two structurally related 'hits' demonstrated activity in both of these screens that is similar (but less potent) to that observed for SF3B1 targeted agents such as SD6 (as detailed above). The most potent of these confirmed hits are shown in FIG. 10, CGP-7451A (1) and Aminopurvalanol A (2).

These two confirmed hits, CGP-74514A (1) (Imbach et al. (1999) Bioorg Med Chem Lett 9: 91-6) and aminopurvalanol A (2) (Chang et al. (1999) Chem Biol 6: 361-75) are known to inhibit cyclin-dependent kinases (CDKs), and in particular CDK1 (Chang et al. (1999) Chem Biol 6: 361-75). Compound 1 was reportedly optimized for selective CDK1 activity through a significant analoging effort (Imbach et al. (1999) Bioorg Med Chem Lett 9: 91-6). However, structurally similar compounds have been reported to have a very broad spectrum of biological activities (Chang et al. (1999) Chem Biol 6: 361-75), which indicates that this inhibitor class may also inhibit other important protein kinases. In order to narrow down the possible identity of the target class that led to exon-skipping in the assay, additional commercially available selective kinfFIGase inhibitor tool compounds that have shown cell-based activity were screened (Uitdehaag et al. (2012) Br J Pharmacol 166: 858-76). The compounds that were evaluated included the CDK selective clinical compound dinaciclib (a nanomolar inhibitor of CDK1, CDK2, CDK5, and CDK9) (Parry et al. (2010) Mol Cancer Ther 9: 2344-53), SRPIN340 (selective serine arginine protein kinase (SRPK) 1 inhibitor ($K_i$=0.89 µM; this compound inhibits SRPK1 and SRPK2 but does not significantly inhibit other SRPKs such as CLK1 and CLK4, or other classes of SR kinases) (Fukuhara et al. (2006) Proc Natl Acad Sci USA 103: 11329-33). All of these compounds were found to be inactive (at 10 µM) in the MDM2-Luc assay, which eliminated SRPK1, SRPK2, CDK1, CDK2, CDK5 and CDK9 as the likely targets that are responsible for the observed activity in this MDM2-Luc cell-based assay.

In contrast to the lack of activity of the tool compounds discussed above, the CLK1/2/4 cell-active inhibitor KH-CB19 showed modest activity in the MDM2-Luc assay (as detailed above) (Fedorov et al. (2011) Chem Biol 18: 67-76). Without wishing to be bound by theory, these results, taken together with the recent observations of pronounced modulation of splicing by CLK inhibitor compounds such as Ariki compound-2 (see FIG. 1) (Araki et al. (2015) PLoS One 10: e0116929), suggest that CLK inhibition was responsible for the alternate splicing effects seen with compounds 1 and 2. In order to explore the CLKs as possible targets, and to better understand the structure-activity relationships (SAR), additional new structurally related analogs along with the associated CLK biochemical inhibition data were clearly needed.

9. Development of Novel Drug-Like Synthetic Spliceosome Modulators

A set of analogs containing some of the pharmacophore features of 1 and/or 2 (see Scheme 1 and Table 6) were prepared using well-precedented chemistry that has been used to make similar analogs (Imbach et al. (1999) *Bioorg Med Chem Lett* 9: 91-6; Chang et al. (1999) *Chem Biol* 6: 361-75; Oumata et al. (2008) *J Med Chem* 51: 5229-42), in order to explore the nature of the pharmacophore that led to the observed activation of the triple-exon skipping in this assay (Shi et al. (2015) *Pharmacol Res Perspect* 3: e00158). As can be seen by inspection of Table 3, replacement of the $N^7$ nitrogen with CH completely abrogated all activity at 10 µM (compound 11), as did acetylation of the basic primary amine (compound 12), and dramatically reduced activity by replacement of the valanol group of 2 with an unsubstituted methyl ether (compound 13). The absolute and relative stereochemistry of the cyclohexane diamine also affected the activity. By combining potential interaction features from both 1 and 2 into compound 14 and into the acetanilide derivative 15, strong MDM2-Luc activity was observed (as detailed above). Thus, without wishing to be bound by theory, this set of compounds has identified some of the critical geometric and interaction pharmacophore features that lead to activation in the MDM2-Luc assay.

SCHEME 1.

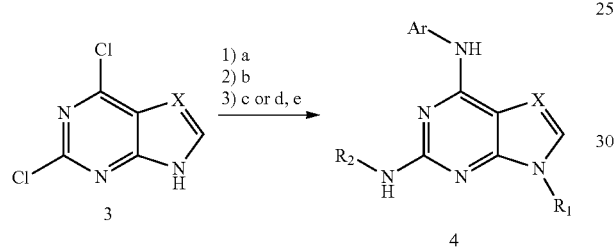

Reagents and conditions:
(a) EtBr or i-PrI, $K_2CO_3$, DMSO; (b) $ArNH_2$, TEA, BuOH, 100° C., 16 h; (c) $R_2NH_2$, TEA, NMP, 160° C., 16 h; (d) Boc—$R_2NH_2$, DIPEA, 110° C.; (e) TFA, $CH_2Cl_2$, rt, 1 h.

TABLE 6$^A$

| Compound | Ar | X | $R_1$ | $R_2$—NH | MDM2/Luc |
|---|---|---|---|---|---|
| CGP-74514A (1) | 3-Cl-phenyl | N | Et | cyclohexyl-NHMe, NH2 (+/-) | Active |
| 5 | 3-Cl-phenyl | N | Et | cyclohexyl-NHMe, NH2 | Active |
| 6 | 3-Cl-phenyl | N | Et | cyclohexyl-NHMe, NH2 | Active |
| 7 | 3-Cl-phenyl | N | i-Pr | cyclohexyl-NHMe, NH2 | Active |
| 8 | 3-Cl-phenyl | N | i-Pr | cyclohexyl-NHMe, NH2 | Active |
| 9 | 3-Cl-phenyl | N | i-Pr | cyclohexyl-NHMe, NH2 | Active |
| 10 | 3-Cl-phenyl | N | i-Pr | cyclohexyl-NHMe, NH2 | Active |
| 11 | 3-Cl-phenyl | CH | i-Pr | cyclohexyl-NHMe, NH2 (+/-) | NA |
| 12 | 3-Cl-phenyl | N | Et | cyclohexyl-NHMe, AcNH (+/-) | NA |
| 13 | 3-Cl-phenyl | N | i-Pr | MeO-CH2CH2-NHMe | NA |

TABLE 6[A]-continued

![Structure D: pyrimidine-fused imidazole with Ar-NH at position 6, R2-NH at position 2, R1 at position 9, X at position 8]

| Compound | Ar | X | R₁ | R₂—NH | MDM2/Luc |
|---|---|---|---|---|---|
| 14 | 3-Cl-5-NH₂-phenyl | N | i-Pr | (cyclohexyl with NHMe and NH₂, (+/-)) | Active |
| 15 | 3-Cl-5-AcNH-phenyl | N | i-Pr | (cyclohexyl with NHMe and NH₂, (+/-)) | Active |

[a]Active means a significant MDM2-Luc reporter response (greater than approximately which is statistically significant over DMSO control, where DMSO is set as Luc-Fold = 1.0) in luciferase activation based on the average of three experiments. Sudemycin D6 serves a positive control.
Abbreviations: NA, not active. See Experimental Section for more details.

Figure 11:
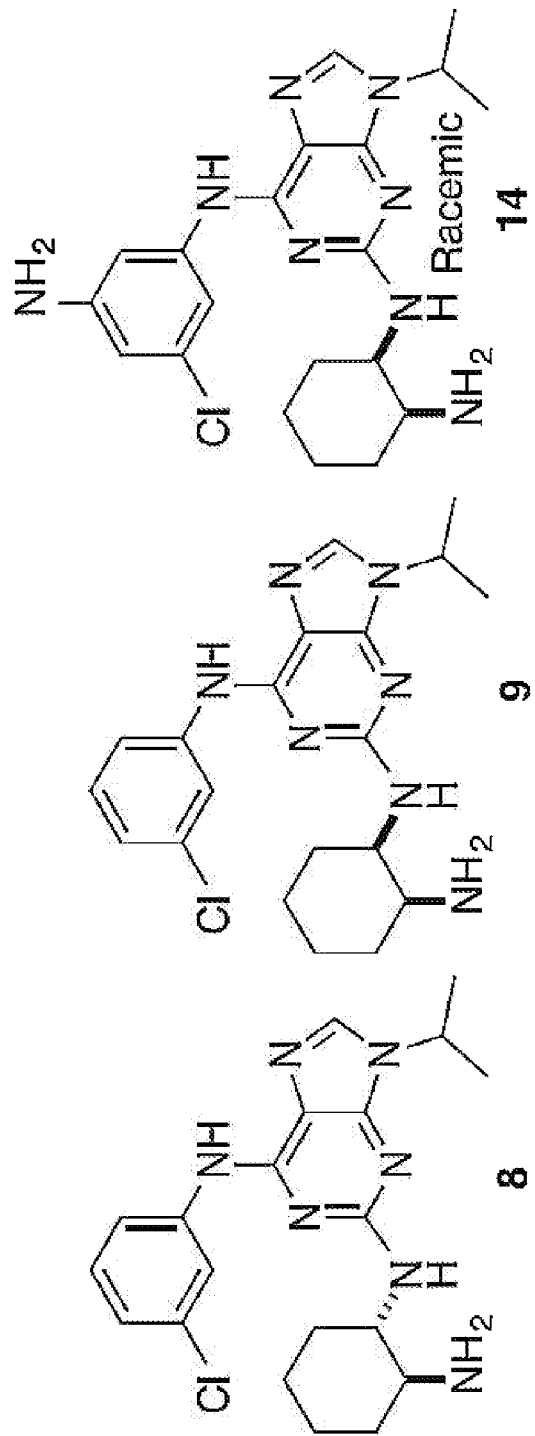
FIG. 11 shows representative chemical structures of compounds 8, 9, and 14, which demonstrated active CLK inhibition when profiled against 22 oncogenic kinases.
Figure 12A:
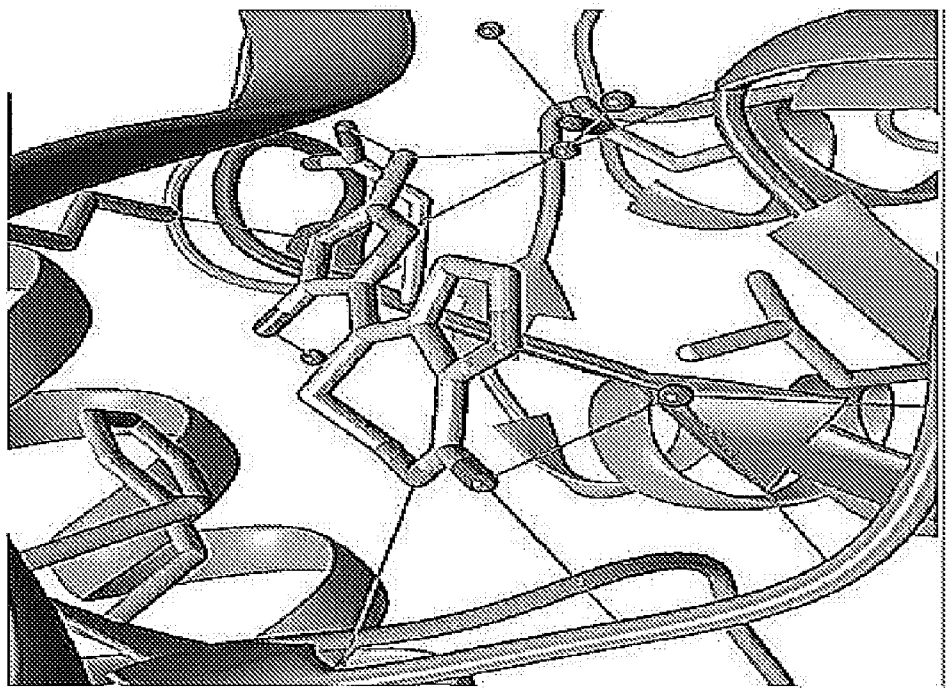
FIG. 12A shows a representative illustration of the co-crystal structures of debromohymenialdisine (K0010) bound to CLK1 using the published coordinates (Hasegawa et al. (2011) *ACS Chem. Biol.* 6: 229-33), indicating the hydrogen bonds to the ligand.
Figure 12B:
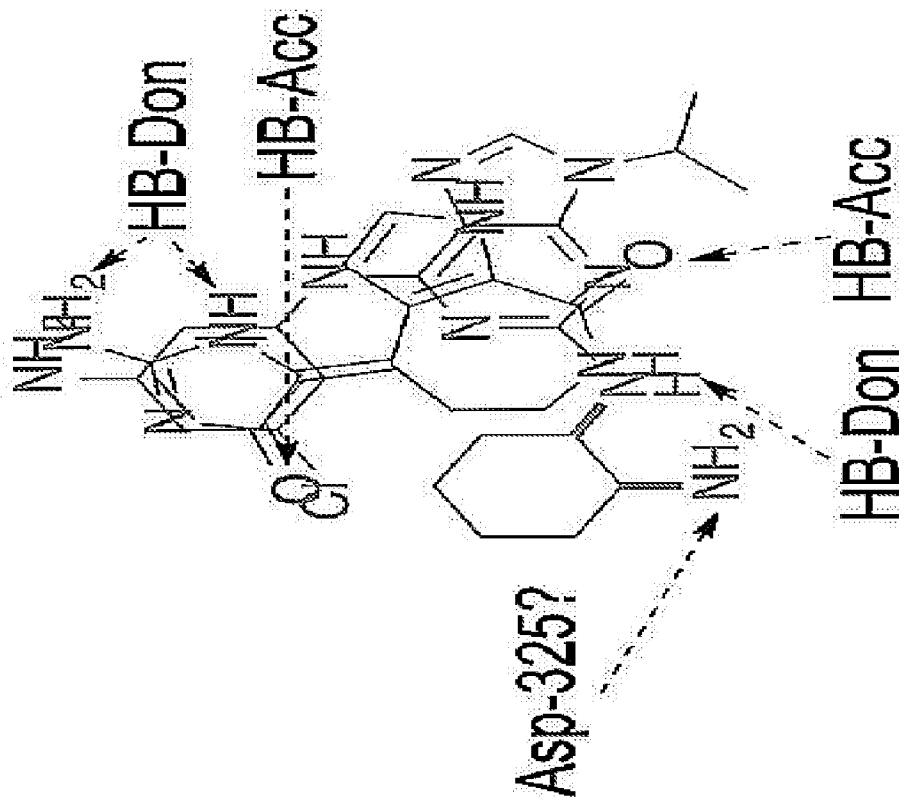
FIG. 12B shows a representative illustration of a 2D overlay of the hydrogen bond pharmacophore features from K0010 (blue) over the structure of CLK inhibitor 14 (shown in grey) from Table 3. (Abbreviations: HB-Don=hydrogen-bond donor: HB-Acc=hydrogen-bond acceptor.)
Figure 13:
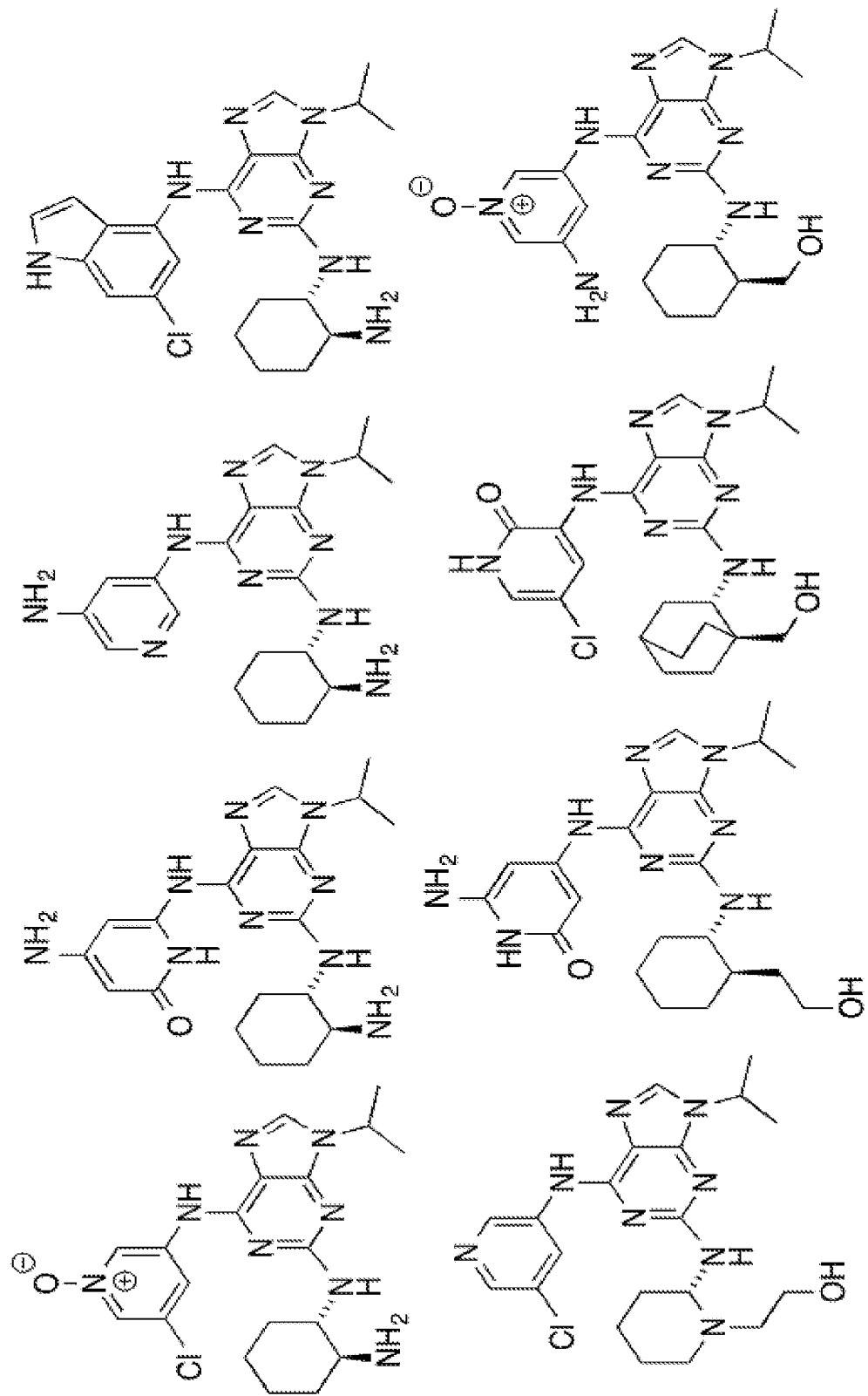
FIG. 13 shows representative illustrations of the chemical compound structure examples of focused library compounds to test and explore different pharmacophore hypotheses.
Figure 14:
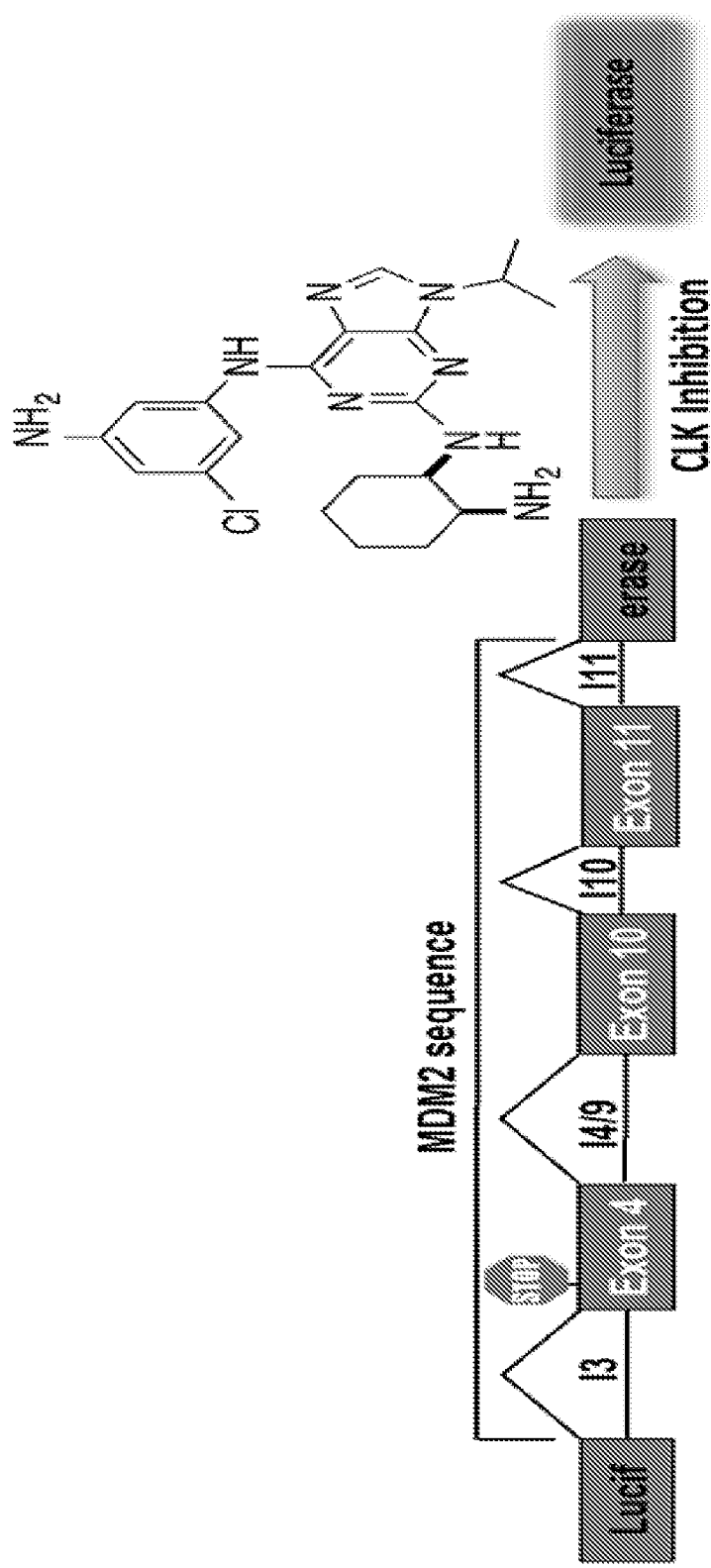
FIG. 14 shows a representative illustration of a compound having CLK inhibition.

Since the pharmacophores present in 1 and 2 do not match the previously reported consensus pharmacophore for agents that target the SF3B1 splicing protein (Lagisetti et al. (2013) *J Med Chem* 56: 10033-44; Lagisetti et al. (2008) *J Med Chem* 51: 6220-4; Lagisetti et al. (2014) *ACS Chem Biol* 9: 643-8), it appeared unlikely that 1 or 2 target the sudemycin D6 binding site on SF3B1. However, since it known that CLK inhibition can lead to modulation of pre-mRNA splicing (Araki et al. (2015) *PLoS One* 10: e0116929), and since it was observed that the weakly cell-active, but selective, CLK inhibitor KH-CB19 shows activity in the MDM2-Luc reporter assay, it was decided to explore the activity of 1 (and the active analogs) in regard to their biochemical inhibition of CLK 1-4 (Table 7). The results summarized in Table 7 clearly show that CGP-74514A (1), which has been considered a selective CDK inhibitor (Dai et al. (2002) *Cell Cycle* 1: 143-52) actually also shows significant inhibition of CLK 1, 2, and 4 and so can be considered a dual CLK/CDK inhibitor. Additionally some of the analogs of 1 and 2 were more active for three of the four CLK subtypes and the potency trend of CLK inhibition across the subtypes is similar to the trend that was observed in the MDM2-Luc reporter assay, in that more potent CLK inhibitors (compounds 9, 10, 14, 15) showed a stronger luciferase response (Luc fold). Interestingly compound 8 shows some modest (~5 fold) selectivity for CLK2 over CLK1 and CLK4 without significant CDK1,4,6 activity and compounds 9, 10, 14 and 15 that showed the strongest Luc activation also show potent CLK inhibition for the 1, 2 and 4 subtypes. Given these data compounds 8, 9, and 14 were selected for kinase profiling against 22 oncogenic kinases (Uitdehaag et al. (2012) *Br J Pharmacol* 166: 858-76) at a concentration of 1 μM in duplicate for each analog (FIG. 11 and as detailed above). This screen showed <50% inhibition against the entire 22 diverse kinase panel for compound 8, with some significant off-target activity for 9 only against Flt3, Src(1-530) and off-target activity for 14 against Flt3, Plk1, and Src(1-530) (as detailed above).

TABLE 7[A]

| Cmpd. | CLK1 | CLK2 | CLK3 | CLK4 | CDK1 | CDK4 | CDK6 |
|---|---|---|---|---|---|---|---|
| CGP-74514A (1) | 148 | 111 | >1000 | 104 | 382 | 573 | >1000 |
| 5 | 868 | 498 | >1000 | >1000 | 546 | >1000 | >1000 |
| 6 | 371 | 190 | >1000 | 498 | >1000 | >1000 | >1000 |
| 7 | 400 | 120 | >1000 | 634 | >1000 | >1000 | >1000 |
| SRI-29329 (8) | 78 | 16 | >1000 | 86 | >1000 | >1000 | >1000 |
| 9 | 38 | 11 | >1000 | 50 | 674 | 541 | >1000 |
| 10 | 74 | 26 | >1000 | 70 | >1000 | >1000 | >1000 |
| 14 | 18 | 16 | >1000 | 54 | 973 | >1000 | >1000 |
| 15 | 19 | 13 | >1000 | 64 | >1000 | 930 | >1000 |

IC₅₀ (nM)

TABLE 8[A]

![Structure: purine core with HN-Ar at 6, R2-NH at 2, isopropyl at N9]

| Compound | Ar | R2-NH |
|---|---|---|
| SRI-30129 16 | 3-Cl-5-NH₂-phenyl | (cyclohexyl with NHMe and NH₂) |
| SRI-30130 17 | 3-Cl-5-NH₂-phenyl | (cyclohexyl with NHMe and NH₂) |
| SRI-30131 18 | 3-Cl-5-AcNH-phenyl | (cyclohexyl with NHMe and NH₂) |
| SRI-30132 19 | 3-Cl-5-AcNH-phenyl | (cyclohexyl with NHMe and NH₂) |
| SRI-30118 20 | 3-Cl-5-NH₂-phenyl | (cyclohexyl with NHMe and NH₂) |

TABLE 8[A]-continued

| Compound | Ar | R2-NH |
|---|---|---|
| SRI-30119 21 | 3-Cl-5-NH$_2$-phenyl | (cyclohexyl with NH-Me and NH$_2$) |
| SRI-30120 22 | 3-Cl-phenyl | (piperidinyl-NHMe) |
| SRI-30121 23 | 3-Cl-phenyl | (piperidinyl-NHMe) |
| SRI-30125 24 | 3-Cl-phenyl | (pyrrolidinyl-NHMe) |
| SRI-30126 25 | 3-Cl-phenyl | (pyrrolidinyl-NHMe) |

TABLE 9[A]

| | | | IC$_{50}$ (nM) | | | | |
|---|---|---|---|---|---|---|---|
| Cmpd | | CLK1 | CLK2 | CLK3 | CLK4 | CDK1 | CDK4 | CDK6 |
| SRI-30129 | 16 | 17 | 6 | >1000 | 25 | 532 | >1000 | >1000 |
| SRI-30130 | 17 | 21 | 26 | >1000 | 28 | >1000 | >1000 | >1000 |
| SRI-30131 | 18 | 19 | 7 | >1000 | 30 | >1000 | 611 | >1000 |
| SRI-30132 | 19 | 26 | 17 | >1000 | 31 | >1000 | >1000 | >1000 |
| SRI-30118 | 20 | 56 | 14 | >1000 | 124 | >1000 | >1000 | >1000 |
| SRI-30119 | 21 | 274 | 163 | >1000 | 648 | >1000 | >1000 | >1000 |
| SRI-30120 | 22 | 31 | 26 | >1000 | 61 | >1000 | >1000 | >1000 |
| SRI-30121 | 23 | 66 | 34 | >1000 | 102 | >1000 | >1000 | >1000 |
| SRI-30125 | 24 | 71 | 28 | >1000 | 77 | >1000 | >1000 | >1000 |
| SRI-30126 | 25 | 118 | 92 | >1000 | 299 | >1000 | >1000 | >1000 |

[A]Enzyme inhibition of CLK subtypes 1-4 and CDK 1, 4, and 6.

The published co-crystal structures of the CLK selective inhibitor KH-CB19 (Nakajima et al. (1996) *J Antibiot (Tokyo)* 49: 1196-203), and the promiscuous debromohymenialdisine (Hasegawa et al. (2011) *ACS Chem Biol* 6: 229-33), can be helpful in developing a pharmacophore hypothesis (FIG. 5A-B). As shown in FIG. 5A, a hypothetical binding mode is proposed, based on the initial SAR data, the published CLK1/debromohymenialdisine structure (prepared using UCSF Chimera (Liu et al. (2012) *PloS one* 7: e45464)) and the inferred overlays, which together suggest a potentially important charge-charge hydrogen-bond interaction between CLK1 Asp-325 and the basic primary amine in the active selective compounds such as 8, 9, 14, and 15. FIG. 5B illustrates a 2D overlay of the hydrogen bond pharmacophore features from K0010 (blue, top overlay) over the structure of CLK inhibitor 14 (shown in grey, bottom/under structure on which the top overlay is placed) from Table 6. The notation "Asp-325?" refers to a hypothetical interaction with this residue in CLK1, assuming the overlay is correct.

The disclosed triple-exon skipping assay was used to screen a small molecule library (composed of 830 known drugs and 4,359 bioactive compounds (Walters et al. (2014) *PLoS One* 9: e91173)) and have identified initial hits. Using directed chemistry, which included a range of optically pure analogs, potent and selective CLK inhibitors and associated structure-activity relationships were identified. Dose response was used in the MDM2-Luc exon-skipping assay and the orthogonal PCR MDM2 alternate splicing assay in Rh-18 cells to validate the active hits and analogs and as a guide in the development of SAR. Some of the new analogs showed significant activity in the MDM2-Luc assay and are potent biochemical inhibitors of CLK subtypes 1, 2 and 4. Several of these compounds show reasonable overall kinase selectivity, based on data from a total of 29 kinases (including CLK1-4; CDK 1, 4, and 6; and a screen against a panel of 22 oncogenic kinases). It is noted that the well-studied tool compound CGP-74514A (1) shows significantly more biochemical activity against CLK 1, 2, and 4 than either CDK 1 or CDK 2, under the assay conditions that were used. Additionally, it was found that CLK inhibition generally correlated with MDM2-Luc activity in this series of compounds. Thus, compounds that are dual CLK2/CDK1 inhibitors (such as 1) or more specific CLK inhibitors (such as SRI-29329, 8) were identified. This is a remarkable result since CLK2 (Yoshida et al. (2015) *Cancer Res* 75: 1516-26) and CDK1 (Kang et al. (2014) *BMC Cancer* 14: 32) have recently been independently identified as potential targets for breast cancer. Therefore, without wishing to be bound by theory, these active analogs, SAR results, and the MDM2-Luc assay may facilitate the development of new probe and lead molecules with potential application in breast cancer, and other diseases. Additionally the MDM2-Luc assay has proven its utility in the identification of compounds with splicing modulatory activity at targets other than SF3B1. The uniqueness of triple-exon skipping splicing modulatory pharmacophores is remarkable in that none of the FDA approved drugs showed this activity at 10 µM in this assay. Additionally, the observations of overlapping pharmacophores for the CLK and CDK (and potentially structurally related CDK inhibitors) should be considered when interpreting biological results that are based on the cellular or in vivo responses to compounds such as CGP-74514A (1).

I. REFERENCES

Shi, Y.; Joyner, A. S.; Shadrick, W.; Palacios, G.; Lagisetti, C.; Potter, P. M.; Sambucetti, L. C.; Stamm, S.; Webb, T. R. Pharmacodynamic assays to facilitate preclinical and clinical development of pre-mRNA splicing modulatory drug candidates. *Pharmacol Res Perspect* 2015, 3, e00158.

Walters, B. J.; Lin, W.; Diao, S.; Brimble, M.; Iconaru, L. I.; Dearman, J.; Goktug, A.; Chen, T.; Zuo, J. High-throughput screening reveals alsterpaullone, 2-cyanoethyl as a potent p27Kip1 transcriptional inhibitor. *PLoS One* 2014, 9, e91173.

Fan, L.; Lagisetti, C.; Edwards, C. C.; Webb, T. R.; Potter, P. M. Sudemycins, novel small molecule analogues of FR901464, induce alternative gene splicing. *ACS Chem Biol* 2011, 6, 582-9.

Lagisetti, C.; Palacios, G.; Goronga, T.; Freeman, B.; Caufield, W.; Webb, T. R. Optimization of antitumor modulators of pre-mRNA splicing. *J Med Chem* 2013, 56, 10033-44.

Kramer, A. The structure and function of proteins involved in mammalian pre-mRNA splicing. *Annu Rev Biochem* 1996, 65, 367-409.

Wahl, M. C.; Will, C. L.; Luhrmann, R. The spliceosome: design principles of a dynamic RNP machine. *Cell* 2009, 136, 701-18.

Hang, J.; Wan, R.; Yan, C.; Shi, Y. Structural basis of pre-mRNA splicing. *Science* 2015.

Webb, T. R.; Joyner, A. S.; Potter, P. M. The development and application of small molecule modulators of SF3b as therapeutic agents for cancer. *Drug Discovery Today* 2013, 18, 43-49.

Bonnal, S.; Vigevani, L.; Valcarcel, J. The spliceosome as a target of novel antitumour drugs. *Nat Rev Drug Discov* 2012, 11, 847-859.

Kaida, D.; Motoyoshi, H.; Tashiro, E.; Nojima, T.; Hagiwara, M.; Ishigami, K.; Watanabe, H.; Kitahara, T.; Yoshida, T.; Nakajima, H.; Tani, T.; Horinouchi, S.; Yoshida, M. Spliceostatin A targets SF3b and inhibits both splicing and nuclear retention of pre-mRNA. *Nat Chem Biol* 2007, 3, 576-83.

Kotake, Y.; Sagane, K.; Owa, T.; Mimori-Kiyosue, Y.; Shimizu, H.; Uesugi, M.; Ishihama, Y.; Iwata, M.; Mizui, Y. Splicing factor SF3b as a target of the antitumor natural product pladienolide. *Nat Chem Biol* 2007, 3, 570-5.

Hasegawa, M.; Miura, T.; Kuzuya, K.; Inoue, A.; Won Ki, S.; Horinouchi, S.; Yoshida, T.; Kunoh, T.; Koseki, K.; Mino, K.; Sasaki, R.; Yoshida, M.; Mizukami, T. Identification of SAP155 as the target of GEX1A (Herboxidiene), an antitumor natural product. *ACS Chem Biol* 2011, 6, 229-33.

Liu, X.; Biswas, S.; Berg, M. G.; Antapli, C. M.; Xie, F.; Wang, Q.; Tang, M.-C.; Tang, G.-L.; Zhang, L.; Dreyfuss, G.; Cheng, Y.-Q. Genomics-Guided Discovery of Thailanstatins A, B, and C As Pre-mRNA Splicing Inhibitors and Antiproliferative Agents from *Burkholderia thailandensis* MSMB43. *Journal of Natural Products* 2013, 76, 685-693.

Nakajima, H.; Sato, B.; Fujita, T.; Takase, S.; Terano, H.; Okuhara, M. New antitumor substances, FR901463, FR901464 and FR901465. I. Taxonomy, fermentation, isolation, physico-chemical properties and biological activities. *J Antibiot (Tokyo)* 1996, 49, 1196-203.

Nakajima, H.; Hori, Y.; Terano, H.; Okuhara, M.; Manda, T.; Matsumoto, S.; Shimomura, K. New antitumor substances, FR901463, FR901464 and FR901465. II. Activities against experimental tumors in mice and mechanism of action. *J Antibiot (Tokyo)* 1996, 49, 1204-11.

Mizui, Y.; Sakai, T.; Iwata, M.; Uenaka, T.; Okamoto, K.; Shimizu, H.; Yamori, T.; Yoshimatsu, K.; Asada, M. Pladienolides, new substances from culture of *Streptomyces platensis* Mer-11107. III. In vitro and in vivo antitumor activities. *J Antibiot (Tokyo)* 2004, 57, 188-96.

Eskens, F. A.; Ramos, F. J.; Burger, H.; O'Brien, J. P.; Piera, A.; de Jonge, M. J.; Mizui, Y.; Wiemer, E. A.; Carreras, M. J.; Baselga, J.; Tabernero, J. Phase I pharmacokinetic and pharmacodynamic study of the first-in-class spliceosome inhibitor E7107 in patients with advanced solid tumors. *Clin Cancer Res* 2013, 19, 6296-304.

Yoshida, K.; Sanada, M.; Shiraishi, Y.; Nowak, D.; Nagata, Y.; Yamamoto, R.; Sato, Y.; Sato-Otsubo, A.; Kon, A.; Nagasaki, M.; Chalkidis, G.; Suzuki, Y.; Shiosaka, M.; Kawahata, R.; Yamaguchi, T.; Otsu, M.; Obara, N.; Sakata-Yanagimoto, M.; Ishiyama, K.; Mori, H.; Nolte, F.; Hofmann, W. K.; Miyawaki, S.; Sugano, S.; Haferlach, C.; Koeffler, H. P.; Shih, L. Y.; Haferlach, T.; Chiba, S.; Nakauchi, H.; Miyano, S.; Ogawa, S. Frequent pathway mutations of splicing machinery in myelodysplasia. *Nature* 2011, 478, 64-9.

Lagisetti, C.; Palacios, G.; Goronga, T.; Freeman, B.; Caufield, W.; Webb, T. R. Optimization of antitumor modulators of pre-mRNA splicing. *J Med Chem* 2013, 56, 10033-44.

Fedorov, O.; Huber, K.; Eisenreich, A.; Filippakopoulos, P.; King, O.; Bullock, A. N.; Szklarczyk, D.; Jensen, L. J.; Fabbro, D.; Trappe, J.; Rauch, U.; Bracher, F.; Knapp, S. Specific CLK inhibitors from a novel chemotype for regulation of alternative splicing. *Chem Biol* 2011, 18, 67-76.

Araki, S.; Dairiki, R.; Nakayama, Y.; Murai, A.; Miyashita, R.; Iwatani, M.; Nomura, T.; Nakanishi, O. Inhibitors of CLK protein kinases suppress cell growth and induce apoptosis by modulating pre-mRNA splicing. *PLoS One* 2015, 10, e0116929.

Pawellek, A.; McElroy, S.; Samatov, T.; Mitchell, L.; Woodland, A.; Ryder, U.; Gray, D.; Luhrmann, R.; Lamond, A. I. Identification of small molecule inhibitors of pre-mRNA splicing. *J Biol Chem* 2014, 289, 34683-98.

Lagisetti, C.; Pourpak, A.; Jiang, Q.; Cui, X.; Goronga, T.; Morris, S. W.; Webb, T. R. Antitumor compounds based on a natural product consensus pharmacophore. *J Med Chem* 2008, 51, 6220-4.

Lagisetti, C.; Pourpak, A.; Goronga, T.; Jiang, Q.; Cui, X.; Hyle, J.; Lahti, J. M.; Morris, S. W.; Webb, T. R. Synthetic mRNA splicing modulator compounds with in vivo antitumor activity. *J Med Chem* 2009, 52, 6979-90.

Fan, L.; Lagisetti, C.; Edwards, C. C.; Webb, T. R.; Potter, P. M. Sudemycins, novel small molecule analogues of FR901464, induce alternative gene splicing. *ACS Chem Biol* 2011, 6, 582-9.

Gundluru, M. K.; Pourpak, A.; Cui, X.; Morris, S. W.; Webb, T. R. Design, synthesis and initial biological evaluation of a novel pladienolide analog scaffold. *Medchemcomm* 2011, 2, 904-908.

Lagisetti, C.; Yermolina, M. V.; Sharma, L. K.; Palacios, G.; Prigaro, B. J.; Webb, T. R. Pre-mRNA splicing-modulatory pharmacophores: the total synthesis of herboxidiene, a pladienolide-herboxidiene hybrid analog and related derivatives. *ACS Chem Biol* 2014, 9, 643-8.

Effenberger, K. A.; Urabe, V. K.; Prichard, B. E.; Ghosh, A. K.; Jurica, M. S. Interchangeable SF3B1 inhibitors interfere with pre-mRNA splicing at multiple stages. *RNA* 2016, 22, 350-9.

Convertini, P.; Shen, M.; Potter, P. M.; Palacios, G.; Lagisetti, C.; de la Grange, P.; Horbinski, C.; Fondufe-Mittendorf, Y. N.; Webb, T. R.; Stamm, S. Sudemycin E influences alternative splicing and changes chromatin modifications. *Nucleic Acids Res* 2014, 42, 4947-61.

David, C. J.; Manley, J. L. Alternative pre-mRNA splicing regulation in cancer: pathways and programs unhinged. *Genes Dev* 2010, 24, 2343-64.

Ogawa, S. Splicing factor mutations in myelodysplasia. *Int J Hematol* 2012, 96, 438-42.

Damm, F.; Nguyen-Khac, F.; Fontenay, M.; Bernard, O. A. Spliceosome and other novel mutations in chronic lymphocytic leukemia and myeloid malignancies. *Leukemia* 2012, 26, 2027-31.

Murati, A.; Brecqueville, M.; Devillier, R.; Mozziconacci, M. J.; Gelsi-Boyer, V.; Birnbaum, D. Myeloid malignancies: mutations, models and management. *BMC Cancer* 2012, 12, 304.

Cancer Genome Atlas Research, N. Genomic and epigenomic landscapes of adult de novo acute myeloid leukemia. *N Engl J Med* 2013, 368, 2059-74.

Cancer Genome Atlas, N. Comprehensive molecular portraits of human breast tumours. *Nature* 2012, 490, 61-70.

Maguire, S. L.; Leonidou, A.; Wai, P.; Marchio, C.; Ng, C. K.; Sapino, A.; Salomon, A. V.; Reis-Filho, J. S.; Weigelt, B.; Natrajan, R. C. SF3B1 mutations constitute a novel therapeutic target in breast cancer. *J Pathol* 2015, 235, 571-80.

Imielinski, M.; Berger, A. H.; Hammerman, P. S.; Hernandez, B.; Pugh, T. J.; Hodis, E.; Cho, J.; Suh, J.; Capelletti, M.; Sivachenko, A.; Sougnez, C.; Auclair, D.; Lawrence, M. S.; Stojanov, P.; Cibulskis, K.; Choi, K.; de Waal, L.; Sharifnia, T.; Brooks, A.; Greulich, H.; Banerji, S.; Zander, T.; Seidel, D.; Leenders, F.; Ansen, S.; Ludwig, C.; Engel-Riedel, W.; Stoelben, E.; Wolf, J.; Goparju, C.; Thompson, K.; Winckler, W.; Kwiatkowski, D.; Johnson, B. E.; Janne, P. A.; Miller, V. A.; Pao, W.; Travis, W. D.; Pass, H. I.; Gabriel, S. B.; Lander, E. S.; Thomas, R. K.; Garraway, L. A.; Getz, G.; Meyerson, M. Mapping the hallmarks of lung adenocarcinoma with massively parallel sequencing. *Cell* 2012, 150, 1107-20.

Harbour, J. W. Genomic, prognostic, and cell-signaling advances in uveal melanoma. *Am Soc Clin Oncol Educ Book* 2013, 388-91.

Hubert, C. G.; Bradley, R. K.; Ding, Y.; Toledo, C. M.; Herman, J.; Skutt-Kakaria, K.; Girard, E. J.; Davison, J.; Berndt, J.; Corrin, P.; Hardcastle, J.; Basom, R.; Delrow, J. J.; Webb, T.; Pollard, S. M.; Lee, J.; Olson, J. M.; Paddison, P. J. Genome-wide RNAi screens in human brain tumor isolates reveal a novel viability requirement for PHF5A. *Genes Dev* 2013, 27, 1032-45.

Hsu, T. Y.; Simon, L. M.; Neill, N. J.; Marcotte, R.; Sayad, A.; Bland, C. S.; Echeverria, G. V.; Sun, T.; Kurley, S. J.; Tyagi, S.; Karlin, K. L.; Dominguez-Vidana, R.; Hartman, J. D.; Renwick, A.; Scorsone, K.; Bernardi, R. J.; Skinner, S. O.; Jain, A.; Orellana, M.; Lagisetti, C.; Golding, I.; Jung, S. Y.; Neilson, J. R.; Zhang, X. H.; Cooper, T. A.; Webb, T. R.; Neel, B. G.; Shaw, C. A.; Westbrook, T. F. The spliceosome is a therapeutic vulnerability in MYC-driven cancer. *Nature* 2015.

Shi, Y.; Joyner, A. S.; Shadrick, W.; Palacios, G.; Lagisetti, C.; Potter, P. M.; Sambucetti, L. C.; Stamm, S.; Webb, T. R. Pharmacodynamic assays to facilitate preclinical and clinical development of pre-mRNA splicing modulatory drug candidates. *Pharmacol Res Perspect* 2015, 3, e00158.

Walters, B. J.; Lin, W.; Diao, S.; Brimble, M.; Iconaru, L. I.; Dearman, J.; Goktug, A.; Chen, T.; Zuo, J. High-throughput screening reveals alsterpaullone, 2-cyanoethyl as a potent p27Kip1 transcriptional inhibitor. *PLoS One* 2014, 9, e91173.

Imbach, P.; Capraro, H. G.; Furet, P.; Mett, H.; Meyer, T.; Zimmermann, J. 2,6,9-trisubstituted purines: optimization towards highly potent and selective CDK1 inhibitors. *Bioorg Med Chem Lett* 1999, 9, 91-6.

Chang, Y. T.; Gray, N. S.; Rosania, G. R.; Sutherlin, D. P.; Kwon, S.; Norman, T. C.; Sarohia, R.; Leost, M.; Meijer, L.; Schultz, P. G. Synthesis and application of functionally diverse 2,6,9-trisubstituted purine libraries as CDK inhibitors. *Chem Biol* 1999, 6, 361-75.

Uitdehaag, J. C.; Verkaar, F.; Alwan, H.; de Man, J.; Buijsman, R. C.; Zaman, G. J. A guide to picking the most selective kinase inhibitor tool compounds for pharmacological validation of drug targets. *Br J Pharmacol* 2012, 166, 858-76.

Parry, D.; Guzi, T.; Shanahan, F.; Davis, N.; Prabhavalkar, D.; Wiswell, D.; Seghezzi, W.; Paruch, K.; Dwyer, M. P.; Doll, R.; Nomeir, A.; Windsor, W.; Fischmann, T.; Wang, Y.; Oft, M.; Chen, T.; Kirschmeier, P.; Lees, E. M. Dinaciclib (SCH 727965), a novel and potent cyclin-dependent kinase inhibitor. *Mol Cancer Ther* 2010, 9, 2344-53.

Fukuhara, T.; Hosoya, T.; Shimizu, S.; Sumi, K.; Oshiro, T.; Yoshinaka, Y.; Suzuki, M.; Yamamoto, N.; Herzenberg, L. A.; Herzenberg, L. A.; Hagiwara, M. Utilization of host SR protein kinases and RNA-splicing machinery during viral replication. *Proc Natl Acad Sci USA* 2006, 103, 11329-33.

Oumata, N.; Bettayeb, K.; Ferandin, Y.; Demange, L.; Lopez-Giral, A.; Goddard, M. L.; Myrianthopoulos, V.; Mikros, E.; Flajolet, M.; Greengard, P.; Meijer, L.; Galons, H. Roscovitine-derived, dual-specificity inhibitors of cyclin-dependent kinases and casein kinases 1. *J Med Chem* 2008, 51, 5229-42.

Dai, Y.; Dent, P.; Grant, S. Induction of apoptosis in human leukemia cells by the CDK1 inhibitor CGP74514A. *Cell Cycle* 2002, 1, 143-52.

Fabian, M. A.; Biggs, W. H., 3rd; Treiber, D. K.; Atteridge, C. E.; Azimioara, M. D.; Benedetti, M. G.; Carter, T. A.; Ciceri, P.; Edeen, P. T.; Floyd, M.; Ford, J. M.; Galvin, M.; Gerlach, J. L.; Grotzfeld, R. M.; Herrgard, S.; Insko, D. E.; Insko, M. A.; Lai, A. G.; Lelias, J. M.; Mehta, S. A.; Milanov, Z. V.; Velasco, A. M.; Wodicka, L. M.; Patel, H. K.; Zarrinkar, P. P.; Lockhart, D. J. A small molecule-kinase interaction map for clinical kinase inhibitors. *Nat Biotechnol* 2005, 23, 329-36.

Yoshida, T.; Kim, J. H.; Carver, K.; Su, Y.; Weremowicz, S.; Mulvey, L.; Yamamoto, S.; Brennan, C.; Mei, S.; Long, H.; Yao, J.; Polyak, K. CLK2 Is an Oncogenic Kinase and Splicing Regulator in Breast Cancer. *Cancer Res* 2015, 75, 1516-26.

Kang, J.; Sergio, C. M.; Sutherland, R. L.; Musgrove, E. A. Targeting cyclin-dependent kinase 1 (CDK1) but not CDK4/6 or CDK2 is selectively lethal to MYC-dependent human breast cancer cells. *BMC Cancer* 2014, 14, 32.

Chakarova, C. F. et al. Mutations in HPRP3, a third member of pre-mRNA splicing factor genes, implicated in autosomal dominant retinitis pigmentosa. *Hum Mol Genet* 11, 87-92 (2002).

Tanackovic, G. et al. A missense mutation in PRPF6 causes impairment of pre-mRNA splicing and autosomal-dominant retinitis pigmentosa. *Am J Hum Genet* 88, 643-649, doi:10.1016/j.ajhg.2011.04.008 (2011).

Boon, K. L. et al. prp8 mutations that cause human retinitis pigmentosa lead to a U5 snRNP maturation defect in yeast. *Nat Struct Mol Biol* 14, 1077-1083 (2007).

Liu, T. et al. A novel missense SNRNP200 mutation associated with autosomal dominant retinitis pigmentosa in a Chinese family. *PloS one* 7, e45464, doi:10.1371/journal.pone.0045464 (2012).

Vithana, E. N. et al. A human homolog of yeast pre-mRNA splicing gene, PRP31, underlies autosomal dominant retinitis pigmentosa on chromosome 19q13.4 (RP11). *Mol Cell* 8, 375-381 (2001).

He, H. et al. Mutations in U4atac snRNA, a component of the minor spliceosome, in the developmental disorder MOPD I. *Science* 332, 238-240, doi:10.1126/science.1200587 (2011).

Quesada, V. et al. Exome sequencing identifies recurrent mutations of the splicing factor SF3B1 gene in chronic lymphocytic leukemia. *Nature genetics* 44, 47-52, doi:10.1038/ng.1032 (2012).

Makishima, H. et al. Mutations in the spliceosome machinery, a novel and ubiquitous pathway in leukemogenesis. *Blood* 119, 3203-3210, doi:10.1182/blood-2011-12-399774 (2012).

Popowycz, F. et al. Pyrazolo[1,5-a]-1,3,5-triazine as a Purine Bioisostere: Access to Potent Cyclin-Dependent Kinase Inhibitor (R)-Roscovitine Analogue. *Journal of medicinal chemistry* 52, 655-663, doi:10.1021/jm801340z (2009).

Various publications are cited herein, the contents of which are hereby incorporated by reference in their entireties.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula selected from:

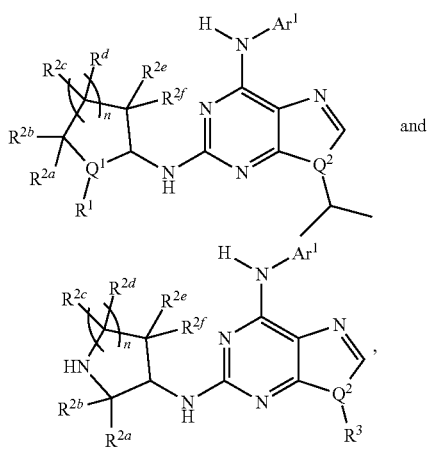

wherein n is selected from 1 and 2;
wherein each of $Q^1$ and $Q^2$ is independently selected from N and CH;
wherein $R^1$ is selected from —OH, —$NHR^4$, —(C1-C4 alkyl)OH, and —(C1-C4 alkyl)$NHR^4$;
wherein $R^4$, when present, is selected from hydrogen and C1-C4 alkyl;
wherein each occurrence of each of $R^{2a}$, $R^{2b}$, $R^{2c}$, $R^{2d}$, $R^{2e}$, and $R^{2f}$ is independently selected from hydrogen and C1-C8 alkyl;
wherein $R^3$ is selected from ethyl and isopropyl; and
wherein $Ar^1$ is selected from monocyclic aryl, 6-membered heteroaryl, and bicyclic heteroaryl, and is substituted with 0-4 groups independently selected from halogen, —OH, —$NH_2$, —CN, —$NO_2$, C1-C4 alkyl, C1-C4 haloalkyl, C1-C4 alkoxy, —NHC(O)(C1-C4 alkyl), C1-C4 alkylamino, and (C1-C4)(C1-C4) dialkylamino,
or a pharmaceutically acceptable salt thereof.

2. The compound of claim 1, wherein n is 2.

3. The compound of claim 1, wherein $Q^2$ is N.

4. The compound of claim 1, wherein $R^1$ is —$NHR^4$.

5. The compound of claim 1, wherein each of $R^{2a}$, $R^{2b}$, $R^{2c}$, $R^{2d}$, $R^{2e}$, and $R^{2f}$ is hydrogen.

6. The compound of claim 1, wherein $Ar^1$ is a moiety having a structure represented by a formula:

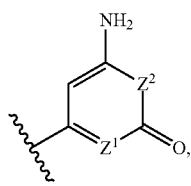
wherein $Z^1$ is selected from CH and N; and
wherein $Z^2$ is selected from $CH_2$ and NH.
7. The compound of claim 1, wherein the compound has a structure represented by a formula selected from:
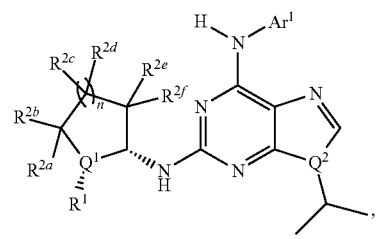
,
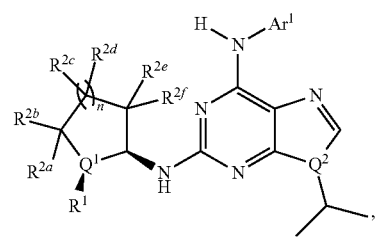
,
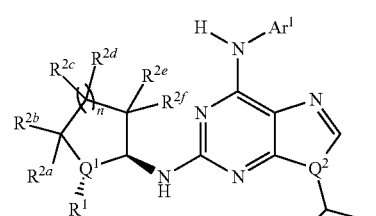
,
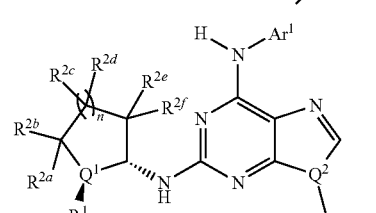
,
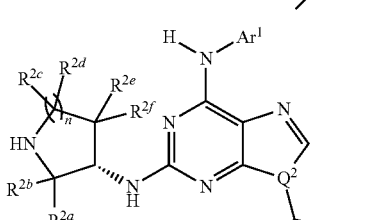
, and
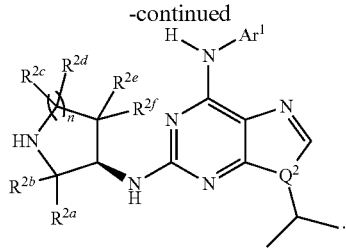
8. The compound of claim 1, wherein the compound is selected from:
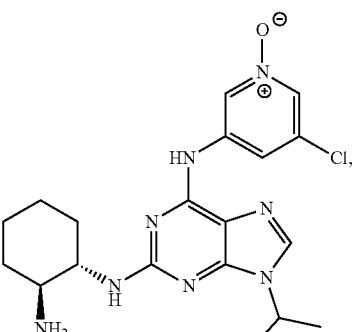
,
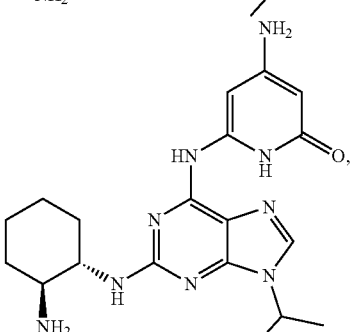
,
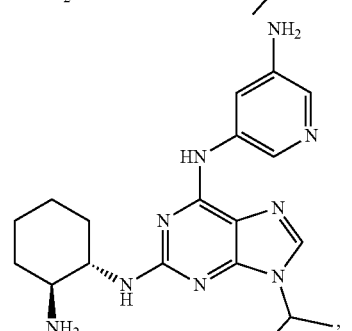
,
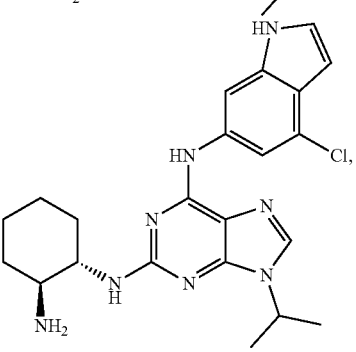
, -continued
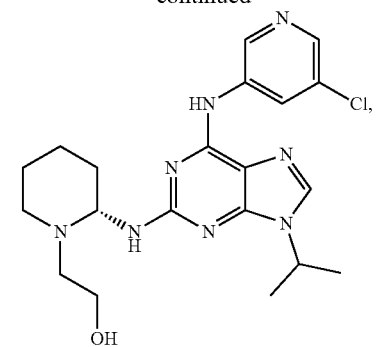
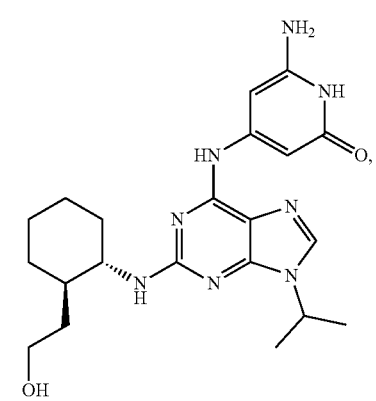
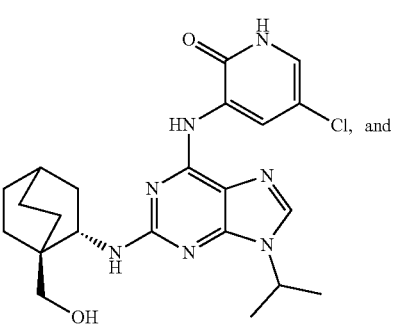
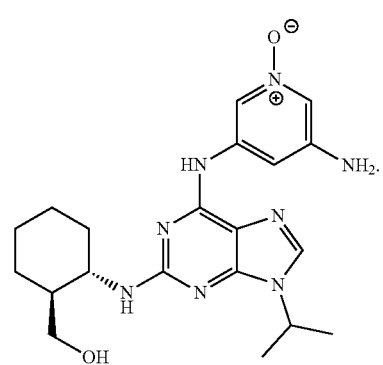
9. The compound of claim 1, wherein the compound is selected from:
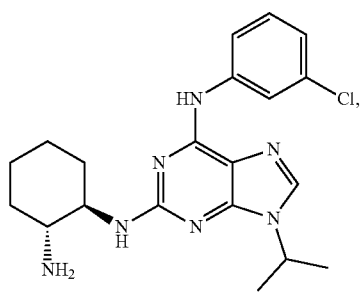
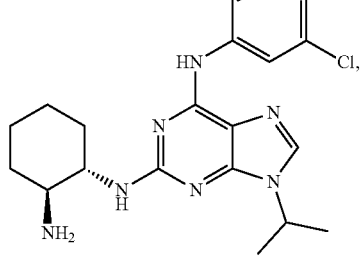
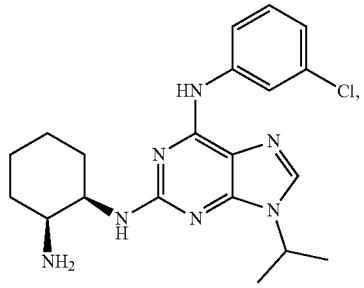
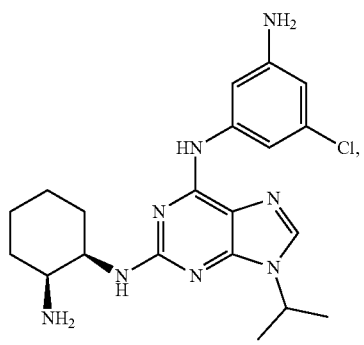
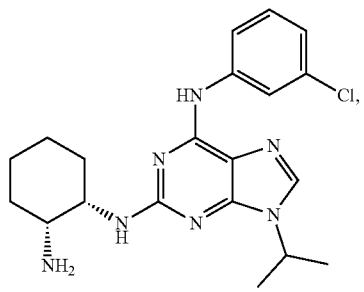

147
-continued

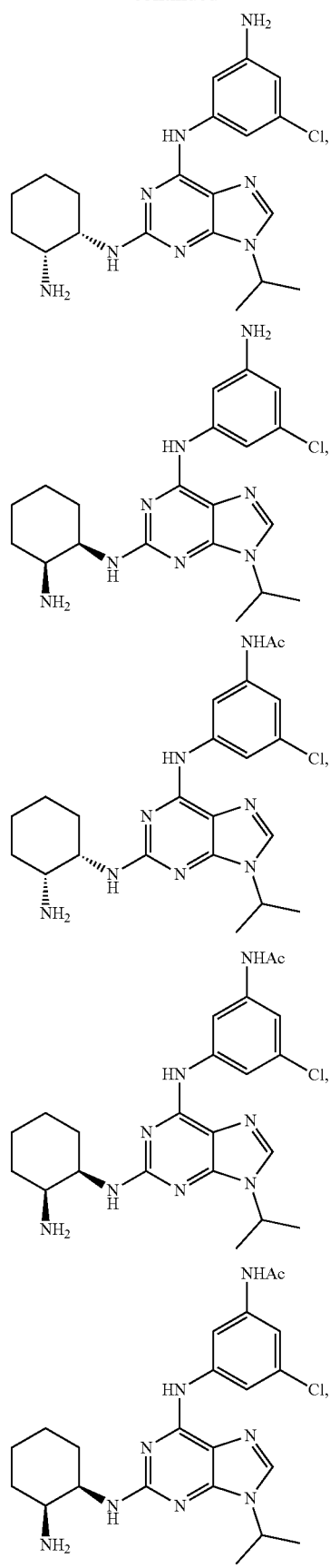

148
-continued

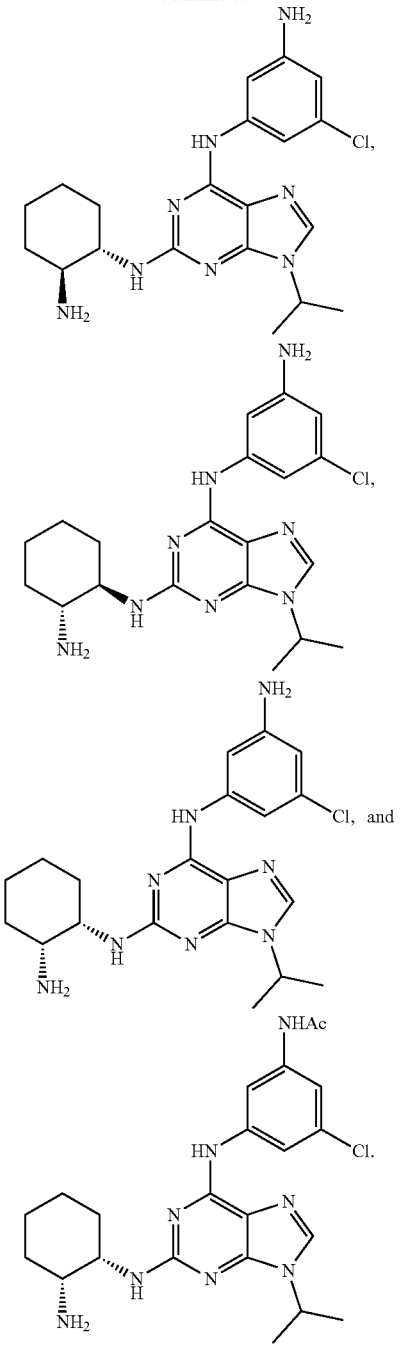

10. A pharmaceutical composition comprising an effective amount of at least one compound of claim 1 and a pharmaceutically acceptable carrier.

11. An in vitro method for inhibiting CLK2 and/or CDK1 in at least one cell, the method comprising the step of contacting the cell with an effective amount of the compound of claim 1.

12. The method of claim 11, wherein $Ar^1$ is a moiety having a structure represented by a formula:

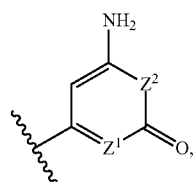

wherein Z¹ is selected from CH and N; and
wherein Z² is selected from CH$_2$ and NH.

13. The method of claim 11, wherein the compound has a structure represented by a formula selected from:

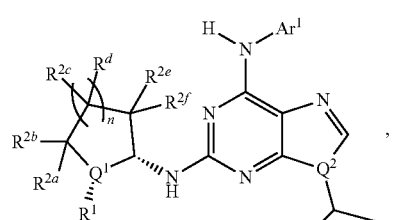

,

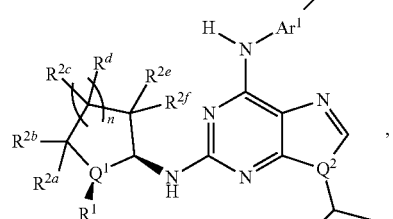

,

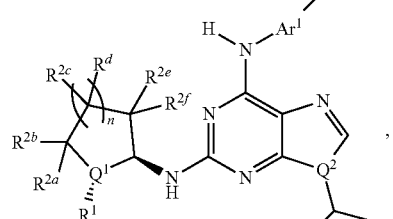

,

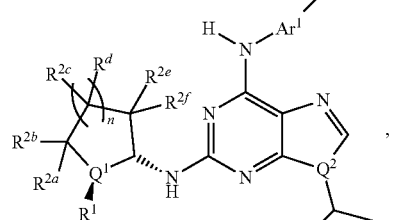

,

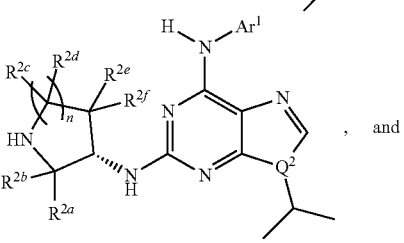

, and

14. The compound of claim 1, wherein the compound has a structure represented by a formula:

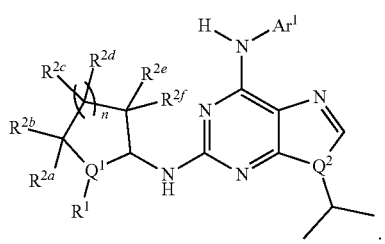

.

15. The compound of claim 1, wherein the compound has a structure represented by a formula:

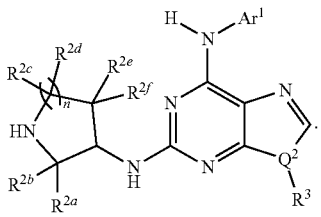

.

16. The compound of claim 1, wherein the compound has a structure represented by a formula:

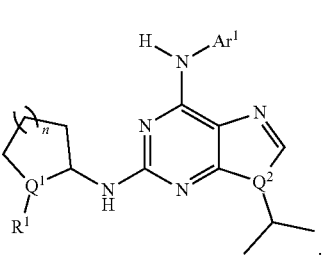

.

17. The compound of claim 1, wherein the compound has a structure represented by a formula:

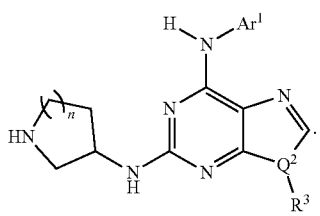

.

* * * * *

```
                        SEQUENCE LISTING

<160> NUMBER OF SEQ ID NOS: 13

<210> SEQ ID NO 1
<211> LENGTH: 16
<212> TYPE: PRT
<213> ORGANISM: Artificial Sequence
<220> FEATURE:
<223> OTHER INFORMATION: Synthetic Construct

<400> SEQUENCE: 1

Glu Arg Met Arg Pro Arg Lys Arg Gln Gly Ser Val Arg Arg Arg Val
1               5                   10                  15

<210> SEQ ID NO 2
<211> LENGTH: 27
<212> TYPE: PRT
<213> ORGANISM: Artificial Sequence
<220> FEATURE:
<223> OTHER INFORMATION: Synthetic Construct

<400> SEQUENCE: 2

Tyr Arg Arg Ala Ala Val Pro Pro Ser Pro Ser Leu Ser Arg His Ser
1               5                   10                  15

Ser Pro His Gln Ser Pro Glu Asp Glu Glu Glu
            20                  25

<210> SEQ ID NO 3
<211> LENGTH: 16
<212> TYPE: PRT
<213> ORGANISM: Artificial Sequence
<220> FEATURE:
<223> OTHER INFORMATION: Synthetic Construct

<400> SEQUENCE: 3

Glu Arg Met Arg Pro Arg Lys Arg Gln Gly Ser Val Arg Arg Arg Val
1               5                   10                  15

<210> SEQ ID NO 4
<211> LENGTH: 27
<212> TYPE: PRT
<213> ORGANISM: Artificial Sequence
<220> FEATURE:
<223> OTHER INFORMATION: Synthetic Construct

<400> SEQUENCE: 4

Tyr Arg Arg Ala Ala Val Pro Pro Ser Pro Ser Leu Ser Arg His Ser
1               5                   10                  15

Ser Pro His Gln Ser Pro Glu Asp Glu Glu Glu
            20                  25
```

<210> SEQ ID NO 5
<211> LENGTH: 12
<212> TYPE: PRT
<213> ORGANISM: Artificial Sequence
<220> FEATURE:
<223> OTHER INFORMATION: Synthetic Construct

<400> SEQUENCE: 5

Glu Ala Ile Tyr Ala Ala Pro Phe Ala Lys Lys Lys
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Synthetic Construct

<400> SEQUENCE: 6

Leu Arg Arg Ala Ser Leu Gly
1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic Construct

<400> SEQUENCE: 7

Ala Lys Arg Arg Arg Leu Ser Ser Leu Arg Ala
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic Construct

<400> SEQUENCE: 8

Glu Ala Ile Tyr Ala Ala Pro Phe Ala Lys Lys Lys
1               5                   10

<210> SEQ ID NO 9
<211> LENGTH: 14
<212> TYPE: PRT
<213> ORGANISM: Artificial Sequence
<220> FEATURE:
<223> OTHER INFORMATION: Synthetic Construct

<400> SEQUENCE: 9

Lys Lys Lys Ser Pro Gly Glu Tyr Val Asn Ile Glu Phe Gly
1               5                   10

<210> SEQ ID NO 10
<211> LENGTH: 23
<212> TYPE: PRT
<213> ORGANISM: Artificial Sequence
<220> FEATURE:
<223> OTHER INFORMATION: Synthetic Construct

<400> SEQUENCE: 10

Lys Lys Lys Lys Glu Arg Leu Leu Asp Asp Arg His Asp Ser Gly Leu
1               5                   10                  15

Asp Ser Met Lys Asp Glu Glu

```
<210> SEQ ID NO 11
<211> LENGTH: 39
<212> TYPE: PRT
<213> ORGANISM: Artificial Sequence
<220> FEATURE:
<223> OTHER INFORMATION: Synthetic Construct

<400> SEQUENCE: 11

Lys Thr Phe Cys Gly Thr Pro Glu Tyr Leu Ala Pro Glu Val Arg Arg
1               5                   10                  15

Glu Pro Arg Ile Leu Ser Glu Glu Gln Glu Met Phe Arg Asp Phe
            20                  25                  30

Asp Tyr Ile Ala Asp Trp Cys
            35

<210> SEQ ID NO 12
<211> LENGTH: 15
<212> TYPE: PRT
<213> ORGANISM: Artificial Sequence
<220> FEATURE:
<223> OTHER INFORMATION: Synthetic Construct

<400> SEQUENCE: 12

Gly Gly Glu Glu Glu Glu Tyr Phe Glu Leu Val Lys Lys Lys Lys
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic Construct

<400> SEQUENCE: 13

Gly Gly Glu Glu Glu Glu Tyr Phe Glu Leu Val Lys Lys Lys Lys
1               5                   10                  15
```